(12) United States Patent
Chamberlain et al.

(10) Patent No.: US 7,820,441 B2
(45) Date of Patent: Oct. 26, 2010

(54) PRODUCTION OF VIRAL VECTORS

(75) Inventors: Jeffrey S. Chamberlain, Seattle, WA (US); Dennis J. Hartigan-O'Connor, Lake Tahoe, CA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 742 days.

(21) Appl. No.: 10/381,153

(22) PCT Filed: Sep. 21, 2001

(86) PCT No.: PCT/US01/29496

§ 371 (c)(1), (2), (4) Date: Oct. 9, 2003

(87) PCT Pub. No.: WO02/27007

PCT Pub. Date: Apr. 4, 2002

(65) Prior Publication Data

US 2004/0087029 A1  May 6, 2004

Related U.S. Application Data

(60) Provisional application No. 60/235,060, filed on Sep. 25, 2000.

(51) Int. Cl.
*C12P 21/00* (2006.01)
*C12P 21/08* (2006.01)
*C12N 15/10* (2006.01)
*C12N 15/11* (2006.01)
*C12N 7/00* (2006.01)
*C12N 15/13* (2006.01)
*C12N 5/10* (2006.01)

(52) U.S. Cl. ............. 435/457; 435/456; 435/325; 424/199.1; 424/233.1; 424/93.21

(58) Field of Classification Search ............... None
See application file for complete search history.

(56) References Cited

U.S. PATENT DOCUMENTS

| | | | | |
|---|---|---|---|---|
| 5,811,238 A | | 9/1998 | Stemmer et al. | 435/6 |
| 5,824,544 A | | 10/1998 | Armentano et al. | 435/320.1 |
| 5,919,676 A | * | 7/1999 | Graham et al. | 435/91.4 |
| 5,932,210 A | | 8/1999 | Gregory et al. | 424/93.2 |
| 6,083,750 A | | 7/2000 | Chamberlain et al. | 435/369 |
| 6,630,346 B1 | * | 10/2003 | Morsy et al. | 435/325 |

FOREIGN PATENT DOCUMENTS

| | | |
|---|---|---|
| EP | 1 016 724 | 7/2000 |
| WO | WO97/25446 | 1/1997 |
| WO | WO 97/25446 * | 7/1997 |
| WO | WO 98 13510 | 4/1998 |
| WO | WO 00 18939 | 4/2000 |
| WO | WO 00 46360 | 8/2000 |

OTHER PUBLICATIONS

Hartigan-O'Connor et al, Improved Production of Gutted Adenovirus in Cells Expressing Adenovirus Preterminal Protein and DNA Polymerase, Journal of Virology, vol. 73(9), Sep. 1999, p. 7835-7841.*
Hartigan-O'Connor et al, Improved Production of Gutted Adenovirus in Cells Expressing Adenovirus Preterminal Protein and DNA Polymerase, Journal of Virology, vol. 73(9), Sep. 1999, STN abstract only.*
Hay et al, Origin of adenovirus DNA replication. Role of the nuclear factor I binding site in vivo, abstract, J Mol Biol, 1985, 186(1), pp. 129-136).*
Amalfitano et al., in Lucy J, and Brown S. (eds): Dystrophin: Gene, Protein, and Cell Biology (Cambridge University Press, 1997), Chpt. 1, 1- 26.
Challberg MD., Rawlins Dr.,"Template requirements for the initiation of adenovirus DNA replication," *P.N.A.S.*, 81(1):100-4 (1984).
Graham, F.L.,"Covalently closed circles of human adenovirus DNA are infectious," *The EMBO J.*, 3:2917-2922 (1984).
Hanahan, D.,"Studies on transformation of *Escherichia coli* with plasmids,"*J. Mol. Biol.*, 166:557-580 (1983).
Hirt, B.,"Selective extraction of polyoma DNA from infected mouse cell cultures,"*J. Mol. Biol.* 26:365-369 (1967).
Pronk et al.,"The adenovirus terminal protein influences binding of replication proteins and changes the origin structure," *Nucleic Acids Research*, 25(10):2293-2300 ( 1993).
Wright, E. et al., "Dual-origin plasmids containing an amplifiable ColE1*ori*; temperature-controlled expression of cloned genes," *Gene* 49(3):311-321 (1986).

* cited by examiner

*Primary Examiner*—Maria B Marvich
(74) *Attorney, Agent, or Firm*—Medlen & Carroll, LLP

(57) ABSTRACT

The present invention relates to methods and compositions for the production of viral vectors. In particular, the present invention provides methods and compositions for faster, higher titer and higher purity production of viral vectors (e.g. adenoviral vectors). In some embodiments, the present invention provides gutted and helper viruses with identical or similar termini. In other embodiments, the present invention provides terminal protein linked adenoviral DNA. In certain embodiments, the present invention provides template extended adenoviral DNA.

17 Claims, 49 Drawing Sheets

A.

| Origin | Structure |
|---|---|
| Natural or TP-primer-modified | ⬭CATCATCAATAA<br>GTAGTAGTTATT |
| Deproteinized or Hirt prep | Serine⌒CATCATCAATAA<br>GTAGTAGTTATT |
| PacI | TAACATCATCAATAA<br>TAATTGTAGTAGTTATT |
| FseI | CCATCATCAATAA<br>GGCCGGTAGTAGTTATT |

B.

```
                     12587                              17756
                       ↓                                  ↓
Wild-type:    GACGA GGCCGGCC TGGTC ... GGCAT GGCCGGCC ACGGC ΔFseI.4:      GACGA AGCCGGCC TGGTC ... GGCAT GGCCGGCT ACGGC
```

C.

FIGURE 3
A.
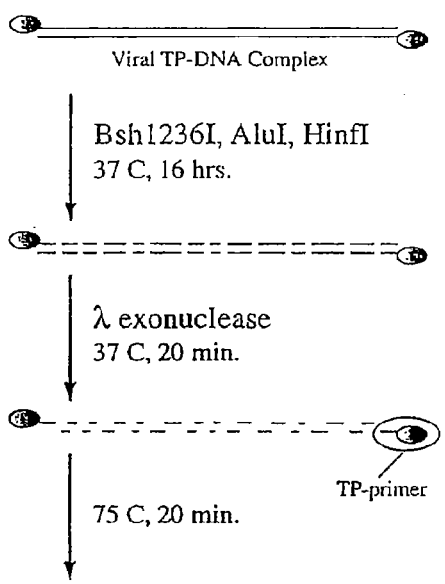
B.
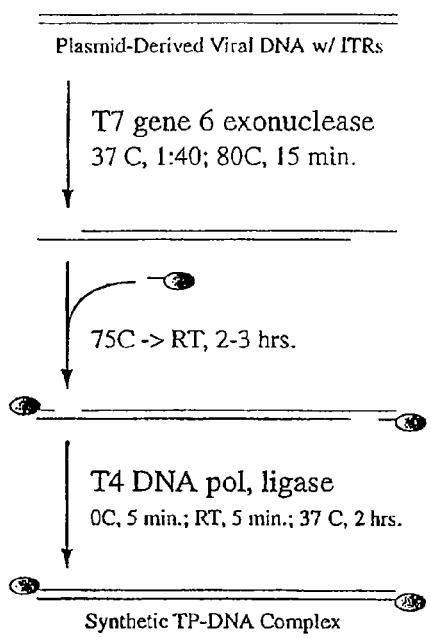

FIGURE 4
A.
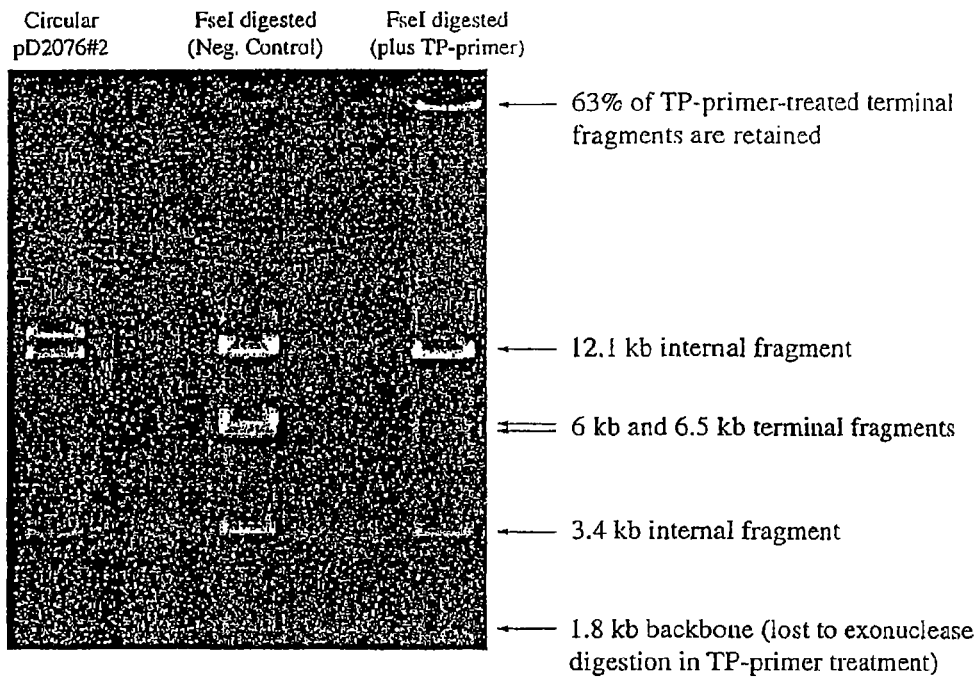
B.
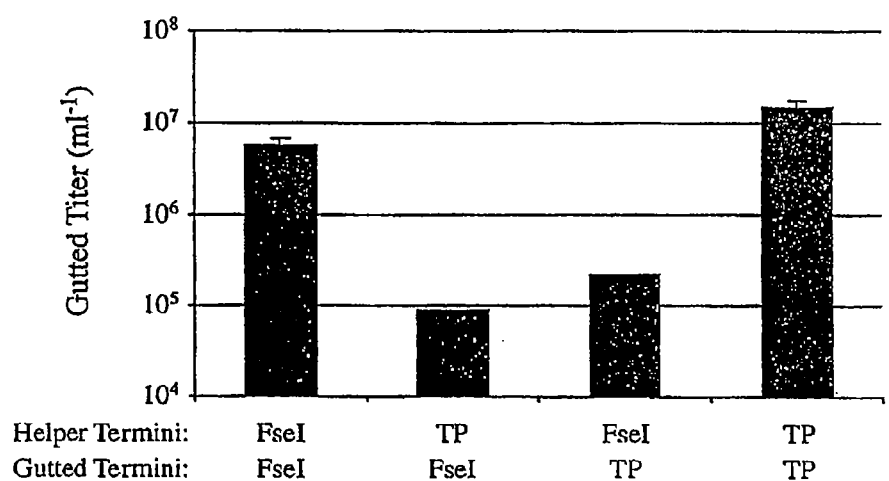

FIGURE 8

```
CATCATCAATAATATACCTTATTTTGGATTGAAGCCAATATGATAATGAGGGGGTGGAGTTTGTGACGTGGCGCGG
GGCGTGGGAACGGGGCGGGTGACGTAGTAGTGTGGCGGAAGTGTGATGTTGCAAGTGTGGCGGAACACATGTATAA
CTTCGTATAATGTATGCTATACGAAGTTATACATGTAAGCGACGGATGTGGCAAAAGTGACGTTTTTGGTGTGCGC
CGGTGTACACAGGAAGTGACAATTTTCGCGCGGTTTTAGGCGGATGTTGTAGTAAATTTGGGCGTAACCGAGTAAG
ATTTGGCCATTTTCGCGGGAAAACTGAATAAGAGGAAGTGAAATCTGAATAATTTTGTGTTACTCATAGCGCGTAA
TATTTGTCTAGGGAGATCTATAACTTCGTATAATGTATGCTATACGAAGTTATTACCGAAGAAATGGCTCGAGATC
TGGAAGGTGCTGAGGTACGATGAGACCCGCACCAGGTGCAGACCCTGCGAGTGTGGCGGTAAACATATTAGGAACC
AGCCTGTGATGCTGGATGTGACCGAGGAGCTGAGGCCCGATCACTTGGTGCTGGCCTGCACCCGCGCTGAGTTTGG
CTCTAGCGATGAAGATACAGATTGAGGTACTGAAATGTGTGGGCGTGGCTTAAGGGTGGGAAAGAATATATAAGGT
GGGGGTCTTATGTAGTTTTGTATCTGTTTTGCAGCAGCCGCCGCCGCCATGAGCACCAACTCGTTTGATGGAAGCA
TTGTGAGCTCATATTTGACAACGCGCATGCCCCATGGGCCGGGGTGCGTCAGAATGTGATGGGCTCCAGCATTGA
TGGTCGCCCCGTCCTGCCCGCAAACTCTACTACCTTGACCTACGAGACCGTGTCTGGAACGCCGTTGGAGACTGCA
GCCTCCGCCGCCGCTTCAGCCGCTGCAGCCACCGCCCGCGGGATTGTGACTGACTTTGCTTTCCTGAGCCCGCTTG
CAAGCAGTGCAGCTTCCCGTTCATCCGCCCGCGATGACAAGTTGACGGCTCTTTTGGCACAATTGGATTCTTTGAC
CCGGGAACTTAATGTCGTTTCTCAGCAGCTGTTGGATCTGCGCCAGCAGGTTTCTGCCCTGAAGGCTTCCTCCCCT
CCCAATGCGGTTTAAAACATAAATAAAAAACCAGACTCTGTTTGGATTTGGATCAAGCAAGTGTCTTGCTGTCTTT
ATTTAGGGGTTTTGCGCGCGCGGTAGGCCCGGGACCAGCGGTCTCGGTCGTTGAGGGTCCTGTGTATTTTTTCCAG
GACGTGGTAAAGGTGACTCTGGATGTTCAGATACATGGGCATAAGCCCGTCTCTGGGGTGGAGGTAGCACCACTGC
AGAGCTTCATGCTGCGGGGTGGTGTTGTAGATGATCCAGTCGTAGCAGGAGCGCTGGGCGTGGTGCCTAAAAATGT
CTTTCAGTAGCAAGCTGATTGCCAGGGGCAGGCCCTTGGTGTAAGTGTTTACAAAGCGGTTAAGCTGGGATGGGTG
CATACGTGGGGATATGAGATGCATCTTGGACTGTATTTTTAGGTTGGCTATGTTCCCAGCCATATCCCTCCGGGGA
TTCATGTTGTGCAGAACCACCAGCACAGTGTATCCGGTGCACTTGGGAAATTTGTCATGTAGCTTAGAAGGAAATG
CGTGGAAGAACTTGGAGACGCCCTTGTGACCTCCAAGATTTTCCATGCATTCGTCCATAATGATGGCAATGGGCCC
ACGGGCGGCGGCCTGGGCGAAGATATTTCTGGGATCACTAACGTCATAGTTGTGTTCCAGGATGAGATCGTCATAG
GCCATTTTTACAAAGCGCGGGCGGAGGGTGCCAGACTGCGGTATAATGGTTCCATCCGGCCCAGGGGCGTAGTTAC
CCTCACAGATTTGCATTTCCCACGCTTTGAGTTCAGATGGGGGATCATGTCTACCTGCGGGGCGATGAAGAAAAC
GGTTTCCGGGGTAGGGGAGATCAGCTGGGAAGAAAGCAGGTTCCTGAGCAGCTGCGACTTACCGCAGCCGGTGGGC
CCGTAAATCACACCTATTACCGGGTGCAACTGGTAGTTAAGAGAGCTGCAGCTGCCGTCATCCCTGAGCAGGGGGG
CCACTTCGTTAAGCATGTCCCTGACTCGCATGTTTTCCCTGACCAAATCCGCCAGAAGGCGCTCGCCGCCCAGCGA
TAGCAGTTCTTGCAAGGAAGCAAAGTTTTTCAACGGTTTGAGACCGTCCGCCGTAGGCATGCTTTTGAGCGTTTGA
CCAAGCAGTTCCAGGCGGTCCCACAGCTCGGTCACCTGCTCTACGGCATCTCGATCCAGCATATCTCCTCGTTTCG
CGGGTTGGGGCGGCTTTCGCTGTACGGCAGTAGTCGGTGCTCGTCCAGACGGGCCAGGGTCATGTCTTTCCACGGG
CGCAGGGTCCTCGTCAGCGTAGTCTGGGTCACGGTGAAGGGGTGCGCTCCGGGCTGCGCGCTGGCCAGGGTGCGCT
TGAGGCTGGTCCTGCTGGTGCTGAAGCGCTGCCGGTCTTCGCCCTGCGCGTCGGCCAGGTAGCATTTGACCATGGT
GTCATAGTCCAGCCCCTCCGCGGCGTGGCCCTTGGCGCGCAGCTTGCCCTTGGAGGAGGCGCCGCACGAGGGGCAG
TGCAGACTTTTGAGGGCGTAGAGCTTGGGCGCGAGAAATACCGATTCCGGGGAGTAGGCATCCGCGCCGCAGGCCC
CGCAGACGGTCTCGCATTCCACGAGCCAGGTGAGCTCTGGCCGTTCGGGGTCAAAAACCAGGTTTCCCCCATGCTT
TTTGATGCGTTTCTTACCTCTGGTTTCCATGAGCCGGTGTCCACGCTCGGTGACGAAAAGGCTGTCCGTGTCCCCG
TATACAGACTTGAGAGGCCTGTCCTCGAGCGGTGTTCCGCGGTCCTCCTCGTATAGAAACTCGGACCACTCTGAGA
CAAAGGCTCGCGTCCAGGCCAGCACGAAGGAGGCTAAGTGGGAGGGGTAGCGGTCGTTGTCCACTAGGGGTCCAC
TCGCTCCAGGGTGTGAAGACACATGTCGCCCTCTTCGGCATCAAGGAAGGTGATTGGTTTGTAGGTGTAGGCCACG
TGACCGGGTGTTCCTGAAGGGGGCTATAAAAGGGGTGGGGCGCGTTCGTCCTCACTCTCTTCCGCATCGCTGT
CTGCGAGGGCCAGCTGTTGGGGTGAGTACTCCCTCTGAAAAGCGGGCATGACTTCTGCGCTAAGATTGTCAGTTTC
CAAAAACGAGGAGGATTTGATATTCACCTGGCCCGCGGTGATGCCTTTGAGGGTGGCCGCATCCATCTGGTCAGAA
AAGACAATCTTTTTGTTGTCAAGCTTGGTGGCAAACGACCCGTAGAGGGCGTTGGACAGCAACTTGGCGATGGAGC
GCAGGGTTTGGTTTTTGTCGCGATCGGCGCGCTCCTTGGCCGCGATGTTTAGCTGCACGTATTCGCGCGCAACGCA
CCGCCATTCGGGAAAGACGGTGGTGCGCTCGTCGGGCACCAGGTGCACGCGCCAACCGCGGTTGTGCAGGGTGACA
AGGTCAACGCTGGTGGCTACCTCTCCGCGTAGGCGCTCGTTGGTCCAGCAGAGGCGGCCGCCCTTGCGCGAGCAGA
ATGGCGGTAGGGGTCTAGCTGCGTCTCGTCCGGGGGTCTGCGTCCACGGTAAAGACCCCGGGCAGCAGGCGCGC
GTCGAAGTAGTCTATCTTGCATCCTTGCAAGTCTAGCGCCTGCTGCCATGCGCGGGCGGCAAGCGCGCGCTCGTAT
GGGTTGAGTGGGGGACCCCATGGCATGGGGTGGGTGAGCGCGAGGCGTACATGCCGCAAATGTCGTAAACGTAGA
GGGGCTCTCTGAGTATTCCAAGATATGTAGGGTAGCATCTTCCACCGCGGATGCTGGCGCGCACGTAATCGTATAG
TTCGTGCGAGGGAGCGAGGAGGTCGGGACCGAGGTTGCTACGGGCGGGCTGCTCTGCTCGGAAGACTATCTGCCTG
AAGATGGCATGTGAGTTGGATGATATGGTTGGACGCTGGAAGACGTTGAAGCTGGCGTCTGTGAGACCTACCGCGT
CACGCACGAAGGAGGCGTAGGAGTCGCGCAGCTTGTTGACCAGCTCGGCGGTGACCTGCACGTCTAGGGCGCAGTA
GTCCAGGGTTTCCTTGATGATGTCATACTTATCCTGTCCCTTTTTTTTCCACAGCTCGCGGTTGAGGACAAACTCT
TCGCGGTCTTTCCAGTACTCTTGGATCGGAAACCCGTCGGCCTCCGAACGGTAAGAGCCTAGCATGTAGAACTGGT
TGACGGCCTGGTAGGCGCAGCATCCCTTTTCTACGGGTAGCGCGTATGCCTGCGCGGCCTTCCGGAGCGAGGTGTG
GGTGAGCGCAAAGGTGTCCCTGACCATGACTTTGAGGTACTGGTATTTGAAGTCAGTGTCGTCGCATCCGCCCTGC
TCCCAGAGCAAAAGTCCGTGCGCTTTTTGAACGCGGATTTGGCAGGGCGAAGGTGACATCGTTGAAGAGTATCT
TTCCCGCGCGAGGCATAAAGTTGCGTGTGATGCGGAAGGGTCCCGGCACCTCGGAACGGTTGTTAATTACCTGGGC
```

FIGURE 8A

```
GGCGAGCACGATCTCGTCAAAGCCGTTGATGTTGTGGCCCACAATGTAAAGTTCCAAGAAGCGCGGGATGCCCTTG
ATGGAAGGCAATTTTTTAAGTTCCTCGTAGGTGAGCTCTTCAGGGGAGCTGAGCCCGTGCTCTGAAAGGGCCCAGT
CTGCAAGATGAGGGTTGGAAGCGACGAATGAGCTCCACAGGTCACGGGCCATTAGCATTTGCAGGTGGTCGCGAAA
GGTCCTAAACTGGCGACCTATGGCCATTTTTTCTGGGGTGATGCAGTAGAAGGTAAGCGGGTCTTGTTCCCAGCGG
TCCCATCCAAGGTTCGCGGCTAGGTCTCGCGCGGCAGTCACTAGAGGCTCATCTCCGCCGAACTTCATGACCAGCA
TGAAGGGCACGAGCTGCTTCCCAAAGGCCCCCATCCAAGTATAGGTCTCTACATCGTAGGTGACAAAGAGACGCTC
GGTGCGAGGATGCGAGCCGATCGGGAAGAACTGGATCTCCCGCCACCAATTGGAGGAGTGGCTATTGATGTGGTGA
AAGTAGAAGTCCCTGCGACGGGCCGAACACTCGTGCTGGCTTTTGTAAAAACGTGCGCAGTACTGGCAGCGGTGCA
CGGGCTGTACATCCTGCACGAGGTTGACCTGACGACCGCGCACAAGGAAGCAGAGTGGGAATTTGAGCCCCTCGCC
TGGCGGGTTTGGCTGGTGGTCTTCTACTTCGGCTGCTTGTCCTTGACCGTCTGGCTGCTCGAGGGGAGTTACGGTG
GATCGGACCACCACGCCGCGCGAGCCCAAAGTCCAGATGTCCGCGCGCGGCGGTCGGAGCTTGATGACAACATCGC
GCAGATGGGAGCTGTCCATGGTCTGGAGCTCCCGCGGCGTCAGGTCAGGCGGGAGCTCCTGCAGGTTTACCTCGCA
TAGACGGGTCAGGGCGCGGGCTAGATCCAGGTGATACCTAATTTCCAGGGGCTGGTTGGTGGCGGCGTCGATGGCT
TGCAAGAGGCCGCATCCCCGCGGCGCGACTACGGTACCGCGCGGCGGGCGGTGGGCCGCGGGGTGTCCTTGGATG
ATGCATCTAAAAGCGGTGACGCGGGCGAGCCCCGGAGGTAGGGGGGCTCCGGACCCGCCGGGAGAGGGGCAGG
GGCACGTCGGCGCCGCGCGGGCAGGAGCTGGTGCTGCGCGCGTAGGTTGCTGGCGAACGCGACGACGCGGCGGT
TGATCTCCTGAATCTGGCGCCTCTGCGTGAAGACGACGGGCCCGGTGAGCTTGAGCCTGAAAGAGAGTTCGACAGA
ATCAATTTCGGTGTCGTTGACGGCGGCCTGGCGCAAAATCTCCTGCACGTCTCCTGAGTTGTCTTGATAGGCGATC
TCGGCCATGAACTGCTCGATCTCTTCCTCCTGGAGATCTCCGCGTCCGGCTCGCTCCACGGTGGCGGCGAGGTCGT
TGGAAATGCGGGCCATGAGCTGCGAGAAGGCGTTGAGGCCTCCCTCGTTCCAGACGCGGCTGTAGACCACGCCCCC
TTCGGCATCGCGGGCGCGCATGACCACCTGCGCGAGATTGAGCTCCACGTGCCGGGCGAAGACGGCGTAGTTTCGC
AGGCGCTGAAAGAGGTAGTTGAGGGTGGTGGCGGTGTGTTCTGCCACGAAGAAGTACATAACCCAGCGTCGCAACG
TGGATTCGTTGATATCCCCCAAGGCCTCAAGGCGCTCCATGGCCTCGTAGAAGTCCACGGCGAAGTTGAAAAACTG
GGAGTTGCGCGCCGACACGGTTAACTCCTCCTCCAGAAGACGGATGAGCTCGGCGACAGTGTCGCGCACCTCGCGC
TCAAAGGCTACAGGGGCCTCTTCTTCTTCTTCAATCTCCTCTTCCATAAGGGCCTCCCCTTCTTCTTCTTCTGGCG
GCGGTGGGGAGGGGGACACGGCGGCGACGACGGCGCACCGGGAGGCGGTCGACAAAGCGCTCGATCATCTCCCC
GCGGCGACGGCGCATGGTCTCGGTGACGCGCGCGGCCGTTCTCGCGGGGCGCAGTTGGAAGACGCCGCCCGTCATG
TCCCGGTTATGGGTTGGCGGGGGCTGCCATGCGGCAGGGATACGGCGCTAACGATGCATCTCAACAATTGTTGTG
TAGGTACTCCGCCGCCGAGGGACCTGAGCGAGTCCGCATCGACCGGATCGGAAAACCTCTCGAGAAAGGCGTCTAA
CCAGTCACAGTCGCAAGGTAGGCTGAGCACCGTGGCGGGCGGCAGCGGGCGGCGGTCGGGGTTGTTTCTGGCGGAG
GTGCTGCTGATGATGTAATTAAAGTAGGCGGTCTTGAGACGGCGGATGGTCGACAGAAGCACCATGTCCTTGGGTC
CGGCCTGCTGAATGCGCAGGCGGTCGGCCATGCCCCAGGCTTCGTTTTGACATCGGCGCAGGTCTTTGTAGTAGTC
TTGCATGAGCCTTTCTACCGGCACTTCTTCTTCTCCTTCCTCTTGTCCTGCATCTCTTGCATCTATCGCTGCGGCG
GCGGCGGAGTTTGGCCGTAGGTGGCGCCCTCTTCCTCCCATGCGTGTGACCCCGAAGCCCTCATCGGCTGAAGCA
GGGCTAGGTCGGCGACAACGCGCTCGGCTAATATGGCCTGCTGCACCTGCGTGAGGGTAGACTGGAAGTCATCCAT
GTCCACAAAGCGGTGGTATGCGCCCGTGTTGATGGTGTAAGTGCAGTTGGCCATAACGGACCAGTTAACGGTCTGG
TGACCCGGCTGCGAGAGCTCGGTGTACCTGAGACGCGAGTAAGCCCTCGAGTCAAATACGTAGTCGTTGCAAGTCC
GCACCAGGTACTGGTATCCCACCCAAAAAGTGCGGCGGCGGCTGGCGGTAGAGGGGCCAGCGTAGGGTGGCCGGGGC
TCCGGGGGCGAGATCTTCCAACATAAGGCGATGATATCCGTAGATGTACCTGGACATCCAGGTGATGCCGGCGGCG
GTGGTGGAGGCGCGCGGAAAGTCGCGGACGCGGTTCCAGATGTTGCGCAGCGGCAAAAAGTGCTCCATGGTCGGGA
CGCTCTGGCCGGTCAGGCGCGCGCAATCGTTGACGCTCTACCGTGCAAAAGGAGAGCCTGTAAGCGGGCACTCTTC
CGTGGTCTGGTGGATAAATTCGCAAGGGTATCATGGCGGACGACCGGGGTTCGAGCCCCGTATCCGGCCGTCCGCC
GTGATCCATGCGGTTACCGCCCGCGTGTCGAACCCAGGTGTGCGACGTCAGACAACGGGGAGTGCTCCTTTTGGC
TTCCTTCCAGGCGCGGCGGCTGCTGCGCTAGCTTTTTTGGCCACTGGCCGCGCGCAGCGTAAGCGGTTAGGCTGGA
AAGCGAAAGCATTAAGTGGCTCGCTCCCTGTAGCCGGAGGGTTATTTTCCAAGGGTTGAGTCGCGGGACCCCCGGT
TCGAGTCTCGGACCGGCCGGACTGCGGCGAACGGGGGTTTGCCTCCCCGTCATGCAAGACCCCGCTTGCAAATTCC
TCCGGAAACAGGGACGAGCCCCTTTTTTGCTTTTCCCAGATGCATCCGGTGCTGCGGCAGATGCGCCCCCTCCTC
AGCAGCGGCAAGAGCAAGAGCAGCGGCAGACATGCAGGGCACCCTCCCCTCCTCCTACCGCGTCAGGAGGGGCGAC
ATCCGCGGTTGACGCGGCAGCAGATGGTGATTACGAACCCCCGCGGCGCCGGGCCCGGCCACTACCTGGACTTGGAG
GAGGGCGAGGGCCTGGCGCGGCTAGGAGCGCCCTCTCCTGAGCGGTACCCAAGGGTGCAGCTGAAGCGTGATACGC
GTGAGGCGTACGTGCCGCGGCAGAACCTGTTTCGCGACCGCGAGGGAGAGGAGCCCGAGGAGATGCGGGATCGAAA
GTTCCACGCAGGGCGCGAGCTGCGGCATGGCCTGAATCGCGAGCGGTTGCTGCGCGAGGAGGACTTTGAGCCCGAC
GCGCGAACCGGGATTAGTCCCGCGCGCGCACACGTGGCGGCCGCCGACCTGGTAACCGCATACGAGCAGACGGTGA
ACCAGGAGATTAACTTTCAAAAAAGCTTTAACAACCACGTGCGTACGCTTGTGGCGCGCGAGGAGGTGGCTATAGG
ACTGATGCATCTGTGGGACTTTGTAAGCGCGCTGGAGCAAAACCCAAATAGCAAGCCGCTCATGGCGCAGCTGTTC
CTTATAGTGCAGCACAGCAGGGACAACGAGGCATTCAGGGATGCGCTGCTAAACATAGTAGAGCCCGAGGGCCGCT
GGCTGCTCGATTTGATAAACATCCTGCAGAGCATAGTGGTGCAGGAGCGCAGCTTGAGCCTGGCTGACAAGGTGGC
CGCCATCAACTATTCCATGCTTAGCCTGGGCAAGTTTTACGCCCGCAAGATATACCATACCCCTTACGTTCCCATA
GACAAGGAGGTAAAGATCGAGGGGTTCTACATGCGCATGGCGCTGAAGGTGCTTACCTTGAGCGACGACCTGGGCG
TTTATCGCAACGAGCGCATCCACAAGGCCGTGAGCGTGAGCCGGCGGCGCGAGCTCAGCGACCGCGAGCTGATGCA
CAGCCTGCAAAGGGCCCTGGCTGGCACGGGCAGCGGCGATAGAGAGGCCGAGTCCTACTTTGACGCGGGCGCTGAC
```

FIGURE 8B

```
CTGCGCTGGGCCCCAAGCCGACGCGCCCTGGAGGCAGCTGGGGCCGGACCTGGGCTGGCGGTGGCACCCGCGCGCG
CTGGCAACGTCGGCGGCGTGGAGGAATATGACGAGGACGATGAGTACGAGCCAGAGGACGGCGAGTACTAAGCGGT
GATGTTTCTGATCAGATGATGCAAGACGCAACGGACCCGGCGGTGCGGGCGGCGCTGCAGAGCCAGCCGTCCGGCC
TTAACTCCACGGACGACTGGCGCCAGGTCATGGACCGCATCATGTCGCTGACTGCGCGCAATCCTGACGCGTTCCG
GCAGCAGCCGCAGGCCAACCGGCTCTCCGCAATTCTGGAAGCGGTGGTCCCGGCGCGCGCAAACCCCACGCACGAG
AAGGTGCTGGCGATCGTAAACGCGCTGGCCGAAAACAGGGCCATCCGGCCCGACGAGGCCGGCCTGGTCTACGACG
CGCTGCTTCAGCGCGTGGCTCGTTACAACAGCGGCAACGTGCAGACCAACCTGGACCGGCTGGTGGGGATGTGCG
CGAGGCCGTGGCGCAGCGTGAGCGCGCGCAGCAGCAGGGCAACCTGGGCTCCATGGTTGCACTAAACGCCTTCCTG
AGTACACAGCCCGCCAACGTGCCGCGGGGACAGGAGGACTACACCAACTTTGTGAGCGCACTGCGGCTAATGGTGA
CTGAGACACCGCAAAGTGAGGTGTACCAGTCTGGGCCAGACTATTTTTTCCAGACCAGTAGACAAGGCCTGCAGAC
CGTAAACCTGAGCCAGGCTTTCAAAAACTTGCAGGGGCTGTGGGGGGTGCGGGCTCCCACAGGCGACCGCGCGACC
GTGTCTAGCTTGCTGACGCCCAACTCGCGCCTGTTGCTGCTGCTAATAGCGCCCTTCACGGACAGTGGCAGCGTGT
CCCGGGACACATACCTAGGTCACTTGCTGACACTGTACCGCGAGGCCATAGGTCAGGCGCATGTGGACGAGCATAC
TTTCCAGGAGATTACAAGTGTCAGCCGCGCGCTGGGGCAGGAGGACACGGGCAGCCTGGAGGCAACCCTAAACTAC
CTGCTGACCAACCGGCGGCAGAAGATCCCCTCGTTGCACAGTTTAAACAGCGAGGAGGAGCGCATTTTGCGCTACG
TGCAGCAGAGCGTGAGCCTTAACCTGATGCGCGACGGGGTAACGCCCAGCGTGGCGCTGGACATGACCGCGCGCAA
CATGGAACCGGGCATGTATGCCTCAAACCGGCCGTTTATCAACCGCCTAATGGACTACTTGCATCGCGCGGCCGCC
GTGAACCCCGAGTATTTCACCAATGCCATCTTGAACCCGCACTGGCTACCGCCCCCTGGTTTCTACACCGGGGAT
TCGAGGTGCCCGAGGGTAACGATGGATTCCTCTGGGACGACATAGACGACAGCGTGTTTTCCCCGCAACCGCAGAC
CCTGCTAGAGTTGCAACAGCGCGAGCAGGCAGAGGCGGCCTGCGAAAGGAAAGCTTCCGCAGGCCAAGCAGCTTG
TCCGATCTAGGCGCTGCGGCCCCGCGGTCAGATGCTAGTAGCCCATTTCCAAGCTTGATAGGGTCTCTTACCAGCA
CTCGCACCACCCGCCCGCGCCTGCTGGGCGAGGAGGAGTACCTAAACAACTCGCTGCTGCAGCCGCAGCGCGAAAA
AAACCTGCCTCCGGCATTTCCCAACAACGGGATAGAGAGCCTAGTGGACAAGATGAGTAGATGGAAGACGTACGCG
CAGGAGCACAGGGACGTGCCAGGCCCGCGCCCGCCCACCCGTCGTCAAAGGCACGACCGTCAGCGGGGTCTGGTGT
GGGAGGACGATGACTCGGCAGACGACAGCAGCGTCCTGGATTTGGGAGGGAGTGGCAACCCGTTTGCGCACCTTCG
CCCCAGGCTGGGGAGAATGTTTTAAAAAAAAAAAAGCATGATGCAAAATAAAAAACTCACCAAGGCCATGGCACCG
AGCGTTGGTTTTCTTGTATTCCCCTTAGTATGCGGCGCGCGGCGATGTATGAGGAAGGTCCTCCTCCCTCCTACGA
GAGTGTGGTGAGCGCGGCGCCAGTGGCGGCGGCGCTGGGTTCTCCCTTCGATGCTCCCCTGGACCCGCCGTTTGTG
CCTCCGCGGTACCTGCGGCCTACCGGGGGGAGAAACAGCATCCGTTACTCTGAGTTGGCACCCCTATTCGACACCA
CCCGTGTGTACCTGGTGGACAACAAGTCAACGGATGTGGCATCCCTGAACTACCAGAACGACCACAGCAACTTTCT
GACCACGGTCATTCAAAACAATGACTACAGCCCGGGGGAGGCAAGCACACAGACCATCAATCTTGACGACCGGTCG
CACTGGGGCGGCGACCTGAAAACCATCCTGCATACCAACATGCCAAATGTGAACGAGTTCATGTTTACCAATAAGT
TTAAGGCGCGGGTGATGGTGTCGCGCTTGCCTACTAAGGACAATCAGGTGGAGCTGAAATACGAGTGGGTGGAGTT
CACGCTGCCCGAGGGCAACTACTCCGAGACCATGACCATAGACCTTATGAACAACGCGATCGTGGAGCACTACTTG
AAAGTGGGCAGACAGAACGGGGTTCTGGAAAGCGACATCGGGGTAAAGTTTGACACCCGCAACTTCAGACTGGGGT
TTGACCCCGTCACTGGTCTTGTCATGCCTGGGGTATATACAAACGAAGCCTTCCATCCAGACATCATTTTGCTGCC
AGGATGCGGGGTGGACTTCACCCACAGCCGCCTGAGCAACTTGTTGGGCATCCGCAAGCGGCAACCCTTCCAGGAG
GGCTTTAGGATCACCTACGATGATCTGGAGGGTGGTAACATTCCCGCACTGTTGGATGTGGACGCCTACCAGGCGA
GCTTGAAAGATGACACCGAACAGGGCGGGGGTGGCGCAGGCGGCAGCAACAGCAGTGGCAGCGGCGCGGAAGAGAA
CTCCAACGCGGCAGCCGCGGCAATGCAGCCGGTGGAGGACATGAACGATCATGCCATTCGCGGCGACACCTTTGCC
ACACGGGCTGAGGAGAAGCGCGCTGAGGCCGAAGCAGCGGCCGAAGCTGCCGCCCCCGCTGCGCAACCCGAGGTCG
AGAAGCCTCAGAAGAAACCGGTGATCAAACCCCTGACAGAGGACAGCAAGAAACGCAGTTACAACCTAATAAGCAA
TGACAGCACCTTCACCCAGTACCGCAGCTGGTACCTTGCATACAACTACGGCGACCCTCAGACCGGAATCCGCTCA
TGGACCCTGCTTTGCACTCCTGACGTAACCTGCGGCTCGGAGCAGGTCTACTGGTCGTTGCCAGACATGATGCAAG
ACCCCGTGACCTTCCGCTCCACGCGCCAGATCAGCAACTTTCCGGTGGTGGGCGCCGAGCTGTTGCCCGTGCACTC
CAAGAGCTTCTACAACGACCAGGCCGTCTACTCCCAACTCATCCGCCAGTTTACCTCTCTGACCCACGTGTTCAAT
CGCTTTCCCGAGAACCAGATTTTGGCGCGCCCGCCAGCCCCCACCATCACCACCGTCAGTGAAAACGTTCCTGCTC
TCACAGATCACGGGACGCTACCGCTGCGCAACAGCATCGGAGGAGTCCAGCGAGTGACCATTACTGACGCCAGACG
CCGCACCTGCCCCTACGTTTACAAGGCCCTGGGCATAGTCTCGCCGCGCGTCCTATCGAGCCGCACTTTTTGAGCA
AGCATGTCCATCCTTATATCGCCCAGCAATAACACAGGCTGGGGCCTGCGCTTCCCAAGCAAGATGTTTGGCGGGG
CCAAGAAGCGCTCCGACCAACACCCAGTGCGCGTGCGCGGGCACTACCGCGCGCCCTGGGGCGCGCACAAACGCGG
CCGCACTGGGCGCACCACCGTCGATGACGCCATCGACGCGGTGGTGGAGGAGGCGCGCAACTACACGCCCACGCCG
CCACCAGTGTCCACAGTGGACGCGGCCATTCAGACCGTGGTGCGCGGAGCCCGGCGCTATGCTAAAATGAAGAGAC
GGCGGAGGCGCGTAGCACGTCGCCACCGCCGCGACCCGGCACTGCGCCCAACGCGGCGGCGGCCCTGCTTAA
CCGCGCACGTCGCACCGGCCGACGGCGGCCATGGCCGCTCGAAGGCTGGCCGCGGGTATTGTCACTGTGCCC
CCCAGGTCCAGGCGACGAGCGGCCGCCGCAGCAGCCGCGGCCATTAGTGCTATGACTCAGGGTCGCAGGGGCAACG
TGTATTGGGTGCGCGACTCGGTTAGCGGCCTGCGCGTGCCCGTGCGCACCCGCCCCCGCGCAACTAGATTGCAAG
AAAAAACTACTTAGACTCGTACTGTTGTATGTATCCAGCGGCGGCGGCGCGCAACGAAGCTATGTCCAAGCGCAAA
ATCAAAGAAGAGATGCTCCAGGTCATCGCGCCGGAGATCTATGGCCCCCCGAAGAAGGAAGAGCAGGATTACAAGC
CCCGAAAGCTAAAGCGGGTCAAAAAGAAAAAGAAAGATGATGATGATGAACTTGACGACGAGGTGGAACTGCTGCA
CGCTACCGCGCCCAGGCGACGGGTACAGTGGAAAGGTCGACGCGTAAAACGTGTTTTGCGACCCGGCACCACCGTA
```

FIGURE 8C

```
GTCTTTACGCCCGGTGAGCGCTCCACCCGCACCTACAAGCGCGTGTATGATGAGGTGTACGGCGACGAGGACCTGC
TTGAGCAGGCCAACGAGCGCCTCGGGGAGTTTGCCTACGGAAAGCGGCATAAGGACATGCTGGCGTTGCCGCTGGA
CGAGGGCAACCCAACACCTAGCCTAAAGCCCGTAACACTGCAGCAGGTGCTGCCCGCGTTGCACCGTCCGAAGAA
AAGCGCGGCCTAAAGCGCGAGTCTGGTGACTTGGCACCCACCGTGCAGCTGATGGTACCCAAGCGCCAGCGACTGG
AAGATGTCTTGGAAAAAATGACCGTGGAACCTGGGCTGGAGCCCGAGGTCCGCGTGCGGCCAATCAAGCAGGTGGC
GCCGGGACTGGGCGTGCAGACCGTGGACGTTCAGATACCCACTACCAGTAGCACCAGTATTGCCACCGCCACAGAG
GGCATGGAGACACAAACGTCCCCGGTTGCCTCAGCGGTGGCGGATGCCGCGGTGCAGGCGGTCGCTGCGGCCGCGT
CCAAGACCTCTACGGAGGTGCAAACGGACCCGTGGATGTTTCGCGTTTCAGCCCCCGGCGCCCGCGCGGTTCGAG
GAAGTACGGCGCCGCCAGCGCGCTACTGCCCGAATATGCCCTACATCCTTCCATTGCGCCTACCCCCGGCTATCGT
GGCTACACCTACCGCCCCAGAAGACGAGCAACTACCCGACGCCGAACCACCACTGGAACCGCCGCCGCCGTCGCC
GTCGCCAGCCCGTGCTGGCCCCGATTTCCGTGCGCAGGGTGGCTCGCGAAGGAGGCAGGACCCTGGTGCTGCCAAC
AGCGCGCTACCACCCCAGCATCGTTTAAAAGCCGGTCTTTGTGGTTCTTGCAGATATGGCCCTCACCTGCCGCCTC
CGTTTCCCGGTGCCGGGATTCCGAGGAAGAATGCACCGTAGGAGGGGCATGGCCGGCCACGGCCTGACGGCGGCA
TGCGTCGTGCGCACCACCGGCGGCGGCGCGTCGCACCGTCGCATGCGCGGCGGTATCCTGCCCCTCCTTATTCC
ACTGATCGCCGCGGCGATTGGCGCCGTGCCCGGAATTGCATCCGTGGCCTTGCAGGCGCAGAGACACTGATTAAAA
ACAAGTTGCATGTGGAAAAATCAAAATAAAAAGTCTGGACTCTCACGCTCGCTTGGTCCTGTAACTATTTTGTAGA
ATGGAAGACATCAACTTTGCGTCTCTGGCCCCGCGACACGGCTCGCGCCCGTTCATGGGAAACTGGCAAGATATCG
GCACCAGCAATATGAGCGGTGGCGCCTTCAGCTGGGGCTCGCTGTGGAGCGGCATTAAAAATTTCGGTTCCACCGT
TAAGAACTATGGCAGCAAGGCCTGGAACAGCAGCACAGGCCAGATGCTGAGGGATAAGTTGAAAGAGCAAAATTTC
CAACAAAAGGTGGTAGATGGCCTGGCCTCTGGCATTAGCGGGGTGGTGGACCTGGCCAACCAGGCAGTGCAAAATA
AGATTAACAGTAAGCTTGATCCCCGCCCTCCCGTAGAGGAGCCTCCACCGGCCGTGGAGACAGTGTCTCCAGAGGG
GCGTGGCGAAAAGCGTCCGCGCCCCGACAGGGAAGAAACTCTGGTGACGCAAATAGACGAGCCTCCCTCGTACGAG
GAGGCACTAAAGCAAGGCCTGCCCACCACCCGTCCCATCGCGCCCATGGCTACCGGAGTGCTGGGCCAGCACACAC
CCGTAACGCTGGACCTGCCTCCCCCCGCCGACACCCAGCAGAAACCTGTGCTGCCAGGCCCGACCGCCGTTGTTGT
AACCCGTCCTAGCCGCGCGTCCCTGCGCCGCGCCGCCAGCGGTCCGCGATCGTTGCGGCCCGTAGCCAGTGGCAAC
TGGCAAAGCACACTGAACAGCATCGTGGGTCTGGGGGTGCAATCCCTGAAGCGCCGACGATGCTTCTGAATAGCTA
ACGTGTCGTATGTGTGTCATGTATGCGTCCATGTCGCCGCCAGAGGAGCTGCTGAGCCGCCGCGCGCCCGCTTTCC
AAGATGGCTACCCCTTCGATGATGCCGCAGTGGTCTTACATGCACATCTCGGGCCAGGACGCCTCGGAGTACCTGA
GCCCCGGGCTGGTGCAGTTTGCCCGCGCCACCGAGACGTACTTCAGCCTGAATAACAAGTTTAGAAACCCCACGGT
GGCGCCTACGCACGACGTGACCACAGACGCGTCCCAGCGTTTGACGCTGCGTTCATCCCTGTGGACCGTGAGGAT
ACTGCGTACTCGTACAAGGCGCGGTTCACCCTAGCTGTGGGTGATAACCGTGTGCTGGACATGGCTTCCACGTACT
TTGACATCCGCGGCGTGCTGGACAGGGGCCCTACTTTTAAGCCCTACTCTGGCACTGCCTACAACGCCCTGGCTCC
CAAGGGTGCCCCAAATCCTTGCGAATGGGATGAAGCTGCTACTGCTCTTGAAATAAACCTAGAAGAAGAGGACGAT
GACAACGAAGACGAAGTAGACGAGCAAGCTGAGCAGCAAAAAACTCACGTATTTGGGCAGGCGCCTTATTCTGGTA
TAAATATTACAAAGGAGGGTATTCAAATAGGTGTCGAAGGTCAAACACCTAAATATGCCGATAAAACATTTCAACC
TGAACCTCAAATAGGAGAATCTCAGTGGTACGAAACTGAAATTAATCATGCAGCTGGGAGAGTCCTTAAAAAGACT
ACCCCAATGAAACCATGTTACGGTTCATATGCAAAACCCACAAATGAAAATGGAGGGCAAGGCATTCTTGTAAAGC
AACAAAATGGAAAGCTAGAAAGTCAAGTGGAAATGCAATTTTTCTCAACTACTGAGGCGACCGCAGGCAATGGTGA
TAACTTGACTCCTAAAGTGGTATTGTACAGTGAAGATGTAGATATAGAAACCCCAGACACTCATATTTCTTACATG
CCCACTATTAAGGAAGGTAACTCACGAGAACTAATGGGCCAACAATCTATGCCCAACAGGCCTAATTACATTGCTT
TTAGGGACAATTTTATTGGTCTAATGTATTACAACAGCACGGGTAATATGGGTGTTCTGGCGGGCCAAGCATCGCA
GTTGAATGCTGTTGTAGATTTGCAAGACAGAAACACAGAGCTTTCATACCAGCTTTTGCTTGATTCCATTGGTGAT
AGAACCAGGTACTTTTCTATGTGGAATCAGGCTGTTGACAGCTATGATCCAGATGTTAGAATTATTGAAAATCATG
GAACTGAAGATGAACTTCCAAATTACTGCTTTCCACTGGGAGGTGTGATTAATACAGAGACTCTTACCAAGGTAAA
ACCTAAAACAGGTCAGGAAAATGGATGGGAAAAAGATGCTACAGAATTTCAGATAAAAATGAAATAAGAGTTGGA
AATAATTTTGCCATGGAAATCAATCTAAATGCCAACCTGTGCAGGAAATTTCCTGTACTCCAACATAGCGCTGATT
TGCCCGACAAGCTAAAGTACAGTCCTTCCAACGTAAAAATTTCTGATAACCCAAACACCTACGACTACATGAACAA
GCGAGTGGTGGCTCCCGGGTTAGTGGACTGCTACATTAACCTTGGAGCACGCTGGTCCCTTGACTATATGGACAAC
GTCAACCCATTTAACCACCACCGCAATGCTGGCCTGCGCTACCGCTCAATGTTGCTGGGCAATGGTCGCTATGTGC
CCTTCCACATCCAGGTGCCTCAGAAGTTCTTTGCCATTAAAAACCTCCTTCTCCTGCCGGGCTCATACACCTACGA
GTGGAACTTCAGGAAGGATGTTAACATGGTTCTGCAGAGCTCCCTAGGAAATGACCTAAGGGTTGACGGAGCCAGC
ATTAAGTTTGATAGCATTTGCCTTTACGCCACCTTCTTCCCCATGGCCCACAACACCGCCTCCACGCTTGAGGCCA
TGCTTAGAAACGACACCAACGACCAGTCCTTTAACGACTATCTCTCCGCCGCCAACATGCTCTACCCTATACCCGC
CAACGCTACCAACGTGCCCATATCCATCCCCTCCCGCAACTGGGCGGCTTTCCGCGGCTGGGCCTTCACGCGCCTT
AAGACTAAGGAAACCCCATCACTGGGCTCGGGCTACGACCCTTATTACACCTACTCTGGCTCTATACCCTACCTAG
ATGGAACCTTTTACCTCAACCACACCTTTAAGAAGGTGGCCATTACCTTTGACTCTTCTGTCAGCTGGCCTGGCAA
TGACCGCCTGCTTACCCCAACGAGTTTGAAATTAAGCGCTCAGTTGACGGGGAGGGTTACAACGTTGCCCAGTGT
AACATGACCAAAGACTGGTTCCTGGTACAAATGCTAGCTAACTACAACATTGGCTACCAGGGCTTCTATATCCCAG
AGAGCTACAAGGACCGCATGTACTCCTTCTTTAGAAACTTCCAGCCCATGAGCCGTCAGGTGGTGGATGATACTAA
ATACAAGGACTACCAACAGGTGGGCATCCTACACCAACACAACAACTCTGGATTTGTTGGCTACCTTGCCCCCACC
ATGCGCGAAGGACAGGCCTACCCTGCTAACTTCCCCTATCCGCTTATAGGCAAGACCGCAGTTGACAGCATTACCC
```

FIGURE 8D

```
AGAAAAAGTTTCTTTGCGATCGCACCCTTTGGCGCATCCCATTCTCCAGTAACTTTATGTCCATGGGCGCACTCAC
AGACCTGGGCCAAAACCTTCTCTACGCCAACTCCGCCCACGCGCTAGACATGACTTTTGAGGTGGATCCCATGGAC
GAGCCCACCCTTCTTTATGTTTTGTTTGAAGTCTTTGACGTGGTCCGTGTGCACCGGCCGCACCGCGGCGTCATCG
AAACCGTGTACCTGCGCACGCCCTTCTCGGCCGGCAACGCCACAACATAAAGAAGCAAGCAACATCAACAACAGCT
GCCGCCATGGGCTCCAGTGAGCAGGAACTGAAAGCCATTGTCAAAGATCTTGGTTGTGGGCCATATTTTTGGGCA
CCTATGACAAGCGCTTTCCAGGCTTTGTTTCTCCACACAAGCTCGCCTGCGCCATAGTCAATACGGCCGGTCGCGA
GACTGGGGGCGTACACTGGATGGCCTTTGCCTGGAACCCGCACTCAAAAACATGCTACCTCTTTGAGCCCTTTGGC
TTTTCTGACCAGCGACTCAAGCAGGTTTACCAGTTTGAGTACGAGTCACTCCTGCGCCGTAGCGCCATTGCTTCTT
CCCCCGACCGCTGTATAACGCTGGAAAAGTCCACCCAAAGCGTACAGGGGCCCAACTCGGCCGCCTGTGGACTATT
CTGCTGCATGTTTCTCCACGCCTTTGCCAACTGGCCCCAAACTCCCATGGATCACAACCCCACCATGAACCTTATT
ACCGGGGTACCCAACTCCATGCTCAACAGTCCCCAGGTACAGCCCACCCTGCGTCGCAACCAGGAACAGCTCTACA
GCTTCCTGGAGCGCCACTCGCCCTACTTCCGCAGCCACAGTGCGCAGATTAGGAGCGCCACTTCTTTTGTCACTT
GAAAAACATGTAAAAATAATGTACTAGAGACACTTTCAATAAAGGCAAATGCTTTTATTTGTACACTCTCGGGTGA
TTATTTACCCCCACCCTTGCCGTCTGCGCCGTTTAAAAATCAAAGGGGTTCTGCCGCGCATCGCTATGCGCCACTG
GCAGGGACACGTTGCGATACTGGTGTTTAGTGCTCCACTTAAACTCAGGCACAACCATCCGCGCAGCTCGGTGAA
GTTTTCACTCCACAGGCTGCGCACCATCACCAACGCGTTTAGCAGGTCGGGCGCCGATATCTTGAAGTCGCAGTTG
GGGCCTCCGCCCTGCGCGCGCGAGTTGCGATACACAGGGTTGCAGCACTGGAACACTATCAGCGCCGGGTGGTGCA
CGCTGGCCAGCACGCTCTTGTCGGAGATCAGATCCGCGTCCAGGTCCTCCGCGTTGCTCAGGGCGAACGGAGTCAA
CTTTGGTAGCTGCCTTCCCAAAAGGGCGCGTGCCCAGGCTTTGAGTTGCACTCGCACCGTAGTGGCATCAAAAGG
TGACCGTGCCCGGTCTGGGCGTTAGGATACAGCGCCTGCATAAAAGCCTTGATCTGCTTAAAAGCCACCTGAGCCT
TTGCGCCTTCAGAGAAGAACATGCCGCAAGACTTGCCGGAAAACTGATTGGCCGGACAGGCCGCGTCGTGCACGCA
GCACCTTGCGTCGGTGTTGGAGATCTGCACCACATTTCGGCCCCACCGGTTCTTCACGATCTTGGCCTTGCTAGAC
TGCTCCTTCAGCGCGCGCTGCCCGTTTTCGCTCGTCACATCCATTTCAATCACGTGCTCCTTATTTATCATAATGC
TTCCGTGTAGACACTTAAGCTCGCCTTCGATCTCAGCGCAGCGGTGCAGCCACAACGCGCAGCCCGTGGGCTCGTG
ATGCTTGTAGGTCACCTCTGCAAACGACTGCAGGTACGCCTGCAGGAATCGCCCCATCATCGTCACAAAGGTCTTG
TTGCTGGTGAAGGTCAGCTGCAACCCGCGGTGCTCCTCGTTCAGCCAGGTCTTGCATACGGCCGCCAGAGCTTCCA
CTTGGTCAGGCAGTAGTTTGAAGTTCGCCTTTAGATCGTTATCCACGTGGTACTTGTCCATCAGCGCGCGCGCAGC
CTCCATGCCCTTCTCCCACGCAGACACGATCGGCACACTCAGCGGGTTCATCACCGTAATTTCACTTTCCGCTTCG
CTGGGCTCTTCCTCTTCCTCTTGCGTCCGCATACCACGCGCCACTGGGTCGTCTTCATTCAGCCGCCGCACTGTGC
GCTTACCTCCTTTGCCATGCTTGATTAGCACCGGTGGGTTGCTGAAACCCACCATTTGTAGCGCCACATCTTCTCT
TTCTTCCTCGCTGTCCACGATTACCTCTGGTGATGGCGGGCGCTCGGGCTTGGGAGAAGGGCGCTTCTTTTTCTTC
TTGGGCGCAATGGCCAAATCCGCCGCCGAGGTCGATGGCCGCGGGCTGGGTGTGCGCGCACCAGCGCGTCTTGTG
ATGAGTCTTCCTCGTCCTCGGACTCGATACGCCGCCTCATCCGCTTTTTTGGGGCGCCCGGGGAGGCGGCGGCGA
CGGGGACGGGGACGACACGTCCTCCATGGTTGGGGGACGTCGCGCCGCACCGCGTCCGCGCTCGGGGGTGGTTTCG
CGCTGCTCCTCTTCCCGACTGGCCATTTCCTTCTCCTATAGGCAGAAAAAGATCATGGAGTCAGTCGAGAAGAAGG
ACAGCCTAACCGCCCCCTCTGAGTTCGCCACCACCGCCTCCACCGATGCCGCCAACGCGCCTACCACCTTCCCCGT
CGAGGCACCCCGCTTGAGGAGGAGGAAGTGATTATCGAGCAGGACCCAGGTTTTGTAAGCGAAGACGACGAGGAC
CGCTCAGTACCAACAGAGGATAAAAAGCAAGACCAGGACAACGCAGAGGCAAACGAGGAACAAGTCGGGCGGGGGG
ACGAAAGGCATGGCGACTACCTAGATGTGGGAGACGACGTGCTGTTGAAGCATCTGCAGCGCCAGTGCGCCATTAT
CTGCGACGCGTTGCAAGAGCGCAGCGATGTGCCCCTCGCCATAGCGGATGTCAGCCTTGCCTACGAACGCCACCTA
TTCTCACCGCGCGTACCCCCCAAACGCCAAGAAAACGGCACATGCGAGCCCAACCCGCGCCTCAACTTCTACCCCG
TATTTGCCGTGCCAGAGGTGCTTGCCACCTATCACATCTTTTTCCAAAACTGCAAGATACCCCTATCCTGCCGTGC
CAACCGCAGCCGAGCGGACAAGCAGCTGGCCTTGCGGCAGGGCGCTGTCATACCTGATATCGCCCTCGCTCAACGAA
GTGCCAAAAATCTTTGAGGGTCTTGGACGCGACGAGAAGCGCGCGGCAAACGCTCTGCAACAGGAAAACAGCGAAA
ATGAAAGTCACTCTGGAGTGTTGGTGGAACTCGAGGGTGACAACGCGCGCCTAGCCGTACTAAAACGCAGCATCGA
GGTCACCCACTTTGCCTACCCGGCACTTAACCTACCCCCAAGGTCATGAGCACAGTCATGAGTGAGCTGATCGTG
CGCCGTGCGCAGCCCCTGGCAGGGGGATGCAAATTTGCAAGAACAAACAGAGGAGGGCCTACCCGCAGTTGGCGACG
AGCAGCTAGCGCGCTGGCTTCAAACGCGCAGACCTGCCGACTTGGAGGAGCGACGCAAACTAATGATGGCCGCAGT
GCTCGTTACCGTGGAGCTTGAGTGCATGCAGCGGTTCTTTGCTGACCCGGAGATGCAGCGCAAGCTAGAGGAAACA
TTGCACTACACCTTTCGACAGGGCTACGTACGCCAGGCCTGCAAGATCTCCAACGTGGAGCTCTGCAACCTGGTCT
CCTACCTTGGAATTTTGCACGAAAACCGCCTTGGGCAAAACGTGCTTCATTCCACGCTCAAGGGCGAGGCGCGCCG
CGACTACGTCCGCGACTGCGTTTACTTATTTCTATGCTACACCTGGCAGACGGCCATGGGCGTTTGGCAGCAGTGC
TTGGAGGAGTGCAACCTCAAGGAGCTGCAGAAACTGCTAAAGCAAAACTTGAAGGACCTATGGACGGCCTTCAACG
AGCGCTCCGTGGCCGCGCACCTGGCGGACATCATTTTCCCCGAACGCCTGCTTAAAACCCTGCAACAGGGTCTGCC
AGACTTCACCAGTCAAAGCATGTTGCAGAACTTTAGGAACTTTATCCTAGAGCGCTCAGGAATCTTGCCCGCCACC
TGCTGTGCACTTCCTAGCGACTTTGTGCCCATTAAGTACCGCGAATGCCCTCCGCCGCTTTGGGGCCACTGCTACC
TTCTGCAGCTAGCCAACTACCTTGCCTACCACTCTGACATAATGGAAGACGTGAGCGGTGACGGTCTACTGGAGTG
TCACTGTCGCTGCAACCTATGCACCCCGCACCGCTCCCTGGTTTGCAATTCGCAGCTGCTTAACGAAAGTCAAATT
ATCGGTACCTTTGAGCTGCAGGGTCCCTCGCCTGACGAAAAGTCCGCGGCTCCGGGGTTGAAACTCACTCCGGGGC
TGTGGACGTCGGCTTACCTTCGCAAATTTGTACCTGAGGACTACCACGCCCACGAGATTAGGTTCTACGAAGACCA
ATCCCGCCCGCCAAATGCGGAGCTTACCGCCTGCGTCATTACCCAGGGCCACATTCTTGGCCAATTGCAAGCCATC
```

FIGURE 8E

```
AACAAAGCCCGCCAAGAGTTTCTGCTACGAAAGGGACGGGGGGTTTACTTGGACCCCCAGTCCGGCGAGGAGCTCA
ACCCAATCCCCCGCCGCCGCAGCCCTATCAGCAGCAGCCGCGGGCCCTTGCTTCCCAGGATGGCACCCAAAAGA
AGCTGCAGCTGCCGCCGCCACCCACGGACGAGGAGGAATACTGGGACAGTCAGGCAGAGGAGGTTTTGGACGAGGA
GGAGGAGGACATGATGGAAGACTGGGAGAGCCTAGACGAGGAAGCTTCCGAGGTCGAAGAGGTGTCAGACGAAACA
CCGTCACCCTCGGTCGCATTCCCCTCGCCGGCGCCCCAGAAATCGGCAACCGGTTCCAGCATGGCTACAACCTCCG
CTCCTCAGGCGCCGCCGGCACTGCCCGTTCGCCGACCCAACCGTAGATGGGACACCACTGGAACCAGGGCCGGTAA
GTCCAAGCAGCCGCCGCCGTTAGCCCAAGAGCAACAACAGCGCCAAGGCTACCGCTCATGGCGCGGGCACAAGAAC
GCCATAGTTGCTTGCTTGCAAGACTGTGGGGGCAACATCTCCTTCGCCCGCCGCTTTCTTCTCTACCATCACGGCG
TGGCCTTCCCCCGTAACATCCTGCATTACTACCGTCATCTCTACAGCCCATACTGCACCGGCGGCAGCGGCAGCGG
CAGCAACAGCAGCGGCCACACAGAAGCAAAGGCGACCGGATAGCAAGACTCTGACAAAGCCCAAGAAATCCACAGC
GGCGGCAGCAGCAGGAGGAGGAGCGCTGCGTCTGGCGCCCAACGAACCCGTATCGACCCGCGAGCTTAGAAACAGG
ATTTTTCCCACTCTGTATGCTATATTTCAACAGAGCAGGGCCAAGAACAAGAGCTGAAAATAAAAAACAGGTCTC
TGCGATCCCTCACCCGCAGCTGCCTGTATCACAAAAGCGAAGATCAGCTTCGGCGCACGCTGGAAGACGCGGAGGC
TCTCTTCAGTAAATACTGCGCGCTGACTCTTAAGGACTAGTTTCGCGCCCTTTCTCAAATTTAAGCGCGAAAACTA
CGTCATCTCCAGCGGCCACACCCGGCGCCAGCACCTGTCGTCAGCGCCATTATGAGCAAGGAAATTCCCACGCCCT
ACATGTGGAGTTACCAGCCACAAATGGGACTTGCGGCTGGAGCTGCCCAAGACTACTCAACCCGAATAAACTACAT
GAGCGCGGGACCCCACATGATATCCCGGGTCAACGGAATCCGCGCCCACCGAAACCGAATTCTCTTGGAACAGGCG
GCTATTACCACCACACCTCGTAATAACCTTAATCCCCGTAGTTGGCCCGCTGCCCTGGTGTACCAGGAAAGTCCCG
CTCCCACCACTGTGGTACTTCCCAGAGACGCCCAGGCCGAAGTTCAGATGACTAACTCAGGGGCGCAGCTTGCGGG
CGGCTTTCGTCACAGGGTGCGGTCGCCCGGGCAGGGTATAACTCACCTGACAATCAGAGGGCGAGGTATTCAGCTC
AACGACGAGTCGGTGAGCTCCTCGCTTGGTCTCCGTCCGACGGGACATTTCAGATCGGCGGCGCCGGCCGTCCTT
CATTCACGCCTCGTCAGGCAATCCTAACTCTGCAGACCTCGTCCTCTGAGCCGCGCTCTGGAGGCATTGGAACTCT
GCAATTTATTGAGGAGTTTGTGCCATCGGTCTACTTTAACCCCTTCTCGGGACCTCCCGGCCACTATCCGGATCAA
TTTATTCCTAACTTTGACGCGGTAAAGGACTCGGCGGACGGCTACGACTGAATGTTAAGTGGAGAGGCAGAGCAAC
TGCGCCTGAAACACCTGGTCCACTGTCGCCGCCACAAGTGCTTTGCCCGCGACTCCGGTGAGTTTTGCTACTTTGA
ATTGCCCGAGGATCATATCGAGGGCCCGGCGCACGGCGTCCGGCTTACCGCCCAGGGAGAGCTTGCCCGTAGCCTG
ATTCGGGAGTTTACCCAGCGCCCCCTGCTAGTTGAGCGGGACAGGGGACCCTGTGTTCTCACTGTGATTTGCAACT
GTCCTAACCTTGGATTACATCAAGATCCTCTAGTTAATTAACAGCTTGCATGCCTGCAGGTCGACGGATCGGGAGA
TCTCGGCCGCATATTAAGTGCATTGTTCTCGATACCGCTAAGTGCATTGTTCTCGTTAGCTCGATGGACAAGTGCA
TTGTTCTCTTGCTGAAAGCTCGATGGACAAGTGCATTGTTCTCTTGCTGAAAGCTCGATGGACAAGTGCATTGTTC
TCTTGCTGAAAGCTCAGTACCCGGGAGTACCCTCGACCGCCGGAGTATAAATAGAGGCGCTTCGTCTACGGAGCGA
CAATTCAATTCAAACAAGCAAAGTGAACACGTCGCTAAGCGAAAGCTAAGCAAATAAACAAGCGCAGCTGAACAAG
CTAAACAATCTGCAGTAAAGTGCAAGTTAAAGTGAATCAATTAAAAGTAACCAGCAACCAAGTAAATCAACTGCAA
CTACTGAAATCTGCCAAGAAGTAATTATTGAATACAAGAAGAGAACTCTGAATACTTTCAACAAGTTACCGAGAAA
GAAGAACTCACACACAGCTAGCGTTTAAACTTAAGCTTCACCATGGTGGGCCCTGCATGCTGCTGCTGCTGCTGC
TGCTGGGCCTGAGGCTACAGCTCTCCCTGGGCATCATCCTAGTTGAGGAGGAGAACCCGGACTTCTGGAACCGCGA
GGCAGCCGAGGCCCTGGGTGCCGCCAAGAAGCTGCAGCCTGCACAGACAGCCGCCAAGAACCTCATCATCTTCCTG
GGCGATGGGGTGGGGGTGTCTACGGTGACAGCTGCCAGGATCCTAAAAGGGCAGAAGAAGGACAAACTGGGGCCTG
AGATACCCCTGGCCATGGACCGCTTCCCATATGTGGCTCTGTCCAAGACATACAATGTAGACAAACATGTGCCAGA
CAGTGGAGCCACAGCCACGGCCTACCTGTGCGGGGTCAAGGGCAACTTCCAGACCATTGGCTTGAGTGCAGCCGCC
CGCTTTAACCAGTGCAACACGACACGCGGCAACGAGGTCATCTCCGTGATGAATCGGGCCAAGAAAGCAGGGAAGT
CAGTGGGAGTGGTAACCACCACACGAGTGCAGCACGCCCTCGCCAGCCGGCACCTACGCCCACACGGTGAACCGCAA
CTGGTACTCGGACGCCGACGTGCCTGCCTCGGCCCGCCAGGAGGGGTGCCAGGACATCGCTACGCAGCTCATCTCC
AACATGGACATTGACGTGATCCTAGGTGGGGCCGAAAGTACATGTTTCGCATGGGAACCCCAGACCCTGAGTACC
CAGATGACTACAGCCAAGGTGGGACCAGGCTGGACGGGAAGAATCTGGTGCAGGAATGGCTGGCGAAGCACCAGGG
TGCCCGGTACGTGTGGAACCGCACTGAGCTCATGCGGGCTTCCCTGGACCCGTCTGTGGCCCATCTCATGGGTCTC
TTTGAGCCTGGAGACATGAAATACGAGATCCACCGAGACTCCACACTGGACCCCTCCCTGATGGAGATGACAGAGG
CTGCCCTGCGCCTGCTGAGCAGGAACCCCCGCGGCTTCTTCCTCTTCGTGGAGGGTGGTCGCATCGACCATGGTCA
TCATGAAAGCAGGGCTTACCGGGCACTGACTGAGACGATCATGTTCGACGACGCCATTGAGAGGCGGGCCAGCTC
ACCAGCGAGGAGGACACGCTGAGCCTCGTCACTGCCGACCACTCCCACGTCTTCTCCTTCGGAGGCTGCCCCCTGC
GAGGGGGCTCCATCTTCGGGCTGGCCCCTGGCAAGGCCCGGGACAGGAAGGCCTACGACGGTCCTCCTATACGGAAA
CGGTCCAGGCTATGTGCTCAAGGACGCGGCGCCCGGCCGGATGTTACCGAGAGCGAGAGCGGGAGCCCCGAGTATCGG
CAGCAGTCAGCAGTGCCCCTGGACGAAGAGACCCACGCAGGCGAGGACGTGCGGTGTTCGCGCGCGGCCCGCAGG
CGCACCTGGTTCACGGCGTGCAGGAGCAGACCTTCATAGCGCACGTCATGGCCTTCGCCGCCTGCCTGGAGCCCTA
CACCGCCTGCGACCTGGCGCCCCCGCCGGCACCACCGACGCCGCGCACCCGGGGCGGTCCGTGGTCCCCGCGTTG
CTTCCTCTGCTGGCCGGGACCCTGCTGCTGCTGGAGACGGCCACTGCTCCCTGAGTGTCCCGTCCCTGGGCTCCT
GCTTCCCCATCCCGGAGTTCTCCTGCTCCCCGCCTCCTGTCGTCCTGCCTGGCCTCCAGCCCGAGTCGTCATCCCC
GGAGTCCCTATACAGAGGTCCTGCCATGGAACCTTCCCCTCCCCGTGCGCTCTGGGGACTGAGCCCATGACACCAA
ACCTGCCCCTTGGCTGCTCTCGGACTCCCTACCCCAACCCCAGGGACAGATCTGGCCAGATTTGTAAAACAAATAG
ATTTTAGGCCCAAAGATTATTTAAAGCATTGCCTGGAACGCAGTGAGTTTTTGTTAGAAAAGAGAATAATTCAAAG
TGGCATTGCTTTGCTTCTTATGTTAATTTGGTACAGACCTGTGGCTGAGTTTGCTCAAAGTATTCAGAGCAGAATT
```

FIGURE 8F

```
GTGGAGTGGAAAGAGAGATTGGACAAAGAGTTTAGTTTGTCAGTGTATCAAAAAATGAAGTTTAATGTGGCTATGG
GAATTGGAGTTTTAGATTGGCTAAGAAACAGTGATGATGATGATGAAGACAGCCAGGAAAATGCTGATAAAAATGA
AGATGGTGGGGAGAAGAACATGGAAGACTCAGGGCATGAAACAGGCATTGATTCACAGTCCCAAGGCTCATTTCAG
GCCCCTCAGTCCTCACAGTCTGTTCATGATCATAATGACCATACCACATTTGTAGAGGTTTTACTTGCTTTAAAA
AACCTCCCACACCTCCCCCTGAACCTGAAACATAAAATGAATGCAATTGTTGTTGTTAACTTGTTTATTGCAGCTT
ATAATGGTTACAAATAAAGCAATAGCATCACAAATTTCACAAATAAAGCATTTTTTTCACTGCATTCTAGTTGTGG
TTTGTCCAAACTCATCAATGTATCTTATCATGTCTGGATCCCCAGGAAGCTCCTCTGTGTCCTCATAAACCCTAAC
CTCCTCTACTTGAGAGGACATTCCAATCATAGGCTGCCCATCCACCCTCTGTGTCCTCCTGTTAATTAGGTCACTT
AACAAAAAGGAAATTGGGTAGGGGTTTTTCACAGACCGCTTTCTAAGGGTAATTTTAAAATATCTGGGAAGTCCCT
TCCACTGCTGTGTTCCAGAAGTGTTGGTAAACAGCCCACAAATGTCAACAGCAGAAACATACAAGCTGTCAGCTTT
GCACAAGGGCCCAACACCCTGCTCATCAAGAAGCACTGTGGTTGCTGTGTTAGTAATGTGCAAAACAGGAGGCACA
TTTTCCCCACCTGTGTAGGTTCCAAAATATCTAGTGTTTTCATTTTTACTTGGATCAGGAACCCAGCACTCCACTG
GATAAGCATTATCCTTATCCAAAACAGCCTTGTGGTCAGTGTTCATCTGCTGACTGTCAACTGTAGCATTTTTGG
GGTTACAGTTTGAGCAGGATATTTGGTCCTGTAGTTTGCTAACACACCCTGCAGCTCCAAAGGTTCCCCACCAACA
GCAAAAAATGAAAATTTGACCCTTGAATGGGTTTTCCAGCACCATTTTCATGAGTTTTTTGTGTCCCTGAATGCA
AGTTTAACATAGCAGTTACCCCAATAACCTCAGTTTTAACAGTAACAGCTTCCACATCAAAATATTTCCACAGGT
TAAGTCCTCATTTAAATTAGGCAAAGGAATTCCACTTCCCACTGCCTTGCTTCCGTCTCCCATTCAAACTTTTATC
AACTGACATTATTCTAAGTAAAATCCTCTTCATTATGTTGTCAGCAATCCATTGCTTGAAGGCCTGGCTCCCCAGA
ACCCCTCGACTGGTATGTCTTCTCCTAGAATACTCCAGAAGAAAAGGAGTGTATGAAGATAGTGACTGCACATTAA
AATGACTGAAACCATAGTAAATTAGGATGAGATTCTGGGCAGATAAACAGACAGCTGGCTAGGATCATTTTTTAT
GCCTTGGACTTCTTTGGCAATCTGTTGAAGCCTGACATTCCTCAGAATAATGTTTTAAAGCCCAACAATAAGACCC
TGTAGCACATATAATAAGTACTGCAGTTTTGAAGTAGTGATAAGCATAAATGATATTTGATATATTTATTATAAC
TGTAATGAGATGTGTACATATCTGTGACTTCATAGGTACTGATTGTACTACTGTGATTTTTTGCCTACTTTCAAA
ATGAAAAGGAATGCTTAATTTCAGTTAGAGGTTAGTAAAGACAAATAGGTAATTTTCTTCTCCAGTGAAGAGCATG
GCGCCCCTTGCTATTCATGGACGCTTGCTTAAAGACTTGTACACAGGCTTGCTTTGTATCAACCTATGACTTCCCC
TTACAGCCGATGATAGGTTTTTATTTGCACCTCCTTCGTGTACAAAGACAGTTTTGGTGGCTACGCCATCATTAAA
CTCATTATTATCATGCTTAAGCCTATAGATGTATCCAGTTCTTCTGTTACATAATTGAAGCTGTAGTGAATTGTCT
ATCTTAAACTGCATCGCTAACTGACTACATTTCACACTTCATTTGCTTCCAACATAGACTAACCTTCTTGGATGTC
CACTATTATTTGAACTTTTGAGATTTTTTTTCCTATTTCTAATATCTTAAAATTTCAGAAGACTTAAAGTTTTGCA
ACTACAGGGCTCCATATAGACATCTAGCTTGAATTTATACACTTTCTTTCATTGATGTCCCTGGACTAAAAAATGT
TAAATATTTCTAACCGCTGTACTTAAAGTCCATTACAAACGAAGACTACTGTTGTTAAGTTGAATAGGCATCTTAT
ATATTTTTCACCGGTGCAATAAATAACTTCTATTCCCTTCTAACATCTGCTTGCGTTGCACTGAGAGTACACTATT
GATTAGCAATAGGTTCGTGATTACAGCCCTTCTATAATTAATTGTTAGGTTAACATATTATTCATAAAATATTATT
TTATTAATTTTTACTTGATTTGCTACTGGATGCTTAGAAATAGCTATGAGTATATTGGTAGAACCAGTACTTATAT
TTTATTACATTTTTACATTTCATAAAATTTAAGTGATATAAAAATCCTGAGGAAGTATGCCACAAAAGTGGTCTCA
GTGGAAATTTAAATATGTTAACATTTATTTTTAAAATGTAGCGTGAAATAGACAACTTTAAAAGCTCAGCTTAAAA
AAAAAACTCAAGGAAGCTGAACTTGACTTTTTAAAGCACTGAAGTGCAATATTTAATGTAGGTCAACATGTTTAAA
TGGGAAAATTTTTTTCCTAATTACAGCCAAATCCCTAGCTGTAATTAACTTAAAATTTGTATACTATTTCACAACA
GAGTCAGCATATACCACTTTCTTATAAAATTAGAAAGATCTAAAATTTTAGAGCTTATTGGTGAAACAGGCATAT
TGCTACATCTTTGTTTATAAATTATAATGTGCCTTTAGAGCCCAATAACAGATAACAAGATTTTGAAAATTCAGGT
GAATTAGAGTTATCAGAGGGAATGTTAATACACTCTATTCAAATACTATATGAGTAAGACATTTAAAATAGGAAAC
AATACTTTATATATTAAAAAAAATTAATCTTCCAGTCGATTTAATCCACTTTATGAATTCATTTAAATCGATTTAA
ATTCGAATTAATTAACTAGAGTACCCGGGGATCTTATTCCCTTTAACTAATAAAAAAAAATAATAAAGCATCACTT
ACTTAAAATCAGTTAGCAAATTTCTGTCCAGTTTATTCAGCAGCACCTCCTTGCCCTCCTCCCAGCTCTGGTATTG
CAGCTTCCTCCTGGCTGCAAACTTTCTCCACAATCTAAATGGAATGTCAGTTTCCTCCTGTTCCTGTCCATCCGCA
CCCACTATCTTCATGTTGTTGCAGATGAAGCGCGCAAGACCGTCTGAAGATACCTTCAACCCCGTGTATCCATATG
ACACGGAAACCGGTCCTCCAACTGTGCCTTTTCTTACTCCTCCCTTTGTATCCCCCAATGGGTTTCAAGAGAGTCC
CCCTGGGGTACTCTCTTTGCGCCTATCCGAACCTCTAGTTACCTCCAATGGCATGCTTGCGCTCAAAATGGGCAAC
GGCCTCTCTCTGGACGAGGCCGGCAACCTTACCTCCCAAAATGTAACCACTGTGAGCCCACCTCTCAAAAAAACCA
AGTCAAACATAAACCTGGAAATATCTGCACCCCTCACAGTTACCTCAGAAGCCCTAACTGTGGCTGCCGCCGCACC
TCTAATGGTCGCGGGCAACACACTCACCATGCAATCACAGGCCCCGCTAACCGTGCACGACTCCAAACTTAGCATT
GCCACCCAAGGACCCCTCACAGTGTCAGAAGGAAAGCTAGCCCTGCAAACATCAGGCCCCCTCACCACCACCGATA
GCAGTACCCTTACTATCACTGCCTCACCCCCTCTAACTACTGCCACTGGTAGCTTGGGCATTGACTTGAAAGAGCC
CATTTATACACAAAATGGAAAACTAGGACTAAAGTACGGGGCTCCTTTGCATGTAACAGACGACCTAAACACTTTG
ACCGTAGCAACTGGTCCAGGTGTGACTATTAATAATACTTCCTTGCAAACTAAAGTTACTGGAGCCTTGGGTTTTG
ATTCACAAGGCAATATGCAACTTAATGTAGCAGGAGGACTAAGGATTGATTCTCAAAACAGACGCCTTATACTTGA
TGTTAGTTATCCGTTTGATGCTCAAAACCAACTAAATCTAAGACTAGGACAGGGCCCTCTTTTTATAAACTCAGCC
CACAACTTGGATATTAACTACAACAAAGGCCTTTACTTGTTTACAGCTTCAAACAATTCCAAAAAGCTTGAGGTTA
ACCTAAGCACTGCCAAGGGGTTGATGTTTGACGCTACAGCCATAGCCATTAATGCAGGAGATGGGCTTGAATTTGG
TTCACCTAATGCACCCAAACACAAATCCCCTCAAAACAAAAATTGGCCATGGCCTAGAATTTGATTCAAACAAGGCT
ATGGTTCCTAAACTAGGAACTGGCCTTAGTTTTGACAGCACAGGTGCCATTACAGTAGGAAACAAAAATAATGATA
```

FIGURE 8G

```
AGCTAACTTTGTGGACCACACCAGCTCCATCTCCTAACTGTAGACTAAATGCAGAGAAAGATGCTAAACTCACTTT
GGTCTTAACAAAATGTGGCAGTCAAATACTTGCTACAGTTTCAGTTTTGGCTGTTAAAGGCAGTTTGGCTCCAATA
TCTGGAACAGTTCAAAGTGCTCATCTTATTATAAGATTTGACGAAAATGGAGTGCTACTAAACAATTCCTTCCTGG
ACCCAGAATATTGGAACTTTAGAAATGGAGATCTTACTGAAGGCACAGCCTATACAAACGCTGTTGGATTTATGCC
TAACCTATCAGCTTATCCAAAATCTCACGGTAAAACTGCCAAAAGTAACATTGTCAGTCAAGTTTACTTAAACGGA
GACAAAACTAAACCTGTAACACTAACCATTACACTAAACGGTACACAGGAAACAGGAGACACAACTCCAAGTGCAT
ACTCTATGTCATTTTCATGGGACTGGTCTGGCCACAACTACATTAATGAAATATTTGCCACATCCTCTTACACTTT
TTCATACATTGCCCAAGAATAAAGAATCGTTTGTGTTATGTTTCAACGTGTTTATTTTTCAATTGCAGAAAATTTC
AAGTCATTTTTCATTCAGTAGTATAGCCCCACCACCACATAGCTTATACAGATCACCGTACCTTAATCAAACTCAC
AGAACCCTAGTATTCAACCTGCCACCTCCCTCCCAACACACAGAGTACACAGTCCTTTCTCCCCGGCTGGCCTTAA
AAAGCATCATATCATGGGTAACAGACATATTCTTAGGTGTTATATTCCACACGGTTTCCTGTCGAGCCAAACGCTC
ATCAGTGATATTAATAAACTCCCCGGGCAGCTCACTTAAGTTCATGTCGCTGTCCAGCTGCTGAGCCACAGGCTGC
TGTCCAACTTGCGGTTGCTTAACGGGCGGCGAAGGAGAAGTCCACGCCTACATGGGGGTAGAGTCATAATCGTGCA
TCAGGATAGGGCGGTGGTGCTGCAGCAGCGCGCGAATAAACTGCTGCCGCCGCCGCTCCGTCCTGCAGGAATACAA
CATGGCAGTGGTCTCCTCAGCGATGATTCGCACCGCCCGCAGCATAAGGCGCCTTGTCCTCCGGGCACAGCAGCGC
ACCCTGATCTCACTTAAATCAGCACAGTAACTGCAGCACAGCACCACAATATTGTTCAAAATCCCACAGTGCAAGG
CGCTGTATCCAAAGCTCATGGCGGGGACCACAGAACCCACGTGGCCATCATACCACAAGCGCAGGTAGATTAAGTG
GCGACCCCTCATAAACACGCTGGACATAAACATTACCTCTTTTGGCATGTTGTAATTCACCACCTCCCGGTACCAT
ATAAACCTCTGATTAAACATGGCGCCATCCACCACCATCCTAAACCAGCTGGCCAAAACCTGCCCGCCGGCTATAC
ACTGCAGGGAACCGGGACTGGAACAATGACAGTGGAGAGCCCAGGACTCGTAACCATGGATCATCATGCTCGTCAT
GATATCAATGTTGGCACAACACAGGCACACGTGCATACACTTCCTCAGGATTACAAGCTCCTCCCGCGTTAGAACC
ATATCCCAGGGAACAACCCATTCCTGAATCAGCGTAAATCCCACACTGCAGGGAAGACCTCGCACGTAACTCACGT
TGTGCATTGTCAAAGTGTTACATTCGGGCAGCAGCGGATGATCCTCCAGTATGGTAGCGCGGGTTTCTGTCTCAAA
AGGAGGTAGACGATCCCTACTGTACGGAGTGCGCCGAGACAACCGAGATCGTGTTGGTCGTAGTGTCATGCCAAAT
GGAACGCCGGACGTAGTCATATTTCCTGAAGCAAAACCAGGTGCGGGCGTGACAAACAGATCTGCGTCTCCGGTCT
CGCCGCTTAGATCGCTCTGTGTAGTAGTTGTAGTATATCCACTCTCTCAAAGCATCCAGGCGCCCCCTGGCTTCGG
GTTCTATGTAAACTCCTTCATGCGCCGCTGCCCTGATAACATCCACCACCGCAGAATAAGCCACACCCAGCCAACC
TACACATTCGTTCTGCGAGTCACACACGGGAGGAGCGGGAAGAGCTGGAAGAACCATGTTTTTTTTTTATTCCAA
AAGATTATCCAAAACCTCAAAATGAAGATCTATTAAGTGAACGCGCTCCCCTCCGGTGGCGTGGTCAAACTCTACA
GCCAAGAACAGATAATGGCATTTGTAAGATGTTGCACAATGGCTTCCAAAAGGCAAACGGCCCTCACGTCCAAGT
GGACGTAAAGGCTAAACCCTTCAGGGTGAATCTCCTCTATAAACATTCCAGCACCTTCAACCATGCCCAAATAATT
CTCATCTCGCCACCTTCTCAATATATCTCTAAGCAAATCCCGAATATTAAGTCCGGCCATTGTAAAAATCTGCTCC
AGAGCGCCCTCCACCTTCAGCCTCAAGCAGCGAATCATGATTGCAAAAATTCAGGTTCCTCACAGACCTGTATAAG
ATTCAAAAGCGGAACATTAACAAAAATACCGCGATCCCGTAGGTCCCTTCGCAGGGCCAGCTGAACATAATCGTGC
AGGTCTGCACGGACCAGCGCGGCCACTTCCCCGCCAGGAACCTTGACAAAAGAACCCACACTGATTATGACACGCA
TACTCGGAGCTATGCTAACCAGCGTAGCCCCGATGTAAGCTTTGTTGCATGGGCGGCGATATAAAATGCAAGGTGC
TGCTCAAAAAATCAGGCAAAGCCTCGCGCAAAAAAGAAAGCACATCGTAGTCATGCTCATGCAGATAAAGGCAGGT
AAGCTCCGGAACCACCACAGAAAAAGACACCATTTTTCTCTCAAACATGTCTGCGGGTTCTGCATAAACACAAAA
TAAAATAACAAAAAAACATTTAAACATTAGAAGCCTGTCTTACAACAGGAAAAACAACCCTTATAAGCATAAGACG
GACTACGGCCATGCCGGCGTGACCGTAAAAAACTGGTCACCGTGATTAAAAAGCACCACCGACAGCTCCTCGGTC
ATGTCCGGAGTCATAATGTAAGACTCGGTAAACACATCAGGTTGATTCATCGGTCAGTGCTAAAAAGCGACCGAAA
TAGCCCGGGGGAATACATACCCGCAGGCGTAGAGACAACATTACAGCCCCCATAGGAGGTATAACAAAATTAATAG
GAGAGAAAAACACATAAACACCTGAAAAACCCTCCTGCCTAGGCAAAATAGCACCCTCCCGCTCCAGAACAACATA
CAGCGCTTCACAGCGGCAGCCTAACAGTCAGCCTTACCAGTAAAAAGAAAACCTATTAAAAAAACACCACTCGAC
ACGGCACCAGCTCAATCAGTCACAGTGTAAAAAGGGCCAAGTGCAGAGCGAGTATATATAGGACTAAAAAATGAC
GTAACGGTTAAAGTCCACAAAAAACACCCAGAAAACCGCACGCGAACCTACGCCCAGAAACGAAAGCCAAAAAACC
CACAACTTCCTCAAATCGTCACTTCCGTTTTCCCACGTTACGTCACTTCCCATTTTAAGAAAACTACAATTCCCAA
CACATACAAGTTACTCCGCCCTAAAACCTACGTCACCCGCCCCGTTCCCACGCCCCGCGCCACGTCACAAACTCCA
CCCCCTCATTATCATATTGGCTTCAATCCAAAATAAGGTATATTATTGATGATG
```

FIGURE 9 (pBSX sequence, SEQ ID NO:12)

```
CTAAATTGTAAGCGTTAATATTTTGTTAAAATTCGCGTTAAATTTTTGTTAAATCAGCTCATTTTTTAACCAATAG
GCCGAAATCGGCAAAATCCCTTATAAATCAAAAGAATAGACCGAGATAGGGTTGAGTGTTGTTCCAGTTTGGAACA
AGAGTCCACTATTAAAGAACGTGGACTCCAACGTCAAAGGGCGAAAAACCGTCTATCAGGGCGATGGCCCACTACG
TGAACCATCACCCTAATCAAGTTTTTTGGGGTCGAGGTGCCGTAAAGCACTAAATCGGAACCCTAAAGGGAGCCCC
CGATTTAGAGCTTGACGGGGAAAGCCGGCGAACGTGGCGAGAAAGGAAGGGAAGAAAGCGAAAGGAGCGGGCGCTA
GGGCGCTGGCAAGTGTAGCGGTCACGCTGCGCGTAACCACCACACCCGCCGCGCTTAATGCGCCGCTACAGGGCGC
GTCCCATTCGCCATTCAGGCTGCGCAACTGTTGGGAAGGGCGATCGGTGCGGGCCTCTTCGCTATTACGCCAGCTG
GCGAAAGGGGGATGTGCTGCAAGGCGATTAAGTTGGGTAACGCCAGGGTTTTCCCAGTCACGACGTTGTAAAACGA
CGGCCAGTGAGCGCGCGTAATACGACTCACTATAGGGCGAATTGGAGCTTACGTATTAATTAAGGCGCCGCGGTGG
CGGCCGCTCTAGAACTAGTGGATCCCCCGGGCTGCAGGAATTCGGCCGCCTAGGCCACGCGTAAGCTTATCGATAC
CGTCGACCTCGAGGGGGGGCCCGGTACCCAGCTTTTGTTCCCTTTAGTGAGGGTTAATTGCGCGCTTGGCGTAATC
ATGGTCATAGCTGTTTCCTGTGTGAAATTGTTATCCGCTCACAATTCCACACAACATACGAGCCGGAAGCATAAAG
TGTAAAGCCTGGGGTGCCTAATGAGTGAGCTAACTCACATTAATTGCGTTGCGCTCACTGCCCGCTTTCCAGTCGG
GAAACCTGTCGTGCCAGCTGCATTAATGAATCGGCCAACGCGCGGGGAGAGGCGGTTTGCGTATTGGGCGCTCTTC
CGCTTCCTCGCTCACTGACTCGCTGCGCTCGGTCGTTCGGCTGCGGCGAGCGGTATCAGCTCACTCAAAGGCGGTA
ATACGGTTATCCACAGAATCAGGGGATAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCATAGCTCAC
GCTGTAGGTATCTCAGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGCCACTGGCAGCAGCC
ACTGGTAACAGGATTAGCAGAGCGAGGTATGTAGGCGGTGCTACAGAGTTCTTGAAGTGGTGGCCTAACTACGGCT
ACACTAGAAGGACAGTATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGCAGCAGATTACGCGCAGAAAAAAAGGA
TCTCAAGAAGATCCTTTGATCTTTTCTACGGGGTCTGACGCTCAGTGGAACGAAAACTCACGTTAAGGGATTTTGG
TCATGAGATTATCAAAAAGGATCTTCACCTAGATCCTTTTAAATTAAAAATGAAGTTTTAAATCAATCTAAAGTAT
ATATGAGTAAACTTGGTCTGACAGTTACCAATGCTTAATCAGTGAGGCACCTATCTCAGCGATCTGTCTATTTCGT
TCATCCATAGTTGCCTGACTCCCCGTCGTGTAGATAACTACGATACGGGAGGGCTTACCATCTGGCCCCAGTGCTG
CAATGATACCGCGAGACCCACGCTCACCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGGCTT
CATTCAGCTCCGGTTCCCAACGATCAAGGCGAGTTACATGATCCCCCATGTTGTGCAAAAAAGCGGTTAGCTCCTT
CGGTCCTCCGATCGTTGTCAGAAGTAAGTTGGCCGCAGTGTTATCACTCATGGTTATGGCAGCACTGCATAATTCT
CTTACTGTCATGCCATCCGTAAGATGCTTTTCTGTGACTGGTGAGTACTCAACCAAGTCATTCTGAGAATAGTGTA
TGCGGCGACCGAGTTGCTCTTGCCCGGCGTCAATACGGGATAATACCGCGCCACATAGCAGAACTTTAAAAGTGCT
CATCATTGGAAAACGTTCTTCGGGGCGAAAACTCTCAAGGATCTTACCGCTGTTGAGATCCAGTTCGATGTAACCC
ACTCGTGCACCCAACTGATCTTCAGCATCTTTTACTTTCACCAGCGTTTCTGGGTGAGCAAAAACAGGAAGGCAAA
ATGCCGCAAAAAAGGGAATAAGGGCGACACGGAAATGTTGAATACTCATACTCTTCCTTTTTCAATATTATTGAAG
CATTTATCAGGGTTATTGTCTCATGAGCGGATACATATTTGAATGTATTTAGAAAAATAAACAAATAGGGGTTCCG
CGCACATTTCCCCGAAAAGTGCCAC
```

FIGURE 11 ΔFseI.4 (SEQ ID

```
CATCATCAATAATATACCTTATTTTGGATTGAAGCCAATATGATAATGAGGGGGTGGAGTTTGTGACGTGGCGCGG
GGCGTGGGAACGGGGCGGGTGACGTAGTAGTGTGGCGGAAGTGTGATGTTGCAAGTGTGGCGGAACACATGTATAA
CTTCGTATAATGTATGCTATACGAAGTTATACATGTAAGCGACGGATGTGGCAAAAGTGACGTTTTTGGTGTGCGC
CGGTGTACACAGGAAGTGACAATTTTCGCGCGGTTTTAGGCGGATGTTGTAGTAAATTTGGGCGTAACCGAGTAAG
ATTTGGCCATTTTCGCGGGAAAACTGAATAAGAGGAAGTGAAATCTGAATAATTTTGTGTTACTCATAGCGCGTAA
TATTTGTCTAGGGAGATCTATAACTTCGTATAATGTATGCTATACGAAGTTATTACCGAAGAAATGGCTCGAGATC
TGGAAGGTGCTGAGGTACGATGAGACCCGCACCAGGTGCAGACCCTGCGAGTGTGGCGGTAAACATATTAGGAACC
AGCCTGTGATGCTGGATGTGACCGAGGAGCTGAGGCCCGATCACTTGGTGCTGGCCTGCACCCGCGCTGAGTTTGG
CTCTAGCGATGAAGATACAGATTGAGGTACTGAAATGTGTGGGCGTGGCTTAAGGGTGGGAAAGAATATATAAGGT
GGGGGTCTTATGTAGTTTTGTATCTGTTTTGCAGCAGCCGCCGCCGCCATGAGCACCAACTCGTTTGATGGAAGCA
TTGTGAGCTCATATTTGACAACGCGCATGCCCCATGGGCCGGGGTGCGTCAGAATGTGATGGGCTCCAGCATTGA
TGGTCGCCCCGTCCTGCCCGCAAACTCTACTACCTTGACCTACGAGACCGTGTCTGGAACGCCGTTGGAGACTGCA
GCCTCCGCCGCCGCTTCAGCCGCTGCAGCCACCGCCCGCGGGATTGTGACTGACTTTGCTTTCCTGAGCCCGCTTG
CAAGCAGTGCAGCTTCCCGTTCATCCGCCCGCGATGACAAGTTGACGGCTCTTTTGGCACAATTGGATTCTTTGAC
CCGGGAACTTAATGTCGTTTCTCAGCAGCTGTTGGATCTGCGCCAGCAGGTTTCTGCCCTGAAGGCTTCCTCCCCT
CCCAATGCGGTTTAAAACATAAATAAAAAACCAGACTCTGTTTGGATTTGGATCAAGCAAGTGTCTTGCTGTCTTT
ATTTAGGGGTTTTGCGCGCGCGGTAGGCCCGGGACCAGCCGGTCTCGGTCGTTGAGGGTCCTGTGTATTTTTCCAG
GACGTGGTAAAGGTGACTCTGGATGTTCAGATACATGGCATAAGCCCGTCTCTGGGGTGGAGGTAGCACCACTGC
AGAGCTTCATGCTGCGGGTGGTGTTGTAGATGATCCAGTCGTAGCAGGAGCGCTGGGCGTGGTGCCTAAAAATGT
CTTTCAGTAGCAAGCTGATTGCCAGGGGCAGGCCCTTGGTGTAAGTGTTTACAAAGCGGTTAAGCTGGGATGGGTG
CATACGTGGGGATATGAGATGCATCTTGGACTGTATTTTTAGGTTGGCTATGTTCCCAGCCATATCCCTCCGGGGA
TTCATGTTGTGCAGAACCACCAGCACAGTGTATCCGGTGCACTTGGGAAATTTGTCATGTAGCTTAGAAGGAAATG
CGTGGAAGAACTTGGAGACGCCCTTGTGACCTCCAAGATTTTCCATGCATTCGTCCATAATGATGGCAATGGGCCC
ACGGGCGGCGGCCTGGGCGAAGATATTTCTGGGATCACTAACGTCATAGTTGTGTTCCAGGATGAGATCGTCATAG
GCCATTTTTACAAAGCGCGGGCGGAGGGTGCCAGACTGCGGTATAATGGTTCCATCCGGCCCAGGGGCGTAGTTAC
CCTCACAGATTTGCATTTCCCACGCTTTGAGTTCAGATGGGGGATCATGTCTACCTGCGGGGCGATGAAGAAAAC
GGTTTCCGGGGTAGGGGAGATCAGCTGGGAAGAAAGCAGGTTCCTGAGCAGCTGCGACTTACCGCAGCCGGTGGGC
CCGTAAATCACACCTATTACCGGGTGCAACTGGTAGTTAAGAGAGCTGCAGCTGCCGTCATCCCTGAGCAGGGGGG
CCACTTCGTTAAGCATGTCCCTGACTCGCATGTTTTCCCTGACCAAATCGCCAGAAGGCGCTCGCCGCCCAGCGA
TAGCAGTTCTTGCAAGGAAGCAAAGTTTTTCAACGGTTTGAGACCGTCCGCCGTAGGCATGCTTTTGAGCGTTTGA
CCAAGCAGTTCCAGGCGGTCCCACAGCTCGGTCACCTGCTCTACGGCATCTCGATCCAGCATATCTCCTCGTTTCG
CGGGTTGGGGCGGCTTTCGCTGTACGGCAGTAGTCGGTGCTCGTCCAGACGGGCCAGGGTCATGTCTTTCCACGGG
CGCAGGGTCCTCGTCAGCGTAGTCTGGGTCACGGTGAAGGGGTGCGCTCCGGGCTGCGCGCTGGCCAGGGTGCGCT
TGAGGCTGGTCCTGCTGGTGCTGAAGCGCTGCCGGTCTTCGCCCTGCGCGTCGGCCAGGTAGCATTTGACCATGGT
GTCATAGTCCAGCCCCTCCGCGGCGTGGCCCTTGGCGCGCAGCTTGCCCTTGGAGGAGGCGCCGCACGAGGGGCAG
TGCAGACTTTTGAGGGCGTAGAGCTTGGGCGCGAGAAATACCGATTCCGGGGAGTAGGCATCCGCGCCGCAGGCCC
CGCAGACGGTCTCGCATTCCACGAGCCAGGTGAGCTCTGGCCGTTCGGGGGTCAAAAACCAGGTTTCCCCCATGCTT
TTTGATGCGTTTCTTACCTCTGGTTTCCATGAGCCGGTGTCCACGCTCGGTGACGAAAAGGCTGTCCGTGTCCCG
TATACAGACTTGAGAGGCCTGTCCTCGAGCGGTGTTCCGCGGTCCTCCTCGTATAGAAACTCGGACCACTCTGAGA
CAAAGGCTCGCGTCCAGGCCAGCACGAAGGAGGCTAAGTGGGAGGGGTAGCGGTCGTTGTCCACTAGGGGGTCCAC
TCGCTCCAGGGTGTGAAGACACATGTCGCCCTCTTCGGCATCAAGGAAGGTGATTGGTTTGTAGGTGTAGGCCACG
TGACCGGGTGTTCCTGAAGGGGGCTATAAAAGGGGTGGGGCGCGTTCGTCCTCACTCTCTTCCGCATCGCTGT
CTGCGAGGGCCAGCTGTTGGGGTGAGTACTCCCTCTGAAAAGCGGGCATGACTTCTGCGCTAAGATTGTCAGTTTC
CAAAAACGAGGAGGATTTGATATTCACCTGGCCCGCGGTGATGCCTTTGAGGGTGGCCGCATCCATCTGGTCAGAA
AAGACAATCTTTTTGTTGTCAAGCTTGGTGGCAAACGACCCGTAGAGGGCGTTGGACAGCAACTTGGCGATGGAGC
GCAGGGTTTGGTTTTTGTCGCGATCGGCGCGCTCCTTGGCCGCGATGTTTAGCTGCACGTATTCGCGCGCAACGCA
CCGCCATTCGGGAAAGACGGTGGTGCGCTCGTCGGGCACCAGGTGCACGCGCCAACCGCGGTTGTGCAGGGTGACA
AGGTCAACGCTGGTGGCTACCTCTCCGCGTAGGCGCTCGTTGGTCCAGCAGAGGCGGCCGCCCTTGCGCGAGCAGA
ATGGCGGTAGGGGTCTAGCTGCGTCTCGTCCGGGGGTCTGCGTCCACGGTAAAGACCCCGGGCAGCAGGCGCGC
GTCGAAGTAGTCTATCTTGCATCCTTGCAAGTCTAGCGCCTGCTGCCATGCGCGGGCGGCAAGCGCGCGCTCGTAT
GGGTTGAGTGGGGGACCCCATGGCATGGGTGGGTGAGCGCGGAGGCGTACATGCCGCAAATGTCGTAAACGTAGA
GGGGCTCTCTGAGTATTCCAAGATATGTAGGGTAGCATCTTCCACCGCGGATGCTGGCGCGCACGTAATCGTATAG
TTCGTGCGAGGGAGCGAGGAGGTCGGGACCGAGGTTGCTACGGCGGGCTGCTCTGCTCGGAAGACTATCTGCCTG
AAGATGGCATGTGAGTTGGATGATATGGTTGGACGCTGGAAGACGTTGAAGCTGGCGTCTGTGAGACCTACCGCGT
CACGCACGAAGGAGGCGTAGGAGTCGCGCAGCTTGTTGACCAGCTCGGCGGTGACCTGCACGTCTAGGGCGCAGTA
GTCCAGGGTTTCCTTGATGATGTCATACTTATCCTGTCCCTTTTTTTTCCACAGCTCGCGGTTGAGGACAAACTCT
TCGCGGTCTTTCCAGTACTCTTGGATCGGAAACCCGTCCGGCCTCCGAACGGTAAGAGCCTAGCATGTAGAACTGGT
TGACGGCCTGGTAGGCGCAGCATCCCTTTTCTACGGGTAGCGCGTATGCCTGCGCGGCCTTCCGGAGCGAGGTGTG
GGTGAGCGCAAAGGTGTCCCTGACCATGACTTTGAGGTACTGGTATTTGAAGTCAGTGTCGTCGCATCCGCCCTGC
TCCCAGAGCAAAAAGTCCGTGCGCTTTTTGGAACGCGGATTTGGCAGGGCGAAGGTGACATCGTTGAAGAGTATCT
TTCCCGCGCGAGGCATAAAGTTGCGTGTGATGCGGAAGGGTCCCGGCACCTCGGAACGGTTGTTAATTACCTGGGC
```

FIGURE 11 (cont.)

```
GGCGAGCACGATCTCGTCAAAGCCGTTGATGTTGTGGCCCACAATGTAAAGTTCCAAGAAGCGCGGGATGCCCTTG
ATGGAAGGCAATTTTTTAAGTTCCTCGTAGGTGAGCTCTTCAGGGGAGCTGAGCCCGTGCTCTGAAAGGGCCCAGT
CTGCAAGATGAGGGTTGGAAGCGACGAATGAGCTCCACAGGTCACGGGCCATTAGCATTTGCAGGTGGTCGCGAAA
GGTCCTAAACTGGCGACCTATGGCCATTTTTTCTGGGGTGATGCAGTAGAAGGTAAGCGGGTCTTGTTCCCAGCGG
TCCCATCCAAGGTTCGCGGCTAGGTCTCGCGCGGCAGTCACTAGAGGCTCATCTCCGCCGAACTTCATGACCAGCA
TGAAGGGCACGAGCTGCTTCCCAAAGGCCCCCATCCAAGTATAGGTCTCTACATCGTAGGTGACAAAGAGACGCTC
GGTGCGAGGATGCGAGCCGATCGGGAAGAACTGGATCTCCCGCCACCAATTGGAGGAGTGGCTATTGATGTGGTGA
AAGTAGAAGTCCCTGCGACGGGCCGAACACTCGTGCTGGCTTTTGTAAAAACGTGCGCAGTACTGGCAGCGGTGCA
CGGGCTGTACATCCTGCACGAGGTTGACCTGACGACCGCGCACAAGGAAGCAGAGTGGGAATTTGAGCCCCTCGCC
TGGCGGGTTTGGCTGGTGGTCTTCTACTTCGGCGCTTGTCCTTGACCGTCTGGCTGCTCGAGGGGAGTTACGGTG
GATCGGACCACCACGCCGCGCGAGCCCAAAGTCCAGATGTCCGCGCGCGGCGGTCGGAGCTTGATGACAACATCGC
GCAGATGGGAGCTGTCCATGGTCTGGAGCTCCCGCGGCGTCAGGTCAGGCGGGAGCTCCTGCAGGTTTACCTCGCA
TAGACGGGTCAGGGCGCGGGCTAGATCCAGGTGATACCTAATTTCCAGGGGCTGGTTGGTGGCGGCGTCGATGGCT
TGCAAGAGGCCGCATCCCCGCGGCGCGACTACGGTACCGCGCGGCGGGCGGTGGGCCGCGGGGGTGTCCTTGGATG
ATGCATCTAAAAGCGGTGACGCGGGCGAGCCCCCGGAGGTAGGGGGGGCTCCGGACCCGCCGGGAGAGGGGGCAGG
GGCACGTCGGCGCCGCGCGCGGGCAGGAGCTGGTGCTGCGCGCGTAGGTTGCTGGCGAACGCGACGACGCGGCGGT
TGATCTCCTGAATCTGGCGCCTCTGCGTGAAGACGACGGGCCCGGTGAGCTTGAGCCTGAAAGAGAGTTCGACAGA
ATCAATTTCGGTGTCGTTGACGGCGGCCTGGCGCAAAATCTCCTGCACGTCTCCTGAGTTGTCTTGATAGGCGATC
TCGGCCATGAACTGCTCGATCTCTTCCTCCTGGAGATCTCCGCGTCCGGCTCGCTCCACGGTGGCGGCGAGGTCGT
TGGAAATGCGGGCCATGAGCTGCGAGAAGGCGTTGAGGCCTCCCTCGTTCCAGACGCGGCTGTAGACCACGCCCCC
TTCGGCATCGCGGGCGCGCATGACCACCTGCGCGAGATTGAGCTCCACGTGCCGGGCGAAGACGGCGTAGTTTCGC
AGGCGCTGAAAGAGGTAGTTGAGGGTGGTGGCGGTGTGTTCTGCCACGAAGAAGTACATAACCCAGCGTCGCAACG
TGGATTCGTTGATATCCCCCAAGGCCTCAAGGCGCTCCATGGCCTCGTAGAAGTCCACGGCGAAGTTGAAAAACTG
GGAGTTGCGCGCCGACACGGTTAACTCCTCCTCCAGAAGACGGATGAGCTCGGCGACAGTGTCGCGCACCTCGCGC
TCAAAGGCTACAGGGGCCTCTTCTTCTTCTTCAATCTCCTCTTCCATAAGGGCCTCCCCTTCTTCTTCTTCTGGCG
GCGGTGGGGAGGGGGACACGGCGGCGACGACGGCGCACCGGGAGGCGGTCGACAAAGCGCTCGATCATCTCCCC
GCGGCGACGGCGCATGGTCTCGGTGACGGCGCGGCCGTTCTCGCGGGGCGCAGTTGGAAGACGCCGCCCGTCATG
TCCCGGTTATGGGTTGGCGGGGGGCTGCCATGCGGCAGGGATACGGCGCTAACGATGCATCTCAACAATTGTTGTG
TAGGTACTCCGCCGCCGAGGGACCTGAGCGAGTCCGCATCGACCGGATCGGAAAACCTCTCGAGAAAGGCGTCTAA
CCAGTCACAGTCGCAAGGTAGGCTGAGCACCGTGGCGGGCGGCAGCGGGCGGCGGTCGGGGTTGTTTCTGGCGGAG
GTGCTGCTGATGATGTAATTAAAGTAGGCGGTCTTGAGACGGCGGATGGTCGACAGAAGCACCATGTCCTTGGGTC
CGGCCTGCTGAATGCGCAGGCGGTCGGCCATGCCCCAGGCTTCGTTTTGACATCGGCGCAGGTCTTTGTAGTAGTC
TTGCATGAGCCTTTCTACCGGCACTTCTTCTTCTCCTTCCTCTTGTCCTGCATCTCTTGCATCTATCGCTGCGGCG
GCGGCGGAGTTTGGCCGTAGGTGGCGCCCTCTTCCTCCCATGCGTGTGACCCCGAAGCCCCTCATCGGCTGAAGCA
GGGCTAGGTCGGCGACAACGCGCTCGGCTAATATGGCCTGCTGCACCTGCGTGAGGGTAGACTGGAAGTCATCCAT
GTCCACAAAGCGGTGGTATGCGCCCGTGTTGATGGTGTAAGTGCAGTTGGCCATAACGGACCAGTTAACGGTCTGG
TGACCCGGCTGCGAGAGCTCGGTGTACCTGAGACGCGAGTAAGCCCTCGAGTCAAATACGTAGTCGTTGCAAGTCC
GCACCAGGTACTGGTATCCCACCAAAAAGTGCGGCGGCGGCTGGCGGTAGAGGGGCCAGCGTAGGGTGGCCGGGGC
TCCGGGGGCGAGATCTTCCAACATAAGGCGATGATATCCGTAGATGTACCTGGACATCCAGGTGATGCCGGCGGCG
GTGGTGGAGGCGCGCGGAAAGTCGCGGACGCGGTTCCAGATGTTGCGCAGCGGCAAAAAGTGCTCCATGGTCGGGA
CGCTCTGGCCGGTCAGGCGCGCGCAATCGTTGACGCTCTACCGTGCAAAAGGAGAGCCTGTAAGCGGGCACTCTTC
CGTGGTCTGGTGGATAAATTCGCAAGGGTATCATGGCGGACGACCGGGGTTCGAGCCCCGTATCCGGCCGTCCGCC
GTGATCCATGCGGTTACCGCCCGCGTGTCGAACCCAGGTGTGCGACGTCAGACAACGGGGGAGTGCTCCTTTTGGC
TTCCTTCCAGGCGCGGCGGCTGCTGCGCTAGCTTTTTTGGCCACTGGCCGCGCGCAGCGTAAGCGGTTAGGCTGGA
AAGCGAAAGCATTAAGTGGCTCGCTCCCTGTAGCCGGAGGGTTATTTTCCAAGGGTTGAGTCGCGGGACCCCCGGT
TCGAGTCTCGGACCGGCCGGACTGCGGCGAACGGGGGTTTGCCTCCCCGTCATGCAAGACCCCGCTTGCAAATTCC
TCCGGAAACAGGGACGAGCCCCTTTTTTGCTTTTCCCAGATGCATCCGGTGCTGCGGCAGATGCGCCCCCCTCCTC
AGCAGCGGCAAGAGCAAGAGCAGCGGCAGACATGCAGGGCACCCTCCCCTCCTCCTACCGCGTCAGGAGGGGCGAC
ATCCGCGGTTGACGCGGCAGCAGATGGTGATTACGAACCCCCGCGGCGCCGGGCCCGGCACTACCTGGACTTGGAG
GAGGGCGAGGGCCTGGCGCGGCTAGGAGCGCCCTCTCCTGAGCGGTACCCAAGGGTGCAGCTGAAGCGTGATACGC
GTGAGGCGTACGTGCCGGCAGAACCTGTTTCGCGACCGCGAGGGAGAGGAGCCCGAGGAGATGCGGGATCGAAA
GTTCCACGCAGGGCGCGAGCTGCGGCATGGCCTGAATCGCGAGCGGTTGCTGCGCGAGGAGGACTTTGAGCCCGAC
GCGCGAACCGGGATTAGTCCCGCGCGCGCACACGTGGCGGCCGCCGACCTGGTAACCGCATACGAGCAGACGGTGA
ACCAGGAGATTAACTTTCAAAAAAGCTTTAACAACCACGTGCGTACGCTTGTGGCGCGCGAGGAGGTGGCTATAGG
ACTGATGCATCTGTGGGACTTTGTAAGCGCGCTGGAGCAAAACCCAAATAGCAAGCCGCTCATGGCGCAGCTGTTC
CTTATAGTGCAGCACAGCAGGGACAACGAGGCATTCAGGGATGCGCTGCTAAACATAGTAGAGCCCGAGGGCCGCT
GGCTGCTCGATTTGATAAACATCCTGCAGAGCATAGTGGTGCAGGAGCGCAGCTTGAGCCTGGCTGACAAGGTGGC
CGCCATCAACTATTCCATGCTTAGCCTGGGCAAGTTTTACGCCCGCAAGATATACCATACCCCTTACGTTCCCATA
GACAAGGAGGTAAAGATCGAGGGGTTCTACATGCGCATGGCGCTGAAGGTGCTTACCTTGAGCGACGACCTGGGCG
TTTATCGCAACGAGCGCATCCACAAGGCCGTGAGCGTGAGCCGGCGGCGCGAGCTCAGCGACCGCGAGCTGATGCA
CAGCCTGCAAAGGGCCCTGGCTGGCACGGGCAGCGGCGATAGAGAGGCCGAGTCCTACTTTGACGCGGGCGCTGAC
```

FIGURE 11 (cont.)

```
CTGCGCTGGGCCCCAAGCCGACGCGCCCTGGAGGCAGCTGGGGCCGGACCTGGGCTGGCGGTGGCACCCGCGCGCG
CTGGCAACGTCGGCGGCGTGGAGGAATATGACGAGGACGATGAGTACGAGCCAGAGGACGGCGAGTACTAAGCGGT
GATGTTTCTGATCAGATGATGCAAGACGCAACGGACCCGGCGGTGCGGGCGGCGCTGCAGAGCCAGCCGTCCGGCC
TTAACTCCACGGACGACTGGCGCCAGGTCATGGACCGCATCATGTCGCTGACTGCGCGCAATCCTGACGCGTTCCG
GCAGCAGCCGCAGGCCAACCGGCTCTCCGCAATTCTGGAAGCGGTGGTCCCGGCGCGCGCAAACCCCACGCACGAG
AAGGTGCTGGCGATCGTAAACGCGCTGGCCGAAAACAGGGCCATCCGGCCCGACGAAGCCGGCCTGGTCTACGACG
CGCTGCTTCAGCGCGTGGCTCGTTACAACAGCGGCAACGTGCAGACCAACCTGGACCGGCTGGTGGGGATGTGCG
CGAGGCCGTGGCGCAGCGTGAGCGCGCGCAGCAGCAGGGCAACCTGGGCTCCATGGTTGCACTAAACGCCTTCCTG
AGTACACAGCCCGCCAACGTGCCGCGGGGACAGGAGGACTACACCAACTTTGTGAGCGCACTGCGGCTAATGGTGA
CTGAGACACCGCAAAGTGAGGTGTACCAGTCTGGGCCAGACTATTTTTTCCAGACCAGTAGACAAGGCCTGCAGAC
CGTAAACCTGAGCCAGGCTTTCAAAAACTTGCAGGGGCTGTGGGGGGTGCGGGCTCCCACAGGCGACCGCGCGACC
GTGTCTAGCTTGCTGACGCCCAACTCGCGCCTGTTGCTGCTGCTAATAGCGCCCTTCACGGACAGTGGCAGCGTGT
CCCGGGACACATACCTAGGTCACTTGCTGACACTGTACCGCGAGGCCATAGGTCAGGCGCATGTGGACGAGCATAC
TTTCCAGGAGATTACAAGTGTCAGCCGCGCGCTGGGGCAGGAGGACACGGGCAGCCTGGAGGCAACCCTAAACTAC
CTGCTGACCAACCGGCGGCAGAAGATCCCCTCGTTGCACAGTTTAAACAGCGAGGAGGAGCGCATTTTGCGCTACG
TGCAGCAGAGCGTGAGCCTTAACCTGATGCGCGACGGGGTAACGCCCAGCGTGGCGCTGGACATGACCGCGCGCAA
CATGGAACCGGCATGTATGCCTCAAACCGGCCGTTTATCAACCGCCTAATGGACTACTTGCATCGCGCGGCCGCC
GTGAACCCCGAGTATTTCACCAATGCCATCTTGAACCCGCACTGGCTACCGCCCCCTGGTTTCTACACCGGGGAT
TCGAGGTGCCCGAGGGTAACGATGGATTCCTCTGGGACGACATAGACGACAGCGTGTTTTCCCCGCAACCGCAGAC
CCTGCTAGAGTTGCAACAGCGCGAGCAGGCAGGAGGCGGCGCTGCGAAAGGAAGGCTTCCGCAGGCCAAGCAGCTTG
TCCGATCTAGGCGCTGCGGCCCCGCGGTCAGATGCTAGTAGCCCATTTCCAAGCTTGATAGGGTCTCTTACCAGCA
CTCGCACCACCCGCCCGCGCCTGCTGGGCGAGGAGGAGTACCTAAACAACTCGCTGCTGCAGCCGCAGCGCGAAAA
AAACCTGCCTCCGGCATTTCCCAACAACGGGATAGAGAGCCTAGTGGACAAGATGAGTAGATGGAAGACGTACGCG
CAGGAGCACAGGGACGTGCCAGGCCCGCGCCCGCCCACCCGTCGTCAAAGGCACGACCGTCAGCGGGGTCTGGTGT
GGGAGGACGATGACTCGGCAGACGACAGCAGCGTCCTGGATTTGGGAGGGAGTGGCAACCCGTTTGCGCACCTTCG
CCCCAGGCTGGGGAGAATGTTTTAAAAAAAAAAAAAGCATGATGCAAAATAAAAAACTCACCAAGGCCATGGCACCG
AGCGTTGGTTTTCTTGTATTCCCCTTAGTATGCGGCGCGCGGCGATGTATGAGGAAGGTCCTCCTCCCTCCTACGA
GAGTGTGGTGAGCGCGGCGCCAGTGGCGGCGGCGCTGGGTTCTCCCTTCGATGCTCCCCTGGACCCGCCGTTTGTG
CCTCCGCGGTACCTGCGGCCTACCGGGGGGAGAAACAGCATCCGTTACTCTGAGTTGGCACCCCTATTCGACACCA
CCCGTGTGTACCTGGTGGACAACAAGTCAACGGATGTGGCATCCCTGAACTACCAGAACGACCACAGCAACTTTCT
GACCACGGTCATTCAAAACAATGACTACAGCCCGGGGGAGGCAAGCACACAGACCATCAATCTTGACGACCGGTCG
CACTGGGGCGGCGACCTGAAAACCATCCTGCATACCAACATGCCAAATGTGAACGAGTTCATGTTTACCAATAAGT
TTAAGGCGCGGGTGATGGTGTCGCGCTTGCCTACTAAGGACAATCAGGTGGAGCTGAAATACGAGTGGGTGGAGTT
CACGCTGCCCGAGGGCAACTACTCCGAGACCATGACCATAGACCTTATGAACAACGCGATCGTGGAGCACTACTTG
AAAGTGGGCAGACAGAACGGGGTTCTGGAAAGCGACATCGGGGTAAAGTTTGACACCCGCAACTTCAGACTGGGGT
TTGACCCCGTCACTGGTCTTGTCATGCCTGGGGTATATACAAACGAAGCCTTCCATCCAGACATCATTTTGCTGCC
AGGATGCGGGGTGGACTTCACCCACAGCCGCCTGAGCAACTTGTTGGGCATCCGCAAGCGGCAACCCTTCCAGGAG
GGCTTTAGGATCACCTACGATGATCTGGAGGGTGGTAACATTCCCGCACTGTTGGATGTGGACGCCTACCAGGCGA
GCTTGAAAGATGACACCGAACAGGGCGGGGGTGGCGCAGGCGGCAGCAACAGCAGTGGCAGCGGCGCGGAAGAGAA
CTCCAACGCGGCAGCCGCGGCAATGCAGCCGGTGGAGGACATGAACGATCATGCCATTCGCGGCGACACCTTTGCC
ACACGGGCTGAGGAGAAGCGCGCTGAGGCCGAAGCAGCGGCCGAAGCTGCCGCCCCCGCTGCGCAACCCGAGGTCG
AGAAGCCTCAGAAGAAACCGGTGATCAAACCCCTGACAGAGGACAGCAAGAAACGCAGTTACAACCTAATAAGCAA
TGACAGCACCTTCACCCAGTACCGCAGCTGGTACCTTGCATACAACTACGGCGACCCTCAGACCGGAATCCGCTCA
TGGACCCTGCTTTGCACTCCTGACGTAACCTGCGGCTCGGAGCAGGTCTACTGGTCGTTGCCAGACATGATGCAAG
ACCCCGTGACCTTCCGCTCCACGCGCCAGATCAGCAACTTTCCGGTGGTGGGCGCCGAGCTGTTGCCCGTGCACTC
CAAGAGCTTCTACAACGACCAGGCCGTCTACTCCCAACTCATCCGCCAGTTTACCTCTCTGACCCACGTGTTCAAT
CGCTTTCCCGAGAACCAGATTTTGGCGCGCCCAGCCCCCACCATCACCACCGTCAGTGAAAACGTTCCTCTC
TCACAGATCACGGGACGCTACCGCTGCGCAACAGCATCGAGGAGTCCAGCGAGTGACCATTACTGACGCCAGACG
CCGCACCTGCCCCTACGTTTACAAGGCCCTGGGCATAGTCTCGCCGCGCGTCCTATCGAGCCGCACTTTTTGAGCA
AGCATGTCCATCCTTATATCGCCCAGCAATAACACAGGCTGGGGCCTGCGCTTCCCAAGCAAGATGTTTGGCGGGG
CCAAGAAGCGCTCCGACCAACACCCAGTGCGCGTGCGCGGGCACTACCGCGCGCCCTGGGCGCGCACAAACGCGG
CCGCACTGGGCGCACCACCGTCGATGACGCCATCGACGCGGTGGTGGAGGAGGCGCGCAACTACACGCCCACGCCG
CCACCAGTGTCCACAGTGGACGCGGCCATTCAGACCGTGGTGCGCGGAGCCCGGCGCTATGCTAAAATGAAGAGAC
GGCGGAGGCGCGTAGCACGTCGCCACCGCCGCCGACCCGGCACTGCCGCCCAACGCGCGGCGGCGGCCCTGCTTAA
CCGCGCACGTCGCACCGGCCGACGGGCGGCCATGCGGGCCGCTCGAAGGCTGGCCGCGGGTATTGTCACTGTGCCC
CCCAGGTCCAGGCGACGAGCGGCCGCCGCAGCAGCCGCGGCCATTAGTGCTATGACTCAGGGTCGCAGGGGCAACG
TGTATTGGGTGCGCGACTCGGTTAGCGGCCTGCGCGTGCCCGTGCGCACCCGCCCCCGCGCAACTAGATTGCAAG
AAAAAACTACTTAGACTCGTACTGTTGTATGTATCCAGCGGCGGCGGCGCGCAACGAAGCTATGTCCAAGCGCAAA
ATCAAAGAAGAGATGCTCCAGGTCATCGCGCCGGAGATCTATGCCCCCCGAAGAAGGAAGAGCAGGATTACAAGC
CCCGAAAGCTAAAGCGGGTCAAAAAGAAAAAGAAAGATGATGATGATGAACTTGACGACGAGGTGGAACTGCTGCA
CGCTACCGCGCCCAGGCGACGGGTACAGTGGAAAGGTCGACGCGTAAAACGTGTTTTGCGACCCCGGCACCACCGTA
```

FIGURE 11 (cont.)

```
GTCTTTACGCCCGGTGAGCGCTCCACCCGCACCTACAAGCGCGTGTATGATGAGGTGTACGGCGACGAGGACCTGC
TTGAGCAGGCCAACGAGCGCCTCGGGGAGTTTGCCTACGGAAAGCGGCATAAGGACATGCTGGCGTTGCCGCTGGA
CGAGGGCAACCCAACACCTAGCCTAAAGCCCGTAACACTGCAGCAGGTGCTGCCCGCGCTTGCACCGTCCGAAGAA
AAGCGCGGCCTAAAGCGCGAGTCTGGTGACTTGGCACCCACCGTGCAGCTGATGGTACCCAAGCGCCAGCGACTGG
AAGATGTCTTGGAAAAAATGACCGTGGAACCTGGGCTGGAGCCCGAGGTCCGCGTGCGGCCAATCAAGCAGGTGGC
GCCGGGACTGGGCGTGCAGACCGTGGACGTTCAGATACCCACTACCAGTAGCACCAGTATTGCCACCGCCACAGAG
GGCATGGAGACACAAACGTCCCCGGTTGCCTCAGCGGTGGCGGATGCCGCGGTGCAGGCGGTCGCTGCGGCCGCGT
CCAAGACCTCTACGGAGGTGCAAACGGACCCGTGGATGTTTCGCGTTTCAGCCCCCCGGCGCCCGCGCGGTTCGAG
GAAGTACGGCGCCGCCAGCGCGCTACTGCCCGAATATGCCCTACATCCTTCCATTGCGCCTACCCCCGGCTATCGT
GGCTACACCTACCGCCCCAGAAGACGAGCAACTACCCGACGCCGAACCACCACTGGAACCCGCCGCCGCCGTCGCC
GTCGCCAGCCCGTGCTGGCCCCGATTTCCGTGCGCAGGGTGGCTCGCGAAGGAGGCAGGACCCTGGTGCTGCCAAC
AGCGCGCTACCACCCCAGCATCGTTTAAAAGCCGGTCTTTGTGGTTCTTGCAGATATGGCCCTCACCTGCCGCCTC
CGTTTCCCGGTGCCGGGATTCCGAGGAAGAATGCACCGTAGGAGGGCATGGCCGGCTACGGCCTGACGGGCGGCA
TGCGTCGTGCGCACCACCGGCGGCGGCGCGCGTCGCACCGTCGCATGCGCGGCGGTATCCTGCCCCTCCTTATTCC
ACTGATCGCCGCGGCGATTGGCGCCGTGCCCGGAATTGCATCCGTGGCCTTGCAGGCGCAGAGACACTGATTAAAA
ACAAGTTGCATGTGGAAAAATCAAAATAAAAAGTCTGGACTCTCACGCTCGCTTGGTCCTGTAACTATTTTGTAGA
ATGGAAGACATCAACTTTGCGTCTCTGGCCCCGCGACACGGCTCGCGCCCGTTCATGGGAAACTGGCAAGATATCG
GCACCAGCAATATGAGCGGTGGCGCCTTCAGCTGGGCTCGCTGTGGAGCGGCATTAAAAATTTCGGTTCCACCGT
TAAGAACTATGGCAGCAAGGCCTGGAACAGCAGCACAGGCCAGATGCTGAGGGATAAGTTGAAAGAGCAAATTTC
CAACAAAAGGTGGTAGATGGCCTGGCCTCTGGCATTAGCGGGGTGGTGGACCTGGCCAACCAGGCAGTGCAAAATA
AGATTAACAGTAAGCTTGATCCCCGCCCTCCCGTAGAGGAGCCTCCACCGGCCGTGGAGACAGTGTCTCCAGAGGG
GCGTGGCGAAAAGCGTCCGCGCCCCGACAGGGAAGAAACTCTGGTGACGCAAATAGACGAGCCTCCCTCGTACGAG
GAGGCACTAAAGCAAGGCCTGCCCACCACCCGTCCCATCGCGCCCATGGCTACCGGAGTGCTGGGCCAGCACACAC
CCGTAACGCTGGACCTGCCTCCCCCGCCGACACCCAGCAGAAACCTGTGCTGCCAGGCCCGACCGCCGTTGTTGT
AACCCGTCCTAGCCGCGCGTCCCTGCGCCGCGCCGCCAGCGGTCCGCGATCGTTGCGGCCCGTAGCCAGTGGCAAC
TGGCAAAGCACACTGAACAGCATCGTGGGTCTGGGGGTGCAATCCCTGAAGCGCCGACGATGCTTCTGAATAGCTA
ACGTGTCGTATGTGTGTCATGTATGCGTCCATGTCGCCGCCAGAGGAGCTGCTGAGCCGCCGCGCGCCCGCTTTCC
AAGATGGCTACCCCTTCGATGATGCCGCAGTGGTCTTACATGCACATCTCGGGCCAGGACGCCTCGGAGTACCTGA
GCCCCGGGCTGGTGCAGTTTGCCCGCGCCACCGAGACGTACTTCAGCCTGAATAACAAGTTTAGAAACCCCACGGT
GGCGCCTACGCCACGACGTGACCACAGACCGGTCCCAGCGTTTGACGCTGCGGTTCATCCCTGTGGACCGTGAGGAT
ACTGCGTACTCGTACAAGGCGCGGTTCACCCTAGCTGTGGGTGATAACCGTGTGCTGGACATGGCTTCCACGTACT
TTGACATCCGCGGCGTGCTGGACAGGGGCCCTACTTTTAAGCCCTACTCTGGCACTGCCTACAACGCCCTGGCTCC
CAAGGGTGCCCCAAATCCTTGCGAATGGGATGAAGCTGCTACTGCTCTTGAAATAAACCTAGAAGAAGAGGACGAT
GACAACGAAGACGAAGTAGACGAGCAAGCTGAGCAGCAAAAAACTCACGTATTTGGGCAGGCGCCTTATTCTGGTA
TAAATATTACAAAGGAGGGTATTCAAATAGGTGTCGAAGGTCAAACACCTAAATATGCCGATAAAACATTTCAACC
TGAACCTCAAATAGGAGAATCTCAGTGGTACGAAACTGAAATTAATCATGCAGCTGGGAGAGTCCTTAAAAAGACT
ACCCCAATGAAACCATGTTACGGTTCATATGCAAAACCCACAAATGAAAATGGAGGGCAAGGCATTCTTGTAAAGC
AACAAAATGGAAAGCTAGAAAGTCAAGTGGAAATGCAATTTTTCTCAACTACTGAGGCGACCGCAGGCAATGGTGA
TAACTTGACTCCTAAAGTGGTATTGTACAGTGAAGATGTAGATATAGAAACCCCAGACACTCATATTTCTTACATG
CCCACTATTAAGGAAGGTAACTCACGAGAACTAATGGGCCAACAATCTATGCCCAACAGGCCTAATTACATTGCTT
TTAGGGACAATTTTATTGGTCTAATGTATTACAACAGCACGGGTAATATGGGTGTTCTGGCGGGCCAAGCATCGCA
GTTGAATGCTGTTGTAGATTTGCAAGACAGAAACACAGAGCTTTCATACCAGCTTTTGCTTGATTCCATTGGTGAT
AGAACCAGGTACTTTTCTATGTGGAATCAGGCTGTTGACAGCTATGATCCAGATGTTAGAATTATTGAAAATCATG
GAACTGAAGATGAACTTCCAAATTACTGCTTTCCACTGGGAGGTGTGATTAATACAGAGACTCTTACCAAGGTAAA
ACCTAAAACAGGTCAGGAAAATGGATGGGAAAAAGATGCTACAGAATTTTCAGATAAAAATGAAATAAGAGTTGGA
AATAATTTTGCCATGGAAATCAATCTAAATGCCAACCTGTGGAGAAATTTCCTGTACTCCAACATAGCGCTGTATT
TGCCCGACAAGCTAAAGTACAGTCCTTCCAACGTAAAAATTTCTGATAACCCAAACACCTACGACTACATGAACAA
GCGAGTGGTGGCTCCCGGGTTAGTGGACTGCTACATTAACCTTGGAGCACGCTGGTCCCTTGACTATATGGACAAC
GTCAACCCATTTAACCACCACCGCAATGCTGGCCTGCGCTACCGCTCAATGTTGCTGGGCAATGGTCGCTATGTGC
CCTTCCACATCCAGGTGCCTCAGAAGTTCTTTGCCATTAAAAACCTCCTTCTCCTGCCGGGCTCATACACCTACGA
GTGGAACTTCAGGAAGGATGTTAACATGGTTCTGCAGAGCTCCCTAGGAAATGACCTAAGGGTTGACGGAGCCAGC
ATTAAGTTTGATAGCATTTGCCTTTACGCCACCTTCTTCCCCATGGCCCACAACACCGCCTCCACGCTTGAGGCCA
TGCTTAGAAACGACACCAACGACCAGTCCTTTAACGACTATCTCTCCGCCGCCAACATGCTCTACCCTATACCCGC
CAACGCTACCAACGTGCCCATATCCATCCCCTCCCGCAACTGGGCGGCTTTCCGCGGCTGGGCCTTCACGCGCCTT
AAGACTAAGGAAACCCCATCACTGGGCTCGGGCTACGACCCTTATTACACCTACTCTGGCTCTATACCCTACCTAG
ATGGAACCTTTTACCTCAACCACACCTTTAAGAAGGTGGCCATTACCTTTGACTCTTCTGTCAGCTGGCCTGGCAA
TGACCGCCTGCTTACCCCCAACGAGTTTGAAATTAAGCGCTCAGTTGACGGGGAGGGTTACAACGTTGCCCAGTGT
AACATGACCAAAGACTGGTTCCTGGTACAAATGCTAGCTAACTACAACATTGGCTACCAGGGCTTCTATATCCCAG
AGAGCTACAAGGACCGCATGTACTCCTTCTTTAGAAACTTCCAGCCCATGAGCCGTCAGGTGGTGATGATACTAA
ATACAAGGACTACCAACAGGTGGGCATCCTACACCAACACAACAACTCTGGATTTGTTGGCTACCTTGCCCCCACC
ATGCGCGAAGGACAGGCCTACCCTGCTAACTTCCCCTATCCGCTTATAGGCAAGACCGCAGTTGACAGCATTACCC
```

FIGURE 11 (cont.)

```
AGAAAAAGTTTCTTTGCGATCGCACCCTTTGGCGCATCCCATTCTCCAGTAACTTTATGTCCATGGGCGCACTCAC
AGACCTGGGCCAAAACCTTCTCTACGCCAACTCCGCCCACGCGCTAGACATGACTTTTGAGGTGGATCCCATGGAC
GAGCCCACCCTTCTTTATGTTTTGTTTGAAGTCTTTGACGTGGTCCGTGTGCACCGGCCGCACCGCGGCGTCATCG
AAACCGTGTACCTGCGCACGCCCTTCTCGGCCGGCAACGCCACAACATAAAGAAGCAAGCAACATCAACAACAGCT
GCCGCCATGGGCTCCAGTGAGCAGGAACTGAAAGCCATTGTCAAAGATCTTGGTTGTGGGCCATATTTTTTGGGCA
CCTATGACAAGCGCTTTCCAGGCTTTGTTTCTCCACACAAGCTCGCCTGCGCCATAGTCAATACGGCCGGTCGCGA
GACTGGGGGCGTACACTGGATGGCCTTTGCCTGGAACCCGCACTCAAAAACATGCTACCTCTTTGAGCCCTTTGGC
TTTTCTGACCAGCGACTCAAGCAGGTTTACCAGTTTGAGTACGAGTCACTCCTGCGCCGTAGCGCCATTGCTTCTT
CCCCCGACCGCTGTATAACGCTGGAAAAGTCCACCCAAAGCGTACAGGGGCCCAACTCGGCCGCCTGTGGACTATT
CTGCTGCATGTTTCTCCACGCCTTTGCCAACTGGCCCCAAACTCCCATGGATCACAACCCCACCATGAACCTTATT
ACCGGGGTACCCAACTCCATGCTCAACAGTCCCCAGGTACAGCCCACCCTGCGTCGCAACCAGGAACAGCTCTACA
GCTTCCTGGAGCGCCACTCGCCCTACTTCCGCAGCCACAGTGCGCAGATTAGGAGCGCCACTTCTTTTTGTCACTT
GAAAAACATGTAAAAATAATGTACTAGAGACACTTTCAATAAAGGCAAATGCTTTTATTTGTACACTCTCGGGTGA
TTATTTACCCCCACCCTTGCCGTCTGCGCCGTTTAAAAATCAAAGGGGTTCTGCCGCGCATCGCTATGCGCCACTG
GCAGGGACACGTTGCGATACTGGTGTTTAGTGCTCCACTTAAACTCAGGCACAACCATCCGCGGCAGCTCGGTGAA
GTTTTCACTCCACAGGCTGCGCACCATCACCAACGCGTTTAGCAGGTCGGGCGCCGATATCTTGAAGTCGCAGTTG
GGGCCTCCGCCCTGCGCGCGCGAGTTGCGATACACAGGGTTGCAGCACTGGAACACTATCAGCGCCGGTGGTGCA
CGCTGGCCAGCACGCTCTTGTCGGAGATCAGATCCGCGTCCAGGTCCTCCGCGTTGCTCAGGGCGAACGGAGTCAA
CTTTGGTAGCTGCCTTCCCAAAAAGGGCGCGTGCCCAGGCTTTGAGTTGCACTCGCACCGTAGTGGCATCAAAAGG
TGACCGTGCCCGGTCTGGGCGTTAGGATACAGCGCCTGCATAAAAGCCTTGATCTGCTTAAAAGCCACCTGAGCCT
TTGCGCCTTCAGAGAAGAACATGCCGCAAGACTTGCCGGAAAACTGATTGGCCGGACAGGCCGCGTCGTGCACGCA
GCACCTTGCGTCGGTCGTTGGAGATCTGCACCACATTTCGGCCCCACCGGTTCTTCACGATCTTGGCCTTGCTAGAC
TGCTCCTTCAGCGCGCGCTGCCCGTTTTCGCTCGTCACATCCATTTCAATCACGTGCTCCTTATTTATCATAATGC
TTCCGTGTAGACACTTAAGCTCGCCTTCGATCTCAGCGCAGCGGTGCAGCCACAACGCGCAGCCCGTGGGCTCGTG
ATGCTTGTAGGTCACCTCTGCAAACGACTGCAGGTACGCCTGCAGGAATCGCCCCATCATCGTCACAAAGGTCTTG
TTGCTGGTGAAGGTCAGCTGCAACCCGCGGTGCTCCTCGTTCAGCCAGGTCTTGCATACGGCCGCCAGAGCTTCCA
CTTGGTCAGGCAGTAGTTTGAAGTTCGCCTTTAGATCGTTATCCACGTGGTACTTGTCCATCAGCGCGCGCGCAGC
CTCCATGCCCTTCTCCCACGCAGACACGATCGGCACACTCAGCGGGTTCATCACCGTAATTTCACTTTCCGCTTCG
CTGGGCTCTTCCTCTTCCTCTTGCGTCCGCATACCACGCGCCACTGGGTCGTCTTCATTCAGCCGCCGCACTGTGC
GCTTACCTCCTTTGCCATGCTTGATTAGCACCGGTGGGTTGCTGAAACCCACCATTTGTAGCGCCACATCTTCTCT
TTCTTCCTCGCTGTCCACGATTACCTCTGGTGATGGCGGGCGCTCGGGCTTGGGAGAAGGGCGCTTCTTTTTCTTC
TTGGGCGCAATGGCCAAATCCGCCGCCGAGGTCGATGGCCGCGGGCTGGGTGTGCGCGGCACCAGCGCGTCTTGTG
ATGAGTCTTCCTCGTCCTCGGACTCGATACGCCGCCTCATCCGCTTTTTTGGGGGCGCCCGGGGAGGCGGCGGCGA
CGGGGACGGGGACGACACGTCCTCCATGGTTGGGGGACGTCGCGCCGCACCGCGTCCGCGCTCGGGGTGGTTTCG
CGCTGCTCCTCTTCCCGACTGGCCATTTCCTTCTCCTATAGGCAGAAAAAGATCATGGAGTCAGTCGAGAAGAAGG
ACAGCCTAACCGCCCCCTCTGAGTTCGCCACCACCGCCTCCACCGATGCCGCCAACGCGCCTACCACCTTCCCCGT
CGAGGCACCCCCGCTTGAGGAGGAGGAAGTGATTATCGAGCAGGACCCAGGTTTTGTAAGCGAAGACGACGAGGAC
CGCTCAGTACCAACAGAGGATAAAAAGCAAGACCAGGACAACGCAGAGGCAAACGAGGAACAAGTCGGGCGGGGGG
ACGAAAGGCATGGCGACTACCTAGATGTGGGAGACGACGTGCTGTTGAAGCATCTGCAGCGCCAGTGCGCCATTAT
CTGCGACGCGTTGCAAGAGCGCAGCGATGTGCCCCTCGCCATAGCGGATGTCAGCCTTGCCTACGAACGCCACCTA
TTCTCACCGCGCGTACCCCCCAAACGCCAAGAAAACGGCACATGCGAGCCCAACCCGCGCCTCAACTTCTACCCCG
TATTTGCCGTGCCAGAGGTGCTTGCCACCTATCACATCTTTTTCCAAAACTGCAAGATACCCCTATCCTGCCGTGC
CAACCGCAGCCGAGCGGACAAGCAGCTGGCCTTGCGGCAGGGCGCTGTCATACCTGATATCGCCTCGCTCAACGAA
GTGCCAAAAATCTTTGAGGGTCTTGGACGCGACGAGAAGCGCGCGGCAAACGCTCTGCAACAGGAAAACAGCGAAA
ATGAAAGTCACTCTGGAGTGTTGGTGGAACTCGAGGGTGACAACGCGCGCCTAGCCGTACTAAAACGCAGCATCGA
GGTCACCCACTTTGCCTACCCGGCACTTAACCTACCCCCAAGGTCATGAGCACAGTCATGAGTGAGCTGATCGTG
CGCCGTGCGCAGCCCCTGGAGAGGGATGCAAATTTGCAAGAACAAACAGAGGAGGGCCTACCCGCAGTTGGCGACG
AGCAGCTAGCGCGCTGGCTTCAAACGCGCGAGCCTGCCGACTTGGAGGAGCGACGCAAACTAATGATGGCCGCAGT
GCTCGTTACCGTGGAGCTTGAGTGCATGCAGCGGTTCTTTGCTGACCCGGAGATGCAGCGCAAGCTAGAGGAAACA
TTGCACTACACCTTTCGACAGGGCTACGTACGCCAGGCCTGCAAGATCTCCAACGTGGAGTCTCTGCAACCTGGTCT
CCTACCTTGGAATTTTGCACGAAAACCGCCTTGGGCAAAACGTGCTTCATTCCACGCTCAAGGGCGAGGCGCGCCG
CGACTACGTCCGCGACTGCGTTTACTTATTTCTATGCTACACCTGGCAGACGGCCATGGGCGTTTGGCAGCAGTGC
TTGGAGGAGTGCAACCTCAAGGAGCTGCAGAAACTGCTAAAGCAAAACTTGAAGGACCTATGGACGGCCTTCAACG
AGCGCTCCGTGGCCGCGCACCTGGCGGACATCATTTTCCCCGAACGCCTGCTTAAAACCCTGCAACAGGGTCTGCC
AGACTTCACCAGTCAAAGCATGTTGCAGAACTTTAGGAACTTTATCCTAGAGCGCTCAGGAATCTTGCCCGCCACC
TGCTGTGCACTTCCTAGCGACTTTGTGCCCATTAAGTACCGCGAATGCCCTCCGCCGCTTTGGGCCACTGCTACC
TTCTGCAGCTAGCCAACTACCTTGCCTACCACTCTGACATAATGGAAGACGTGAGCGGTGACGGTCTACTGGAGTG
TCACTGTCGCTGCAACCTATGCACCCCGCACCGCTCCCTGGTTTGCAATTCGCAGCTGCTTAACGAAAGTCAAATT
ATCGGTACCTTTGAGCTGCAGGGTCCCTCGCCTGACGAAAAGTCCGCGGCTCCGGGGTTGAAACTCACTCCGGGGC
TGTGGACGTCGGCTTACCTTCGCAAATTTGTACCTGAGGACTACCACGCCCACGAGATTAGGTTCTACGAAGACCA
ATCCCGCCCGCCAAATGCGGAGCTTACCGCCTGCGTCATTACCCAGGGCCACATTCTTGGCCAATTGCAAGCCATC
```

FIGURE 11 (cont.)

```
AACAAAGCCCGCCAAGAGTTTCTGCTACGAAAGGGACGGGGGGTTTACTTGGACCCCCAGTCCGGCGAGGAGCTCA
ACCCAATCCCCCGCCGCCGCAGCCCTATCAGCAGCAGCCGCGGGCCCTTGCTTCCCAGGATGGCACCCAAAAGA
AGCTGCAGCTGCCGCCGCCACCCACGGACGAGGAGGAATACTGGGACAGTCAGGCAGAGGAGGTTTTGGACGAGGA
GGAGGAGGACATGATGGAAGACTGGGAGAGCCTAGACGAGGAAGCTTCCGAGGTCGAAGAGGTGTCAGACGAAACA
CCGTCACCCTCGGTCGCATTCCCCTCGCCGGCGCCCCAGAAATCGGCAACCGGTTCCAGCATGGCTACAACCTCCG
CTCCTCAGGCGCCGCCGGCACTGCCCGTTCGCCGACCCAACCGTAGATGGGACACCACTGGAACCAGGGCCGGTAA
GTCCAAGCAGCCGCCGCCGTTAGCCCAAGAGCAACAACAGCGCCAAGGCTACCGCTCATGGCGCGGGCACAAGAAC
GCCATAGTTGCTTGCTTGCAAGACTGTGGGGGCAACATCTCCTTCGCCCGCCGCTTTCTTCTCTACCATCACGGCG
TGGCCTTCCCCCGTAACATCCTGCATTACTACCGTCATCTCTACAGCCCATACTGCACCGGCGGCAGCGGCAGCGG
CAGCAACAGCAGCGGCCACACAGAAGCAAAGGCGACCGGATAGCAAGACTCTGACAAAGCCCAAGAAATCCACAGC
GGCGGCAGCAGCAGGAGGAGGAGCGCTGCGTCTGGCGCCCAACGAACCCGTATCGACCCGCGAGCTTAGAAACAGG
ATTTTTCCCACTCTGTATGCTATATTTCAACAGAGCAGGGGCCAAGAACAAGAGCTGAAAATAAAAAACAGGTCTC
TGCGATCCCTCACCCGCAGCTGCCTGTATCACAAAAGCGAAGATCAGCTTCGCGCACGCTGGAAGACGCGGAGGC
TCTCTTCAGTAAATACTGCGCGCTGACTCTTAAGGACTAGTTTCGCGCCCTTTCTCAAATTTAAGCGCGAAAACTA
CGTCATCTCCAGCGGCCACACCCGGCGCCAGCACCTGTCGTCAGCGCCATTATGAGCAAGGAAATTCCCACGCCCT
ACATGTGGAGTTACCAGCCACAAATGGGACTTGCGGCTGGAGCTGCCCAAGACTACTCAACCCGAATAAACTACAT
GAGCGCGGGACCCCACATGATATCCCGGGTCAACGGAATCCGCGCCCACCGAAACCGAATTCTCTTGGAACAGGCG
GCTATTACCACCACACCTCGTAATAACCTTAATCCCCGTAGTTGGCCCGCTGCCCTGGTGTACCAGGAAAGTCCCG
CTCCCACCACTGTGGTACTTCCCAGAGACGCCCAGGCCGAAGTTCAGATGACTAACTCAGGGGCGCAGCTTGCGGG
CGGCTTTCGTCACAGGGTGCGGTCGCCCGGGCAGGGTATAACTCACCTGACAATCAGAGGGCGAGGTATTCAGCTC
AACGACGAGTCGGTGAGCTCCTCGCTTGGTCTCCGTCCGGACGGGACATTTCAGATCGGCGGCGCCGGCCGTCCTT
CATTCACGCCTCGTCAGGCAATCCTAACTCTGCAGACCTCGTCCTCTGAGCCGCGCTCTGGAGGCATTGGAACTCT
GCAATTTATTGAGGAGTTTGTGCCATCGGTCTACTTTAACCCCTTCTCGGGACCTCCCGGCCACTATCCGGATCAA
TTTATTCCTAACTTTGACGCGGTAAAGGACTCGGCGGACGGCTACGACTGAATGTTAAGTGGAGAGGCAGAGCAAC
TGCGCCTGAAACACCTGGTCCACTGTCGCCGCCACAAGTGCTTTGCCCGCGACTCCGGTGAGTTTTGCTACTTTGA
ATTGCCCGAGGATCATATCGAGGGCCCGGCGCACGGCGTCCGGCTTACCGCCCAGGGAGAGCTTGCCCGTAGCCTG
ATTCGGAGTTTACCCAGCGCCCCCTGCTAGTTGAGCGGGACAGGGGACCCTGTGTTCTCACTGTGATTTGCAACT
GTCCTAACCTTGGATTACATCAAGATCCTCTAGTTAATTAACAGCTTGCATGCCTGCAGGTCGACGGATCGGGAGA
TCTCGGCCGCATATTAAGTGCATTGTTCTCGATACCGCTAAGTGCATTGTTCTCGTTAGCTCGATGGACAAGTGCA
TTGTTCTCTTGCTGAAAGCTCGATGGACAAGTGCATTGTTCTCTTGCTGAAAGCTCGATGGACAAGTGCATTGTTC
TCTTGCTGAAAGCTCAGTACCCGGGAGTACCCTCGACCGCCGGAGTATAAATAGAGGCGCTTCGTCTACGGAGCGA
CAATTCAATTCAAACAAGCAAAGTGAACACGTCGCTAAGCGAAAGCTAAGCAAATAAACAAGCGCAGCTGAACAAG
CTAAACAATCTGCAGTAAAGTGCAAGTTAAAGTGAATCAATTAAAAGTAACCAGCAACCAAGTAAATCAACTGCAA
CTACTGAAATCTGCCAAGAAGTAATTATTGAATACAAGAAGAGAACTCTGAATACTTTCAACAAGTTACCGAGAAA
GAAGAACTCACACACAGCTAGCGTTTAAACTTAAGCTTCACCATGGTGGGGCCCTGCATGCTGCTGCTGCTGCTGC
TGCTGGGCCTGAGGCTACAGCTCTCCCTGGGCATCATCCTAGTTGAGGAGGAGAACCCGGACTTCTGGAACCGCGA
GGCAGCCGAGGCCCTGGGTGCCGCCAAGAAGCTGCAGCCTGCACAGACAGCCGCCAAGAACCTCATCATCTTCCTG
GGCGATGGGGTGGGGGTGTCTACGGTGACAGCTGCCAGGATCCTAAAAGGGCAGAAGAAGGACAAACTGGGGCCTG
AGATACCCCTGGCCATGGACCGCTTCCCATATGTGGCTCTGTCCAAGACATACAATGTAGACAAACATGTGCCAGA
CAGTGGAGCCACAGCCACGGCCTACCTGTGCGGGGTCAAGGGCAACTTCCAGACCATTGGCTTGAGTGCAGCCGCC
CGCTTTAACCAGTGCAACACGACACGCGGCAACGAGGTCATCTCCGTGATGAATCGGGCCAAGAAAGCAGGGAAGT
CAGTGGGAGTGGTAACCACCACACGAGTGCAGCACGCCTCGCCAGCCGGCACCTACGCCCACACGGTGAACCGCAA
CTGGTACTCGGACGCCGACGTGCCTGCCTCGGCCCGCCAGGAGGGGTGCCAGGACATCGCTACGCAGCTCATCTCC
AACATGGACATTGACGTGATCCTAGGTGGGGGCCGAAAGTACATGTTTCGCATGGGAACCCCAGACCCTGAGTACC
CAGATGACTACAGCCAAGGTGGGACCAGGCTGGACGGGAAGAATCTGGTGCAGGAATGGCTGGCGAAGCACCAGGG
TGCCCGGTACGTGTGGAACCGCACTGAGCTCATGCAGGCTTCCCTGGACCCGTCTGTGGCCCATCTCATGGGTCTC
TTTGAGCCTGGAGACATGAAATACGAGATCCACCGAGACTCCACACTGGACCCCTCCCTGATGGAGATGACAGAGG
CTGCCCTGCGCCTGCTGAGCAGGAACCCCCGCGGCTTCTTCCTCTTCGTGGAGGGTGGTCGCATCGACCATGGTCA
TCATGAAAGCAGGGCTTACCGGGCACTGACTGAGACGATCATGTTCGACGACGCCATTGAGAGGGCGGGCCAGCTC
ACCAGCGAGGAGGACACGCTGAGCTCGTCACTGCCGACCACTCCCACGTCTTCTCCTTCGGAGGCTGCCCCCTGC
GAGGGGGCTCCATCTTCGGGCTGGCCCCTGGCAAGGCCCGGGACAGGAAGGCCTACACGGTCCTCCTATACGGAAA
CGGTCCAGGCTATGTGCTCAAGGACGGCGCCCGGCCGGATGTTACCGAGAGCGAGAGCGGGAGCCCCGAGTATCGG
CAGCAGTCAGCAGTGCCCCTGGACGAAGAGACCCACGCAGGCGAGGACGTGGCGGTGTTCGCGCGCGGCCCGCAGG
CGCACCTGGTTCACGGCGTGCAGGAGCAGACCTTCATAGCGCACGTCATGGCCTTCGCCGCCTGCCTGGAGCCCTA
CACCGCCTGCGACCTGGCGCCCCCGCCGGCACCACCGACGCCGCGCACCCGGGGCGGTCCGTGGTCCCCGCGTTG
CTTCCTCTGCTGGCCGGGACCCTGCTGCTGCTGGAGACGGCCACTGCTCCCTGAGTGTCCCGTCCCTGGGGCTCCT
GCTTCCCCATCCCGGAGTTCTCCTGCTCCCCGCCTCCTGTCGTCCTGCCTGGCCTCCAGCCCGAGTCGTCATCCCC
GGAGTCCCTATACAGAGGTCCTGCCATGGAACCTTCCCCGTGCGCTCTGGGGACTGAGCCCATGACACCAA
ACCTGCCCCTTGGCTGCTCTCGGACTCCCTACCCCAACCCCAGGGACAGATCTGCCAGATTTGTAAAACAAATAG
ATTTTAGGCCCAAAGATTATTTAAAGCATTGCCTGGAACGCAGTGAGTTTTTGTTAGAAAAGAGAATAATTCAAAG
TGGCATTGCTTTGCTTCTTATGTTAATTTGGTACAGACCTGTGGCTGAGTTTGCTCAAAGTATTCAGAGCAGAATT
```

FIGURE 11 (cont.)

```
GTGGAGTGGAAAGAGAGATTGGACAAAGAGTTTAGTTTGTCAGTGTATCAAAAAATGAAGTTTAATGTGGCTATGG
GAATTGGAGTTTTAGATTGGCTAAGAAACAGTGATGATGATGATGAAGACAGCCAGGAAATGCTGATAAAAATGA
AGATGGTGGGGAGAAGAACATGGAAGACTCAGGGCATGAAACAGGCATTGATTCACAGTCCCAAGGCTCATTTCAG
GCCCCTCAGTCCTCACAGTCTGTTCATGATCATAATCAGCCATACCACATTTGTAGAGGTTTTACTTGCTTTAAAA
AACCTCCCACACCTCCCCCTGAACCTGAAACATAAAATGAATGCAATTGTTGTTGTTAACTTGTTTATTGCAGCTT
ATAATGGTTACAAATAAAGCAATAGCATCACAAATTTCACAAATAAAGCATTTTTTTCACTGCATTCTAGTTGTGG
TTTGTCCAAACTCATCAATGTATCTTATCATGTCTGGATCCCCAGGAAGCTCCTCTGTGTCCTCATAAACCCTAAC
CTCCTCTACTTGAGAGGACATTCCAATCATAGGCTGCCCATCCACCCTCTGTGTCCTCCTGTTAATTAGGTCACTT
AACAAAAAGGAAATTGGGTAGGGGTTTTTCACAGACCGCTTTCTAAGGGTAATTTTAAAATATCTGGGAAGTCCCT
TCCACTGCTGTGTTCCAGAAGTGTTGGTAAACAGCCCACAAATGTCAACAGCAGAAACATACAAGCTGTCAGCTTT
GCACAAGGGCCCAACACCCTGCTCATCAAGAAGCACTGTGGTTGCTGTGTTAGTAATGTGCAAAACAGGAGGCACA
TTTTCCCCACCTGTGTAGGTTCCAAAATATCTAGTGTTTTCATTTTTACTTGGATCAGGAACCCAGCACTCCACTG
GATAAGCATTATCCTTATCCAAAACAGCCTTGTGGTCAGTGTTCATCTGCTGACTGTCAACTGTAGCATTTTTGG
GGTTACAGTTTGAGCAGGATATTTGGTCCTGTAGTTTGCTAACACACCCTGCAGCTCCAAAGGTTCCCCACCAACA
GCAAAAAAATGAAAATTTGACCCTTGAATGGGTTTTCCAGCACCATTTTCATGAGTTTTTTGTGTCCCTGAATGCA
AGTTTAACATAGCAGTTACCCCAATAACCTCAGTTTTAACAGTAACAGCTTCCCACATCAAAATATTTCCACAGGT
TAAGTCCTCATTTAAATTAGGCAAAGGAATTCCACTTCCCACTGCCTTGCTTCCGTCTCCCATTCAAACTTTTATC
AACTGACATTATTCTAAGTAAAATCCTCTTCATTATGTTGTCAGCAATCCATTGCTTGAAGGCCTGGCTCCCAGA
ACCCCTCGACTGGTATGTCTTCTCCTAGAATACTCCAGAAGAAAAGGAGTGTATGAAGATAGTGACTGCACATTAA
AATGACTGAAACCATAGTAAATTAGGATGAGATTCTGGGCAGATAAACAGACAGCTGGCTAGGATCATTTTTTTAT
GCCTTGGACTTCTTTGGCAATCTGTTGAAGCCTGACATTCCTCAGAATAATGTTTTAAAGCCCAACAATAAGACCC
TGTAGCACATATAATAAGTACTGCAGTTTTGAAGTAGTGATAAGCATAAATGATATTTTGATATATTTATTATAAC
TGTAATGAGATGTGTACATATCTGTGACTTCATAGGTACTGATTGTACTACTGTGATTTTTTGCCTACTTTCAAA
ATGAAAAGGAATGCTTAATTTCAGTTAGAGGTTAGTAAAGACAAATAGGTAATTTTCTTCCAGTGAAGAGCATG
GCGCCCCTTGCTATTCATGGACGCTTGCTTAAAGACTTGTACACAGGCTTGCTTTGTATCAACCTATGACTTCCCC
TTACAGCCGATGATAGGTTTTTATTTGCACCTCCTTCGTGTACAAAGACAGTTTTGGTGGCTACGCCATCATTAAA
CTCATTATTATCATGCTTAAGCCTATAGATGTATCCAGTTCTTCTGTTACATAATTGAAGCTGTAGTGAATTGTCT
ATCTTAAACTGCATCGCTAACTGACTACATTTCACACTTCATTTGCTTCCAACATAGACTAACCTTCTTGGATGTC
CACTATTATTTGAACTTTTGAGATTTTTTTTCCTATTTCTAATATCTTAAAATTTCAGAAGACTTAAAGTTTTGCA
ACTACAGGGCTCCATATAGACATCTAGCTTGAATTTATACACTTTCTTTCATTGATGTCCCTGGACTAAAAAATGT
TAAATATTTCTAACCGCTGTACTTAAAGTCCATTACAAACGAAGACTACTGTTGTTAAGTTGAATAGGCATCTTAT
ATATTTTTCACCGGTGCAATAAATAACTTCTATTCCCTTCTAACATCTGCTTGCGTTGCACTGAGAGTACACTATT
GATTAGCAATAGGTTCGTGATTACAGCCCCTTCTATAATTAATTGTTAGGTTAACATATTATTCATAAAATATTATT
TTATTAATTTTTACTTGATTTGCTACTGGATGCTTAGAAATAGCTATGAGTATATTGGTAGAACCAGTACTTATAT
TTTATTACATTTTTACATTTCATAAAATTTAAGTGATATAAAAATCCTGAGGAAGTATGCCACAAAAGTGGTCTCA
GTGGAAATTTAAATATGTTAACATTTATTTTTAAAATGTAGCGTGAAATAGACAACTTTAAAAGCTCAGCTTAAAA
AAAAAACTCAAGGAAGCTGAACTTGACTTTTTAAAGCACTGAAGTGCAATATTTAATGTAGGTCAACATGTTTAAA
TGGGAAAATTTTTTTCCTAATTACAGCCAAATCCCTAGCTGTAATTAACTTAAAATTTGTATACTATTTCACAACA
GAGTCAGCATATACCACTTTCTTATAAAATTAGAAAGATCTAAAATTTTAGAGCTTATTTGGTGAAACAGGCATAT
TGCTACATCTTTGTTTATAAATTATAATGTGCCTTTAGAGCCCAATAACAGATAACAAGATTTTGAAAATTCAGGT
GAATTAGAGTTATCAGAGGGAATGTTAATACACTCTATTCAAATACTATATGAGTAAGACATTTAAAATAGGAAAC
AATACTTTATATATTAAAAAAAATTAATCTTCCAGTCGATTTAATCCACTTTATGAATTCATTTAAATCGATTTAA
ATTCGAATTAATTAACTAGAGTACCCGGGGATCTTATTCCCTTTAACTAATAAAAAAAAATAATAAAGCATCACTT
ACTTAAAATCAGTTAGCAAATTTCTGTCCAGTTTATTCAGCAGCACCTCCTTGCCCTCCTCCCAGCTCTGGTATTG
CAGCTTCCTCCTGGCTGCAAACTTTCTCCACAATCTAAATGGAATGTCAGTTTCCTCCTGTTCCTGTCCATCCGCA
CCCACTATCTTCATGTTGTTGCAGATGAAGCGCGCAAGACCGTCTGAAGATACCTTCAACCCCGTGTATCCATATG
ACACGGAAACCGGTCCTCCAACTGTGCCTTTTCTTACTCCTCCCTTTGTATCCCCCAATGGGTTTCAAGAGAGTCC
CCCTGGGGTACTCTCTTTGCGCCTATCCGAACCTCTAGTTACCTCCAATGGCATGCTTGCGCTCAAAATGGGCAAC
GGCCTCTCTCTGGACGAGGCCGGCAACCTTACCTCCCAAAATGTAACCACTGTGAGCCCACCTCTCAAAAAAACCA
AGTCAAACATAAACCTGGAAATATCTGCACCCCTCACAGTTACCTCAGAAGCCCTAACTGTGGCTGCCGCCGCACC
TCTAATGGTCGCGGGCAACACACTCACCATGCAATCACAGGCCCCGCTAACCGTGCACGACTCCAAACTTAGCATT
GCCACCCAAGGACCCCTCACAGTGTCAGAAGGAAAGCTAGCCCTGCAAACATCAGGCCCCCTCACCACCACCGATA
GCAGTACCCTTACTATCACTGCCTCACCCCCTCTAACTACTGCCACTGGTAGCTTGGGCATTGACTTGAAAGAGCC
CATTTATACACAAAATGGAAAACTAGGACTAAAGTACGGGCTCCTTTGCATGTAACAGACGACCTAAACACTTTG
ACCGTAGCAACTGGTCCAGGTGTGACTATTAATAATACTTCCTTGCAAACTAAAGTTACTGGAGCCTTGGGTTTTG
ATTCACAAGGCAATATGCAACTTAATGTAGCAGGAGGACTAAGGATTGATTCTCAAAACAGACGCCTTATACTTGA
TGTTAGTTATCCGTTTGATGCTCAAAACCAACTAAATCTAAGACTAGGACAGGGCCCTCTTTTTATAAACTCAGCC
CACAACTTGGATATTAACTACAACAAAGGCCTTTACTTGTTTACAGCTTCAAACAATTCCAAAAAGCTTGAGGTTA
ACCTAAGCACTGCCAAGGGGTTGATGTTTGACGCTACAGCCATAGCCATTAATGCAGGAGATGGGCTTGAATTTGG
TTCACCTAATGCACCAAACACAAATCCCCTCAAAACAAAAATTGGCCATGGCCTAGAATTTGATTCAAACAAGGCT
ATGGTTCCTAAACTAGGAACTGGCCTTAGTTTTGACAGCACAGGTGCCATTACAGTAGGAAACAAAAATAATGATA
```

FIGURE 11 (cont.)

```
AGCTAACTTTGTGGACCACACCAGCTCCATCTCCTAACTGTAGACTAAATGCAGAGAAAGATGCTAAACTCACTTT
GGTCTTAACAAAATGTGGCAGTCAAATACTTGCTACAGTTTCAGTTTTGGCTGTTAAAGGCAGTTTGGCTCCAATA
TCTGGAACAGTTCAAAGTGCTCATCTTATTATAAGATTTGACGAAAATGGAGTGCTACTAAACAATTCCTTCCTGG
ACCCAGAATATTGGAACTTTAGAAATGGAGATCTTACTGAAGGCACAGCCTATACAAACGCTGTTGGATTTATGCC
TAACCTATCAGCTTATCCAAAATCTCACGGTAAAACTGCCAAAAGTAACATTGTCAGTCAAGTTTACTTAAACGGA
GACAAAACTAAACCTGTAACACTAACCATTACACTAAACGGTACACAGGAAACAGGAGACACAACTCCAAGTGCAT
ACTCTATGTCATTTTCATGGGACTGGTCTGGCCACAACTACATTAATGAAATATTTGCCACATCCTCTTACACTTT
TTCATACATTGCCCAAGAATAAAGAATCGTTTGTGTTATGTTTCAACGTGTTTATTTTTCAATTGCAGAAAATTTC
AAGTCATTTTTCATTCAGTAGTATAGCCCCACCACCACATAGCTTATACAGATCACCGTACCTTAATCAAACTCAC
AGAACCCTAGTATTCAACCTGCCACCTCCCTCCCAACACACAGAGTACACAGTCCTTTCTCCCCGGCTGGCCTTAA
AAAGCATCATATCATGGGTAACAGACATATTCTTAGGTGTTATATTCCACACGGTTTCCTGTCGAGCCAAACGCTC
ATCAGTGATATTAATAAACTCCCCGGGCAGCTCACTTAAGTTCATGTCGCTGTCCAGCTGCTGAGCCACAGGCTGC
TGTCCAACTTGCGGTTGCTTAACGGGCGGCGAAGGAGAAGTCCACGCCTACATGGGGGTAGAGTCATAATCGTGCA
TCAGGATAGGGCGGTGGTGCTGCAGCAGCGCGCGAATAAACTGCTGCCGCCGCCGCTCCGTCCTGCAGGAATACAA
CATGGCAGTGGTCTCCTCAGCGATGATTCGCACCGCCCGCAGCATAAGGCGCCTTGTCCTCCGGGCACAGCAGCGC
ACCCTGATCTCACTTAAATCAGCACAGTAACTGCAGCACAGCACCACAATATTGTTCAAAATCCCACAGTGCAAGG
CGCTGTATCCAAAGCTCATGGCGGGGACCACAGAACCCACGTGGCCATCATACCACAAGCGCAGGTAGATTAAGTG
GCGACCCCTCATAAACACGCTGGACATAAACATTACCTCTTTTGGCATGTTGTAATTCACCACCTCCCGGTACCAT
ATAAACCTCTGATTAAACATGGCGCCATCCACCACCATCCTAAACCAGCTGGCCAAAACCTGCCCGCCGGCTATAC
ACTGCAGGGAACCGGGACTGGAACAATGACAGTGGAGAGCCCAGGACTCGTAACCATGGATCATCATGCTCGTCAT
GATATCAATGTTGGCACAACACAGGCACACGTGCATACACTTCCTCAGGATTACAAGCTCCTCCCGCGTTAGAACC
ATATCCCAGGGAACAACCCATTCCTGAATCAGCGTAAATCCCACACTGCAGGGAAGACCTCGCACGTAACTCACGT
TGTGCATTGTCAAAGTGTTACATTCGGGCAGCAGCGGATGATCCTCCAGTATGGTAGCGCGGGTTTCTGTCTCAAA
AGGAGGTAGACGATCCCTACTGTACGGAGTGCGCCGAGACAACCGAGATCGTGTTGGTCGTAGTGTCATGCCAAAT
GGAACGCCGGACGTAGTCATATTTCCTGAAGCAAAACCAGGTGCGGGCGTGACAAACAGATCTGCGTCTCCGGTCT
CGCCGCTTAGATCGCTCTGTGTAGTAGTTGTAGTATATCCACTCTCTCAAAGCATCCAGGCGCCCCCTGGCTTCGG
GTTCTATGTAAACTCCTTCATGCGCCGCTGCCCTGATAACATCCACCACCGCAGAATAAGCCACACCCAGCCAACC
TACACATTCGTTCTGCGAGTCACACACGGGAGGAGCGGGAAGAGCTGGAAGAACCATGTTTTTTTTTTATTCCAA
AAGATTATCCAAAACCTCAAAATGAAGATCTATTAAGTGAACGCGCTCCCCTCCGGTGGCGTGGTCAAACTCTACA
GCCAAAGAACAGATAATGGCATTTGTAAGATGTTGCACAATGGCTTCCAAAAGGCAAACGGCCCTCACGTCCAAGT
GGACGTAAAGGCTAAACCCTTCAGGGTGAATCTCCTCTATAAACATTCCAGCACCTTCAACCATGCCCAAATAATT
CTCATCTCGCCACCTTCTCAATATATCTCTAAGCAAATCCCGAATATTAAGTCCGGCCATTGTAAAAATCTGCTCC
AGAGCGCCCTCCACCTTCAGCCTCAAGCAGCGAATCATGATTGCAAAAATTCAGGTTCCTCACAGACCTGTATAAG
ATTCAAAAGCGGAACATTAACAAAAATACCGCGATCCCGTAGGTCCCTTCGCAGGGCCAGCTGAACATAATCGTGC
AGGTCTGCACGGACCAGCGCGGCCACTTCCCCGCCAGGAACCTTGACAAAAGAACCCACACTGATTATGACACGCA
TACTCGGAGCTATGCTAACCAGCGTAGCCCCGATGTAAGCTTTGTTGCATGGGCGGCGATATAAAATGCAAGGTGC
TGCTCAAAAAATCAGGCAAAGCCTCGCGCAAAAAAGAAAGCACATCGTAGTCATGCTCATGCAGATAAAGGCAGGT
AAGCTCCGGAACCACCACAGAAAAAGACACCATTTTTCTCTCAAACATGTCTGCGGGTTTCTGCATAAACACAAAA
TAAAATAACAAAAAAACATTTAAACATTAGAAGCCTGTCTTACAACAGGAAAAACAACCCTTATAAGCATAAGACG
GACTACGGCCATGCCGGCGTGACCGTAAAAAAACTGGTCACCGTGATTAAAAAGCACCACCGACAGCTCCTCGGTC
ATGTCCGGAGTCATAATGTAAGACTCGGTAAACACATCAGGTTGATTCATCGGTCAGTGCTAAAAAGCGACCGAAA
TAGCCCGGGGGAATACATACCCGCAGGCGTAGAGACAACATTACAGCCCCCATAGGAGGTATAACAAAATTAATAG
GAGAGAAAAACACATAAACACCTGAAAAACCCTCCTGCCTAGGCAAAATAGCACCCTCCCGCTCCAGAACAACATA
CAGCGCTTCACAGCGGCAGCCTAACAGTCAGCCTTACCAGTAAAAAAGAAAACCTATTAAAAAAACACCACTCGAC
ACGGCACCAGCTCAATCAGTCACAGTGTAAAAAAGGGCCAAGTGCAGAGCGAGTATATATAGGACTAAAAAATGAC
GTAACGGTTAAAGTCCACAAAAAACACCCAGAAAACCGCACGCGAACCTACGCCCAGAAACGAAAGCCAAAAACC
CACAACTTCCTCAAATCGTCACTTCCGTTTTCCCACGTTACGTAACTTCCCATTTTAAGAAAACTACAATTCCCAA
CACATACAAGTTACTCCGCCCTAAAACCTACGTCACCCGCCCCGTTCCCACGCCCCGCGCCACGTCACAAACTCCA
CCCCCTCATTATCATATTGGCTTCAATCCAAAATAAGGTATATTATTGATGATG
``` pD2076#2: A Linear Gutted Virus Carrying Human Dystrophin

FIGURE 13
TP-DNA Complex from (+)lox(+)pol Helper
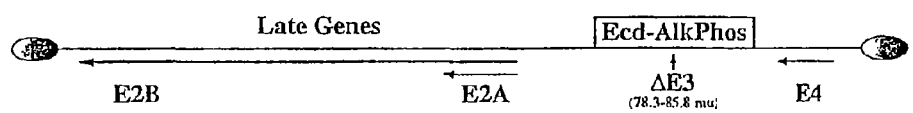
Deproteinized Hirt Prep DNA from ΔFseI.4
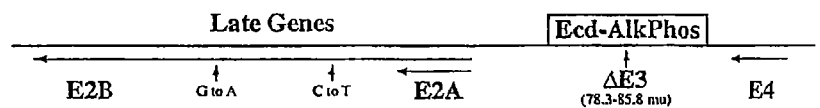
pD1940#3 or pD1940#6
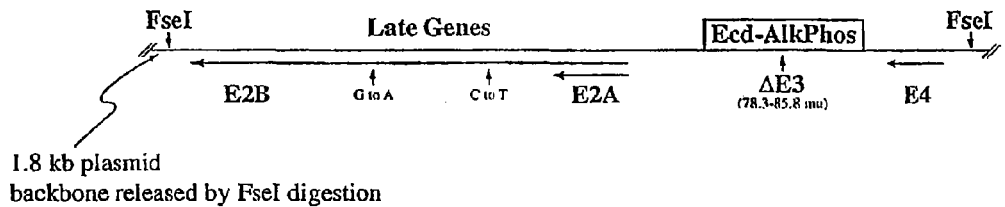
1.8 kb plasmid
backbone released by FseI digestion

FIGURE 14 pD1940 sequence (SEQ ID NO:13)

```
CTAAATTGTAAGCGTTAATATTTTGTTAAAATTCGGCCGGCCATCATCAATAATATACCTTATTTTGGATTGAAGC
CAATATGATAATGAGGGGGTGGAGTTTGTGACGTGGCGCGGGGCGTGGGAACGGGGCGGGTGACGTAGTAGTGTGG
CGGAAGTGTGATGTTGCAAGTGTGGCGGAACACATGTATAACTTCGTATAATGTATGCTATACGAAGTTATACATG
TAAGCGACGGATGTGGCAAAAGTGACGTTTTTGGTGTGCGCCGGTGTACACAGGAAGTGACAATTTTCGCGCGGTT
TTAGGCGGATGTTGTAGTAAATTTGGGCGTAACCGAGTAAGATTTGGCCATTTTCGCGGGAAAACTGAATAAGAGG
AAGTGAAATCTGAATAATTTTGTGTTACTCATAGCGCGTAATATTTGTCTAGGGAGATCTATAACTTCGTATAATG
TATGCTATACGAAGTTATTACCGAAGAAATGGCTCGAGATCTGGAAGGTGCTGAGGTACGATGAGACCCGCACCAG
GTGCAGACCCTGCGAGTGTGGCGGTAAACATATTAGGAACCAGCCTGTGATGCTGGATGTGACCGAGGAGCTGAGG
CCCGATCACTTGGTGCTGGCCTGCACCCGCGCTGAGTTTGGCTCTAGCGATGAAGATACAGATTGAGGTACTGAAA
TGTGTGGGCGTGGCTTAAGGGTGGGAAAGAATATATAAGGTGGGGGTCTTATGTAGTTTTGTATCTGTTTTGCAGC
AGCCGCCGCCGCCATGAGCACCAACTCGTTTGATGGAAGCATTGTGAGCTCATATTTGACAACGCGCATGCCCCCA
TGGGCCGGGGTGCGTCAGAATGTGATGGGCTCCAGCATTGATGGTCGCCCCGTCCTGCCCGCAAACTCTACTACCT
TGACCTACGAGACCGTGTCTGGAACGCCGTTGGAGACTGCAGCCTCCGCCGCCGCTTCAGCCGCTGCAGCCACCGC
CCGCGGGATTGTGACTGACTTTGCTTTCCTGAGCCCGCTTGCAAGCAGTGCAGCTTCCCGTTCATCCGCCCGCGAT
GACAAGTTGACGGCTCTTTTGGCACAATTGGATTCTTTGACCCGGGAACTTAATGTCGTTTCTCAGCAGCTGTTGG
ATCTGCGCCAGCAGGTTTCTGCCCTGAAGGCTTCCTCCCCTCCCAATGCGGTTTAAAACATAAATAAAAAACCAGA
CTCTGTTTGGATTTGGATCAAGCAAGTGTCTTGCTGTCTTTATTTAGGGGTTTTGCGCGCGCGGTAGGCCCGGGAC
CAGCGGTCTCGGTCGTTGAGGGTCCTGTGTATTTTTTCCAGGACGTGGTAAAGGTGACTCTGGATGTTCAGATACA
TGGGCATAAGCCCGTCTCTGGGGTGGAGGTAGCACCACTGCAGAGCTTCATGCTGCGGGTGGTGTTGTAGATGAT
CCAGTCGTAGCAGGAGCGCTGGGCGTGGTGCCTAAAAATGTCTTTCAGTAGCAAGCTGATTGCCAGGGGCAGGCCC
TTGGTGTAAGTGTTTACAAAGCGGTTAAGCTGGGATGGGTGCATACGTGGGGATATGAGATGCATCTTGGACTGTA
TTTTTAGGTTGGCTATGTTCCCAGCCATATCCCTCCGGGGATTCATGTTGTGCAGAACCACCAGCACAGTGTATCC
GGTGCACTTGGGAAATTTGTCATGTAGCTTAGAAGGAAATGCGTGGAAGAACTTGGAGACGCCCTTGTGACCTCCA
AGATTTTCCATGCATTCGTCCATAATGATGGCAATGGGCCCACGGGCGGCGGCCTGGGCGAAGATATTTCTGGGAT
CACTAACGTCATAGTTGTGTTCCAGGATGAGATCGTCATAGGCCATTTTTACAAAGCGCGGGCGGAGGGTGCCAGA
CTGCGGTATAATGGTTCCATCCGGCCCAGGGGCGTAGTTACCCTCACAGATTTGCATTTCCCACGCTTTGAGTTCA
GATGGGGGATCATGTCTACCTGCGGGCGATGAAGAAAACGGTTTCCGGGGTAGGGGAGATCAGCTGGGAAGAAA
GCAGGTTCCTGAGCAGCTGCGACTTACCGCAGCCGGTGGGCCCGTAAATCACACCTATTACCGGGTGCAACTGGTA
GTTAAGAGAGCTGCAGCTGCCGTCATCCCTGAGCAGGGGGCCACTTCGTTAAGCATGTCCCTGACTCGCATGTTT
TCCCTGACCAAATCCGCCAGAAGGCGCTCGCCGCCCAGCGATAGCAGTTCTTGCAAGGAAGCAAAGTTTTTCAACG
GTTTGAGACCGTCCGCCGTAGGCATGCTTTTGAGCGTTTGACCAAGCAGTTCCAGGCGGTCCCACAGCTCGGTCAC
CTGCTCTACGGCATCTCGATCCAGCATATCTCCTCGTTTCGCGGGTTGGGGCGGCTTTCGCTGTACGGCAGTAGTC
GGTGCTCGTCCAGACGGGCCAGGGTCATGTCTTTCCACGGGCGCAGGGTCCTCGTCAGCGTAGTCTGGGTCACGGT
GAAGGGGTGCGCTCCGGGCTGCGCGCTGGCCAGGGTGCGCTTGAGGCTGGTCCTGCTGGTGCTGAAGCGCTGCCGG
TCTTCGCCCTGCGCGTCGGCCAGGTAGCATTTGACCATGGTGTCATAGTCCAGCCCCTCCGCGGCGTGGCCCTTGG
CGCGCAGCTTGCCCTTGGAGGAGGCGCCGCACGAGGGCAGTGCAGACTTTTGAGGGCGTAGAGCTTGGGCGCGAG
AAATACCGATTCCGGGGAGTAGGCATCCGCGCCGCAGGCCCCGCAGACGGTCTCGCATTCCACGAGCCAGGTGAGC
TCTGGCCGTTCGGGGTCAAAAACCAGGTTTCCCCCATGCTTTTTGATGCGTTTCTTACCTCTGGTTTCCATGAGCC
GGTGTCCACGCTCGGTGACGAAAAGGCTGTCCGTGTCCCGTATACAGACTTGAGAGGCCTGTCCTCGAGCGGTGT
TCCGCGGTCCTCCTCGTATAGAAACTCGGACCACTCTGAGACAAAGGCTCGCGTCCAGGCCAGCACGAAGGAGGCT
AAGTGGGAGGGGTAGCGGTCGTTGTCCACTAGGGGTCCACTCGCTCCAGGGTGGTGAAGACACATGTCGCCCTCTT
CGGCATCAAGGAAGGTGATTGGTTTGTAGGTGTAGGCCACGTGACCGGGTGTTCCTGAAGGGGGCTATAAAAGGG
GGTGGGGGCGCGTTCGTCCTCACTCTCTTCCGCATCCGTCTGCGAGGGCCAGCTGTTGGGGTGAGTACTCCCTC
TGAAAAGCGGGCATGACTTCTGCGCTAAGATTGTCAGTTTCCAAAAACGAGGAGGATTTGATATTCACCTGGCCCG
CGGTGATGCCTTTGAGGGTGGCCGCATCCATCTGGTCAGAAAAGACAATCTTTTTGTTGTCAAGCTTGGTGGCAAA
CGACCCGTAGAGGGCGTTGGACAGCAACTTGGCGATGGAGCGCAGGGTTTGGTTTTTGTCGCGATCGGCGCGCTCC
TTGGCCGCGATGTTTAGCTGCACGTATTCGCGCGCAACGCACCGCCATTCGGGAAAGACGGTGGTGCGCTCGTCGG
GCACCAGGTGCACGCGCCAACCGCGGTTGTGCAGGGTGACAAGGTCAACGCTGGTGGCTACCTCTCCGCGTAGGCG
CTCGTTGGTCCAGCAGAGGCGGCCGCCCTTGCGCGAGCAGAATGGCGGTAGGGGTCTAGCTGCGTCTCGTCCGGG
GGGTCTGCGTCCACGGTAAAGACCCCGGGCAGCAGGCGCGCGTCGAAGTAGTCTATCTTGCATCCTTGCAAGTCTA
GCGCCTGCTGCCATGCGCGGGCGGCAAGCGCGCGCTCGTATGGGTTGAGTGGGGACCCCATGGCATGGGTGGGT
GAGCGCGGAGGCGTACATGCCGCAAATGTCGTAAACGTAGAGGGGCTCTCTGAGTATTCCAAGATATGTAGGGTAG
CATCTTCCACCGCGGATGCTGGCGCGCACGTAATCGTATAGTTCGTGCGAGGGAGCGAGGAGGTCGGGACCGAGGT
TGCTACGGGCGGCTGCTCTGCTCGGAAGACTATCTGCCTGAAGATGGCATGTGAGTTGGATGATATGGTTGGACG
CTGGAAGACGTTGAAGCTGGCGTCTGTGAGACCTACCGCGTCACGCACGAAGGAGGCGTAGGAGTCGCGCAGCTTG
TTGACCAGCTCGGCGGTGACCTGCACGTCTAGGGCGCAGTAGTCCAGGGTTTCCTTGATGATGTCATACTTATCCT
GTCCCTTTTTTTCCACAGCTCGCGGTTGAGGACAAACTCTTCGCGGTCTTTCCAGTACTCTTGGATCGGAAACCC
GTCGGCCTCCGAACGGTAAGAGCCTAGCATGTAGAACTGGTTGACGGCCTGGTAGGCGCAGCATCCCTTTTCTACG
GGTAGCGCGTATGCCTGCGCGGCCTTCCGGAGCGAGGTGTGGGTGAGCGCAAAGGTGTCCCTGACCATGACTTTGA
GGTACTGGTATTTGAAGTCAGTGTCGTCGCATCCGCCCTGCTCCCAGAGCAAAAAGTCCGTGCGCTTTTTGGAACG
CGGATTTGGCAGGGCGAAGGTGACATCGTTGAAGAGTATCTTTCCCGCGCGAGGCATAAAGTTGCGTGTGATGCGG
```

FIGURE 14 (cont.)

```
AAGGGTCCCGGCACCTCGGAACGGTTGTTAATTACCTGGGCGGCGAGCACGATCTCGTCAAAGCCGTTGATGTTGT
GGCCCACAATGTAAAGTTCCAAGAAGCGCGGGATGCCCTTGATGGAAGGCAATTTTTTAAGTTCCTCGTAGGTGAG
CTCTTCAGGGGAGCTGAGCCCGTGCTCTGAAAGGGCCCAGTCTGCAAGATGAGGGTTGGAAGCGACGAATGAGCTC
CACAGGTCACGGGCCATTAGCATTTGCAGGTGGTCGCGAAAGGTCCTAAACTGGCGACCTATGGCCATTTTTTCTG
GGGTGATGCAGTAGAAGGTAAGCGGGTCTTGTTCCCAGCGGTCCCATCCAAGGTTCGCGGCTAGGTCTCGCGCGGC
AGTCACTAGAGGCTCATCTCCGCCGAACTTCATGACCAGCATGAAGGGCACGAGCTGCTTCCCAAAGGCCCCCATC
CAAGTATAGGTCTCTACATCGTAGGTGACAAAGAGACGCTCGGTGCGAGGATGCGAGCCGATCGGGAAGAACTGGA
TCTCCCGCCACCAATTGGAGGAGTGGCTATTGATGTGGTGAAAGTAGAAGTCCCTGCGACGGGCCGAACACTCGTG
CTGGCTTTTGTAAAAACGTGCGCAGTACTGGCAGCGGTGCACGGGCTGTACATCCTGCACGAGGTTGACCTGACGA
CCGCGCACAAGGAAGCAGAGTGGGAATTTGAGCCCCTCGCCTGGCGGGTTTGGCTGGTGGTCTTCTACTTCGGCTG
CTTGTCCTTGACCGTCTGGCTGCTCGAGGGGAGTTACGGTGGATCGGACCACCACGCCGCGCGAGCCCAAAGTCCA
GATGTCCGCGCGGCGGTCGGAGCTTGATGACAACATCGCGCAGATGGGAGCTGTCCATGGTCTGGAGCTCCCGC
GGCGTCAGGTCAGGCGGGAGCTCCTGCAGGTTTACCTCGCATAGACGGGTCAGGGCGCGGGCTAGATCCAGGTGAT
ACCTAATTTCCAGGGGCTGGTTGGTGGCGGCGTCGATGGCTTGCAAGAGGCCGCATCCCCGCGGCGCGACTACGGT
ACCGCGCGGCGGCGGTGGGCCGCGGGGTGTCCTTGGATGATGCATCTAAAAGCGGTGACGCGGGCGAGCCCCG
GAGGTAGGGGGGGCTCCGGACCCGCCGGGAGAGGGGGCAGGGCACGTCGGCGCCGCGCGGGCAGGAGCTGGTG
CTGCGCGCGTAGGTTGCTGGCGAACGCGACGACGCGGCGGTTGATCTCCTGAATCTGGCGCCTCTGCGTGAAGACG
ACGGGCCCGGTGAGCTTGAGCCTGAAAGAGAGTTCGACAGAATCAATTTCGGTGTCGTTGACGGCGGCCTGGCGCA
AAATCTCCTGCACGTCTCCTGAGTTGTCTTGATAGGCGATCTCGGCCATGAACTGCTCGATCTCTTCCTCCTGGAG
ATCTCCGCGTCCGGCTCGCTCCACGGTGGCGGCGAGGTCGTTGGAAATGCGGGCCATGAGCTGCGAGAAGGCGTTG
AGGCCTCCCTCGTTCCAGACGCGGCTGTAGACCACGCCCCCTTCGGCATCGCGGGCGCGCATGACCACCTGCGCGA
GATTGAGCTCCACGTGCCGGGCGAAGACGGCGTAGTTTCGCAGGCGCTGAAAGAGGTAGTTGAGGGTGGTGGCGGT
GTGTTCTGCCACGAAGAAGTACATAACCCAGCGTCGCAACGTGGATTCGTTGATATCCCCAAGGCCTCAAGGCGC
TCCATGGCCTCGTAGAAGTCCACGGCGAAGTTGAAAAACTGGGAGTTGCGCGCCGACACGGTTAACTCCTCCTCCA
GAAGACGGATGAGCTCGGCGACAGTGTCGCGCACCTCGCGCTCAAAGGCTACAGGGGCCTCTTCTTCTTCTTCAAT
CTCCTCTTCCATAAGGGCCTCCCCTTCTTCTTCTTCTGGCGGCGGTGGGGAGGGGGACACGGCGGCGACGACGG
CGCACCGGGAGGCGGTCGACAAAGCGCTCGATCATCTCCCCGCGGCGACGGCGCATGGTCTCGGTGACGGCGCGGC
CGTTCTCGCGGGGGCGCAGTTGGAAGACGCCGCCCGTCATGTCCCGGTTATGGGTTGGCGGGGGGCTGCCATGCGG
CAGGGATACGGCGCTAACGATGCATCTCAACAATTGTTGTGTAGGTACTCCGCCGCCGAGGGACCTGAGCGAGTCC
GCATCGACCGGATCGGAAAACCTCTCGAGAAAGGCGTCTAACCAGTCACAGTCGCAAGGTAGGCTGAGCACCGTGG
CGGGCGGCAGCGGGCGGCGGTCGGGGTTGTTTCTGGCGGAGGTGCTGCTGATGATGTAATTAAAGTAGGCGGTCTT
GAGACGGCGGATGGTCGACAGAAGCACCATGTCCTTGGGTCCGGCCTGCTGAATGCGCAGGCGGTCGGCCATGCCC
CAGGCTTCGTTTTGACATCGGCGCAGGTCTTTGTAGTAGTCTTGCATGAGCCTTTCTACCGGCACTTCTTCTTCTC
CTTCCTCTTGTCCTGCATCTCTTGCATCTATCGCTGCGGCGGCGGCGGAGTTTGGCCGTAGGTGGCGCCCTCTTCC
TCCCATGCGTGTGACCCCGAAGCCCCTCATCGGCTGAAGCAGGGCTAGGTCGGCGACAACGCGCTCGGCTAATATG
GCCTGCTGCACCTGCGTGAGGGTAGACTGGAAGTCATCCATGTCCACAAAGCGGTGGTATGCGCCCGTGTTGATGG
TGTAAGTGCAGTTGGCCATAACGGACCAGTTAACGGTCTGGTGACCCGGCTGCGAGAGCTCGGTGTACCTGAGACG
CGAGTAAGCCCTCGAGTCAAATACGTAGTCGTTGCAAGTCCGCACCAGGTACTGGTATCCCACCAAAAAGTGCGGC
GGCGGCTGGCGGTAGAGGGGCCAGCGTAGGGTGGCCGGGGCTCCGGGGCGAGATCTTCCAACATAAGGCGATGAT
ATCCGTAGATGTACCTGGACATCCAGGTGATGCCGGCGGCGGTGGTGGAGGCGCGCGGAAAGTCGCGGACGCGGTT
CCAGATGTTGCGCAGCGGCAAAAAGTGCTCCATGGTCGGGACGCTCTGGCCGGTCAGGCGCGCGCAATCGTTGACG
CTCTACCGTGCAAAAGGAGAGCCTGTAAGCGGGCACTCTTCCGTGGTCTGGTGGATAAATTCGCAAGGGTATCATG
GCGGACGACCGGGGTTCGAGCCCCGTATCCGGCCGTCCGCCGTGATCCATGCGGTTACCGCCCGCGTGTCGAACCC
AGGTGTGCGACGTCAGACAACGGGGAGTGCTCCTTTTGGCTTCCTTCCAGGCGCGGCGGCTGCTGCGCTAGCTTT
TTTGGCCACTGGCCGCGCGCAGCGTAAGCGGTTAGGCTGGAAAGCGAAAGCATTAAGTGGCTCGCTCCCTGTAGCC
GGAGGGTTATTTTCCAAGGGTTGAGTCGCGGGACCCCCGGTTCGAGTCTCGGACCGGCCGGACTGCGGCGAACGGG
GGTTTGCCTCCCCGTCATGCAAGACCCCGCTTGCAAATTCCTCCGGAAACAGGGACGAGCCCCTTTTTTGCTTTTC
CCAGATGCATCCGGTGCTGCGGCAGATGCGCCCCCCTCCTCAGCAGCGGCAAGAGCAAGAGCAGCGGCAGACATGC
AGGGCACCCTCCCCTCCTCCTACCGCGTCAGGAGGGGCGACATCCGCGGTTGACGCGGCAGCAGATGGTGATTACG
AACCCCGCGGCGCCGGGCCCGGCACTACCTGGACTTGGAGGAGGGCGAGGGCCTGGCGCGGCTAGGAGCGCCCTC
TCCTGAGCGGTACCCAAGGGTGCAGCTGAAGCGTGATACGCGTGAGGCGTACGTGCCGCGGCAGAACCTGTTTCGC
GACCGCGAGGGAGAGGAGCCCGAGGAGATGCGGGATCGAAAGTTCCACGCAGGGCGCGAGCTGCGGCATGGCCTGA
ATCGCGAGCGGTTGCTGCGCGAGGAGGACTTTGAGCCCGACGCGGCGAACCGGGATTAGTCCCGCGCGCACACGT
GGCGGCCGCCGACCTGGTAACCGCATACGAGCAGACGGTGAACCAGGAGATTAACTTTCAAAAAAGCTTTAACAAC
CACGTGCGTACGCTTGTGGCGCGCGAGGAGGTGGCTATAGGACTGATGCATCTGTGGGACTTTGTAAGCGCGCTGG
AGCAAAACCCAAATAGCAAGCCGCTCATGGCGCAGCTGTTCCTTATAGTGCAGCACAGCAGGGACAACGAGGCATT
CAGGGATGCGCTGCTAAACATAGTAGAGCCCGAGGGCCGCTGGCTGCTCGATTTGATAAACATCCTGCAGAGCATA
GTGGTGCAGGAGCGCAGCTTGAGCCTGGCTGACAAGGTGGCCGCCATCAACTATTCCATGCTTAGCCTGGGCAAGT
TTTACGCCCGCAAGATATACCATACCCCTTACGTTCCCATAGACAAGGAGGTAAAGATCGAGGGGTTCTACATGCG
CATGGCGCTGAAGGTGCTTACCTTGAGCGACGACCTGGGCGTTTATCGCAACGAGCGCATCCACAAGGCCGTGAGC
GTGAGCCGGCGGCGCGAGCTCAGCGACCGCGAGCTGATGCACAGCCTGCAAAGGGCCCTGGCTGGCACGGGCAGCG
```

FIGURE 14 (cont.)

```
GCGATAGAGAGGCCGAGTCCTACTTTGACGCGGGCGCTGACCTGCGCTGGGCCCCAAGCCGACGCGCCCTGGAGGC
AGCTGGGGCCGGACCTGGGCTGGCGGTGGCACCCGCGCGCGCTGGCAACGTCGGCGGCGTGGAGGAATATGACGAG
GACGATGAGTACGAGCCAGAGGACGGCGAGTACTAAGCGGTGATGTTTCTGATCAGATGATGCAAGACGCAACGGA
CCCGGCGGTGCGGGCGGCGCTGCAGAGCCAGCCGTCCGGCCTTAACTCCACGGACGACTGGCGCCAGGTCATGGAC
CGCATCATGTCGCTGACTGCGCGCAATCCTGACGCGTTCCGGCAGCAGCCGCAGGCCAACCGGCTCTCCGCAATTC
TGGAAGCGGTGGTCCCGGCGCGCGCAAACCCCACGCACGAGAAGGTGCTGGCGATCGTAAACGCGCTGGCCGAAAA
CAGGGCCATCCGGCCCGACGAAGCCGGCCTGGTCTACGACGCGCTGCTTCAGCGCGTGGCTCGTTACAACAGCGGC
AACGTGCAGACCAACCTGGACCGGCTGGTGGGGGATGTGCGCGAGGCCGTGGCGCAGCGTGAGCGCGCGCAGCAGC
AGGGCAACCTGGGCTCCATGGTTGCACTAAACGCCTTCCTGAGTACACAGCCCGCCAACGTGCCGCGGGACAGGA
GGACTACACCAACTTTGTGAGCGCACTGCGGCTAATGGTGACTGAGACACCGCAAAGTGAGGTGTACCAGTCTGGG
CCAGACTATTTTTTCCAGACCAGTAGACAAGGCCTGCAGACCGTAAACCTGAGCCAGGCTTTCAAAAACTTGCAGG
GGCTGTGGGGGGTGCGGGCTCCCACAGGCGACCGCGCGACCGTGTCTAGCTTGCTGACGCCCAACTCGCGCCTGTT
GCTGCTGCTAATAGCGCCCTTCACGGACAGTGGCAGCGTGTCCCGGGACACATACCTAGGTCACTTGCTGACACTG
TACCGCGAGGCCATAGGTCAGGCGCATGTGGACGAGCATACTTTCCAGGAGATTACAAGTGTCAGCCGCGCGCTGG
GGCAGGAGGACACGGGCAGCCTGGAGGCAACCCTAAACTACCTGCTGACCAACCGGCGGCAGAAGATCCCCTCGTT
GCACAGTTTAAACAGCGAGGAGGAGCGCATTTTGCGCTACGTGCAGCAGAGCGTGAGCCTTAACCTGATGCGCGAC
GGGGTAACGCCCAGCGTGGCGCTGGACATGACCGCGCGCAACATGGAACCGGGCATGTATGCCCTCAAACCGGCCGT
TTATCAACCGCCTAATGGACTACTTGCATCGCGCGGCCGCCGTGAACCCCGAGTATTTCACCAATGCCATCTTGAA
CCCGCACTGGCTACCGCCCCTGGTTTCTACACCGGGGATTCGAGGTGCCCGAGGGTAACGATGGATTCCTCTGG
GACGACATAGACGACAGCGTGTTTTCCCCGCAACCGCAGACCCTGCTAGAGTTGCAACAGCGCGAGCAGGCAGAGG
CGGCGCTGCGAAAGGAAAGCTTCCGCAGGCCAAGCAGCTTGTCCGATCTAGGCGCTGCGGCCCCGCGGTCAGATGC
TAGTAGCCCATTTCCAAGCTTGATAGGGTCTCTTACCAGCACTCGCACCACCCGCCCGCGCCTGCTGGGCGAGGAG
GAGTACCTAAACAACTCGCTGCTGCAGCCGCAGCGCGAAAAAAACCTGCCTCCGGCATTTCCCAACAACGGGATAG
AGAGCCTAGTGGACAAGATGAGTAGATGGAAGACGTACGCGCAGGAGCACAGGGACGTGCCAGGCCCGCGCCCGCC
CACCCGTCGTCAAAGGCACGACCGTCAGCGGGGTCTGGTGTGGGAGGACGATGACTCGGCAGACGACAGCAGCGTC
CTGGATTTGGGAGGGAGTGGCAACCCGTTTGCGCACCTTCGCCCCAGGCTGGGGAGAATGTTTTAAAAAAAAAAA
GCATGATGCAAAATAAAAAACTCACCAAGGCCATGGCACCGAGCGTTGGTTTTCTTGTATTCCCCTTAGTATGCGG
CGCGCGGCGATGTATGAGGAAGGTCCTCCTCCCTCCTACGAGAGTGTGGTGAGCGCGGCGCCAGTGGCGGCGGCGC
TGGGTTCTCCCTTCGATGCTCCCCTGGACCCGCCGTTTGTGCCTCCGCGGTACCTGCGGCCTACCGGGGGAGAAA
CAGCATCCGTTACTCTGAGTTGGCACCCCTATTCGACACCACCCGTGTGTACCTGGTGGACAACAAGTCAACGGAT
GTGGCATCCCTGAACTACCAGAACGACCACAGCAACTTTCTGACCACGGTCATTCAAAACAATGACTACAGCCCGG
GGGAGGCAAGCACACAGACCATCAATCTTGACGACCGGTCGCACTGGGGCGGCGACCTGAAAACCATCCTGCATAC
CAACATGCCAAATGTGAACGAGTTCATGTTTACCAATAAGTTTAAGGCGCGGGTGATGGTGTCGCGCTTGCCTACT
AAGGACAATCAGGTGGAGCTGAAATACGAGTGGGTGGAGTTCACGCTGCCCGAGGGCAACTACTCCGAGACCATGA
CCATAGACCTTATGAACAACGCGATCGTGGAGCACTACTTGGAAGTGGGCAGACAGAACGGGGTTCTGGAAAGCGA
CATCGGGGTAAAGTTTGACACCCGCAACTTCAGACTGGGGTTTGACCCCGTCACTGGTCTTGTCATGCCTGGGGTA
TATACAAACGAAGCCTTCCATCCAGACATCATTTTGCTGCCAGGATGCGGGGTGGACTTCACCCACAGCCGCCTGA
GCAACTTGTTGGGCATCCGCAAGCGGCAACCCTTCCAGGAGGGCTTTAGGATCACCTACGATGATCTGGAGGGTGG
TAACATTCCCGCACTGTTGGATGTGGACGCCTACCAGGCGAGCTTGAAAGATGACACCGAACAGGGCGGGGGTGGC
GCAGGCGGCAGCAACAGCAGTGGCAGCGGCGCGGAAGAGAACTCCAACGCGGCAGCCGCGGCAATGCAGCCGGTGG
AGGACATGAACGATCATGCCATTCGCGGCGACACCTTTGCCACACGGGCTGAGGAGAAGCGCGCTGAGGCGAAGC
AGCGGCCGAAGCTGCCGCCCCCGCTGCGCAACCCGAGGTCGAGAAGCCTCAGAAGAAACCGGTGATCAAACCCCTG
ACAGAGGACAGCAAGAAACGCAGTTACAACCTAATAAGCAATGACAGCACCTTCACCCAGTACCGCAGCTGGTACC
TTGCATACAACTACGGCGACCCTCAGACCGGAATCCGCTCATGGACCCTGCTTTGCACTCCTGACGTAACCTGCGG
CTCGGAGCAGGTCTACTGGTCGTTGCCAGACATGATGCAAGACCCCGTGACCTTCCGCTCCACGCGCCAGATCAGC
AACTTTCCGGTGGTGGGCGCCGAGCTGTTGCCCGTGCACTCCAAGAGCTTCTACAACGACCAGGCCGTCTACTCCC
AACTCATCCGCCAGTTTACCTCTCTGACCCACGTGTTCAATCGCTTTCCGGAGAACCAGATTTTGGCGCGCCCGCC
AGCCCCCACCATCACCACCGTCAGTGAAAACGTTCCTGCTCTCACAGATCACGGGACGCTACCGCTGCGCAACAGC
ATCGGAGGAGTCCAGCGAGTGACCATTACTGACGCCAGACGCCGCACCTGCCCCTACGTTTACAAGGCCCTGGGCA
TAGTCTCGCCGCGCGTCCTATCGAGCCGCACTTTTTGAGCAAGCATGTCCATCCTTATATCGCCCAGCAATAACAC
AGGCTGGGGCCTGCGCTTCCCAAGCAAGATGTTTGGCGGGGCCAAGAAGCGCTCCGACCAACACCCAGTGCGCGTG
CGCGGGCACTACCGCGCGCCTGGGGCGCGCACAAACGCGGCCGCACTGGGCGCACCACCGTCGATGACGCCATCG
ACGCGGTGGTGGAGGAGGCGCGCAACTACACGCCCACGCCGCCACCAGTGTCCACAGTGGACGCGGCCATTCAGAC
CGTGGTGCGCGGAGCCCGGCGCTATGCTAAAATGAAGAGACGGCGGAGGCGCGTAGCACGTCGCCACCGCCGCCGA
CCCGGCACTGCCGCCCAACGCGCGGCGGCGGCCCTGCTTAACCGCGCACGTCGCACCGGCCGACGGGCGGCCATGC
GGGCCGCTCGAAGGCTGGCCGCGGGTATTGTCACTGTGCCCCCAGGTCCAGGCGACGAGCGGCCGCCGCAGCAGC
CGCGGCCATTAGTGCTATGACTCAGGGTCGCAGGGGCAACGTGTATTGGGTGCGCGACTCGGTTAGCGGCCTGCGC
GTGCCCGTGCGCACCCGCCCCCCGCGCAACTAGATTGCAAGAAAAACTACTTAGACTCGTACTGTTGTATGTATC
CAGCGGCGGCGGCGCAACGAAGCTATGTCCAAGCGCAAATCAAAGAAGAGATGCTCCAGGTCATCGCGCCGGA
GATCTATGGCCCCCCGAAGAAGGAAGAGCAGGATTACAAGCCCCGAAAGCTAAAGCGGGTCAAAAAGAAAAGAAA
GATGATGATGATGAACTTGACGACGAGGTGGAACTGCTGCACGCTACCGCGCCCAGGCGACGGGTACAGTGGAAAG
```

FIGURE 14 (cont.)

```
GTCGACGCGTAAAACGTGTTTTGCGACCCGGCACCACCGTAGTCTTTACGCCCGGTGAGCGCTCCACCCGCACCTA
CAAGCGCGTGTATGATGAGGTGTACGGCGACGAGGACCTGCTTGAGCAGGCCAACGAGCGCCTCGGGGAGTTTGCC
TACGGAAAGCGGCATAAGGACATGCTGGCGTTGCCGCTGGACGAGGGCAACCCAACACCTAGCCTAAAGCCCGTAA
CACTGCAGCAGGTGCTGCCCGCGCTTGCACCGTCCGAAGAAAAGCGCGGCCTAAAGCGCGAGTCTGGTGACTTGGC
ACCCACCGTGCAGCTGATGGTACCCAAGCGCCAGCGACTGGAAGATGTCTTGGAAAAAATGACCGTGGAACCTGGG
CTGGAGCCCGAGGTCCGCGTGCGGCCAATCAAGCAGGTGGCGCCGGGACTGGGCGTGCAGACCGTGGACGTTCAGA
TACCCACTACCAGTAGCACCAGTATTGCCACCGCCACAGAGGGCATGGAGACACAAACGTCCCCGGTTGCCTCAGC
GGTGGCGGATGCCGCGGTGCAGGCGGTCGCTGCGGCCGCGTCCAAGACCTCTACGGAGGTGCAAACGGACCCGTGG
ATGTTTCGCGTTTCAGCCCCCGGCGCCCGCGCGGTTCGAGGAAGTACGGCGCCGCCAGCGCGCTACTGCCCGAAT
ATGCCCTACATCCTTCCATTGCGCCTACCCCGGCTATCGTGGCTACACCTACCGCCCAGAAGACGAGCAACTAC
CCGACGCCGAACCACCACTGGAACCCGCCGCCGCCGTCGCCGTCGCCAGCCCGTGCTGGCCCCGATTTCCGTGCGC
AGGGTGGCTCGCGAAGGAGGCAGGACCCTGGTGCTGCCAACAGCGCGCTACCACCCCAGCATCGTTTAAAAGCCGG
TCTTTGTGGTTCTTGCAGATATGGCCCTCACCTGCCGCCTCCGTTTCCCGGTGCCGGGATTCCGAGGAAGAATGCA
CCGTAGGAGGGCATGGCCGGCTACGGCCTGACGGGCGGCATGCGTCGTGCGCACCACCGGCGGCGGCGCGCGTCG
CACCGTCGCATGCGCGGCGGTATCCTGCCCCTCCTTATTCCACTGATCGCCGCGGCGATTGGCGCCGTGCCCGGAA
TTGCATCCGTGGCCTTGCAGGCGCAGAGACACTGATTAAAAACAAGTTGCATGTGGAAAAATCAAATAAAAAGTC
TGGACTCTCACGCTCGCTTGGTCCTGTAACTATTTTGTAGAATGGAAGACATCAACTTTGCGTCTCTGGCCCCGCG
ACACGGCTACGCCCGTTCATGGGAAACTGGCAAGATATCGGCACCAGCAATATGAGCGGTGGCGCCTTCAGCTGG
GGCTCGCTGTGGAGCGGCATTAAAAATTTCGGTTCCACCGTTAAGAACTATGGCAGCAAGGCCTGGAACAGCAGCA
CAGGCCAGATGCTGAGGGATAAGTTGAAAGAGCAAAATTTCCAACAAAAGGTGGTAGATGGCCTGGCCTCTGGCAT
TAGCGGGGTGGTGGACCTGGCCAACCAGGCAGTGCAAAATAAGATTAACAGTAAGCTTGATCCCCGCCCTCCCGTA
GAGGAGCCTCCACCGGCCGTGGAGACAGTGTCTCCAGAGGGGCGTGGCGAAAAGCGTCCGCGCCCCGACAGGGAAG
AAACTCTGGTGACGCAAATAGACGAGCCTCCCTCGTACGAGGAGGCACTAAAGCAAGGCCTGCCCACCACCCGTCC
CATCGCGCCCATGGCTACCGGAGTGCTGGGCCAGCACACACCCGTAACGCTGGACCTGCCTCCCCCGCCGACACC
CAGCAGAAACCTGTGCTGCCAGGCCCGACCGCCGTTGTTGTAACCCGTCCTAGCCGCGCGTCCCTGCGCCGCGCCG
CCAGCGGTCCGCGATCGTTGCGGCCCGTAGCCAGTGGCAACTGGCAAAGCACACTGAACAGCATCGTGGGTCTGGG
GGTGCAATCCCTGAAGCGCCGACGATGCTTCTGAATAGCTAACGTGTCGTATGTGTGTCATGTATGCGTCCATGTC
GCCGCCAGAGGAGCTGCTGAGCCGCCGCGCGCCCGCTTTCCAAGATGGCTACCCCTTCGATGATGCCGCAGTGGTC
TTACATGCACATCTCGGGCCAGGACGCCTCGGAGTACCTGAGCCCCGGGCTGGTGCAGTTTGCCCGCGCCACCGAG
ACGTACTTCAGCCTGAATAACAAGTTTAGAAACCCCACGGTGGCGCCTACGCACGACGTGACCACAGACCGGTCCC
AGCGTTTGACGCTGCGGTTCATCCCTGTGGACCGTGAGGATACTGCGTACTCGTACAAGGCGCGGTTCACCCTAGC
TGTGGGTGATAACCGTGTGCTGGACATGGCTTCCACGTACTTTGACATCCGCGGCGTGCTGGACAGGGGCCCTACT
TTTAAGCCCTACTCTGGCACTGCCTACAACGCCCTGGCTCCCAAGGGTGCCCCAAATCCTTGCGAATGGGATGAAG
CTGCTACTGCTCTTGAAATAAACCTAGAAGAAGAGGACGATGACAACGAAGACGAAGTAGACGAGCAAGCTGAGCA
GCAAAAAACTCACGTATTTGGGCAGGCGCCTTATTCTGGTATAAATATTACAAAGGAGGGTATTCAAATAGGTGTC
GAAGGTCAAACACCTAAATATGCCGATAAAACATTTCAACCTGAACCTCAAATAGGAGAATCTCAGTGGTACGAAA
CTGAAATTAATCATGCAGCTGGGAGTCCTTAAAAAGACTACCCCAATGAAACCATGTTACGGTTCATATGCAAA
ACCCACAAATGAAAATGGAGGGCAAGGCATTCTTGTAAAGCAACAAAATGGAAAGCTAGAAAGTCAAGTGGAAATG
CAATTTTTCTCAACTACTGAGGCGACCGCAGGCAATGGTGATAACTTGACTCCTAAAGTGGTATTGTACAGTGAAG
ATGTAGATATAGAAACCCCAGACACTCATATTTCTTACATGCCCACTATTAAGGAAGGTAACTCACGAGAACTAAT
GGGCCAACAATCTATGCCCAACAGGCCTAATTACATTGCTTTTAGGGACAATTTTATTGGTCTAATGTATTACAAC
AGCACGGGTAATATGGGTGTTCTGGCGGGCCAAGCATCGCAGTTGAATGCTGTTGTAGATTTGCAAGACAGAAACA
CAGAGCTTTCATACCAGCTTTTGCTTGATTCCATTGGTGATAGAACCAGGTACTTTTCTATGTGGAATCAGGCTGT
TGACAGCTATGATCCAGATGTTAGAATTATTGAAAATCATGGAACTGAAGATGAACTTCCAAATTACTGCTTTCCA
CTGGGAGGTGTGATTAATACAGAGACTCTTACCAAGGTAAAACCTAAAACAGGTCAGGAAAATGGATGGGAAAAAG
ATGCTACAGAATTTTCAGATAAAAATGAAATAAGAGTTGGAAATAATTTTGCCATGGAAATCAATCTAAATGCCAA
CCTGTGGAGAAATTTCCTGTACTCCAACATAGCGCTGTATTTGCCCGACAAGCTAAAGTACAGTCCTTCCAACGTA
AAAATTTCTGATAACCCAAACACCTACGACTACATGAACAAGCGAGTGGTGGCTCCGGGTTAGTGGACTGCTACA
TTAACCTTGGAGCACGCTGGTCCCTTGACTATATGGACAACGTCAACCCATTTAACCACCACCGCAATGCTGGCCT
GCGCTACCGCTCAATGTTGCTGGGCAATGGTCGCTATGTGCCCTTCCACATCCAGGTGCCTCAGAAGTTCTTTGCC
ATTAAAAACCTCCTTCTCCTGCCGGGCTCATACACCTACGAGTGGAACTTCAGGAAGGATGTTAACATGGTTCTGC
AGAGCTCCCTAGGAAATGACCTAAGGGTTGACGGAGCCAGCATTAAGTTTGATAGCATTTGCCTTTACGCCACCTT
CTTCCCCATGGCCCACAACACCGCCTCCACGCTTGAGGCCATGCTTAGAAACGACACCAACGACCAGTCCTTTAAC
GACTATCTCTCCGCCGCCAACATGCTCTACCCTATACCCGCCAACGCTACCAACGTGCCCATATCCATCCCCTCCC
GCAACTGGGCGGCTTTCCGCGGCTGGGCCTTCACGCGCCTTAAGCATAAGGAAACCCCATCACTGGGCTCGGGCTA
CGACCCTTATTACACCTACTCTGGCTCTATACCCTACCTAGATGGAACCTTTTACCTCAACCACACCCTTTAAGAAG
GTGGCCATTACCTTTGACTCTTCTGTCAGCTGGCCTGGCAATGACCGCCTGCTTACCCCCAACGAGTTTGAAATTA
AGCGCTCAGTTGACGGGGAGGGTTACAACGTTGCCCAGTGTAACATGACCAAAGACTGGTTCCTGGTACAAATGCT
AGCTAACTACAACATTGGCTACCAGGGCTTCTATATCCCAGAGAGCTACAAGGACCGCATGTACTCCTTCTTTAGA
AACTTCCAGCCCATGAGCCGTCAGGTGGTGGATGATACTAAATACAAGGACTACCAACAGGTGGGCATCCTACACC
AACACAACAACTCTGGATTTGTTGGCTACCTTGCCCCCACCATGCGCGAAGGACAGGCCTACCCTGCTAACTTCCC
```

FIGURE 14 (cont.)

```
CTATCCGCTTATAGGCAAGACCGCAGTTGACAGCATTACCCAGAAAAAGTTTCTTTGCGATCGCACCCTTTGGCGC
ATCCCATTCTCCAGTAACTTTATGTCCATGGGCGCACTCACAGACCTGGGCCAAAACCTTCTCTACGCCAACTCCG
CCCACGCGCTAGACATGACTTTTGAGGTGGATCCCATGGACGAGCCCACCCTTCTTTATGTTTTGTTTGAAGTCTT
TGACGTGGTCCGTGTGCACCGGCCGCACCGCGGCGTCATCGAAACCGTGTACCTGCGCACGCCCTTCTCGGCCGGC
AACGCCACAACATAAAGAAGCAAGCAACATCAACAACAGCTGCCGCCATGGGCTCCAGTGAGCAGGAACTGAAAGC
CATTGTCAAAGATCTTGGTTGTGGGCCATATTTTTTGGGCACCTATGACAAGCGCTTTCCAGGCTTTGTTTCTCCA
CACAAGCTCGCCTGCGCCATAGTCAATACGGCCGGTCGCGAGACTGGGGGCGTACACTGGATGGCCTTTGCCTGGA
ACCCGCACTCAAAAACATGCTACCTCTTTGAGCCCTTTGGCTTTTCTGACCAGCGACTCAAGCAGGTTTACCAGTT
TGAGTACGAGTCACTCCTGCGCCGTAGCGCCATTGCTTCTTCCCCCGACCGCTGTATAACGCTGGAAAAGTCCACC
CAAAGCGTACAGGGGCCCAACTCGGCCGCCTGTGGACTATTCTGCTGCATGTTTCTCCACGCCTTTGCCAACTGGC
CCCAAACTCCCATGGATCACAACCCCACCATGAACCTTATTACCGGGGTACCCAACTCCATGCTCAACAGTCCCCA
GGTACAGCCCACCCTGCGTCGCAACCAGGAACAGCTCTACAGCTTCCTGGAGCGCCACTCGCCCTACTTCCGCAGC
CACAGTGCGCAGATTAGGAGCGCCACTTCTTTTTGTCACTTGAAAAACATGTAAAAATAATGTACTAGAGACACTT
TCAATAAAGGCAAATGCTTTTATTTGTACACTCTCGGGTGATTATTTACCCCCACCCTTGCCGTCTGCGCCGTTTA
AAAATCAAAGGGGTTCTGCCGCGCATCGCTATGCGCCACTGGCAGGGACACGTTGCGATACTGGTGTTTAGTGCTC
CACTTAAACTCAGGCACAACCATCCGCGGCAGCTCGGTGAAGTTTTCACTCCACAGGCTGCGCACCATCACCAACG
CGTTAGCAGGTCGGGCGCCGATATCTTGAAGTCGCAGTTGGGGCCTCCGCCCTGCGCGCGCGAGTTGCGATACAC
AGGGTTGCAGCACTGGAACACTATCAGCGCGGGTGGTGCACGCTGGCCAGCACGCTCTTGTCGGAGATCAGATCC
GCGTCCAGGTCCTCCGCGTTGCTCAGGGCGAACGGAGTCAACTTTGGTAGCTGCCTTCCCAAAAAGGGCGCGTGCC
CAGGCTTTGAGTTGCACTCGCACCGTAGTGGCATCAAAAGGTGACCGTGCCCGGTCTGGGCGTTAGGATACAGCGC
CTGCATAAAAGCCTTGATCTGCTTAAAAGCCACCTGAGCCTTTGCGCCTTCAGAGAAGAACATGCCGCAAGACTTG
CCGGAAAACTGATTGGCCGGACAGGCCGCGTCGTGCACGCAGCACCTTGCGTCGGTGTTGGAGATCTGCACCACAT
TTCGGCCCCACCGGTTCTTCACGATCTTGGCCTTGCTAGACTGCTCCTTCAGCGCGCGCTGCCCGTTTTCGCTCGT
CACATCCATTTCAATCACGTGCTCCTTATTTATCATAATGCTTCCGTGTAGACACTTAAGCTCGCCTTCGATCTCA
GCGCAGCGGTGCAGCCACAACGCGCAGCCCGTGGGCTCGTGATGCTTGTAGGTCACCTCTGCAAACGACTGCAGGT
ACGCCTGCAGGAATCGCCCCATCATCGTCACAAAGGTCTTGTTGCTGGTGAAGGTCAGCTGCAACCCGCGGTGCTC
CTCGTTCAGCCAGGTCTTGCATACGGCCGCCAGAGCTTCCACTTGGTCAGGCAGTAGTTTGAAGTTCGCCTTTAGA
TCGTTATCCACGTGGTACTTGTCCATCAGCGCGCGCGCAGCCTCCATGCCCTTCTCCCACGCAGACACGATCGGCA
CACTCAGCGGGTTCATCACCGTAATTTCACTTTCCGCTTCGCTGGGCTCTTCCTCTTCCTCTTGCGTCCGCATACC
ACGCGCCACTGGGTCGTCTTCATTCAGCCGCCGCACTGTGCGCTTACCTCCTTTGCCATGCTTGATTAGCACCGGT
GGGTTGCTGAAACCCACCATTTGTAGCGCCACATCTTCTCTTTCTTCCTCGCTGTCCACGATTACCTCTGGTGATG
GCGGGCGCTCGGGCTTGGGAGAAGGGCGCTTCTTTTTCTTCTTGGGCGCAATGGCCAAATCCGCCGCCGAGGTCGA
TGGCCGCGGGCTGGGTGTGCGCGGCACCAGCGCGTCTTGTGATGAGTCTTCCTCGTCCTCGGACTCGATACGCCGC
CTCATCCGCTTTTTTGGGGGCGCCCGGGGAGGCGGCGGCGACGGGGACGGGGACGACACGTCCTCCATGGTTGGGG
GACGTCGCGCCGCACCGCGTCCGCGCTCGGGGGTGGTTTCGCGCTGCTCCTCTTCCCGACTGGCCATTTCCTTCTC
CTATAGGCAGAAAAAGATCATGGAGTCAGTCGAGAAGAAGGACAGCCTAACCGCCCCCTCTGAGTTCGCCACCACC
GCCTCCACCGATGCCGCCAACGCGCCTACCACCTTCCCCGTCGAGGCACGCCCGCTTGAGGAGGAGGAAGTGATTA
TCGAGCAGGACCCAGGTTTTGTAAGCGAAGACGACGAGGACGCCTCAGTACCAACAGAGGATAAAAAGCAAGACCA
GGACAACGCAGAGGCAAACGAGGAACAAGTCGGGCGGGGGACGAAAGGCATGGCGACTACCTAGATGTGGGAGAC
GACGTGCTGTTGAAGCATCTGCAGCGCCAGTGCGCCATTATCTGCGACGCGTTGCAAGAGCGCAGCGATGTGCCCC
TCGCCATAGCGGATGTCAGCCTTGCCTACGAACGCCACCTATTCTCACCGCGCGTACCCCCAAACGCCAAGAAAA
CGGCACATGCGAGCCCAACCCGCGCCTCAACTTCTACCCCGTATTTGCCGTGCCAGAGGTGCTTGCCACCTATCAC
ATCTTTTTCCAAAACTGCAAGATACCCCTATCCTGCCGTGCCAACCGCAGCCGAGCGGACAAGCAGCTGGCCTTGC
GGCAGGGCGCTGTCATACCTGATATCGCCTCGCTCAACGAAGTGCCAAAAATCTTTGAGGGTCTTGGACGCGACGA
GAAGCGCGCGGCAAACGCTCTGCAACAGGAAAACAGCGAAAATGAAAGTCACTCTGGAGTGTTGGTGGAACTCGAG
GGTGACAACGCGCGCCTAGCCGTACTAAAACGCAGCATCGAGGTCACCCACTTTGCCTACCCGGCACTTAACCTAC
CCCCCAAGGTCATGAGCACAGTCATGAGTGAGCTGATCGTGCGCCGTGCGCAGCCCCTGGAGAGGGATGCAAATTT
GCAAGAACAAACAGAGGAGGGCCTACCCGCAGTTGGCGACGAGCAGCTAGCGCGCTGGCTTCAAACGCGCGAGCCT
GCCGACTTGGAGGAGCGACGCAAACTAATGATGGCCGCAGTGCTCGTTACCGTGGAGCTTGAGTGCATGCAGCGGT
TCTTTGCTGACCCGGAGATGCAGCGCAAGCTAGAGGAAACATTGCACTACACCTTCCGACAGGGCTACGTACGCCA
GGCCTGCAAGATCTCCAACGTGGAGCTCTGCAACCTGGTCTCCTACCTTGGAATTTTGCACGAAAACCGCCTTGGG
CAAAACGTGCTTCATTCCACGCTCAAGGGCGAGGCGCGCCGCGACTACGTCCGCGACTGCGTTTACTTATTTCTAT
GCTACACCTGGCAGACGGCCATGGGCGTTTGGCAGCAGTGCTTGGAGGAGTGCAACCTCAAGGAGCTGCAGAAACT
GCTAAAGCAAAACTTGAAGGACCTATGGACGGCCTTCAACGAGCGCTCCGTGGCCGCGCACCTGGCGGACATCATT
TTCCCCGAACGCCTGCTTAAAACCCTGCAACAGGGTCTGCCAGACTTCACCAGTCAAAGCATGTTGCAGAACTTTA
GGAACTTTATCCTAGAGCGCTCAGGAATCTTGCCCGCCACCTGCTGTGCACTTCCTAGCGACTTTGTGCCCATTAA
GTACCGCGAATGCCCTCCGCCGCTTTGGGGCCACTGCTACCTTCTGCAGCTAGCCAACTACCTTGCCTACCACTCT
GACATAATGGAAGACGTGAGCGGTGACGGTCTACTGGAGTGTCACTGTCGCTGCAACCTATGCACCCGCACCGCT
CCCTGGTTTGCAATTCGCAGCTGCTTAACGAAAGTCAAATTATCGGTACCTTTGAGCTGCAGGGTCCCTCGCCTGA
CGAAAAGTCCGCGGCTCCGGGGTTGAAACTCACTCCGGGGCTGTGGACGTCGGCTTACCTTCGCAAATTTGTACCT
GAGGACTACCACGCCCACGAGATTAGGTTCTACGAAGACCAATCCCGCCCGCCAAATGCGGAGCTTACCGCCTGCG
```

FIGURE 14 (cont.)

```
TCATTACCCAGGGCCACATTCTTGGCCAATTGCAAGCCATCAACAAAGCCCGCCAAGAGTTTCTGCTACGAAAGGG
ACGGGGGTTTACTTGGACCCCCAGTCCGGCGAGGAGCTCAACCCAATCCCCCCGCCGCCGCAGCCCTATCAGCAG
CAGCCGCGGGCCCTTGCTTCCCAGGATGGCACCCAAAAAGAAGCTGCAGCTGCCGCCGCCACCCACGGACGAGGAG
GAATACTGGGACAGTCAGGCAGAGGAGGTTTTGGACGAGGAGGAGGAGGACATGATGGAAGACTGGGAGAGCCTAG
ACGAGGAAGCTTCCGAGGTCGAAGAGGTGTCAGACGAAACACCGTCACCCTCGGTCGCATTCCCCTCGCCGGCGCC
CCAGAAATCGGCAACCGGTTCCAGCATGGCTACAACCTCCGCTCCTCAGGCGCCGCCGGCACTGCCCGTTCGCCGA
CCCAACCGTAGATGGGACACCACTGGAACCAGGGCCGGTAAGTCCAAGCAGCCGCCGCCGTTAGCCCAAGAGCAAC
AACAGCGCCAAGGCTACCGCTCATGGCGCGGGCACAAGAACGCCATAGTTGCTTGCTTGCAAGACTGTGGGGGCAA
CATCTCCTTCGCCCGCCGCTTTCTTCTCTACCATCACGGCGTGGCCTTCCCCCGTAACATCCTGCATTACTACCGT
CATCTCTACAGCCCATACTGCACCGGCGGCAGCGGCAGCGGCAGCAACAGCAGCGGCCACACAGAAGCAAAGGCGA
CCGGATAGCAAGACTCTGACAAAGCCCAAGAAATCCACAGCGGCGGCAGCAGCAGGAGGAGGAGCGCTGCGTCTGG
CGCCCAACGAACCCGTATCGACCCGCGAGCTTAGAAACAGGATTTTTCCCACTCTGTATGCTATATTTCAACAGAG
CAGGGGCCAAGAACAAGAGCTGAAAATAAAAAACAGGTCTCTGCGATCCCTCACCCGCAGCTGCCTGTATCACAAA
AGCGAAGATCAGCTTCGGCGCACGCTGGAAGACGCGGAGGCTCTCTTCAGTAAATACTGCGCGCTGACTCTTAAGG
ACTAGTTTCGCGCCCTTTCTCAAATTTAAGCGCGAAAACTACGTCATCTCCAGCGGCCACACCCGGCGCCAGCACC
TGTCGTCAGCGCCATTATGAGCAAGGAAATTCCCACGCCCTACATGTGGAGTTACCAGCCACAAATGGGACTTGCG
GCTGGAGCTGCCCAAGACTACTCAACCCGAATAAACTACATGAGCGCGGGACCCCACATGATATCCCGGGTCAACG
GAATCCGCGCCCACCGAAACCGAATTCTCTTGGAACAGGCGGCTATTACCACCACACCTCGTAATAACCTTAATCC
CCGTAGTTGGCCCGCTGCCCTGGTGTACCAGGAAAGTCCGCTCCCACCACTGTGGTACTTCCCAGAGACGCCCAG
GCCGAAGTTCAGATGACTAACTCAGGGGCGCAGCTTGCGGGCGGCTTTCGTCACAGGGTGCGGTCGCCCGGGCAGG
GTATAACTCACCTGACAATCAGAGGGCGAGGTATTCAGCTCAACGACGAGTCGGTGAGCTCCTCGCTTGGTCTCCG
TCCGGACGGGACATTTCAGATCGGCGGCGCCGGCCGTCCTTCATTCACGCCTCGTCAGGCAATCCTAACTCTGCAG
ACCTCGTCCTCTGAGCCGCGCTCTGGAGGCATTGGAACTCTGCAATTTATTGAGGAGTTTGTGCCATCGGTCTACT
TTAACCCCTTCTCGGGACCTCCCGGCCACTATCCGGATCAATTTATTCCTAACTTTGACGCGGTAAAGGACTCGGC
GGACGGCTACGACTGAATGTTAAGTGGAGAGGCAGAGCAACTGCGCCTGAAACACCTGGTCCACTGTCGCCGCCAC
AAGTGCTTTGCCCGCGACTCCGGTGAGTTTTGCTACTTTGAATTGCCCGAGGATCATATCGAGGGCCCGGCGCACG
GCGTCCGGCTTACCGCCCAGGGAGAGCTTGCCCGTAGCCTGATTCGGGAGTTTACCCAGCGCCCCTGCTAGTTGA
GCGGGACAGGGGACCCTGTGTTCTCACTGTGATTTGCAACTGTCCTAACCTTGGATTACATCAAGATCCTCTAGTT
AATTAACAGCTTGCATGCCTGCAGGTCGACGGATCGGGAGATCTCGGCCGCATATTAAGTGCATTGTTCTCGATAC
CGCTAAGTGCATTGTTCTCGTTAGCTCGATGGACAAGTGCATTGTTCTCTTGCTGAAAGCTCGATGGACAAGTGCA
TTGTTCTCTTGCTGAAAGCTCGATGGACAAGTGCATTGTTCTCTTGCTGAAAGCTCAGTACCCGGGAGTACCCTCG
ACCGCCGGAGTATAAATAGAGGCGCTTCGTCTACGGAGCGACAATTCAATTCAAACAAGCAAAGTGAACACGTCGC
TAAGCGAAAGCTAAGCAAATAAACAAGCGCAGCTGAACAAGCTAAACAATCTGCAGTAAAGTGCAAGTTAAAGTGA
ATCAATTAAAAGTAACCAGCAACCAAGTAAATCAACTGCAACTACTGAAATCTGCCAAGAAGTAATTATTGAATAC
AAGAAGAGAACTCTGAATACTTTCAACAAGTTACCGAGAAAGAAGAACTCACACACAGCTAGCGTTTAAACTTAAG
CTTCACCATGGTGGGGCCCTGCATGCTGCTGCTGCTGCTGCTGGGCCTGAGGCTACAGCTCTCCCTGGGCATC
ATCCTAGTTGAGGAGGAGAACCCGGACTTCTGGAACCGCGAGGCAGCCGAGGCCCTGGGTGCCGCCAAGAAGCTGC
AGCCTGCACAGACAGCCGCCAAGAACCTCATCATCTTCCTGGGCGATGGGGTGGGGGTGTCTACGGTGACAGCTGC
CAGGATCCTAAAAGGGCAGAAGAAGGACAAACTGGGGCCTGAGATACCCCTGGCCATGGACCGCTTCCCATATGTG
GCTCTGTCCAAGACATACAATGTAGACAAACATGTGCCAGACAGTGGAGCCACAGCCACGGCCTACCTGTGCGGGG
TCAAGGGCAACTTCCAGACCATTGGCTTGAGTGCAGCCGCCCGCTTTAACCAGTGCAACACGACACGCGGCAACGA
GGTCATCTCCGTGATGAATCGGGCCAAGAAAGCAGGGAAGTCAGTGGGAGTGGTAACCACCACACGAGTGCAGCAC
GCCTCGCCAGCCGGCACCTACGCCCACACGGTGAACCGCAACTGGTACTCGGACGCCGACGTGCCTGCCTCGGCCC
GCCAGGAGGGGTGCCAGGACATCGCTACGCAGCTCATCTCCAACATGGACATTGACGTGATCCTAGGTGGGGCCG
AAAGTACATGTTTCGCATGGGAACCCCAGACCCTGAGTACCCAGATGACTACAGCCAAGGTGGGACCAGGCTGGAC
GGGAAGAATCTGGTGCAGGAATGGCTGGCGAAGCACCAGGGTGCCCGGTACGTGTGGAACCGCACTGAGCTCATGC
GGGCTTCCCTGGACCCGTCTGTGGCCCATCTCATGGGTCTCTTTGAGCCTGGAGACATGAAATACGAGATCCACCG
AGACTCCACACTGGACCCCTCCCTGATGGAGATGACAGAGGCTGCCCTGCGCCTGCTGAGCAGGAACCCCCGCGGC
TTCTTCCTCTTCGTGGAGGGTGGTCGCATCGACCATGGTCATCATGAAAGCAGGGCTTACCGGGCACTGACTGAGA
CGATCATGTTCGACGACGCCATTGAGAGGGCGGGCCAGCTCACCAGCGAGGAGGACACGCTGAGCCTCGTCACTGC
CGACCACTCCCACGTCTTCTCCTTCGGAGGCTGCCCCCTGCGAGGGGCTCCATCTTCGGGCTGGCCCCTGGCAAG
GCCCGGGACAGGAAGGCCTACACGGTCCTCCTATACGGAAACGGTCCAGGCTATGTGCTCAAGGACGGCGCCCGGC
CGGATGTTACCGAGAGCGAGAGCGGGCCCCGAGTATCGCAGCAGTCAGCAGTGCCCCTGGACGAAGAGACCCA
CGCAGGCGAGGACGTGGCGGTGTTCGCGCGCGGCCCGCAGGCGCACCTGGTTCACGGCGTGCAGGAGCAGACCTTC
ATAGCGCACGTCATGGCCTTCGCCGCCTGCCTGGAGCCCTACACCGCCTGCGACCTGGCGCCCCCGCCGGCACCA
CCGACGCCGCGCACCCGGGGCGGTCCGTGGTCCCCGCGTTGCTTCCTCTGCTGGCCGGGACCCTGCTGCTGCTGGA
GACGGCCACTGCTCCCTGAGTGTCCCGTCCCTGGGGCTCCTGCTTCCCCATCCCGGAGTTCTCCTGCTCCCCGCCT
CCTGTCGTCCTGCCTGGCCTCCAGCCCGAGTCGTCATCCCCGGAGTCCCTATACAGAGGTCCTGCCATGGAACCTT
CCCCTCCCCGTGCGCTCTGGGGACTGAGCCCATGACACCCAAACCTGCCCCTTGGCTGCTCTCGGACTCCCTACCCC
AACCCCAGGGACAGATCTGGCCAGATTTGTAAAACAAATAGATTTTAGGCCCAAAGATTATTTAAAGCATTGCCTG
GAACGCAGTGAGTTTTTGTTAGAAAAGAGAATAATTCAAAGTGGCATTGCTTTGCTTCTTATGTTAATTTGGTACA
```

FIGURE 14 (cont.)

```
GACCTGTGGCTGAGTTTGCTCAAAGTATTCAGAGCAGAATTGTGGAGTGGAAAGAGAGATTGGACAAAGAGTTTAG
TTTGTCAGTGTATCAAAAAATGAAGTTTAATGTGGCTATGGGAATTGGAGTTTTAGATTGGCTAAGAAACAGTGAT
GATGATGATGAAGACAGCCAGGAAATGCTGATAAAAATGAAGATGGTGGGGAGAAGAACATGGAAGACTCAGGGC
ATGAAACAGGCATTGATTCACAGTCCCAAGGCTCATTTCAGGCCCCTCAGTCCTCACAGTCTGTTCATGATCATAA
TCAGCCATACCACATTTGTAGAGGTTTTACTTGCTTTAAAAAACCTCCCACACCTCCCCCTGAACCTGAAACATAA
AATGAATGCAATTGTTGTTGTTAACTTGTTTATTGCAGCTTATAATGGTTACAAATAAAGCAATAGCATCACAAAT
TTCACAAATAAAGCATTTTTTTCACTGCATTCTAGTTGTGGTTTGTCCAAACTCATCAATGTATCTTATCATGTCT
GGATCCCCAGGAAGCTCCTCTGTGTCCTCATAAACCCTAACCTCCTCTACTTGAGAGGACATTCCAATCATAGGCT
GCCCATCCACCCTCTGTGTCCTCCTGTTAATTAGGTCACTTAACAAAAAGGAAATTGGGTAGGGGTTTTTCACAGA
CCGCTTTCTAAGGGTAATTTTAAAATATCTGGGAAGTCCCTTCCACTGCTGTGTTCCAGAAGTGTTGGTAAACAGC
CCACAAATGTCAACAGCAGAAACATACAAGCTGTCAGCTTTGCACAAGGGCCCAACACCCTGCTCATCAAGAAGCA
CTGTGGTTGCTGTGTTAGTAATGTGCAAAACAGGAGGCACATTTTCCCCACCTGTGTAGGTTCCAAAATATCTAGT
GTTTTCATTTTTACTTGGATCAGGAACCCAGCACTCCACTGGATAAGCATTATCCTTATCCAAAACAGCCTTGTGG
TCAGTGTTCATCTGCTGACTGTCAACTGTAGCATTTTTGGGGTTACAGTTTGAGCAGGATATTTGGTCCTGTAGT
TTGCTAACACACCCTGCAGCTCCAAAGGTTCCCCACCAACAGCAAAAAAATGAAAATTTGACCCTTGAATGGGTTT
TCCAGCACCATTTTCATGAGTTTTTTGTGTCCCTGAATGCAAGTTTAACATAGCAGTTACCCCAATAACCTCAGTT
TTAACAGTAACAGCTTCCCACATCAAAATATTTCCACAGGTTAAGTCCTCATTTAAATTAGGCAAAGGAATTCCAC
TTCCCACTGCCTTGCTTCCGTCTCCCATTCAAACTTTTATCAACTGACATTATTCTAAGTAAAATCCTCTTCATTA
TGTTGTCAGCAATCCATTGCTTGAAGGCCTGGCTCCCCAGAACCCTCGACTGGTATGTCTTCTCCTAGAATACTC
CAGAAGAAAAGGAGTGTATGAAGATAGTGACTGCACATTAAAATGACTGAAACCATAGTAAATTAGGATGAGATTC
TGGGCAGATAAACAGACAGCTGGCTAGGATCATTTTTTTATGCCTTGGACTTCTTTGGCAATCTGTTGAAGCCTGA
CATTCCTCAGAATAATGTTTTAAAGCCCAACAATAAGACCCTGTAGCACATATAATAAGTACTGCAGTTTTGAAGT
AGTGATAAGCATAAATGATATTTTGATATATTTATTATAACTGTAATGAGATGTGTACATATCTGTGACTTCATAG
GTACTGATTGTACTACTGTGATTTTTTTGCCTACTTTCAAAATGAAAAGGAATGCTTAATTTCAGTTAGAGGTTAG
TAAAGACAAATAGGTAATTTTCTTCTCCAGTGAAGAGCATGGCGCCCCTTGCTATTCATGGACGCTTGCTTAAAGA
CTTGTACACAGGCTTGCTTTGTATCAACCTATGACTTCCCCTTACAGCCGATGATAGGTTTTTATTTGCACCTCCT
TCGTGTACAAAGACAGTTTTGGTGGCTACGCCATCATTAAACTCATTATTATCATGCTTAAGCCTATAGATGTATC
CAGTTCTTCTGTTACATAATTGAAGCTGTAGTGAATTGTCTATCTTAAACTGCATCGCTAACTGACTACATTTCAC
ACTTCATTTGCTTCCAACATAGACTAACCTTCTTGGATGTCCACTATTATTTGAACTTTTGAGATTTTTTTCCTA
TTTCTAATATCTTAAAATTTCAGAAGACTTAAAGTTTTGCAACTACAGGGCTCCATATAGACATCTAGCTTGAATT
TATACACTTTCTTTCATTGATGTCCCTGGACTAAAAATGTTAAATATTTCTAACCGCTGTACTTAAAGTCCATTA
CAAACGAAGACTACTGTTGTTAAGTTGAATAGGCATCTTATATATTTTCACCGGTGCAATAAATAACTTCTATTC
CCTTCTAACATCTGCTTGCGTTGCACTGAGAGTACACTATTGATTAGCAATAGGTTCGTGATTACAGCCCTTCTAT
AATTAATTGTTAGGTTAACATATTATTCATAAAATATTATTTATTAATTTTTACTTGATTTGCTACTGGATGCTT
AGAAATAGCTATGAGTATATTGGTAGAACCAGTACTTATATTTTATTACATTTTTACATTTCATAAAATTTAAGTG
ATATAAAAATCCTGAGGAAGTATGCCACAAAAGTGGTCTCAGTGGAAATTTAAATATGTTAACATTTATTTTAAA
ATGTAGCGTGAAATAGACAACTTTAAAAGCTCAGCTTAAAAAAAAAACTCAAGGAAGCTGAACTTGACTTTTTAAA
GCACTGAAGTGCAATATTTAATGTAGGTCAACATGTTTAAATGGGAAAATTTTTTCCTAATTACAGCCAAATCCC
TAGCTGTAATTAACTTAAAATTTGTATACTATTTCACAACAGAGTCAGCATATACCACTTTCTTATAAAATTAGAA
AGATCTAAAATTTTAGAGCTTATTTGGTGAAACAGGCATATTGCTACATCTTTGTTTATAAATTATAATGTGCCTT
TAGAGCCCAATAACAGATAACAAGATTTTGAAAATTCAGGTGAATTAGAGTTATCAGAGGGAATGTTAATACACTC
TATTCAAATACTATATGAGTAAGACATTTAAAATAGGAAACAATACTTTATATATTAAAAAAAATTAATCTTCCAG
TCGATTTAATCCACTTTATGAATTCATTTAAATCGATTTAAATTCGAATTAATTAACTAGAGTACCCGGGGATCTT
ATTCCCTTTAACTAATAAAAAAAAATAATAAAGCATCACTTACTTAAAATCAGTTAGCAAATTTCTGTCCAGTTTA
TTCAGCAGCACCTCCTTGCCCTCCTCCCAGCTCTGGTATTGCAGCTTCCTCCTGGCTGCAAACTTTCTCCACAATC
TAAATGGAATGTCAGTTTCCTCCTGTTCCTGTCCATCCGCACCCACTATCTTCATGTTGTTGCAGATGAAGCGCGC
AAGACCGTCTGAAGATACCTTCAACCCCGTGTATCCATATGACACGGAAACCGGTCCTCCAACTGTGCCTTTTCTT
ACTCCTCCCTTTGTATCCCCCAATGGGTTTCAAGAGAGTCCCCCTGGGGTACTCTCTTTGCGCCTATCCGAACCTC
TAGTTACCTCCAATGGCATGCTTGCGCTCAAAATGGGCAACGGCCTCTCTCTGGACGAGGCCGGCAACCTTACCTC
CCAAAATGTAACCACTGTGAGCCCACCTCTCAAAAAACCAAGTCAAACATAAACCTGGAAATATCTGCACCCCTC
ACAGTTACCTCAGAAGCCCTAACTGTGGCTGCCGCCGCACCTCTAATGGTCGCGGGCAACACACTCACCATGCAAT
CACAGGCCCCGCTAACCGTGCACGACTCCAAACTTAGCATTGCCACCCAAGGACCCCTCACAGTGTCAGAAGGAAA
GCTAGCCCTGCAAACATCAGGCCCCCTCACCACCACCGATAGCAGTACCCTTACTATCACTGCCTCACCCCCTCTA
ACTACTGCCACTGGTAGCTTGGGCATTGACTTGAAAGAGCCCATTTATACACAAAATGGAAAACTAGGACTAAAGT
ACGGGGCTCCTTTGCATGTAACAGACGACCTAAACACTTTGACCGTAGCAACTGGTCCAGGTGTGACTATTAATAA
TACTTCCTTGCAAACTAAAGTTACTGGAGCCTTGGGTTTTGATTCACAAGGCAATATGCAACTTAATGTAGCAGGA
GGACTAAGGATTGATTCTCAAAACAGACGCGCCTTATACTTGATGTTAGTTATCCGTTTGATGCTCAAAACCAACTAA
ATCTAAGACTAGGACAGGGCCCTCTTTTTATAAACTCAGCCCACAACTTGGATATTAACTACAACAAAGGCCTTTA
CTTGTTTACAGCTTCAAACAATTCCAAAAAGCTTGAGGTTAACCTAAGCACTGCCAAGGGGTTGATGTTTGACGCT
ACAGCCATAGCCATTAATGCAGGAGATGGGCTTGAATTTGGTTCACCTAATGCACCAAACACAAATCCCCTCAAAA
CAAAAATTGGCCATGGCCTAGAATTTGATTCAAACAAGGCTATGGTTCCTAAACTAGGAACTGGCCTTAGTTTTGA
```

FIGURE 14 (cont.)

```
CAGCACAGGTGCCATTACAGTAGGAAACAAAAATAATGATAAGCTAACTTTGTGGACCACACCAGCTCCATCTCCT
AACTGTAGACTAAATGCAGAGAAAGATGCTAAACTCACTTTGGTCTTAACAAAATGTGGCAGTCAAATACTTGCTA
CAGTTTCAGTTTTGGCTGTTAAAGGCAGTTTGGCTCCAATATCTGGAACAGTTCAAAGTGCTCATCTTATTATAAG
ATTTGACGAAAATGGAGTGCTACTAAACAATTCCTTCCTGGACCCAGAATATTGGAACTTTAGAAATGGAGATCTT
ACTGAAGGCACAGCCTATACAAACGCTGTTGGATTTATGCCTAACCTATCAGCTTATCCAAAATCTCACGGTAAAA
CTGCCAAAAGTAACATTGTCAGTCAAGTTTACTTAAACGGAGACAAAACTAAACCTGTAACACTAACCATTACACT
AAACGGTACACAGGAAACAGGAGACACAACTCCAAGTGCATACTCTATGTCATTTTCATGGGACTGGTCTGGCCAC
AACTACATTAATGAAATATTTGCCACATCCTCTTACACTTTTTCATACATTGCCCAAGAATAAAGAATCGTTTGTG
TTATGTTTCAACGTGTTTATTTTTCAATTGCAGAAAATTTCAAGTCATTTTTCATTCAGTAGTATAGCCCCACCAC
CACATAGCTTATACAGATCACCGTACCTTAATCAAACTCACAGAACCCTAGTATTCAACCTGCCACCTCCCTCCCA
ACACACAGAGTACACAGTCCTTTCTCCCGGCTGGCCTTAAAAAGCATCATATCATGGGTAACAGACATATTCTTA
GGTGTTATATTCCACACGGTTTCCTGTCGAGCCAAACGCTCATCAGTGATATTAATAAACTCCCCGGGCAGCTCAC
TTAAGTTCATGTCGCTGTCCAGCTGCTGAGCCACAGGCTGCTGTCCAACTTGCGGTTGCTTAACGGGCGGCGAAGG
AGAAGTCCACGCCTACATGGGGTAGAGTCATAATCGTGCATCAGGATAGGCGGTGGTGCTGCAGCAGCGCGCGA
ATAAACTGCTGCCGCCGCTCCGTCCTGCAGGAATACAACATGGCAGTGGTCTCCTCAGCGATGATTCGCACCG
CCCGCAGCATAAGGCGCCTTGTCCTCCGGGCACAGCAGCGCACCCTGATCTCACTTAAATCAGCACAGTAACTGCA
GCACAGCACCACAATATTGTTCAAAATCCCACAGTGCAAGGCGCTGTATCCAAAGCTCATGGCGGGACCACAGAA
CCCACGTGGCCATCATACCACAAGCGCAGGTAGATTAAGTGGCGACCCCTCATAAACACGCTGGACATAAACATTA
CCTCTTTTGGCATGTTGTAATTCACCACCTCCCGGTACCATATAAACCTCTGATTAAACATGGCGCCATCCACCAC
CATCCTAAACCAGCTGGCCAAAACCTGCCCGCCGGCTAGTCATACACTGCAGGGAACCGGGACTGGAACAATGACAGTGG
AGAGCCCAGGACTCGTAACCATGGATCATCATGCTCGTCATGATATCAATGTTGGCACAACACAGGCACACGTGCA
TACACTTCCTCAGGATTACAAGCTCCTCCCGCGTTAGAACCATATCCCAGGGAACAACCCATTCCTGAATCAGCGT
AAATCCCACACTGCAGGGAAGACCTCGCACGTAACTCACGTTGTGCATTGTCAAAGTGTTACATTCGGGCAGCAGC
GGATGATCCTCCAGTATGGTAGCGCGGGTTTCTGTCTCAAAAGGAGGTAGACGATCCCTACTGTACGGAGTGCGCC
GAGACAACCGAGATCGTGTTGGTCGTAGTGTCATGCCAAATGGAACGCCGGACGTAGTCATATTTCCTGAAGCAAA
ACCAGGTGCGGGCGTGACAAACAGATCTGCGTCTCCGGTCTCGCCGCTTAGATCGCTCTGTGTAGTAGTTGTAGTA
TATCCACTCTCTCAAAGCATCCAGGCGCCCCTGGCTTCGGGTTCTATGTAAACTCCTTCATGCGCCGCTGCCCTG
ATAACATCCACCACCGCAGAATAAGCCACACCCAGCCAACCTACACATTCGTTCTGCGAGTCACACACGGGAGGAG
CGGGAAGAGCTGGAAGAACCATGTTTTTTTTTTTATTCCAAAAGATTATCCAAAACCTCAAAATGAAGATCTATTA
AGTGAACGCGCTCCCCTCCGGTGGCGTGGTCAAACTCTACAGCCAAAGAACAGATAATGGCATTTGTAAGATGTTG
CACAATGGCTTCCAAAAGGCAAACGGCCCTCACGTCCAAGTGGACGTAAAGGCTAAACCCTTCAGGGTGAATCTCC
TCTATAAACATTCCAGCACCTTCAACCATGCCCAAATAATTCTCATCTCGCCACCTTCTCAATATATCTCTAAGCA
AATCCCGAATATTAAGTCCGGCCATTGTAAAAATCTGCTCCAGAGCGCCCTCCACCTTCAGCCTCAAGCAGCGAAT
CATGATTGCAAAAATTCAGGTTCCTCACAGACCTGTATAAGATTCAAAAGCGGAACATTAACAAAAATACCGCGAT
CCCGTAGGTCCCTTCGCAGGGCCAGCTGAACATAATCGTGCAGGTCTGCACGGACCAGCGCGGCCACTTCCCCGCC
AGGAACCTTGACAAAAGAACCCACACTGATTATGACACGCATACTCGGAGCTATGCTAACCAGCGTAGCCCCGATG
TAAGCTTTGTTGCATGGCGGCGATATAAAATGCAAGGTGCTCTAAAAATCAGGCAAAGCCTCGCGCAAAAAA
GAAAGCACATCGTAGTCATGCTCATGCAGATAAAGGCAGGTAAGCTCCGGAACCACCACAGAAGAAGACACCATTT
TTCTCTCAAACATGTCTGCGGGTTTCTGCATAAACACAAAATAAAATAACAAAAAAACATTTAAACATTAGAAGCC
TGTCTTACAACAGGAAAAACAACCCTTATAAGCATAAGACGGACTACGGCCATGCCGGCGTGACCGTAAAAAAACT
GGTCACCGTGATTAAAAAGCACCACCGACAGCTCCTCGGTCATGTCCGGAGTCATAATGTAAGACTCGGTAAACAC
ATCAGGTTGATTCATCGGTCAGTGCTAAAAAGCGACCGAAATAGCCCGGGGGAATACATACCCGCAGGCGTAGAGA
CAACATTACAGCCCCCATAGGAGGTATAACAAAATTAATAGGAGAGAAAAACACATAAACACCTGAAAAACCCTCC
TGCCTAGGCAAAATAGCACCCTCCCGCTCCAGAACAACATACAGCGCTTCACAGCGGCAGCCTAACAGTCAGCCTT
ACCAGTAAAAAGAAAACCTATTAAAAAAACACCACTCGACACGGCACCAGCTCAATCAGTCACAGTGTAAAAAAG
GGCCAAGTGCAGAGCGAGTATATATAGGACTAAAAAATGACGTAACGGTTAAAGTCCACAAAAAACACCCAGAAAA
CCGCACGCGAACCTACGCCCAGAAACGAAAGCCAAAAAACCCACAACTTCCTCAAATCGTCACTTCCGTTTTCCCA
CGTTACGTAACTTCCCATTTTAAGAAAACTACAATTCCCAACACATACAAGTTACTCCGCCCTAAAACCTACGTCA
CCCGCCCCGTTCCCACGCCCCGCGCCACGTCACAAACTCCACCCCCTCATTATCATATTGGCTTCAATCCAAAATA
AGGTATATTATTGATGATGGCCGGCCGAATTGAATCAGGGGATAACGCAGGAAAGAACATGTGAGCAAAAGGCCAG
CAAAAGGCCAGGAACCGTAAAAAGGCCGCGTTGCTGGCGTTTTTCCATAGGCTCCGCCCCCCTGACGAGCATCACA
AAAATCGACGCTCAAGTCAGAGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCTCCAAGCTGGGCTGTGTGCACGAAC
CCCCCGTTCAGCCCGACCGCTGCGCCTTATCCGGTAACTATCGTCTTGAGTCCAACCCGGTAAGACACGACTTATC
GCCACTGGCAGCAGCCACTGGTAACAGGATTAGCAGAGCGAGGTATGTAGGCGGTGCTACAGAGTTCTTGAAGTGG
TGGCCTAACTACGGCTACACTAGAAGGACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTTTGCAAGCAGCAGATTAC
GCGCAGAAAAAAAGGATCTCAAGAAGATCCTTTGATCTTTTCTACGGGGTCTGACGCTCAGTGGAACGAAAACTCA
CGTTAAGGGATTTTGGTCATGAGATTATCAAAAGGATCTTCACCTAGATCCTTTTAAATTAAAAATGAAGTTTTA
AATCAATCTAAAGTATATATGAGTAAACTTGGTCTGACAGTTACCAATGCTTAATCAGTGAGGCACCTATCTCAGC
```

FIGURE 14 (cont.)

```
GATCTGTCTATTTCGTTCATCCATAGTTGCCTGACTCCCCGTCGTGTAGATAACTACGATACGGGAGGGCTTACCA
TCTGGCCCCAGTGCTGCAATGATACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGTCTATTAATTGTTGCCGGGAAGC
TAGAGTAAGTAGTTCGCCAGTTAATAGTTTGCGCAACGTTGTTGCCATTGCTACAGGCATCGTGGTGTCACGCTCG
TCGTTTGGTATGGCTTCATTCAGCTCCGGTTCCCAACGATCAAGGCGAGTTACATGATCCCCCATGTTGTGCAAAA
AAGCGGTTAGCTCCTTCGGTCCTCCGATCGTTGTCAGAAGTAAGTTGGCCGCAGTGTTATCACTCATGGTTATGGC
AGCACTGCATAATTCTCTTACTGTCATGCCATCCGTAAGATGCTTTTCTGTGACTGGTGAGTACTCAACCAAGTCA
TTCTGAGAATAGTGTATGCGGCGACCGAGTTGCTCTTGCCCGGCGTCAATACGGGATAATACCGCGCCACATAGCA
GAACTTTAAAAGTGCTCATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAGCGTTTCTGGGTGAGCA
AAAACAGGAAGGCAAAATGCCGCAAAAAAGGGAATAAGGGCGACACGGAAATGTTGAATACTCATACTCTTCCTTT
TTCAATATTATTGAAGCATTTATCAGGGTTATTGTCTCATGAGCGGATACATATTTGAATGTATTTAGAAAAATAA
ACAAATAGGGGTTCCGCGCACATTTCCCCGAAAAGTGCCAC
```

FIGURE 15 pD1962delBbsI-pIX (SEQ ID NO:14)

```
TCTAGAGTCGACCGGTCATGGCTGCGCCCCGACACCCGCCAACACCCGCTGACGCGCCCTGACGGGCTTGTCTGCT
CCCGGCATCCGCTTACAGACAAGCTGTGACCGTCTCCGGGAGCTGCATGTGTCAGAGGTTTTCACCGTCATCACCG
AAACGCGCGAGGCAGCCGGATCATAATCAGCCATACCACATTTGTAGAGGTTTTACTTGCTTTAAAAAACCTCCCC
ACCTCCCCCTGAACCTGAAACATAAAATGAATGCAATTGTTGTTGTTAACTTGTTTATTGCAGCTTATAATGGTTA
CAAATAAAGCAATAGCATCACAAATTTCACAAATAAAGCATTTTTTTCACTGCATTCTAGTTGTGGTTTGTCCAAA
CTCATCAATGTATCTTATCATGTCTGGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCAAAAAAGGGAATAAGGGCGACAC
GGAAATGTTGAATACTCATACTCTTCCTTTTTCAATATTATTGAAGCATTTATCAGGGTTATTGTCTCATGAGCGG
ATACATATTTGAATGTATTTAGAAAAATAAACAAATAGGGGTTCCGCGCACATTTCCCCGAAAAGTGCCACCTGAC
GTCCATTGTTCATTCCACGGACAAAAACAGAGAAAGGAAACGACAGAGGCCAAAAAGCCTCGCTTTCAGCACCTGT
CGTTTCCTTTCTTTTCAGAGGGTATTTTAAATAAAAACATTAAGTTATGACGAAGAAGAACGGAAACGCCTTAAAC
CGGAAAATTTTCATAAATAGCGAAAACCCGCGAGGTCGCCGCCCCGTAACCTGTCGGATCACCGGAAAGGACCCGT
AAAGTGATAATGATTATCATCTAGACTACATCGATGGGTCGTGCGCTCCTTTCGGTCGGGCGCTGCGGGTCGTGGG
GCGGGCGTCAGGCACCGGGCTTGCGGGTCATGCACCAGGTCGCGCGGTCCTTCGGGCACTCGACGTCGGCGGTGAC
GGTGAAGCCGAGCCGCTCGTAGAAGGGGAGGTTGCGGGCGCGGAGGTCTCCAGGAAGGCGGGCACCCCGGCGCGC
TCGGCCGCCTCCACTCCGGGGAGCACGACGGCGCTGCCCAGACCCTTGCCCTGGTGGTCGGGCGAGACGCCGACGG
TGGCCAGGAACCACGCGGGCTCCTTGGGCCGGTGCGGCGCCAGGAGGCCTTCCATCTGTTGCTGCGCGGCCAGCCG
GGAACCGCTCAACTCGGCCATGCGCGGGCCGATCTCGGCGAACACCGCCCCGCTTCGACGCTCTCCGGCGTGGTC
CAGACCGCCACCGCGGCGCCGTCGTCCGCGACCCACACCTTGCCGATGTCGAGCCCGACGGCGCGTGAGGAAGAGTT
CTTGCAGCTCGGTGACCCGCTCGATGTGGCGGTCCGGATCGACGGTGGCGCGTGGCGGGGGGTAGTCGGCGAACGC
GGCGGCGAGGGTGCGTACGGCCCTGGGGACGTCGTCGGCTACGAGCCGCGGCCACCGTGGGCTTGTACTCGGTCATG
GTAAGCTTGCTAGCAGCTGGTACCCAGCTTCTAGAGATCTGACGGTTCACTAAACGAGCTCTGCTTATATAGACCT
CCCACCGTACACGCCTACCGCCCATTTGCGTCAACGGGCGGGGTTATTACGACATTTTGGAAAGTCCCGTTGATT
TTGGTGCCAAAACAAACTCCCATTGACGTCAATGGGGTGGAGACTTGGAAATCCCCGTGAGTCAAACCGCTATCCA
CGCCCATTGGTGTACTGCCAAAACCGCATCACCATGGTAATAGCGATGACTAATACGTAGATGTACTGCCAAGTAG
GAAAGTCCGTAAGGTCATGTACTGGGCATAATGCCAGGCGGGCCATTTACCGTCATTGACGTCAATAGGGGGCGG
ACTTGGCATATGATACACTTGATGTACTGCCAAGTGGGCAGTTTACCGTAAATACTCCACCCATTGACGTCAATGG
AAAGTCCCTATTGGCGTTACTATGGGAACATACGTCATTATTGACGTCAATGGGCGGGGTCGTTGGGCGGTCAGC
CAGGCGGGCCATTTACCGTAAGTTATGTAACGCGGAACTCCATATATGGGCTATGAACTAATGACCCCGTAATTGA
TTACTATTAATAACTAGTCAATAATCAATGTCAACATGGCGGTCATATTGGACATGAGCCAATATAAATGTACATA
TTATGATATAGATACAACGTATGCAATGGCCAATAGCCAATATTGATTTATGCTATATAACCAATGACTAATATGG
CTAATTGCCAATATTGATTCAATGTATAGATCTTCCATACCTACCAGTTCTGCGCCTGCAGCAATGCAACAACGTT
GCCCGGATCTGCGATGATAAGCTGTCAAACATGGAATTGGTCGACTAGCTTGGCACGCCAGAAATCCGCGGTG
GTTTTTGGGGGTCGGGGCGTGTTGGCAGCCACAGACGCCGGTGTTCGTGTCGCGCCAGTACATGCGGTCCATGCC
CAGGCCATCCAAAAACCATGGGTCTGTCTGCTCAGTCCAGTCGTGGACCAGACCCCACGCAACGCCCAAAATAATA
ACCCCCACGAACCATAAACCATTCCCCATGGGGGACCCCGTCCCTAACCCACGGGGCCAGTGGCTATGGCAGGGCC
TGCCGCCCCGACGTTGGCTGCGAGCCCTGGGCCTTCACCCGAACTTGGGGGTGGGGTGGGGAAAAGGAAGAAACG
CGGGCGTATTGGCCCCAATGGGGTCTCGGTGGGGTATCGACAGAGTGCCAGCCCTGGGACCGAACCCCGCGTTTAT
GAACAAACGACCCAACACCCGTGCGTTTTATTCTGTCTTTTTATTGCCGTCATAGCGCGGGTTCCTTCCGGTATTG
TCTCCTTCCGTGTTTCAGTTAGCCTCCCCCATCTCCCCTATTCCTTTGCCCTCGGACGAGTGCTGGGCGTCGGTT
TCCACTATCGGCGAGTACTTCTACACAGCCATCGGTCCAGACGGCCGCGCTTCTGCGGGCGATTTGTGTACGCCCG
ACAGTCCCGGCTCCGGATCGGACGATTGCGTCGCATCGACCCTGCGCCCAAGCTGCATCATCGAAATTGCCGTCAA
CCAAGCTCTGATAGAGTTGGTCAAGACCAATGCGGAGCATATACGCCCGGAGCCGCGGCGATCCTGCAAGCTCCGG
ATGCCTCCGCTCGAAGTAGCGCGTCTGCTGCTCCATACAAGCCAACCACGGCCTCCAGAAGAAGATGTTGGCGACC
TCGTATTGGGAATCCCCGAACATCGCCTCGCTCCAGTCAATGACCGCTGTTATGCGGCCATTGTCCGTCAGGACAT
TGTTGGAGCCGAAATCCGCGTGCACGAGGTGCCGGACTTCGGGGCAGTCCTCGGCCCAAAGCATCAGCTCATCGAG
AGCCTGCGCGACGGACGCACTGACGGTGTCGTCCATCACAGTTTGCCAGTGATACACATGGGGATCAGCAATCGCG
CATATGAAATCACGCCATGTAGTGTATTGACCGATTCCTTGCGGTCCGAATGGGCCGAACCCGCTCGTCTGGCTAA
GATCGGCCGCAGCGCGCGCAAAACCCCTAAATAAAGACAGCAAGACACTTGCTTGATCCAAATCCAAACAGAGTCT
GGTTTTTTATTTATGTTTAAACCGCATTGGGAGGGGAGGAAGCCTTCAGGGCAGAAACCTGCTGGCGCAGATCCA
ACAGCTGCTGAGAAACGACATTAAGTTCCCGGGTCAAAGAATCCAATTGTGCCAAAAGAGCCGTCAACTTGTCATC
GCGGGCGGATGAACGGGAAGCTGCACTGCTTGCAAGCGGGCTCAGGAAAGCAAAGTCAGTCACAATCCCGCGGGCG
GTGGCTGCAGCGGCTGAAGCGGCGGCGGAGGCTGCAGTCTCCAACGGCGTTCCAGACACGGTCTCGTAGGTCAAGG
TAGTAGAGTTTGCGGGCAGGACGGGCGACCATCAATGCTGGAGCCCATCACATTCTGACGCACCCCGGCCCATGG
GGGCATGCGCGTTGTCAAATATGAGCTCACAATGCTTCCATCAAACGAGTTGGTGCTCATGGCGGCGGCGGCTGCT
GCAAAACAGATACAAAACTACATAAGACCCCCACCTTATATATTCTTTCCCACCCGGGATCTGCGGCACGCTGTTG
ACGCTGTTAAGCGGGTCGCTGCAGGGTCGCTCGGTGTTCGAGGCCACACGCGTCACCTTAATATGCGAAGTGGACC
TGGGACCGCGCCGCCCCGACTGCATCTGCGTGTTCGAATTCGCCAATGACAAGACGCTGGGCGGGGTTTGTGTCAT
CATGAACTAAAGACATGCAAATATATTTCTTCCGGGGACACCGCCAGCAAACGCGAGCAACGGGCCACGGGGATG
AAGCAGGGCATGGCGGCCGACGCGCTGGGCTACGTCTTGCTGGCGTTCGCGACGCGAGGCTGGATGGCCTTCCCCA
TTATGATTCTTCTCGCTTCCGGCGGCATCGGGATGCCCGCGTTGCAGGCCATGCTGTCCAGGCAGGTAGATGACGA
```

FIGURE 15 (cont.)

```
CCATCAGGGACAGCTTCAAGGATCGCTCGCGGCTCTTACCAGCCTAACTTCGATCACTGGACCGCTGATCGTCACG
GCGATTTATGCCGCCTCGGCGAGCACATGGAACGGGTTGGCATGGATTGTAGGCGCCGCCCTATACCTTGTCTGCC
TCCCCGCGTTGCGTCGCGGTGCATGGAGCCGGGCCACCTCGACCTGAATGGAAGCCGGCGGCACCTCGCTAACGGA
TTCACCACTCCAAGAATTGGAGCCAATCAATTCTTGCGGAGAACTGTGAATGCGCAAACCAACCCTTGGCAGAACA
TATCCATCGCGTCCGCCATCTCCAGCAGCCGCACGCGGCGCAGCAAAAGGCCAGGAACCGTAAAAAGGCCGCGTTG
CTGGCGTTTTTCCATAGGCTCCGCCCCCTGACGAGCATCACAAAAATCGACGCTCAAGTCAGAGGTGGCGAAACC
CGACAGGACTATAAAGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACGCTGTAGGTATCTCAGT
TCGGTGTAGGTCGTTCGCTCCAAGCTGGGCTGTGTGCACGAACCCCCGTTCAGCCCGACCGCTGCGCCTTATCCG
GTAACTATCGTCTTGAGTCCAACCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTACGGCTACACTAGAAGGACAGTA
TTTGGTATCTGCGCTCTGCTGAAGCCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAAAAAAGGATCTCAAGAAGATCCTTT
GATCTTTTCTACGGGGTCTGACGCTCAGTGGAACGAAAACTCACGTTAAGGGATTTTGGTCATGAGATTATCAAAA
AGGATCTTCACCTAGATCCTTTTAAATTAAAAATGAAGTTTTAAATCAATCTAAAGTATATATGAGTAAACTTGGT
CTGACAGTTACCAATGCTTAATCAGTGAGGCACCTATCTCAGCGATCTGTCTATTTCGTTCATCCATAGTTGCCTG
ACTCCCCGTCGTGTAGATAACTACGATACGGGAGGGCTTACCATCTGGCCCCAGTGCTGCAATGATACCGCGAGAC
CCACGCTCACCGGCTCCAGATTTATCAGCAATAAACCAGCCAGCCGGAAGGGCCGAGCGCAGAAGTGGTCCTGCAA
CTTTATCCGCCTCCATCCAGTCTATTAATTGTTGCCGGGAAGCTAGAGTAAGTAGTTCGCCAGTTAATAGTTTGCG
CAACGTTGTTGCCATTGCTGCAGGCATCGTGGTGTCACGCTCGTCGTTTGGTATGGCTTCATTCAGCTCCGGTTCC
CAACGATCAAGGCGAGTTACATGATCCCCCATGTTGTGCAAAAAAGCGGTTAGCTCCTTCGGTCCTCCGATCGTTG
TCAGAAGTAAGTTGGCCGCAGTGTTATCACTCATGGTTATGGCAGCACTGCATAATTCTCTTACTGTCATGCCATC
CGTAAGATGCTTTTCTGTGACTGGTGAGTACTCAACCAAGTCATTCTGAGAATAGTGTATGCGGCGACCGAGTTGC
TCTTGCCCGGCGTCAACACGGGATAATACCGCGCCACATAGCAGAACTTTAAAAGTGCTCATCATTGGAAAACGTT
CTTCGGGGCGAAAACTCTCAAGGATCTTACCGCTGTTGAGATCCAGTTCGATGTAACCCACTCGTGCACCCAACTG
ATCTTCAGCATCTTTTACTTTCACCAGCGTTTCTGGGTGAGCAAAAACAGGAAGGCAAAATGCCGCAAAAAAGGGA
ATAAGGGCGACACGGAAATGTTGAATACTCATACTCTTCCTTTTTCAATATTATTGAAGCATTTATCAGGGTTATT
GTCTCATGAGCGGATACATATTTGAATGTATTTAGAAAAATAAACAAATAGGGGTTCCGCGCACATTTCCCCGAAA
AGTGCCACCTGACGTCTAAGAAACCATTATTATCATGACATTAACCTATAAAAATAGGCGTATCACGAGGCCCTTC
CCGTAGTCTTCCTGGGCCCCTGGGAGGTACATGTCCCCAGCATTGGTGTAAGAGCTTCAGCCAAGAGTTACACAT
AAAGGCAATGTTGTGTTGCAGTCCACAGACTGCAAAGTCTGCTCCAGGATGAAAGCCACTCAGTGTTGGCAAATGT
GCACATCCATTTATAAGGATGTCAACTACAGTCAGAGAACCCCTTTGTGTTTGGTCCCCCCCGTGTCACATGTGG
AACAGGGCCCAGTTGGCAAGTTGTACCAACCAACTGAAGGGATTACATGCACTGCCCCGCAAGAAGGGGCAGAGA
TGCCGTAGTCAGGTTTAGTTCGTCCGGCGGCGGGGC
```

FIGURE 17 HΔIX#3 (SEQ ID NO:15)

```
CTAAATTGTAAGCGTTAATATTTTGTTAAAATTCGGCCGGCCATCATCAATAATATACCTTATTTTGGATTGAAGC
CAATATGATAATGAGGGGGTGGAGTTTGTGACGTGGCGCGGGGCGTGGGAACGGGGCGGGTGACGTAGTAGTGTGG
CGGAAGTGTGATGTTGCAAGTGTGGCGGAACACATGTATAACTTCGTATAATGTATGCTATACGAAGTTATACATG
TAAGCGACGGATGTGGCAAAAGTGACGTTTTTGGTGTGCGCCGGTGTACACAGGAAGTGACAATTTTCGCGCGGTT
TTAGGCGGATGTTGTAGTAAATTTGGGCGTAACCGAGTAAGATTTGGCCATTTTCGCGGGAAAACTGAATAAGAGG
AAGTGAAATCTGAATAATTTTGTGTTACTCATAGCGCGTAATATTTGTCTAGGGAGATCAATTGGATTCTTTGACC
CGGGAACTTAATGTCGTTTCTCAGCAGCTGTTGGATCTGCGCCAGCAGGTTTCTGCCCTGAAGGCTTCCTCCCCTC
CCAATGCGGTTTAAAACATAAATAAAAAACCAGACTCTGTTTGGATTTGGATCAAGCAAGTGTCTTGCTGTCTTTA
TTTAGGGGTTTTGCGCGCGCGGTAGGCCCGGGACCAGCGGTCTCGGTCGTTGAGGGTCCTGTGTATTTTTTCCAGG
ACGTGGTAAAGGTGACTCTGGATGTTCAGATACATGGGCATAAGCCCGTCTCTGGGGTGGAGGTAGCACCACTGCA
GAGCTTCATGCTGCGGGTGGTGTTGTAGATGATCCAGTCGTAGCAGGAGCGCTGGGCGTGGTGCCTAAAAATGTC
TTTCAGTAGCAAGCTGATTGCCAGGGGCAGGCCCTTGGTGTAAGTGTTTACAAAGCGGTTAAGCTGGGATGGGTGC
ATACGTGGGGATATGAGATGCATCTTGGACTGTATTTTTAGGTTGGCTATGTTCCCAGCCATATCCCTCCGGGGAT
TCATGTTGTGCAGAACCACCAGCACAGTGTATCCGGTGCACTTGGGAAATTTGTCATGTAGCTTAGAAGGAAATGC
GTGGAAGAACTTGGAGACGCCCTTGTGACCTCCAAGATTTTCCATGCATTCGTCCATAATGATGGCAATGGGCCCA
CGGGCGGCGGCCTGGGCGAAGATATTTCTGGGATCACTAACGTCATAGTTGTGTTCCAGGATGAGATCGTCATAGG
CCATTTTTACAAAGCGCGGCGGAGGGTGCCAGACTGCGGTATAATGGTTCCATCCGGCCCAGGGGCGTAGTTACC
CTCACAGATTTGCATTTCCCACGCTTTGAGTTCAGATGGGGGGATCATGTCTACCTGCGGGGCGATGAAGAAACG
GTTTCCGGGGTAGGGGAGATCAGCTGGGAAGAAAGCAGGTTCCTGAGCAGCTGCGACTTACCGCAGCCGGTGGGCC
CGTAAATCACACCTATTACCGGGTGCAACTGGTAGTTAAGAGAGCTGCAGCTGCCGTCATCCCTGAGCAGGGGGGC
CACTTCGTTAAGCATGTCCCTGACTCGCATGTTTTCCCTGACCAAATCCGCCAGAAGGCGCTCGCCGCCCAGCGAT
AGCAGTTCTTGCAAGGAAGCAAAGTTTTTCAACGGTTTGAGACCGTCCGCCGTAGGCATGCTTTTGAGCGTTTGAC
CAAGCAGTTCCAGGCGGTCCCACAGCTCGGTCACCTGCTCTACGGCATCTCGATCCAGCATATCTCCTCGTTTCGC
GGGTTGGGGCGGCTTTCGCTGTACGGCAGTAGTCGGTGCTCGTCCAGACGGGCCAGGGTCATGTCTTTCCACGGGC
GCAGGGTCCTCGTCAGCGTAGTCTGGGTCACGGTGAAGGGGTGCGCTCCGGGCTGCGCGCTGGCCAGGGTGCGCTT
GAGGCTGGTCCTGCTGGTGCTGAAGCGCTGCCGGTCTTCGCCCTGCGCGTCGGCCAGGTAGCATTTGACCATGGTG
TCATAGTCCAGCCCCTCGGCGGCGTGGCCCTTGGCGCGCAGCTTGCCCTTGGAGGAGGCGCCGCACGAGGGGCAGT
GCAGACTTTTGAGGGCGTAGAGCTTGGGCGCGAGAAATACCGATTCCGGGGAGTAGGCATCCGCGCCGCAGGCCCC
GCAGACGGTCTCGCATTCCACGAGCCAGGTGAGCTCTGGCCGTTCGGGGTCAAAAACCAGGTTTCCCCCATGCTTT
TTGATGCGTTTCTTACCTCTGGTTTCCATGAGCCGGTGTCCACGCTCGGTGACGAAAAGGCTGTCCGTGTCCCCGT
ATACAGACTTGAGAGGCCTGTCCTCGAGCGGTGTTCCGCGGTCCTCCTCGTATAGAAACTCGGACCACTCTGAGAC
AAAGGCTCGCGTCCAGGCCAGCACGAAGGAGGCTAAGTGGGAGGGGTAGCGGTCGTTGTCCACTAGGGGGTCCACT
CGCTCCAGGGTGTGAAGACACATGTCGCCCTCTTCGGCATCAAGGAAGGTGATTGGTTTGTAGGTGTAGGCCACGT
GACCGGGTGTTCCTGAAGGGGGCTATAAAAGGGGGTGGGGCGCGTTCGTCCTCACTCTCTTCCGCATCGCTGTC
TGCGAGGGCCAGCTGTTGGGGTGAGTACTCCCTCTGAAAAGCGGGCATGACTTCTGCGCTAAGATTGTCAGTTTCC
AAAAACGAGGAGGATTTGATATTCACCTGGCCCGCGGTGATGCCTTTGAGGGTGGCCGCATCCATCTGGTCAGAAA
AGACAATCTTTTTGTTGTCAAGCTTGGTGGCAAACGACCCGTAGAGGGCGTTGGACAGCAACTTGGCGATGGAGCG
CAGGGTTTGGTTTTTGTCGCGATCGGCGCGCTCCTTGGCCGCGATGTTTAGCTGCACGTATTCGCGCGCAACGCAC
CGCCATTCGGGAAAGACGGTGGTGCGCTCGTCGGGCACCAGGTGCACGCGCCAACCGCGGTTGTGCAGGGTGACAA
GGTCAACGCTGGTGGCTACCTCTCCGCGTAGGCGCTCGTTGGTCCAGCAGAGGCGGCCGCCCTTGCGCGAGCAGAA
TGGCGGTAGGGGTCTAGCTGCGTCTCGTCCGGGGGTCTGCGTCCACGGTAAAGACCCCGGGCAGCAGGCGCGCG
TCGAAGTAGTCTATCTTGCATCCTTGCAAGTCTAGCGCCTGCTGCCATGCGCGGGCGGCAAGCGCGCGCTCGTATG
GGTTGAGTGGGGGACCCCATGGCATGGGGTGGTGGCGACGGGCGTACATGCCGCAAATGTCGTAAACGTAGAG
GGGCTCTCTGAGTATTCCAAGATATGTAGGGTAGCATCTTCCACCGCGGATGCTGGCGCGCACGTAATCGTATAGT
TCGTGCGAGGGAGCGAGGAGGTCGGGACCGAGGTTGCTACGGGCGGGCTGCTCTGCTCGGAAGACTATCTGCCTGA
AGATGGCATGTGAGTTGGATGATATGGTTGGACGCTGGAAGACGTTGAAGCTGGCGTCTGTGAGACCTACCGCGTC
ACGCACGAAGGAGGCGTAGGAGTCGCGCAGCTTGTTGACCAGCTCGGCGGTGACCTGCACGTCTAGGGCGCAGTAG
TCCAGGGTTTCCTTGATGATGTCATACTTATCCTGTCCCTTTTTTTTCCACAGCTCGCGGTTGAGGACAAACTCTT
CGCGGTCTTTCCAGTACTCTTGGATCGGAAACCCGTCGGCCTCCGAACGGTAAGAGCCTAGCATGTAGAACTGGTT
GACGGCCTGGTAGGCGCAGCATCCCTTTTCTACGGGTAGCGCGTATGCCTGCGCGGCCTTCCGGAGCGAGGTGTGG
GTGAGCGCAAAGGTGTCCCTGACCATGACTTTGAGGTACTGGTATTTGAAGTCAGTGTCGTCGCATCCGCCCTGCT
CCCAGAGCAAAAAGTCCGTGCGCTTTTTGGAACGCGGATTTGGCAGGGCGAAGGTGACATCGTTGAAGAGTATCTT
TCCCGCGCGAGGCATAAAGTTGCGTGTGATGCGGAAGGGTCCCGGCACCTCGGAACGGTTGTTAATTACCTGGGCG
GCGAGCACGATCTCGTCAAAGCCGTTGATGTTGTGGCCCACAATGTAAAGTTCCAAGAAGCGCGGGATGCCCTTGA
TGGAAGGCAATTTTTTAAGTTCCTCGTAGGTGAGCTCTTCAGGGGAGCTGAGCCCGTGCTCTGAAAGGGCCCAGTC
TGCAAGATGAGGGTTGGAAGCGACGAATGAGCTCCACAGGTCACGGGCCATTAGCATTTGCAGGTGGTCGCGAAAG
GTCCTAAACTGGCGACCTATGGCCATTTTTCTGGGGTGATGCAGTAGAAGGTAAGCGGGTCTTGTTCCCAGCGGT
CCCATCCAAGGTTCGCGGCCTAGGTCTCGCGGCCAGTCACTAGAGGCTCATCTCCGCCGAACTTCATGACCAGCAT
GAAGGGCACGAGCTGCTTCCCAAAGGCCCCCATCCAAGTATAGGTCTCTACATCGTAGGTGACAAAGAGACGCTCG
GTGCGAGGATGCGAGCCGATCGGGAAGAACTGGATCTCCCGCCACCAATTGGAGGAGTGGCTATTGATGTGGTGAA
AGTAGAAGTCCCTGCGACGGGCCGAACACTCGTGCTGGCTTTTGTAAAAACGTGCGCAGTACTGGCAGCGGTGCAC
```

FIGURE 17 (cont.)

```
GGGCTGTACATCCTGCACGAGGTTGACCTGACGACCGCGCACAAGGAAGCAGAGTGGGAATTTGAGCCCCTCGCCT
GGCGGGTTTGGCTGGTGGTCTTCTACTTCGGCTGCTTGTCCTTGACCGTCTGGCTGCTCGAGGGGAGTTACGGTGG
ATCGGACCACCACGCCGCGCGAGCCCAAAGTCCAGATGTCCGCGCGCGGCGGTCGGAGCTTGATGACAACATCGCG
CAGATGGGAGCTGTCCATGGTCTGGAGCTCCCGCGGCGTCAGGTCAGGCGGGAGCTCCTGCAGGTTTACCTCGCAT
AGACGGGTCAGGGCGCGGGCTAGATCCAGGTGATACCTAATTTCCAGGGGCTGGTTGGTGGCGGCGTCGATGGCTT
GCAAGAGGCCGCATCCCCGCGGCGCGACTACGGTACCGCGCGGCGGGCGGTGGGCCGCGGGGGTGTCCTTGGATGA
TGCATCTAAAAGCGGTGACGCGGGCGAGCCCCCGGAGGTAGGGGGGGCTCCGGACCCGCCGGGAGAGGGGGCAGGG
GCACGTCGGCGCCGCGCGCGGGCAGGAGCTGGTGCTGCGCGCGTAGGTTGCTGGCGAACGCGACGACGCGGCGGTT
GATCTCCTGAATCTGGCGCCTCTGCGTGAAGACGACGGGCCCGGTGAGCTTGAGCCTGAAAGAGAGTTCGACAGAA
TCAATTTCGGTGTCGTTGACGGCGGCCTGGCGCAAAATCTCCTGCACGTCTCCTGAGTTGTCTTGATAGGCGATCT
CGGCCATGAACTGCTCGATCTCTTCCTCCTGGAGATCTCCGCGTCCGGCTCGCTCCACGGTGGCGGCGAGGTCGTT
GGAAATGCGGGCCATGAGCTGCGAGAAGGCGTTGAGGCCTCCCTCGTTCCAGACGCGGCTGTAGACCACGCCCCCT
TCGGCATCGCGGGCGCGCATGACCACCTGCGCGAGATTGAGCTCCACGTGCCGGGCGAAGACGGCGTAGTTTCGCA
GGCGCTGAAAGAGGTAGTTGAGGGTGGTGGCGGTGTGTTCTGCCACGAAGAAGTACATAACCCAGCGTCGCAACGT
GGATTCGTTGATATCCCCCAAGGCCTCAAGGCGCTCCATGGCCTCGTAGAAGTCCACGGCGAAGTTGAAAAACTGG
GAGTTGCGCGCCGACACGGTTAACTCCTCCTCCAGAAGACGGATGAGCTCGGCGACAGTGTCGCGCACCTCGCGCT
CAAAGGCTACAGGGGCCTCTTCTTCTTCTTCAATCTCCTCTTCCATAAGGGCCTCCCCTTCTTCTTCTTCTGGCGG
CGGTGGGGGAGGGGGGACACGGCGGCGACGACGGCGCACCGGGAGGCGGTCGACAAAGCGCTCGATCATCTCCCCG
CGGCGACGGCGCATGGTCTCGGTGACGGCGCGGCCGTTCTCGCGGGGCGCAGTTGGAAGACGCCGCCCGTCATGT
CCCGGTTATGGGTTGGCGGGGGCTGCCATGCGGCAGGGATACGGCGCTAACGATGCATCTCAACAATTGTTGTGT
AGGTACTCCGCCGCCGAGGGACCTGAGCGAGTCCGCATCGACCGGATCGGAAAACCTCTCGAGAAAGCGTCTAAC
CAGTCACAGTCGCAAGGTAGGCTGAGCACCGTGGCGGGCGGCAGCGGGCGGCGGTCGGGGTTGTTTCTGGCGGAGG
TGCTGCTGATGATGTAATTAAAGTAGGCGGTCTTGAGACGGCGGATGGTCGACAGAAGCACCATGTCCTTGGGTCC
GGCCTGCTGAATGCGCAGGCGGTCGGCCATGCCCCAGGCTTCGTTTTGACATCGGCGCAGGTCTTTGTAGTAGTCT
TGCATGAGCCTTTCTACCGGCACTTCTTCTTCTCCTTCCTCTTGTCCTGCATCTTTGCATCTATCGCTGCGGCGG
CGGCGGAGTTTGGCCGTAGGTGGCGCCCTCTTCCTCCCATGCGTGTGACCCCGAAGCCCCTCATCGGCTGAAGCAG
GGCTAGGTCGGCGACAACGCGCTCGGCTAATATGGCCTGCTGCACCTGCGTGAGGGTAGACTGGAAGTCATCCATG
TCCACAAAGCGGTGGTATGCGCCCGTGTTGATGGTGTAAGTGCAGTTGGCCATAACGGACCAGTTAACGGTCTGGT
GACCCGGCTGCGAGAGCTCGGTGTACCTGAGACGCGAGTAAGCCCTCGAGTCAAATACGTAGTCGTTGCAAGTCCG
CACCAGGTACTGGTATCCCACCAAAAAGTGCGGCGGCGGCTGGCGGTAGAGGGGCCAGCGTAGGGTGGCCGGGGCT
CCGGGGGCGAGATCTTCCAACATAAGGCGATGATATCCGTAGATGTACCTGGACATCCAGGTGATGCCGGCGGCGG
TGGTGGAGGCGCGCGGAAAGTCGCGGACGCGGTTCCAGATGTTGCGCAGCGGCAAAAAGTGCTCCATGGTCGGGAC
GCTCTGGCCGGTCAGGCGCGCGCAATCGTTGACGCTCTACCGTGCAAAAGGAGAGCCTGTAAGCGGGCACTCTTCC
GTGGTCTGGTGGATAAATTCGCAAGGGTATCATGGCGGACGACCGGGGTTCGAGCCCCGTATCCGGCCGTCCGCCG
TGATCCATGCGGTTACCGCCCGCGTGTCGAACCCAGGTGTGCGACGTCAGACAACGGGGAGTGCTCCTTTTGGCT
TCCTTCCAGGCGCGGCGGCTGCTGCGCTAGCTTTTTTGGCCACTGGCCGCGCGCAGCGTAAGCGGTTAGGCTGGAA
AGCGAAAGCATTAAGTGGCTCGCTCCCTGTAGCCGGAGGGTTATTTTCCAAGGGTTGAGTCGCGGGACCCCCGGTT
CGAGTCTCGGACCGGCCGGACTGCGGCGAACGGGGGTTTGCCTCCCCGTCATGCAAGACCCCGCTTGCAAATTCCT
CCGGAAACAGGGACGAGCCCCTTTTTTGCTTTTCCCAGATGCATCCGGTGCTGCGGCAGATGCGCCCCCCTCCTCA
GCAGCGGCAAGAGCAAGAGCAGCGGCAGACATGCAGGGCACCCTCCCCTCCTCCTACCGCGTCAGGAGGGGCGACA
TCCGCGGTTGACGCGGCAGCAGATGGTGATTACGAACCCCCGCGGCGCCGGGCCCGGCACTACCTGGACTTGGAGG
AGGGCGAGGGCCTGGCGCGGCTAGGAGCGCCCTCTCCTGAGCGGTACCCAAGGGTGCAGCTGAAGCGTGATACGCG
TGAGGCGTACGTGCCGCGGCAGAACCTGTTTCGCGACCGCGAGGGAGAGGAGCCCGAGGAGATGCGGGATCGAAAG
TTCCACGCAGGGCCGAGCTGCGGCATGGCCTGAATCGCGAGCGGTTGCGCGAGGAGGACTTTGAGCCCGACG
CGCGAACCGGGATTAGTCCCGCGCGCGCACACGTGGCGGCGCCGACCTGGTAACGCCATACGAGCAGACGGTGAA
CCAGGAGATTAACTTTCAAAAAGCTTTAACAACCACGTGCGTACGCTTGTGGCGCGCGAGGAGGTGGCTATAGGA
CTGATGCATCTGTGGGACTTTGTAAGCGCGCTGGAGCAAAACCCAAATAGCAAGCCGCTCATGGCGCAGCTGTTCC
TTATAGTGCAGCACAGCAGGGACAACGAGGCATTCAGGGATGCGCTGCTAAACATAGTAGAGCCCGAGGGCCGCTG
GCTGCTCGATTTGATAAACATCCTGCAGAGCATAGTGGTGCAGGAGCGCAGCTTGAGCCTGGCTGACAAGGTGGCC
GCCATCAACTATTCCATGCTTAGCCTGGGCAAGTTTTACGCCCGCAAGATATACCATACCCCTTACGTTCCCATAG
ACAAGGAGGTAAAGATCGAGGGGTTCTACATGCGCATGGCGCTGAAGGTGCTTACCTTGAGCGACGACCTGGGCGT
TTATCGCAACGAGCGCATCCACAAGGCCGTGAGCGTGAGCCGGCGGCGCGAGCTCAGCGACCGCGAGCTGATGCAC
AGCCTGCAAAGGGCCCTGGCTGGCACGGGCAGCGGCGATAGAGAGGCCGAGTCCTACTTTGACGCGGGCGCTGACC
TGCGCTGGGCCCCAAGCCGACGCGCCCTGGAGGCAGCTGGGGCCGGACCTGGGCTGGCGGTGGCACCCGCGCGCGC
TGGCAACGTCGGCGGCGTGGAGGAATATGACGAGGACGATGAGTACGAGCCAGAGGACGGCGAGTACTAAGCGGTG
ATGTTTCTGATCAGATGATGCAAGACGCAACGGACCCGGCGGTGCGGGCGGCGCTGCAGAGCCAGCCGTCCGGCCT
TAACTCCACGGACGACTGGCGCCAGGTCATGGACCGCATCATGTCGCTGACTGCGCGCAATCCTGACGCGTTCCGG
CAGCAGCCGCAGGCCAACCGGCTCTCCGCAATTCTGGAAGCGGTGGTCCCGGCGCGCGCAAACCCCACGCACGAGA
AGGTGCTGGCGATCGTAAACGCGCTGGCCGAAAACAGGGCCATCCGGCCCGACGAAGCCGGCCTGGTCTACGACGC
GCTGCTTCAGCGCGTGGCTCGTTACAACAGCGGCAACGTGCAGACCAACCTGGACCGGCTGGTGGGGATGTGCGC
GAGGCCGTGGCGCAGCGTGAGCGCGCGCAGCAGCAGGGCAACCTGGGCTCCATGGTTGCACTAAACGCCTTCCTGA
```

FIGURE 17 (cont.)

```
GTACACAGCCCGCCAACGTGCCGCGGGGACAGGAGGACTACACCAACTTTGTGAGCGCACTGCGGCTAATGGTGAC
TGAGACACCGCAAAGTGAGGTGTACCAGTCTGGGCCAGACTATTTTTTCCAGACCAGTAGACAAGGCCTGCAGACC
GTAAACCTGAGCCAGGCTTTCAAAAACTTGCAGGGGCTGTGGGGGGTGCGGGCTCCCACAGGCGACCGCGCGACCG
TGTCTAGCTTGCTGACGCCCAACTCGCGCCTGTTGCTGCTGCTAATAGCGCCCTTCACGGACAGTGGCAGCGTGTC
CCGGGACACATACCTAGGTCACTTGCTGACACTGTACCGCGAGGCCATAGGTCAGGCGCATGTGGACGAGCATACT
TTCCAGGAGATTACAAGTGTCAGCCGCGCGCTGGGGCAGGAGGACACGGGCAGCCTGGAGGCAACCCTAAACTACC
TGCTGACCAACCGGCGGCAGAAGATCCCCTCGTTGCACAGTTTAAACAGCGAGGAGGAGCGCATTTTGCGCTACGT
GCAGCAGAGCGTGAGCCTTAACCTGATGCGCGACGGGGTAACGCCCAGCGTGGCGCTGGACATGACCGCGCGCAAC
ATGGAACCGGGCATGTATGCCTCAAACCGGCCGTTTATCAACCGCCTAATGGACTACTTGCATCGCGCGGCCGCCG
TGAACCCGAGTATTTCACCAATGCCATCTTGAACCCGCACTGGCTACCGCCCCTGGTTTCTACACCGGGGATT
CGAGGTGCCCGAGGGTAACGATGGATTCCTCTGGGACGACATAGACGACAGCGTGTTTCCCCGCAACCGCAGACC
CTGCTAGAGTTGCAACAGCGCGAGCAGGCAGAGGCGGCGCTGCGAAAGGAAAGCTTCCGCAGGCCAAGCAGCTTGT
CCGATCTAGGCGCTGCGGCCCCGCGGTCAGATGCTAGTAGCCCATTTCCAAGCTTGATAGGGTCTCTTACCAGCAC
TCGCACCACCCGCCCGCGCCTGCTGGGCGAGGAGGAGTACCTAAACAACTCGCTGCTGCAGCCGCAGCGCGAAAAA
AACCTGCCTCCGGCATTTCCCAACAACGGGATAGAGAGCCTAGTGGACAAGATGAGTAGATGGAAGACGTACGCGC
AGGAGCACAGGGACGTGCCAGGCCCGCGCCCGCCCACCCGTCGTCAAAGGCACGACCGTCAGCGGGTCTGGTGTG
GGAGGACGATGACTCGGCAGACGACAGCAGCGTCCTGGATTTGGGAGGGAGTGGCAACCCGTTTGCGCACCTTCGC
CCCAGGCTGGGGAGAATGTTTTAAAAAAAAAAAAGCATGATGCAAATAAAAAACTCACCAAGGCCATGGCACCGA
GCGTTGGTTTTCTTGTATTCCCCTTAGTATGCGGCGCGGCGATGTATGAGGAAGGTCCTCCTCCCTCCTACGAG
AGTGTGGTGAGCGCGGCGCCAGTGGCGGCGGCGGTTCTCCCTTCGATGCTCCCCTGGACCCGCCGTTTGTGC
CTCCGCGGTACCTGCGGCCTACCGGGGGGAGAAACAGCATCCGTTACTCTGAGTTGGCACCCCTATTCGACACCAC
CCGTGTGTACCTGGTGGACAACAAGTCAACGGATGTGGCATCCCTGAACTACCAGAACGACCACAGCAACTTTCTG
ACCACGGTCATTCAAAACAATGACTACAGCCCGGGGAGGCAAGCACACAGACCATCAATCTTGACGACCGGTCGC
ACTGGGGCGGCGACCTGAAAACCATCCTGCATACCAACATGCCAAATGTGAACGAGTTCATGTTTACCAATAAGTT
TAAGGCGCGGGTGATGGTGTCGCGCTTGCCTACTAAGGACAATCAGGTGGAGCTGAAATACGAGTGGGTGGAGTTC
ACGCTGCCCGAGGGCAACTACTCCGAGACCATGACCATAGACCTTATGAACAACGCGATCGTGGAGCACTACTTGA
AAGTGGGCAGACAGAACGGGGTTCTGGAAAGCGACATCGGGGTAAAGTTTGACACCCGCAACTTCAGACTGGGGTT
TGACCCCGTCACTGGTCTTGTCATGCCTGGGGTATATACAAACGAAGCCTTCCATCCAGACATCATTTTGCTGCCA
GGATGCGGGGTGGACTTCACCCACAGCCGCCTGAGCAACTTGTTGGGCATCCGCAAGCGGCAACCCTTCCAGGAGG
GCTTTAGGATCACCTACGATGATCTGGAGGGTGGTAACATTCCCGCACTGTTGGATGTGGACGCCTACCAGGCGAG
CTTGAAAGATGACACCGAACAGGGCGGGGGTGGCGCAGGCGGCAGCAACAGCAGTGGCAGCGGCGCGGAAGAGAAC
TCCAACGCGGCAGCCGCGGCAATGCAGCCGGTGGAGGACATGAACGATCATGCCATTCGCGGCGACACCTTTGCCA
CACGGGCTGAGGAGAAGCGCGCTGAGGCCGAAGCAGCGGCCGAAGCTGCCGCCCCGCTGCGCAACCCGAGGTCGA
GAAGCCTCAGAAGAAACCGGTGATCAAACCCCTGACAGAGGACAGCAAGAAACGCAGTTACAACCTAATAAGCAAT
GACAGCACCTTCACCCAGTACCGCAGCTGGTACCTTGCATACAACTACGGCGACCCTCAGACCGGAATCCGCTCAT
GGACCCTGCTTTGCACTCCTGACGTAACCTGCGGCTCGGAGCAGGTCTACTGGTCGTTGCCAGACATGATGCAAGA
CCCCGTGACCTTCCGCTCCACGCGCCAGATCAGCAACTTTCCGGTGGTGGGCGCCGAGCTGTTGCCCGTGCACTCC
AAGAGCTTCTACAACGACCAGGCCGTCTACTCCCAACTCATCCGCCAGTTTACCTCTCGACCCCACGTGTTCAATC
GCTTTCCCGAGAACCAGATTTTGCGCGCCCGCCCAGCCCCCACCATCACCACCGTCAGTGAAAACGTTCCTGCTCT
CACAGATCACGGGACGCTACCGCTGCCAACAGCATCGGAGGAGTCCAGCGAGTGACCATTACTGACGCCAGACGC
CGCACCTGCCCCTACGTTTACAAGGCCCTGGGCATAGTCTCGCCGCGCGTCCTATCGAGCCGCACTTTTTGAGCAA
GCATGTCCATCCTTATATCGCCCAGCAATAACACAGGCTGGGGCCTGCGCTTCCCAAGCAAGATGTTTGGCGGGGC
CAAGAAGCGCTCCGACCAACACCCAGTGCGCGTGCGCGGGCACTACGCGCGCCCTGGGCGCGCACAAACGCGGC
CGCACTGGGCGCACCACCGTCGATGACGCCATCGACGCGGTGGTGGAGGAGGCGCGCAACTACACGCCCACGCCGC
CACCAGTGTCCACAGTGGACGCGGCCATTCAGACCGTGGTGCGCGGAGCCCGGCGCTATGCTAAAATGAAGAGACG
GCGGAGGCGCGTAGCACGTCGCCACCGCCGCCGACCCGGCACTGCCGCCCAACGCGCGGCGGCGGCCCTGCTTAAC
CGCGCACGTCGCACCGGCCGACGGGCGGCCATGCGGGCCGCTCGAAGGCTGGCCGCGGGTATTGTCACTGTGCCCC
CCAGGTCCAGGCGACGAGCGGCCGCCGCAGCAGCCGCGGCCATTAGTGCTATGACTCAGGGTCGCAGGGGCAACGT
GTATTGGGTGCGCGACTCGGTTAGCGGCCTGCGCGTGCCCGTGCGCACCCGCCCCCGCGCAACTAGATTGCAAGA
AAAAACTACTTAGACTCGTACTGTTGTATGTATCCAGCGGCGGCGGCGCGCAACGAAGCTATGTCCAAGCGCAAAA
TCAAAGAAGAGATGCTCCAGGTCATCGCGCCGGAGATCTATGGCCCCCGAAGAAGGAAGAGCAGGATTACAAGCC
CCGAAAGCTAAAGCGGGTCAAAAAGAAAAAGAAAGATGATGATGATGAACTTGACGACGAGGTGGAACTGCTGCAC
GCTACCGCGCCCAGGCGACGGGTACAGTGGAAAGGTCGACGCGTAAAACGTGTTTTGCGACCCGGCACCACCGTAG
TCTTTACGCCCGGTGAGCGCTCCACCCGCACCTACAAGCGCGTGTATGATGAGGTGTACGGCGACGAGGACCTGCT
TGAGCAGGCCAACGACGCGCCTCGGGGAGTTTGCCTACGGAAAGCGGCATAAGGACATGCTGGCGTTGCCGCTGGAC
GAGGGCAACCCAACACCTAGCCTAAAGCCCGTAACACTGCAGCAGGTGCTGCCCGCCGCTTGCACCGTCCGAAGAAA
AGCGCGGCCTAAAGCGAGTCTGGTGACTTGGCACCCACCGTGCAGCTGATGTACCCAAGCGCCAGCGACTGGA
AGATGTCTTGGAAAAAATGACCGTGGAACCTGGGCTGGAGCCCGAGGTCCGCGTGCGGCCAATCAAGCAGGTGGCG
CCGGGACTGGGCGTGCAGACCGTGGACGTTCAGATACCCACTACCAGTAGCACCAGTATTGCCACCGCCACAGAGG
GCATGGAGACACAAACGTCCCCGGTTGCCTCAGCGGTGGCGGATGCCGCGGTGCAGGCGGTCGCTGCGGCCGCGTC
CAAGACCTCTACGGAGGTGCAAACGGACCCGTGGATGTTTCGCGTTTCAGCCCCCCGGCGCCCGCGCGGTTCGAGG
```

FIGURE 17 (cont.)

```
AAGTACGGCGCCGCCAGCGCGCTACTGCCCGAATATGCCCTACATCCTTCCATTGCGCCTACCCCCGGCTATCGTG
GCTACACCTACCGCCCCAGAAGACGAGCAACTACCCGACGCCGAACCACCACTGGAACCCGCCGCCGCCGTCGCCG
TCGCCAGCCCGTGCTGGCCCCGATTTCCGTGCGCAGGGTGGCTCGCGAAGGAGGCAGGACCCTGGTGCTGCCAACA
GCGCGCTACCACCCCAGCATCGTTTAAAAGCCGGTCTTTGTGGTTCTTGCAGATATGGCCCTCACCTGCCGCCTCC
GTTTCCCGGTGCCGGGATTCCGAGGAAGAATGCACCGTAGGAGGGGCATGGCCGGCTACGGCCTGACGGGCGGCAT
GCGTCGTGCGCACCACCGGCGGCGGCGCGCGTCGCACCGTCGCATGCGCGGCGGTATCCTGCCCCTCCTTATTCCA
CTGATCGCCGCGGCGATTGGCGCCGTGCCCGGAATTGCATCCGTGGCCTTGCAGGCGCAGAGACACTGATTAAAAA
CAAGTTGCATGTGGAAAAATCAAAATAAAAAGTCTGGACTCTCACGCTCGCTTGGTCCTGTAACTATTTTGTAGAA
TGGAAGACATCAACTTTGCGTCTCTGGCCCCGCGACACGGCTCGCGCCCGTTCATGGGAAACTGGCAAGATATCGG
CACCAGCAATATGAGCGGTGGCGCCTTCAGCTGGGGCTCGCTGTGGAGCGGCATTAAAAATTTCGGTTCCACCGTT
AAGAACTATGGCAGCAAGGCCTGGAACAGCAGCACAGGCCAGATGCTGAGGGATAAGTTGAAAGAGCAAAATTTCC
AACAAAAGGTGGTAGATGGCCTGGCCTCTGGCATTAGCGGGTGGTGGACCTGGCCAACCAGGCAGTGCAAAATAA
GATTAACAGTAAGCTTGATCCCCGCCCTCCCGTAGAGGAGCCTCCACCGGCCGTGGAGACAGTGTCTCCAGAGGGG
CGTGGCGAAAAGCGTCCGCGCCCGACAGGGAAGAAACTCTGGTGACGCAAATAGACGAGCCTCCCTCGTACGAGG
AGGCACTAAAGCAAGGCCTGCCCACCACCCGTCCCATCGCGCCCATGGCTACCGGAGTGCTGGGCCAGCACACACC
CGTAACGCTGGACCTGCCTCCCCCGCCGACACCCAGCAGAAACCTGTGCTGCCAGGCCCGACCGCCGTTGTTGTA
ACCCGTCCTAGCCGCGCGTCCCTGCGCCGCGCCGCCAGCGGTCCGCGATCGTTGCGGCCCGTAGCCAGTGGCAACT
GGCAAAGCACACTGAACAGCATCGTGGGTCTGGGGGTGCAATCCCTGAAGCGCCGACGATGCTTCTGAATAGCTAA
CGTGTCGTATGTGTGTCATGTATGCGTCCATGTCGCCGCCAGAGGAGCTGCTGAGCCGCCGCGCGCCCGCTTTCCA
AGATGGCTACCCCTTCGATGATGCCGCAGTGGTCTTACATGCACATCTCGGGCCAGGACGCCTCGGAGTACCTGAG
CCCCGGGCTGGTGCAGTTTGCCCGCGCCACCGAGACGTACTTCAGCCTGAATAACAAGTTTAGAAACCCCACGGTG
GCGCCTACGCACGACGTGACCACAGACCGGTCCCAGCGTTTGACGCTGCGGTTCATCCCTGTGGACCGTGAGGATA
CTGCGTACTCGTACAAGGCGCGGTTCACCCTAGCTGTGGGTGATAACCGTGTGCTGGACATGGCTTCCACGTACTT
TGACATCCGGCGTGCTGGACAGGGGCCCTACTTTTAAGCCCTACTCTGGCACTGCCTACAACGCCCTGGCTCCC
AAGGGTGCCCCAAATCCTTGCGAATGGGATGAAGCTGCTACTGCTCTTGAAATAAACCTAGAAGAAGAGGACGATG
ACAACGAAGACGAAGTAGACGAGCAAGCTGAGCAGCAAAAAAACTCACGTATTTGGGCAGGCGCCTTATTCTGGTAT
AAATATTACAAAGGAGGGTATTCAAATAGGTGTCGAAGGTCAAACACCTAAATATGCCGATAAAACATTTCAACCT
GAACCTCAAATAGGAGAATCTCAGTGGTACGAAACTGAAATTAATCATGCAGCTGGGAGAGTCCTTAAAAAGACTA
CCCCAATGAAACCATGTTACGGTTCATATGCAAAACCCACAAATGAAAATGGAGGGCAAGGCATTCTTGTAAAGCA
ACAAAATGAAAGCTAGAAAGTCAAGTGGAAATGCAATTTTTCTCAACTACTGAGGCGACCGCAGGCAATGGTGAT
AACTTGACTCCTAAAGTGGTATTGTACAGTGAAGATGTAGATATAGAAACCCCAGACACTCATATTTCTTACATGC
CCACTATTAAGGAAGGTAACTCACGAGAACTAATGGGCCAACAATCTATGCCCAACAGGCCTAATTACATTGCTTT
TAGGGACAATTTTATTGGTCTAATGTATTACAACAGCACGGGTAATATGGGTGTTCTGGCGGCCAAGCATCGCAG
TTGAATGCTGTTGTAGATTTGCAAGACAGAAACACAGAGCTTTCATACCAGCTTTTGCTTGATTCCATTGGTGATA
GAACCAGGTACTTTTCTATGTGGAATCAGGCTGTTGACAGCTATGATCCAGATGTTAGAATTATTGAAAATCATGG
AACTGAAGATGAACTTCCAAATTACTGCTTTCCACTGGGAGGTGTGATTAATACAGAGACTCTTACCAAGGTAAAA
CCTAAAACAGGTCAGGAAAATGGATGGGAAAAAGATGCTACAGAATTTTCAGATAAAAATGAAATAAGAGTTGGAA
ATAATTTTGCCATGGAAATCAATCTAAATGCCAACCTGTGGAGAAATTTCCTGTACTCCAACATAGCGCTGTATTT
GCCCGACAAGCTAAAGTACAGTCCTTCCAACGTAAAAATTTCTGATAACCCAAACACCTACGACTACATGAACAAG
CGAGTGGTGGCTCCCGGGTTAGTGGACTGCTACATTAACCTTGGAGCACGCTGGTCCCCTTGACTATATGGACAACG
TCAACCCATTTAACCACCACGCAATGCTGGCCTGCGCCTCAATGTTGCTGGGCAATGGTCGCTATGTGCC
CTTCCACATCCAGGTGCCTCAGAAGTTCTTTGCCATTAAAAACCTCCTTCTCCTGCCGGGCTCATACACCTACGAG
TGGAACTTCAGGAAGGATGTTAACATGGTTCTGCAGAGCTCCCTAGGAAATGACCTAAGGGTTGACGGAGCCAGCA
TTAAGTTTGATAGCATTTGCCTTTACGCCACCTTCTTCCCCATGGCCCACAACACCGCCTCCACGCTTGAGGCCAT
GCTTAGAAACGACACCAACGACCAGTCCTTTAACGACTATCTCTCCGCCGCCAACATGCTCTACCCTATACCCGCC
AACGCTACCAACGTGCCCATATCCATCCCCTCCCGCAACTGGGCGGCTTTCCGCGGCTGGGCCTTCACGCGCCTTA
AGACTAAGGAAACCCCATCACTGGGCTCGGCTACGACCCTTATTACACCTACTCTGGCTCTATACCCTACCTAGA
TGGAACCTTTTACCTCAACCACACCTTTAAGAAGGTGGCCATTACCTTTGACTCTTCTGTCAGCTGGCCTGGCAAT
GACCGCCTGCTTACCCCCAACGAGTTTGAAATTAAGCGCTCAGTTGACGGGGAGGGTTACAACGTTGCCCAGTGTA
ACATGACCAAAGACTGGTTCCTGGTACAAATGCTAGCTAACTACAACATTGGCTACCAGGGCTTCTATATCCCAGA
GAGCTACAAGGACCGCATGTACTCCTTCTTTAGAAACTTCCAGCCCATGAGCCGTCAGGTGGTGGATGATACTAAA
TACAAGGACTACCAACAGGTGGGCATCCTACACCAACACAACAACTCTGGATTTGTTGGCTACCTTGCCCCCACCA
TGCGCGAAGGACAGGCCTACCCTGCTAACTTCCCCTATCCGCTTATAGGCAAGACCGCAGTTGACAGCATTACCCA
GAAAAAGTTTCTTTGCGATCGCACCCTTTGGCGCATCCCATTCTCCAGTAACTTTATGTCCATGGGCGCACTCACA
GACCTGGGCCAAAACCTTCTCTACGCCAACTCCGCCCACGCGCTAGACATGACTTTTGAGGTGGATCCCATGGACG
AGCCCACCCTTCTTTATGTTTTGTTTGAAGTGCTTTGACGTGGTCCGTGTGCACCGGCCGCACCGCGGCGTCATCGA
AACCCGTGTACCTGCGCACGCCCTTCTCGGCCGGCAACGCCACAACATAAAGAAGCAAGCAACATCAACAACAGCTG
CCGCCATGGGCTCCAGTGAGCAGGAACTGAAAGCCATTGTCAAAGATCTTGGTTGTGGGCCATATTTTTTGGGCAC
CTATGACAAGCGCTTTCCAGGCTTTGTTTCTCCACACAAGCTCGCCTGCGCCATAGTCAATACGGCCGGTCGCGAG
ACTGGGGGCGTACACTGGATGGCCTTTGCCTGGAACCCGCACTCAAAAACATGCTACCTCTTTGAGCCCTTTGGCT
TTTCTGACCAGCGACTCAAGCAGGTTTACCAGTTTGAGTACGAGTCACTCCTGCGCCGTAGCGCCATTGCTTCTTC
```

FIGURE 17 (cont.)

```
CCCCGACCGCTGTATAACGCTGGAAAAGTCCACCCAAAGCGTACAGGGGCCCAACTCGGCCGCCTGTGGACTATTC
TGCTGCATGTTTCTCCACGCCTTTGCCAACTGGCCCCAAACTCCCATGGATCACAACCCCACCATGAACCTTATTA
CCGGGGTACCCAACTCCATGCTCAACAGTCCCCAGGTACAGCCCACCCTGCGTCGCAACCAGGAACAGCTCTACAG
CTTCCTGGAGCGCCACTCGCCCTACTTCCGCAGCCACAGTGCGCAGATTAGGAGCGCCACTTCTTTTTGTCACTTG
AAAAACATGTAAAAATAATGTACTAGAGACACTTTCAATAAAGGCAAATGCTTTTATTTGTACACTCTCGGGTGAT
TATTTACCCCCACCCTTGCCGTCTGCGCCGTTTAAAAATCAAAGGGGTTCTGCCGCGCATCGCTATGCGCCACTGG
CAGGGACACGTTGCGATACTGGTGTTTAGTGCTCCACTTAAACTCAGGCACAACCATCCGCGGCAGCTCGGTGAAG
TTTTCACTCCACAGGCTGCGCACCATCACCAACGCGTTTAGCAGGTCGGGCGCCGATATCTTGAAGTCGCAGTTGG
GGCCTCCGCCCTGCGCGCGCGAGTTGCGATACACAGGGTTGCAGCACTGGAACACTATCAGCGCCGGGTGGTGCAC
GCTGGCCAGCACGCTCTTGTCGGAGATCAGATCCGCGTCCAGGTCCTCCGCGTTGCTCAGGGCGAACGGAGTCAAC
TTTGGTAGCTGCCTTCCAAAAGGGCGCGTGCCCAGGCTTTGAGTTGCACTCGCACCGTAGTGGCATCAAAAGGT
GACCGTGCCCGGTCTGGGCGTTAGGATACAGCGCCTGCATAAAAGCCTTGATCTGCTTAAAAGCCACCTGAGCCTT
TGCGCCTTCAGAGAAGAACATGCCGCAAGACTTGCCGGAAAACTGATTGGCCGGACAGGCCGCGTCGTGCACGCAG
CACCTTGCGTCGGTGTTGGAGATCTGCACCACATTTCGGCCCCACCGGTTCTTCACGATCTTGGCCTTGCTAGACT
GCTCCTTCAGCGCGCGCTGCCCGTTTTCGCTCGTCACATCCATTTCAATCACGTGCTCCTTATTTATCATAATGCT
TCCGTGTAGACACTTAAGCTCGCCTTCGATCTCAGCGCAGCGGTGCAGCCACAACGCGCAGCCCGTGGGCTCGTGA
TGCTTGTAGGTCACCTCTGCAAACGACTGCAGGTACGCCTGCAGGAATCGCCCCATCATCGTCACAAAGGTCTTGT
TGCTGGTGAAGGTCAGCTGCAACCCGCGGTGCTCCTCGTTCAGCCAGGTCTTGCATACGGCCGCCAGAGCTTCCAC
TTGGTCAGGCAGTAGTTTGAAGTTCGCCTTTAGATCGTTATCCACGTGGTACTTGTCCATCAGCGCGCGCAGCC
TCCATGCCCTTCTCCCACGCAGACACGATCGGCACACTCAGCGGGTTCATCACCGTAATTTCACTTTCCGCTTCGC
TGGGCTCTTCCTCTTCCTCTTGCGTCCGCATACCACGCGCCACTGGGTCGTCTTCATTCAGCCGCCGCACTGTGCG
CTTACCTCCTTTGCCATGCTTGATTAGCACCGGTGGGTTGCTGAAACCCACCATTTGTAGCGCCACATCTTCTCTT
TCTTCCTCGCTGTCCACGATTACCTCTGGTGATGGCGGGCGCTCGGGCTTGGGAGAAGGGCGCTTCTTTTTCTTCT
TGGGCGCAATGGCCAAATCCGCCGCCGAGGTCGATGGCCGCGGGCTGGGTGTGCGCGGCACCAGCGCGTCTTGTGA
TGAGTCTTCCTCGTCCTCGGACTCGATACGCCGCCTCATCCGCTTTTTTGGGGGCGCCCGGGGAGGCGGCGGCGAC
GGGGACGGGGACGACACGTCCTCCATGGTTGGGGACGTCGCGCCGCACCGCGTCCGCGCTCGGGGGTGGTTTCGC
GCTGCTCCTCTTCCCGACTGGCCATTTCCTTCTCCTATAGGCAGAAAAAGATCATGGAGTCAGTCGAGAAGAAGGA
CAGCCTAACCGCCCCCTCTGAGTTCGCCACCACCGCCTCCACCGATGCCGCCAACGCGCCTACCACCTTCCCCGTC
GAGGCACCCCCGCCTTGAGGAGGAGGAAGTGATTATCGAGCAGGACCCCAGGTTTTGTAAGCGAAGACGACGAGGACC
GCTCAGTACCAACAGAGGATAAAAAGCAAGACCAGGACAACGCAGAGGCAAACGAGGAACAAGTCGGGCGGGGGA
CGAAAGGCATGGCGACTACCTAGATGTGGGAGACGACGTGCTGTTGAAGCATCTGCAGCGCCAGTGCGCCATTATC
TGCGACGCGTTGCAAGAGCGCAGCGATGTGCCCCTCGCCATAGCGGATGTCAGCCTTGCCTACGAACGCCACCTAT
TCTCACCGCGCGTACCCCCAAACGCCAAGAAAACGGCACATGCGAGCCCAACCCGCGCCTCAACTTCTACCCCGT
ATTTGCCGTGCCAGAGGTGCTTGCCACCTATCACATCTTTTTCCAAAACTGCAAGATACCCCTATCCTGCCGTGCC
AACCGCAGCCGAGCGGACAAGCAGCTGGCCTTGCGGCAGGGCGCTGTCATACCTGATATCGCCTCGCTCAACGAAG
TGCCAAAAATCTTTGAGGGTCTTGGACGCGACGAGAAGCGCGCGGCAAACGCTCTGCAACAGGAAAACAGCGAAAA
TGAAAGTCACTCTGGAGTGTTGGTGGAACTCGAGGGTGACAACGCGCGCCTAGCCGTACTAAAACGCAGCATCGAG
GTCACCCACTTTGCCTACCCGGCACTTAACCTACCCCCCAAGGTCATGAGCACAGTCATGAGTGAGCTGATCGTGC
GCCGTGCGCAGCCCCTGGAGAGGGGATGCAAATTTGCAAGAACAAACAGAGGAGGGCCTACCCGCAGTTGGCGACGA
GCAGCTAGCGCGCTGGCTTCAAACGCGCGAGCCTGCCGACTTGGAGGAGCGACGCAAACTAATGATGGCCGCAGTG
CTCGTTACCGTGGAGCTTGAGTGCATGCAGCGGTTCTTTGCTGACCCGGAGATGCAGCGCAAGCTAGAGGAAACAT
TGCACTACACCTTTCGACAGGGCTACGTACGCCAGGCCTGCAAGATCTCCAACGTGGAGCTCTGCAACCTGGTCTC
CTACCTTGGAATTTTGCACGAAAACCGCCTTGGGCAAAACGTGCTTCATTCCACGCTCAAGGGCGAGGCGCGCCGC
GACTACGTCCGCGACTGCGTTTACTTATTTCTATGCTACACCTGGCAGACGGCCATGGGCGTTTGGCAGCAGTGCT
TGGAGGAGTGCAACCTCAAGGAGCTGCAGAAACTGCTAAAGCAAACTTGAAGGACCTATGGACGGCCTTCAACGA
GCGCTCCGTGGCCGCGCACCTGGCGGACATCATTTTCCCCGAACGCCTGCTTAAAACCCTGCAACAGGGTCTGCCA
GACTTCACCAGTCAAAGCATGTTGCAGAACTTTAGGAACTTTATCCTAGAGCGCTCAGGAATCTTGCCCGCCACCT
GCTGTGCACTTCCTAGCGACTTTGTGCCCATTAAGTACCGCGAATGCCCTCCGCCGCTTTGGGGCCACTGCTACCT
TCTGCAGCTAGCCAACTACCTTGCCTACCACTCTGACATAATGGAAGACGTGAGCGGTGACGGTCTACTGGAGTGT
CACTGTCGCTGCAACCTATGCACCCCGCACCGCTCCCTGGTTTGCAATTCGCAGCTGCTTAACGAAAGTCAAATTA
TCGGTACCTTTGAGCTGCAGGGTCCCTCGCCTGACGAAAAGTCCGCGGCTCCGGGGTTGAAACTCACTCCGGGGCT
GTGGACGTCGGCTTACCTTCGCAAATTTGTACCTGAGGACTACCACGCCCACGAGATTAGGTTCTACGAAGACCAA
TCCCGCCCGCCAAATGCGGAGCTTACCGCCTGCGTCATTACCCAGGGCCACATTCTTGGCCAATTGCAAGCCATCA
ACAAAGCCCGCCAAGAGTTTCTGCTACGAAAGGGACGGGGGGTTTACTTGGACCCCAGTCCGGCGAGGAGCTCAA
CCCAATCCCCCGCCGCCGCAGCCCTATCAGCAGCAGCCGCGGGCCCTTGCTTCCCAGGATGGCACCCAAAAAGAA
GCTGCAGCTGCCGCCGCCACCCACGGACGAGGAGGAATACTGGGACAGTCAGGCAGAGGAGGTTTTGGACGAGGAG
GAGGAGGACATGATGGAAGACTGGGAGAGCCTAGACGAGGAAGCTTCCGAGGTCGAAGAGGTGTCAGACGAAACAC
CGTCACCCTCGGTCGCATTCCCCTCGCCGGCGCCCCAGAAATCGGCAACCGGTTCCAGCATGGCTACAACCTCCGC
TCCTCAGGCGCCGCCGGCACTGCCCGTTCGCCGACCCAACCGTAGATGGGACACCACTGGAACCAGGGCCGGTAAG
TCCAAGCAGCCGCCGCCGTTAGCCCAAGAGCAACAACAGCGCCAAGGCTACCGCTCATGGCGCGGGCACAAGAACG
CCATAGTTGCTTGCTTGCAAGACTGTGGGGGCAACATCTCCTTCGCCCGCCGCTTTCTTCTCTACCATCACGGCGT
```

FIGURE 17 (cont.)

```
GGCCTTCCCCCGTAACATCCTGCATTACTACCGTCATCTCTACAGCCCATACTGCACCGGCGGCAGCGGCAGCGGC
AGCAACAGCAGCGGCCACACAGAAGCAAAGGCGACCGGATAGCAAGACTCTGACAAAGCCCAAGAAATCCACAGCG
GCGGCAGCAGCAGGAGGAGGAGCGCTGCGTCTGGCGCCCAACGAACCCGTATCGACCCGCGAGCTTAGAAACAGGA
TTTTTCCCACTCTGTATGCTATATTTCAACAGAGCAGGGGCCAAGAACAAGAGCTGAAAATAAAAAACAGGTCTCT
GCGATCCCTCACCCGCAGCTGCCTGTATCACAAAAGCGAAGATCAGCTTCGGCGCACGCTGGAAGACGCGGAGGCT
CTCTTCAGTAAATACTGCGCGCTGACTCTTAAGGACTAGTTTCGCGCCCTTTCTCAAATTTAAGCGCGAAAACTAC
GTCATCTCCAGCGGCCACACCCGGCGCCAGCACCTGTCGTCAGCGCCATTATGAGCAAGGAAATTCCCACGCCCTA
CATGTGGAGTTACCAGCCACAAATGGGACTTGCGGCTGGAGCTGCCCAAGACTACTCAACCCGAATAAACTACATG
AGCGCGGGACCCCACATGATATCCCGGGTCAACGGAATCCGCGCCCACCGAAACCGAATTCTCTTGGAACAGGCGG
CTATTACCACCACACCTCGTAATAACCTTAATCCCCGTAGTTGGCCCGCTGCCCTGGTGTACCAGGAAAGTCCCGC
TCCCACCACTGTGGTACTTCCCAGAGACGCCCAGGCCGAAGTTCAGATGACTAACTCAGGGGCGCAGCTTGCGGGC
GGCTTTCGTCACAGGGTGCGGTCGCCCGGGCAGGGTATAACTCACCTGACAATCAGAGGGCGAGGTATTCAGCTCA
ACGACGAGTCGGTGAGCTCCTCGCTTGGTCTCCGTCCGGACGGGACATTTCAGATCGGCGGCGCCGGCCGTCCTTC
ATTCACGCCTCGTCAGGCAATCCTAACTCTGCAGACCTCGTCCTCTGAGCCGCGCTCTGGAGGCATTGGAACTCTG
CAATTTATTGAGGAGTTTGTGCCATCGGTCTACTTTAACCCCTTCTCGGGACCTCCCGGCCACTATCCGGATCAAT
TTATTCCTAACTTTGACGCGGTAAAGGACTCGGCGGACGGCTACGACTGAATGTTAAGTGGAGAGGCAGAGCAACT
GCGCCTGAAACACCTGGTCCACTGTCGCCGCCACAAGTGCTTTGCCCGCGACTCCGGTGAGTTTTGCTACTTTGAA
TTGCCCGAGGATCATATCGAGGGCCCGGCGCACGGCGTCCGGCTTACCGCCAGGGAGAGCTTGCCCGTAGCCTGA
TTCGGGAGTTTACCCAGCGCCCCTGCTAGTTGAGCGGGACAGGGGACCCTGTGTTCTCACTGTGATTTGCAACTG
TCCTAACCTTGGATTACATCAAGATCCTCTAGTTAATTAACAGCTTGCATGCCTGCAGGTCGACGGATCGGGAGAT
CTCGGCCGCATATTAAGTGCATTGTTCTCGATACCGCTAAGTGCATTGTTCTCGTTAGCTCGATGGACAAGTGCAT
TGTTCTCTTGCTGAAAGCTCGATGGACAAGTGCATTGTTCTCTTGCTGAAAGCTCGATGGACAAGTGCATTGTTCT
CTTGCTGAAAGCTCAGTACCCGGGAGTACCCTCGACCGCCGGAGTATAAATAGAGGCGCTTCGTCTACGGAGCGAC
AATTCAATTCAAACAAGCAAAGTGAACACGTCGCTAAGCGAAAGCTAAGCAAATAAACAAGCGCAGCTGAACAAGC
TAAACAATCTGCAGTAAAGTGCAAGTTAAAGTGAATCAATTAAAAGTAACCAGCAACCAAGTAAATCAACTGCAAC
TACTGAAATCTGCCAAGAAGTAATTATTGAATACAAGAAGAGAACTCTGAATACTTTCAACAAGTTACCGAGAAAG
AAGAACTCACACACAGCTAGCGTTTAAACTTAAGCTTCACCATGGTGGGCCCTGCATGCTGCTGCTGCTGCTGCT
GCTGGGCCTGAGGCTACAGCTCTCCCTGGGCATCATCCTAGTTGAGGAGGAGAACCCGGACTTCTGGAACCGCGAG
GCAGCCGAGGCCCTGGGTGCCGCCAAGAAGCTGCAGCCTGCACAGACAGCCGCCAAGAACCTCATCATCTTCCTGG
GCGATGGGGTGGGGTGTCTACGGTGACAGCTGCCAGGATCCTAAAAGGGCAGAAGAAGGACAAACTGGGGCCTGA
GATACCCCTGGCCATGGACCGCTTCCCATATGTGGCTCTGTCCAAGACATACAATGTAGACAAACATGTGCCAGAC
AGTGGAGCCACAGCCACGGCCTACCTGTGCGGGGTCAAGGGCAACTTCCAGACCATTGGCTTGAGTGCAGCCGCCC
GCTTTAACCAGTGCAACACGACACGCGGCAACGAGGTCATCTCCGTGATGAATCGGGCCAAGAAAGCAGGGAAGTC
AGTGGGAGTGGTAACCACCACACGAGTGCAGCACGCCTCGCCAGCCGGCACCTACGCCCACACGGTGAACCGCAAC
TGGTACTCGGACGCCGACGTGCCTGCCTCGGCCCGCCAGGAGGGGTGCCAGGACATCGCTACGCAGCTCATCTCCA
ACATGGACATTGACGTGATCCTAGGTGGGGCCGAAAGTACATGTTTCGCATGGGAACCCCAGACCCTGAGTACCC
AGATGACTACAGCCAAGGTGGGACCAGGCTGGACGGGAAGAATCTGGTGCAGGAATGGCTGGCGAAGCACCAGGGT
GCCCGGTACGTGTGGAACCGCACTGAGCTCATGCGGGCTTCCCTGGACCCGTCTGTGGCCCATCTCATGGGTCTCT
TTGAGCCTGGAGACATGAAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCGCATCGACCATGGTCAT
CATGAAAGCAGGGCTTACCGGGCACTGACTGAGACGATCATGTTCGACGACGCCATTGAGAGGCGGGCCAGCTCA
CCAGCGAGGAGGACACGCTGAGCCTCGTCACTGCCGACCACTCCCACGTCTTCTCCTTCGGAGGCTGCCCCTGCG
AGGGGGCTCCATCTTCGGGCTGGCCCCTGGCAAGGCCCGGGACAGGAAGGCCTACACGGTCCTCCTATACGGAAAC
GGTCCAGGCTATGTGCTCAAGGACGGCGCCCGGCCGGATGTTACCGAGAGCGAGAGCGGGAGCCCCGAGTATCGGC
AGCAGTCAGCAGTGCCCCTGGACGAAGAGACCCACGCAGGCGAGGACGTGGCGGTGTTCGCGCGCGGCCCGCAGGC
GCACCTGGTTCACGGCGTGCAGGAGCAGACCTTCATAGCGCACGTCATGGCCTTCGCCGCCTGCCTGGAGCCCTAC
ACCGCCTGCGACCTGGCGCCCCCGCCGGCACCACCGACGCCGCGCACCCGGGCGGTCCGTGGTCCCGCGTTGC
TTCCTCTGCTGGCCGGGACCCTGCTGCTGCTGGAGACGGCCACTGCTCCCTGAGTGTCCCGTCCCTGGGCTCCTG
CTTCCCCATCCCGGAGTTCTCCTGCTCCCCGCCTCCTGTCGTCCTGCCTGGCCTCCAGCCCGAGTCGTCATCCCCG
GAGTCCCTATACAGAGGTCCTGCCATGGAACCTTCCCCTCCCCGTGCGCTCTGGGGACTGAGCCCATGACACCAAA
CCTGCCCCTTGGCTGCTCTCGGACTCCCTACCCCAACCCCAGGGACAGATCTGGCCAGATTTGTAAAACAAATAGA
TTTTAGGCCCAAAGATTATTTAAAGCATTGCCTGGAACGCAGTGAGTTTTTGTTAGAAAAGAGAATAATTCAAAGT
GGCATTGCTTTGCTTCTTATGTTAATTTGGTACAGACCTGGCTGAGTTTGCTCAAAGTATTCAGAGCAGAATTG
TGGAGTGGAAAGAGAGATTGGACAAAGAGTTTAGTTTGTCAGTGTATCAAAAAATGAAGTTTAATGTGGCTATGGG
AATTGGAGTTTTAGATTGGCTAAGAAACAGTGATGATGATGATGAAGACAGCCAGGAAAATGCTGATAAAAATGAA
GATGGTGGGGAGAAGAACATGGAAGACTCAGGGCATGAAACAGGCATTGATTCACAGTCCCAAGGCTCATTTCAGG
CCCCTCAGTCCTCACAGTCTGTTCATGATCATAATCAGCCATACCACATTTGTAGAGGTTTTACTTGCTTTAAAAA
ACCTCCCACACCTCCCCCTGAACCTGAAACATAAAATGAATGCAATTGTTGTTGTTAACTTGTTTATTGCAGCTTA
TAATGGTTACAAATAAAGCAATAGCATCACAAATTTCACAAATAAAGCATTTTTTCACTGCATTCTAGTTGTGGT
TTGTCCAAACTCATCAATGTATCTTATCATGTCTGGATCCCCAGGAAGCTCCTCTGTGTCCTCATAAACCCTAACC
TCCTCTACTTGAGAGGACATTCCAATCATAGGCTGCCCATCCACCCTCTGTGTCCTCCTGTTAATTAGGTCACTTA
```

FIGURE 17 (cont.)

```
ACAAAAAGGAAATTGGGTAGGGGTTTTTCACAGACCGCTTTCTAAGGGTAATTTTAAAATATCTGGGAAGTCCCTT
CCACTGCTGTGTTCCAGAAGTGTTGGTAAACAGCCCACAAATGTCAACAGCAGAAACATACAAGCTGTCAGCTTTG
CACAAGGGCCCAACACCCTGCTCATCAAGAAGCACTGTGGTTGCTGTGTTAGTAATGTGCAAAACAGGAGGCACAT
TTTCCCCACCTGTGTAGGTTCCAAAATATCTAGTGTTTTCATTTTTACTTGGATCAGGAACCCAGCACTCCACTGG
ATAAGCATTATCCTTATCCAAAACAGCCTTGTGGTCAGTGTTCATCTGCTGACTGTCAACTGTAGCATTTTTTGGG
GTTACAGTTTGAGCAGGATATTTGGTCCTGTAGTTTGCTAACACACCCTGCAGCTCCAAAGGTTCCCCACCAACAG
CAAAAAAATGAAAATTTGACCCTTGAATGGGTTTTCCAGCACCATTTTCATGAGTTTTTTGTGTCCCTGAATGCAA
GTTTAACATAGCAGTTACCCCAATAACCTCAGTTTTAACAGTAACAGCTTCCCACATCAAAATATTTCCACAGGTT
AAGTCCTCATTTAAATTAGGCAAAGGAATTCCACTTCCCACTGCCTTGCTTCCGTCTCCCATTCAAACTTTTATCA
ACTGACATTATTCTAAGTAAAATCCTCTTCATTATGTTGTCAGCAATCCATTGCTTGAAGGCCTGGCTCCCCAGAA
CCCCTCGACTGGTATGTCTTCTCCTAGAATACTCCAGAAGAAAAGGAGTGTATGAAGATAGTGACTGCACATTAAA
ATGACTGAAACCATAGTAAATTAGGATGAGATTCTGGGCAGATAAACAGACAGCTGGCTAGGATCATTTTTTTATG
CCTTGGACTTCTTTGGCAATCTGTTGAAGCCTGACATTCCTCAGAATAATGTTTTAAAGCCCAACAATAAGACCCT
GTAGCACATATAATAAGTACTGCAGTTTTGAAGTAGTGATAAGCATAAATGATATTTGATATATTTATTATAACT
GTAATGAGATGTGTACATATCTGTGACTTCATAGGTACTGATTGTACTACTGTGATTTTTTGCCTACTTTCAAAA
TGAAAAGGAATGCTTAATTTCAGTTAGAGGTTAGTAAAGACAAATAGGTAATTTTCTTCTCCAGTGAAGAGCATGG
CGCCCCTTGCTATTCATGGACGCTTGCTTAAAGACTTGTACACAGGCTTGCTTTGTATCAACCTATGACTTCCCCT
TACAGCCGATAGGTTTTTATTTGCACCTCCTTCGTGTACAAAGACAGTTTTGGTGGCTACGCCATCATTAAAC
TCATTATTATCATGCTTAAGCCTATAGATGTATCCAGTTCTTCTGTTACATAATTGAAGCTGTAGTGAATTGTCTA
TCTTAAACTGCATCGCTAACTGACTACATTTCACACTTCATTTGCTTCCAACATAGACTAACCTTCTTGGATGTCC
ACTATTATTTGAACTTTTGAGATTTTTTTTCCTATTTCTAATATCTTAAAATTTCAGAAGACTTAAAGTTTTGCAA
CTACAGGGCTCCATATAGACATCTAGCTTGAATTTATACACTTTCTTTCATTGATGTCCCTGGACTAAAAAATGTT
AAATATTTCTAACCGCTGTACTTAAAGTCCATTACAAACGAAGACTACTGTTGTTAAGTTGAATAGGCATCTTATA
TATTTTTCACCGGTGCAATAAATAACTTCTATTCCCTTCTAACATCTGCTTGCGTTGCACTGAGAGTACACTATTG
ATTAGCAATAGGTTCGTGATTACAGCCCTTCTATAATTAATTGTTAGGTTAACATATTATTCATAAAATATTATTT
TATTAATTTTTACTTGATTTGCTACTGGATGCTTAGAAATAGCTATGAGTATATTGGTAGAACCAGTACTTATATT
TTATTACATTTTTACATTTCATAAAATTTAAGTGATATAAAAATCCTGAGGAAGTATGCCACAAAAGTGGTCTCAG
TGGAAATTTAAATATGTTAACATTTATTTTTAAAATGTAGCGTGAAATAGACAACTTTAAAAGCTCAGCTTAAAAA
AAAAACTCAAGGAAGCTGAACTTGACTTTTTAAAGCACTGAAGTGCAATATTTAATGTAGGTCAACATGTTTAAAT
GGGAAAATTTTTTCCTAATTACAGCCAAATCCCTAGCTGTAATTAACTTAAAATTTGTATACTATTTCACAACAG
AGTCAGCATATACCACTTTCTTATAAAATTAGAAAGATCTAAAATTTTAGAGCTTATTTGGTGAAACAGGCATATT
GCTACATCTTTGTTTATAAATTATAATGTGCCTTTAGAGCCCAATAACAGATAACAAGATTTTGAAAATTCAGGTG
AATTAGAGTTATCAGAGGGAATGTTAATACACTCTATTCAAATACTATATGAGTAAGACATTTAAAATAGGAAACA
ATACTTTATATATTAAAAAAAATTAATCTTCCAGTCGATTTAATCCACTTTATGAATTCATTTAAATCGATTTAAA
TTCGAATTAATTAACTAGAATACCCGGGGATCTTATTCCCTTTAACTAATAAAAAAAAATAATAAAGCATCACTTA
CTTAAAATCAGTTAGCAAATTTCTGTCCAGTTTATTCAGCAGCACCTCCTTGCCCTCCTCCCAGCTCTGGTATTGC
AGCTTCCTCCTGGCTGCAAACTTTCTCCACAATCTAAATGGAATGTCAGTTTCCTCCTGTTCCTGTCCATCCGCAC
CCACTATCTTCATGTTGTTGCAGATGAAGCGCGCAAGACCGTCTGAAGATACCTTCAACCCCGTGTATCCATATGA
CACGGAAACCGGTCCTCCAACTGTGCCTTTTCTTACTCCTCCCTTTGTATCCCCCAATGGGTTTCAAGAGAGTCCC
CCTGGGGTACTCTCTTTGCGCCTATCCGAACCTCTAGTTACCTCCAATGGCATGCTTGCGCTCAAAATGGGCAACG
GCCTCTCTCTGGACGAGGCCGGCAACCTTACCTCCCAAAATGTAACCACTGTGAGCCCACCTCTCAAAAAAACCAA
GTCAAACATAAACCTGGAAATATCTGCACCCCTCACAGTTACCTCAGAAGCCCTAACTGTGGCTGCCGCCGCACCT
CTAATGGTCGCGGGCAACACACTCACCATGCAATCACAGGCCCCGCTAACCGTGCACGACTCCAAACTTAGCATTG
CCACCCAAGGACCCCTCACAGTGTCAGAAGGAAAGCTAGCCCTGCAAACATCAGGCCCCCTCACCACCACCGATAG
CAGTACCCTTACTATCACTGCCTCACCCCCTCTAACTACTGCCACTGGTAGCTTGGGCATTGACTTGAAAGAGCCC
ATTTATACACAAAATGGAAAACTAGGACTAAAGTACGGGCTCCTTTGCATGTAACAGACGACCTAAACACTTTGA
CCGTAGCAACTGGTCCAGGTGTGACTATTAATAATACTTCCTTGCAAACTAAAGTTACTGGAGCCTTGGGTTTTGA
TTCACAAGGCAATATGCAACTTAATGTAGCAGGAGGACTAAGGATTGATTCTCAAAACAGACGCCTTATACTTGAT
GTTAGTTATCCGTTTGATGCTCAAAACCAACTAAATCTAAGACTAGGACAGGGCCCTCTTTTTATAAACTCAGCCC
ACAACTTGGATATTAACTACAACAAAGGCCTTTACTTGTTTACAGCTTCAAACAATTCCAAAAAGCTTGAGGTTAA
CCTAAGCACTGCCAAGGGGTTGATGTTTGACGCTACAGCCATAGCCATTAATGCAGGAGATGGGCTTGAATTTGGT
TCACCTAATGCACCAAACACAAATCCCCTCAAAACAAAAATTGGCCATGGCCTAGAATTTGATTCAAACAAGGCTA
TGGTTCCTAAACTAGGAACTGGCCTTAGTTTTGACAGCACAGGTGCCATTACAGTAGGAAACAAAAATAATGATAA
GCTAACTTTGTGGACCACACCAGCTCCATCTCCTAACTGTAGACTAAATGCAGAGAAAGATGCTAAACTCACTTTG
GTCTTAACAAAATGTGGCAGTCAAATACTTGCTACAGTTTCAGTTTTGGCTGTTAAAGGCAGTTTGGCTCCAATAT
CTGGAACAGTTCAAAGTGCTCATCTTATTATAAGATTTGACGAAAATGGAGTGCTACTAAACAATTCCTTCCTGGA
CCCAGAATATTGGAACTTTAGAAATGGAGATCTTACTGAAGGCACCCTATACAAACGCTGTTGGATTTATGCCT
AACCTATCAGCTTATCCAAAATCTCACGGTAAAACTGCCAAAAGTAACATTGTCAGTCAAGTTTACTTAAACGGAG
ACAAAACTAAACCTGTAACACTAACCATTACACTAAACGGTACACAGGAAACAGGAGACACAACTCCAAGTGCATA
CTCTATGTCATTTCATGGGACTGGTCTGGCCACAACTACATTAATGAAATATTTGCCACATCCTCTTACACTTTT
TCATACATTGCCCAAGAATAAAGAATCGTTTGTGTTATGTTTCAACGTGTTTATTTTTCAATTGCAGAAAATTTCA
```

FIGURE 17 (cont.)

```
AGTCATTTTTCATTCAGTAGTATAGCCCCACCACCACATAGCTTATACAGATCACCGTACCTTAATCAAACTCACA
GAACCCTAGTATTCAACCTGCCACCTCCCTCCCAACACACAGAGTACACAGTCCTTTCTCCCCGGCTGGCCTTAAA
AAGCATCATATCATGGGTAACAGACATATTCTTAGGTGTTATATTCCACACGGTTTCCTGTCGAGCCAAACGCTCA
TCAGTGATATTAATAAACTCCCCGGGCAGCTCACTTAAGTTCATGTCGCTGTCCAGCTGCTGAGCCACAGGCTGCT
GTCCAACTTGCGGTTGCTTAACGGGCGGCGAAGGAGAAGTCCACGCCTACATGGGGGTAGAGTCATAATCGTGCAT
CAGGATAGGGCGGTGGTGCTGCAGCAGCGCGCGAATAAACTGCTGCCGCCGCCGCTCCGTCCTGCAGGAATACAAC
ATGGCAGTGGTCTCCTCAGCGATGATTCGCACCGCCCGCAGCATAAGGCGCCTTGTCCTCCGGGCACAGCAGCGCA
CCCTGATCTCACTTAAATCAGCACAGTAACTGCAGCACAGCACCACAATATTGTTCAAATCCCACAGTGCAAGGC
GCTGTATCCAAAGCTCATGGCGGGGACCACAGAACCCACGTGGCCATCATACCACAAGCGCAGGTAGATTAAGTGG
CGACCGCTCATAAACACGCTGGACATAAACATTACCTCTTTTGGCATGTTGTAATTCACCACCTCCCGGTACCATA
TAAACCTCTGATTAAACATGGCGCCATCCACCACCATCCTAAACCAGCTGGCCAAAACCTGCCCGCCGGCTATACA
CTGCAGGGAACCGGGACTGGAACAATGACAGTGGAGAGCCCAGGACTCGTAACCATGGATCATCATGCTCGTCATG
ATATCAATGTTGGCACAACACAGGCACACGTGCATACACTTCCTCAGGATTACAAGCTCCTCCCGCGTTAGAACCA
TATCCCAGGGAACAACCCATTCCTGAATCAGCGTAAATCCCACACTGCAGGGAAGACCTCGCACGTAACTCACGTT
GTGCATTGTCAAAGTGTTACATTCGGGCAGCAGCGGATGATCCTCCAGTATGGTAGCGCGGGTTTCTGTCTCAAAA
GGAGGTAGACGATCCCTACTGTACGGAGTGCGCCGAGACAACCGAGATCGTGTTGGTCGTAGTGTCATGCCAAATG
GAACGCCGGACGTAGTCATATTTCCTGAAGCAAAACCAGGTGCGGGCGTGACAAACAGATCTGCGTCTCCGGTCTC
GCCGCTTAGATCGCTCTGTGTAGTAGTTGTAGTATATCCACTCTCTCAAAGCATCCAGGCGCCCCCTGGCTTCGGG
TTCTATGTAAACTCCTTCATGCGCCGCTGCCCTGATAACATCCACCACCGCAGAATAAGCCACACCCAGCCAACCT
ACACATTCGTTCTGCGAGTCACACACGGGAGGAGCGGGAAGAGCTGGAAGAACCATGTTTTTTTTTTTATTCCAAA
AGATTATCCAAAACCTCAAAATGAAGATCTATTAAGTGAACGCGCTCCCCTCCGGTGGCGTGGTCAAACTCTACAG
CCAAAGAACAGATAATGGCATTTGTAAGATGTTGCACAATGGCTTCCAAAAGGCAAACGGCCCTCACGTCCAAGTG
GACGTAAAGGCTAAACCCTTCAGGGTGAATCTCCTCTATAAACATTCCAGCACCTTCAACCATGCCCAAATAATTC
TCATCTCGCCACCTTCTCAATATATCTCTAAGCAAATCCCGAATATTAAGTCCGGCCATTGTAAAAATCTGCTCCA
GAGCGCCCTCCACCTTCAGCCTCAAGCAGCGAATCATGATTGCAAAAATTCAGGTTCCTCACAGACCTGTATAAGA
TTCAAAAGCGGAACATTAACAAAAATACCGCGATCCCGTAGGTCCCTTCGCAGGGCCAGCTGAACATAATCGTGCA
GGTCTGCACGGACCAGCGCGGCCACTTCCCCGCCAGGAACCTTGACAAAAGAACCCACACTGATTATGACACGCAT
ACTCGGAGCTATGCTAACCAGCGTAGCCCCGATGTAAGCTTTGTTGCATGGGCGGCGATATAAAATGCAAGGTGCT
GCTCAAAAAATCAGGCAAAGCCTCGCGCAAAAAGAAAGCACATCGTAGTCATGCTCATGCAGATAAAGGCAGGTA
AGCTCCGGAACCACCACAGAAAAAGACACCATTTTTCTCTCAAACATGTCTGCGGGTTTCTGCATAAACACAAAT
AAAATAACAAAAAAACATTTAAACATTAGAAGCCTGTCTTACAACAGGAAAAACAACCCTTATAAGCATAAGACGG
ACTACGGCCATGCCGGCGTGACCGTAAAAAAACTGGTCACCGTGATTAAAAAGCACCACCAGACAGCTCCTCGGTCA
TGTCCGGAGTCATAATGTAAGACTCGGTAAACACATCAGGTTGATTCATCGGTCAGTGCTAAAAAGCGACCGAAAT
AGCCCGGGGGAATACATACCCGCAGGCGTAGAGACAACATTACAGCCCCCATAGGAGGTATAACAAAATTAATAGG
AGAGAAAAACACATAAACACCTGAAAAACCCTCCTGCCTAGGCAAAATAGCACCCTCCCGCTCCAGAACAACATAC
AGCGCTTCACAGCGGCAGCCTAACAGTCAGCCTTACCAGTAAAAAAGAAAACCTATTAAAAAAACACCACTCGACA
CGGCACCAGCTCAATCAGTCACAGTGTAAAAAAGGGCCAAGTGCAGAGCGAGTATATATAGGACTAAAAAATGACG
TAACGGTTAAAGTCCACAAAAAACACCCAGAAAACCGCACGCGAACCTACGCCCAGAAACGAAAGCCAAAAAACCC
ACAACTTCCTCAAATCGTCACTTCCGTTTTCCCACGTTACGTAACTTCCCATTTTAAGAAAACTACAATTCCCAAC
ACATACAAGTTACTCCGCCCTAAAACCTACGTCACCCGCCCCGTTCCCACGCCCCGCGCCACGTCACAAACTCCAC
CCCCTCATTATCATATTGGCTTCAATCCAAAATAAGGTATATTATTGATGATGGCCGGCCGAATTGAATCAGGGGA
TAACGCAGGAAAGAACATGTGAGCAAAAGGCCAGCAAAAGGCAGGAACCGTAAAAAGGCCGCGTTGCTGGCGTTT
TTCCATAGGCTCCGCCCCCCTGACGAGCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCTCAGTTCGGTGTAG
GTCGTTCGCTCCAAGCTGGGCTGTGTGCACGAACCCCCCGTTCAGCCCGACCGCTGCGCCTTATCCGGTAACTATC
GTCTTGAGTCCAACCCGGTAAGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAGAAGGACAGTATTTGGTATC
TGCGCTCTGCTGAAGCCAGTTACCTTCGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGATCTCAAGAAGATCCTTTGATCTTTTC
TACGGGGTCTGACGCTCAGTGGAACGAAAACTCACGTTAAGGGATTTTGGTCATGAGATTATCAAAAAGGATCTTC
ACCTAGATCCTTTTAAATTAAAAATGAAGTTTTAAATCAATCTAAAGTATATATGAGTAAACTTGGTCTGACAGTT
ACCAATGCTTAATCAGTGAGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGATACCGCGAGACCCACGCTCA
CCGGCTCCAGATTTATCAGCAATAAACCAGCCAGCCGGAAGGGCCGAGCGCAGAAGTGGTCCTGCAACTTTATCCG
CCTCCATCCAGTCTATTAATTGTTGCCGGGAAGCTAGAGTAAGTAGTTCGCCAGTTAATAGTTTGCGCAACGTTGT
TGCCATTGCTACAGGCATCGTGGTGTCACGCTCGTCGTTTGGTATGGCTTCATTCAGCTCCGGTTCCCAACGATCA
AGGCGAGTTACATGATCCCCCATGTTGTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCTCTTACTGTCATGCCATCCGTAAGATG
CTTTTCTGTGACTGGTGAGTACTCAACCAAGTCATTCTGAGAATAGTGTATGCGGCGACCGAGTTGCTCTTGCCCG
GCGTCAATACGGGATAATACCGCGCCACATAGCAGAACTTTAAAAGTGCTCATCATTGGAAAACGTTCTTCGGGGC
```

FIGURE 17 (cont.)

```
GAAAACTCTCAAGGATCTTACCGCTGTTGAGATCCAGTTCGATGTAACCCACTCGTGCACCCAACTGATCTTCAGC
ATCTTTTACTTTCACCAGCGTTTCTGGGTGAGCAAAAACAGGAAGGCAAAATGCCGCAAAAAAGGGAATAAGGGCG
ACACGGAAATGTTGAATACTCATACTCTTCCTTTTTCAATATTATTGAAGCATTTATCAGGGTTATTGTCTCATGA
GCGGATACATATTTGAATGTATTTAGAAAAATAAACAAATAGGGGTTCCGCGCACATTTCCCCGAAAAGTGCCAC
```

FIGURE 18

SEQ ID NO:17   (Ad2 preterminal protein)
MALSVNDCARLTGQSVPTMEHFLPLRNIWNRVRDFPRASTTAAGITWMSRYTYGYHRLMLEDLA
PGAPATLRWPLYRQPPPHFLVGYQYLVRTCNDYVFDSRAYSRLRYTELSQPGHQTVNWSVMANC
TYTINTGAYHRFVDMDDFQSTLTQVQQAILAERVVADLALLQPMRGFGVTRMGGRGRHLRPNSA
AAVAIDARDAGQEEGEEEVPVERLMQDYYKDLRRCQNEAWGMADRLRIQQAGPKDMVLLSTIR
RLKTAYFNYIISSTSARNNPDRHPLPPATVLSLPCDCDWLDAFLERFSDPVDADSLRSLGGGVPTQQ
LLRCIVSAVSLPHGSPPPTHNRDMTGGVFQLRPRENGRAVTETMRRRRGEMIERFVDRLPVRRRRR
RVPPPPPPPEEEEEGEALMEEEIEEEEAPVAFEREVRDTVAELIRLLEEELTVSARNSQFFNFAVDFY
EAMERLEALGDINESTLRRWVMYFFVAEHTATTLNYLFQRLRNYAVFARHVELNLAQVVMRAR
DAEGGVVYSRVWNEGGLNAFSQLMARISNDLAATVERAGRGDLQEEEIEQFMAEIAYQDNSGDV
QEILRQAAVNDTEIDSVELSFRFKLTGPVVFTQRRQIQEINRRVVAFASNLRAQHQLLPARGADVPL
PPLPAGPEPPLPPGARPRHRF*

SEQ ID NO:18   (Ad2 terminal protein)
VFQLRPRENGRAVTETMRRRRGEMIERFVDRLPVRRRRRRVPPPPPPPEEEEEGEALMEEEIEEEEA
PVAFEREVRDTVAELIRLLEEELTVSARNSQFFNFAVDFYEAMERLEALGDINESTLRRWVMYFFV
AEHTATTLNYLFQRLRNYAVFARHVELNLAQVVMRARDAEGGVVYSRVWNEGGLNAFSQLMA
RISNDLAATVERAGRGDLQEEEIEQFMAEIAYQDNSGDVQEILRQAAVNDTEIDSVELSFRFKLTGP
VVFTQRRQIQEINRRVVAFASNLRAQHQLLPARGADVPLPPLPAGPEPPLPPGARPRHRF*

SEQ ID NO:19   (Ad5 preterminal protein)
MALSVNDCARLTGQSVPTMEHFLPLRNIWNRVRDFPRASTTAAGITWMSRYTYGYHRLMLEDLA
PGAPATLRWPLYRQPPPHFLVGYQYLVRTCNDYVFDSRAYSRLRYTELSQPGHQTVNWSVMANC
TYTINTGAYHRFVDMDDFQSTLTQVQQAILAERVVADLALLQPMRGFGVTRMGGRGRHLRPNSA
AAAAIDARDAGQEEGEEEVPVERLMQDYYKDLRRCQNEAWGMADRLRIQQAGPKDMVLLSTIR
RLKTAYFNYIISSTSARNNPDRRPLPPATVLSLPCDCDWLDAFLERFSDPVDADSLRSLGGGVPTQQ
LLRCIVSAVSLPHGSPPPTHNRDMTGGVFQLRPRENGRAVTETMRRRRGEMIERFVDRLPVRRRRR
RVPPPPPPPEEEEGEALMEEEIEEEEAPVAFEREVRDTVAELIRLLEEELTVSARNSQFFNFAVDFY
EAMERLEALGDINESTLRRWVMYFFVAEHTATTLNYLFQRLRNYAVFARHVELNLAQVVMRAR
DAEGGVVYSRVWNEGGLNAFSQLMARISNDLAATVERAGRGDLQEEEIEQFMAEIAYQDNSGDV
QEILRQAAVNDTEIDSVELSFRLKLTGPVVFTQRRQIQEINRRVVAFASNLRAQHQLLPARGADVP
LPPLPAGPEPPLPPGARPRHRF*

SEQ ID NO:20   (Ad5 terminal protein)
VFQLRPRENGRAVTETMRRRRGEMIERFVDRLPVRRRRRRVPPPPPPPEEEEGEALMEEEIEEEEA
PVAFEREVRDTVAELIRLLEEELTVSARNSQFFNFAVDFYEAMERLEALGDINESTLRRWVMYFFV
AEHTATTLNYLFQRLRNYAVFARHVELNLAQVVMRARDAEGGVVYSRVWNEGGLNAFSQLMA
RISNDLAATVERAGRGDLQEEEIEQFMAEIAYQDNSGDVQEILRQAAVNDTEIDSVELSFRLKLTGP
VVFTQRRQIQEINRRVVAFASNLRAQHQLLPARGADVPLPPLPAGPEPPLPPGARPRHRF*

SEQUENCE LISTING

<160> NUMBER OF SEQ ID NOS: 34

<210> SEQ ID NO 1
<211> LENGTH: 36154
<212> TYPE: DNA
<213> ORGANISM: Artificial Sequence
<220> FEATURE:
<223> OTHER INFORMATION: Synthetic

<400> SEQUENCE: 1

```
catcatcaat aatatacctt attttggatt gaagccaata tgataatgag ggggtggagt         60
ttgtgacgtg gcgcggggcg tgggaacggg gcgggtgacg tagtagtgtg gcggaagtgt        120
gatgttgcaa gtgtggcgga acacatgtat aacttcgtat aatgtatgct atacgaagtt        180
atacatgtaa gcgacggatg tggcaaaagt gacgttttg  gtgtgcgccg gtgtacacag        240
gaagtgacaa ttttcgcgcg gttttaggcg gatgttgtag taaatttggg cgtaaccgag        300
taagatttgg ccattttcgc gggaaaactg aataagagga agtgaaatct gaataatttt        360
gtgttactca tagcgcgtaa tatttgtcta gggagatcta taacttcgta taatgtatgc        420
tatacgaagt tattaccgaa gaaatggctc gagatctgga aggtgctgag gtacgatgag        480
acccgcacca ggtgcagacc ctgcgagtgt ggcggtaaac atattaggaa ccagcctgtg        540
atgctggatg tgaccgagga gctgaggccc gatcacttgg tgctggcctg cacccgcgct        600
gagtttggct ctagcgatga agatacagat tgaggtactg aaatgtgtgg gcgtggctta        660
agggtgggaa agaatatata aggtgggggt cttatgtagt tttgtatctg ttttgcagca        720
gccgccgccg ccatgagcac caactcgttt gatggaagca ttgtgagctc atatttgaca        780
acgcgcatgc ccccatgggc cggggtgcgt cagaatgtga tgggctccag cattgatggt        840
cgccccgtcc tgcccgcaaa ctctactacc ttgacctacg agaccgtgtc tggaacgccg        900
ttggagactg cagcctccgc cgccgcttca gccgctgcag ccaccgcccg cgggattgtg        960
actgactttg ctttcctgag cccgcttgca agcagtgcag cttcccgttc atccgcccgc       1020
gatgacaagt tgacggctct tttggcacaa ttggattctt tgacccggga acttaatgtc       1080
gtttctcagc agctgttgga tctgcgccag caggtttctg ccctgaaggc ttcctcccct       1140
cccaatgcgg tttaaaacat aaataaaaaa ccagactctg tttggatttg gatcaagcaa       1200
gtgtcttgct gtctttattt aggggttttg cgcgcgcggt aggcccggga ccagcggtct       1260
cggtcgttga gggtcctgtg tattttttcc aggacgtggt aaaggtgact ctggatgttc       1320
agatacatgg gcataagccc gtctctgggg tggaggtagc accactgcag agcttcatgc       1380
tgcggggtgg tgttgtagat gatccagtcg tagcaggagc gctgggcgtg gtgcctaaaa       1440
atgtctttca gtagcaagct gattgccagg ggcaggccct tggtgtaagt gtttacaaag       1500
cggttaagct gggatgggtg catacgtggg gatatgagat gcatcttgga ctgtatttt        1560
aggttggcta tgttcccagc catatccctc cggggattca tgttgtgcag aaccaccagc       1620
acagtgtatc cggtgcactt gggaaatttg tcatgtagct tagaaggaaa tgcgtggaag       1680
aacttggaga cgcccttgtg acctccaaga ttttccatgc attcgtccat aatgatggca       1740
atgggcccac gggcggcggc ctgggcgaag atatttctgg gatcactaac gtcatagttg       1800
tgttccagga tgagatcgtc ataggccatt ttacaaagc  gcgggcggag ggtgccagac       1860
tgcggtataa tggttccatc cggcccaggg gcgtagttac cctcacagat ttgcatttcc       1920
cacgctttga gttcagatgg ggggatcatg tctacctgcg gggcgatgaa gaaaacggtt       1980
```

```
tccggggtag gggagatcag ctgggaagaa agcaggttcc tgagcagctg cgacttaccg    2040
cagccggtgg gcccgtaaat cacacctatt accgggtgca actggtagtt aagagagctg    2100
cagctgccgt catccctgag cagggggggcc acttcgttaa gcatgtccct gactcgcatg    2160
ttttccctga ccaaatccgc cagaaggcgc tcgccgccca gcgatagcag ttcttgcaag    2220
gaagcaaagt ttttcaacgg tttgagaccg tccgccgtag gcatgctttt gagcgtttga    2280
ccaagcagtt ccaggcggtc ccacagctcg gtcacctgct ctacggcatc tcgatccagc    2340
atatctcctc gtttcgcggg ttggggcggc tttcgctgta cggcagtagt cggtgctcgt    2400
ccagacgggc cagggtcatg tctttccacg ggcgcagggt cctcgtcagc gtagtctggg    2460
tcacggtgaa ggggtgcgct ccgggctgcg cgctggccag ggtgcgcttg aggctggtcc    2520
tgctggtgct gaagcgctgc cggtcttcgc cctgcgcgtc ggccaggtag catttgacca    2580
tggtgtcata gtccagcccc tccgcggcgt ggcccttggc gcgcagcttg cccttggagg    2640
aggcgccgca cgaggggcag tgcagacttt tgagggcgta gagcttgggc gcgagaaata    2700
ccgattccgg ggagtaggca tccgcgccgc aggccccgca gacggtctcg cattccacga    2760
gccaggtgag ctctggccgt tcggggtcaa aaaccaggtt tcccccatgc ttttgatgc    2820 gtttcttacc tctggtttcc atgagccggt gtccacgctc ggtgacgaaa aggctgtccg    2880
tgtccccgta tacagacttg agaggcctgt cctcgagcgg tgttccgcgg tcctcctcgt    2940
atagaaactc ggaccactct gagacaaagg ctcgcgtcca ggccagcacg aaggaggcta    3000
agtgggaggg gtagcggtcg ttgtccacta ggggtccac tcgctccagg gtgtgaagac    3060
acatgtcgcc ctcttcggca tcaaggaagg tgattggttt gtaggtgtag gccacgtgac    3120
cgggtgttcc tgaaggggg ctataaaagg gggtgggggc gcgttcgtcc tcactctctt    3180
ccgcatcgct gtctgcgagg ccagctgtt gggtgagta ctccctctga aaagcgggca    3240
tgacttctgc gctaagattg tcagtttcca aaaacgagga ggatttgata ttcacctggc    3300
ccgcggtgat gcctttgagg gtggccgcat ccatctggtc agaaaagaca atcttttgt    3360 tgtcaagctt ggtggcaaac gacccgtaga gggcgttgga cagcaacttg gcgatggagc    3420
gcagggtttg gttttgtcg cgatcggcgc gctccttggc cgcgatgttt agctgcacgt    3480
attcgcgcgc aacgcaccgc cattcgggaa agacggtggt gcgctcgtcg ggcaccaggt    3540
gcacgcgcca accgcggttg tgcagggtga caaggtcaac gctggtggct acctctccgc    3600
gtaggcgctc gttggtccag cagaggcggc cgcccttgcg cgagcagaat ggcggtaggg    3660
ggtctagctg cgtctcgtcc ggggggtctg cgtccacggt aaagaccccg ggcagcaggc    3720
gcgcgtcgaa gtagtctatc ttgcatcctt gcaagtctag cgcctgctgc catgcgcggg    3780
cggcaagcgc gcgctcgtat gggttgagtg ggggacccca tggcatgggg tgggtgagcg    3840
cggaggcgta catgccgcaa atgtcgtaaa cgtagagggg ctctctgagt attccaagat    3900 atgtaggta gcatcttcca ccgcggatgc tggcgcgcac gtaatcgtat agttcgtgcg    3960
agggagcgag gaggtcggga ccgaggttgc tacgggcggg ctgctctgct cggaagacta    4020
tctgcctgaa gatggcatgt gagttggatg atatggttgg acgctggaag acgttgaagc    4080
tggcgtctgt gagacctacc gcgtcacgca cgaaggaggc gtaggagtcg cgcagcttgt    4140
tgaccagctc ggcggtgacc tgcacgtcta gggcgcagta gtccagggtt tccttgatga    4200
tgtcatactt atcctgtccc ttttttttcc acagctcgcg gttgaggaca aactcttcgc    4260
ggtctttcca gtactcttgg atcggaaacc cgtcggcctc cgaacggtaa gagcctagca    4320
```

```
tgtagaactg gttgacggcc tggtaggcgc agcatccctt ttctacgggt agcgcgtatg    4380
cctgcgcggc cttccggagc gaggtgtggg tgagcgcaaa ggtgtccctg accatgactt    4440
tgaggtactg gtatttgaag tcagtgtcgt cgcatccgcc ctgctcccag agcaaaaagt    4500
ccgtgcgctt tttggaacgc ggatttggca gggcgaaggt gacatcgttg aagagtatct    4560
ttcccgcgcg aggcataaag ttgcgtgtga tgcggaaggg tcccggcacc tcggaacggt    4620
tgttaattac ctgggcggcg agcacgatct cgtcaaagcc gttgatgttg tggcccacaa    4680
tgtaaagttc caagaagcgc gggatgccct tgatggaagg caatttttta agttcctcgt    4740
aggtgagctc ttcaggggag ctgagcccgt gctctgaaag ggcccagtct gcaagatgag    4800
ggttggaagc gacgaatgag ctccacaggt cacgggccat tagcatttgc aggtggtcgc    4860
gaaaggtcct aaactggcga cctatggcca ttttttctgg ggtgatgcag tagaaggtaa    4920
gcgggtcttg ttcccagcgg tcccatccaa ggttcgcggc taggtctcgc gcggcagtca    4980
ctagaggctc atctccgccg aacttcatga ccagcatgaa gggcacgagc tgcttcccaa    5040
aggcccccat ccaagtatag gtctctacat cgtaggtgac aaagagacgc tcggtgcgag    5100
gatgcgagcc gatcgggaag aactggatct cccgccacca attggaggag tggctattga    5160
tgtggtgaaa gtagaagtcc ctgcgacggg ccgaacactc gtgctggctt ttgtaaaaac    5220
gtgcgcagta ctggcagcgg tgcacgggct gtacatcctg cacgaggttg acctgacgac    5280
cgcgcacaag gaagcagagt gggaatttga gcccctcgcc tggcgggttt ggctggtggt    5340
cttctacttc ggctgcttgt ccttgaccgt ctggctgctc gagggagtt acggtggatc    5400 ggaccaccac gccgcgcgag cccaaagtcc agatgtccgc gcgcggcggt cggagcttga    5460
tgacaacatc gcgcagatgg gagctgtcca tggtctggag ctcccgcggc gtcaggtcag    5520
gcgggagctc ctgcaggttt acctcgcata gacgggtcag ggcgcgggct agatccaggt    5580
gatacctaat ttccagggc tggttggtgg cggcgtcgat ggcttgcaag aggccgcatc    5640
cccgcggcgc gactacggta ccgcgcggcg ggcggtgggc cgcggggtg tccttggatg    5700 atgcatctaa aagcggtgac gcgggcgagc ccccggaggt agggggggct ccggacccgc    5760
cgggagaggg ggcaggggca cgtcggcgcc gcgcgcgggc aggagctggt gctgcgcgcg    5820
taggttgctg gcgaacgcga cgacgcggcg gttgatctcc tgaatctggc gcctctgcgt    5880
gaagacgacg ggcccggtga gcttgagcct gaaagagagt tcgacagaat caatttcggt    5940
gtcgttgacg gcgcctggc gcaaaatctc ctgcacgtct cctgagttgt cttgataggc    6000
gatctcggcc atgaactgct cgatctcttc ctcctggaga tctccgcgtc cggctcgctc    6060
cacggtggcg gcgaggtcgt tggaaatgcg ggccatgagc tgcagaagg cgttgaggcc    6120 tccctcgttc cagacgcggc tgtagaccac gcccccttcg gcatcgcggg cgcgcatgac    6180
cacctgcgcg agattgagct ccacgtgccg ggcgaagacg gcgtagtttc gcaggcgctg    6240
aaagaggtag ttgagggtgg tggcggtgtg ttctgccacg aagaagtaca taacccagcg    6300
tcgcaacgtg gattcgttga tatcccccaa ggcctcaagg cgctccatgg cctcgtagaa    6360
gtccacggcg aagttgaaaa actgggagtt gcgcgccgac acggttaact cctcctccag    6420
aagacggatg agctcggcga cagtgtcgcg cacctcgcgc tcaaaggcta caggggcctc    6480
ttcttcttct tcaatctcct cttccataag ggcctcccct tcttcttctt ctggcggcgg    6540
tgggggaggg gggacacggc ggcgacgacg gcgcaccggg aggcggtcga caaagcgctc    6600
gatcatctcc ccgcggcgac ggcgcatggt ctcggtgacg gcgcggccgt tctcgcgggg    6660
gcgcagttgg aagacgccgc ccgtcatgtc ccggttatgg gttggcgggg ggctgccatg    6720
```

```
cggcagggat acggcgctaa cgatgcatct caacaattgt tgtgtaggta ctccgccgcc    6780
gagggacctg agcgagtccg catcgaccgg atcggaaaac ctctcgagaa aggcgtctaa    6840
ccagtcacag tcgcaaggta ggctgagcac cgtggcgggc ggcagcgggc ggcggtcggg    6900
gttgtttctg gcggaggtgc tgctgatgat gtaattaaag taggcggtct tgagacggcg    6960
gatggtcgac agaagcacca tgtccttggg tccggcctgc tgaatgcgca ggcggtcggc    7020
catgccccag gcttcgtttt gacatcggcg caggtctttg tagtagtctt gcatgagcct    7080
ttctaccggc acttcttctt ctccttcctc ttgtcctgca tctcttgcat ctatcgctgc    7140
ggcggcggcg gagtttggcc gtaggtggcg ccctcttcct cccatgcgtg tgaccccgaa    7200
gcccctcatc ggctgaagca gggctaggtc ggcgacaacg cgctcggcta atatggcctg    7260
ctgcacctgc gtgagggtag actggaagtc atccatgtcc acaaagcggt ggtatgcgcc    7320
cgtgttgatg gtgtaagtgc agttggccat aacggaccag ttaacggtct ggtgacccgg    7380
ctgcgagagc tcggtgtacc tgagacgcga gtaagccctc gagtcaaata cgtagtcgtt    7440
gcaagtccgc accaggtact ggtatcccac caaaaagtgc ggcggcggct ggcggtagag    7500
gggccagcgt agggtggccg gggctccggg ggcgagatct tccaacataa ggcgatgata    7560
tccgtagatg tacctggaca tccaggtgat gccggcggcg gtggtggagg cgcgcggaaa    7620
gtcgcggacg cggttccaga tgttgcgcag cggcaaaaag tgctccatgg tcgggacgct    7680
ctggccggtc aggcgcgcgc aatcgttgac gctctaccgt gcaaaaggag agcctgtaag    7740
cgggcactct tccgtggtct ggtggataaa ttcgcaaggg tatcatgcg gacgaccggg    7800 gttcgagccc cgtatccggc cgtccgccgt gatccatgcg gttaccgccc gcgtgtcgaa    7860
cccaggtgtg cgacgtcaga caacggggga gtgctccttt tggcttcctt ccaggcgcgg    7920
cggctgctgc gctagctttt ttggccactg gccgcgcgca gcgtaagcgg ttaggctgga    7980
aagcgaaagc attaagtggc tcgctccctg tagccggagg gttatttttcc aagggttgag    8040 tcgcgggacc cccggttcga gtctcggacc ggccggactg cggcgaacgg gggtttgcct    8100
ccccgtcatg caagacccc cttgcaaatt cctccggaaa cagggacgag cccctttttt    8160
gcttttccca gatgcatccg gtgctgcggc agatgcgccc ccctcctcag cagcggcaag    8220
agcaagagca gcggcagaca tgcagggcac cctcccctcc tcctaccgcg tcaggagggg    8280
cgacatccgc ggttgacgcg gcagcagatg gtgattacga accccgcgg cgccgggccc    8340 ggcactacct ggacttggag gagggcgagg gcctggcgcg gctaggagcg ccctctcctg    8400
agcggtaccc aagggtgcag ctgaagcgtg atacgcgtga ggcgtacgtg ccgcggcaga    8460
acctgtttcg cgaccgcgag ggagaggagc ccgaggagat gcgggatcga aagttccacg    8520
cagggcgcga gctgcggcat ggcctgaatc gcgagcggtt gctgcgcgag gaggactttg    8580
agcccgacgc gcgaaccggg attagtcccg cgcgcgcaca cgtggcggcc gccgacctgg    8640
taaccgcata cgagcagacg gtgaaccagg agattaactt tcaaaaaagc tttaacaacc    8700
acgtgcgtac gcttgtggcg cgcgaggagg tggctatagg actgatgcat ctgtgggact    8760
ttgtaagcgc gctggagcaa aacccaaata gcaagccgct catggcgcag ctgttcctta    8820
tagtgcagca gcagcaggga caacgaggcat tcagggatgc gctgctaaac atagtagagc    8880
ccgagggccg ctggctgctc gatttgataa acatcctgca gagcatagtg gtgcaggagc    8940
gcagcttgag cctggctgac aaggtggccg ccatcaacta ttccatgctt agcctgggca    9000
agttttacgc ccgcaagata taccataccc cttacgttcc catagacaag gaggtaaaga    9060
```

```
tcgagggatt ctacatgcgc atggcgctga aggtgcttac cttgagcgac gacctgggcg   9120
tttatcgcaa cgagcgcatc cacaaggccg tgagcgtgag ccggcggcgc gagctcagcg   9180
accgcgagct gatgcacagc ctgcaaaggg ccctggctgg cacgggcagc ggcgatagag   9240
aggccgagtc ctactttgac gcgggcgctg acctgcgctg ggccccaagc cgacgcgccc   9300
tggaggcagc tggggccgga cctgggctgg cggtggcacc cgcgcgcgct ggcaacgtcg   9360
gcggcgtgga ggaatatgac gaggacgatg agtacgagcc agaggacggc gagtactaag   9420
cggtgatgtt tctgatcaga tgatgcaaga cgcaacggac ccggcggtgc gggcggcgct   9480
gcagagccag ccgtccggcc ttaactccac ggacgactgg cgccaggtca tggaccgcat   9540
catgtcgctg actgcgcgca atcctgacgc gttccggcag cagccgcagg ccaaccggct   9600
ctccgcaatt ctggaagcgg tggtcccggc gcgcgcaaac cccacgcacg agaaggtgct   9660
ggcgatcgta aacgcgctgg ccgaaaacag ggccatccgg cccgacgagg ccggcctggt   9720
ctacgacgcg ctgcttcagc gcgtggctcg ttacaacagc ggcaacgtgc agaccaacct   9780
ggaccggctg gtggggatg tgcgcgaggc cgtggcgcag cgtgagcgcg cgcagcagca   9840
gggcaacctg ggctccatgg ttgcactaaa cgccttcctg agtacacagc ccgccaacgt   9900
gccgcgggga caggaggact acaccaactt tgtgagcgca ctgcggctaa tggtgactga   9960
gacaccgcaa agtgaggtgt accagtctgg gccagactat tttttccaga ccagtagaca  10020
aggcctgcag accgtaaacc tgagccaggc tttcaaaaac ttgcaggggc tgtgggggt   10080
gcgggctccc acaggcgacc gcgcgaccgt gtctagcttg ctgacgccca actcgcgcct  10140
gttgctgctg ctaatagcgc ccttcacgga cagtggcagc gtgtcccggg acacatacct  10200
aggtcacttg ctgacactgt accgcgaggc cataggtcag gcgcatgtgg acgagcatac  10260
tttccaggag attacaagtg tcagccgcgc gctggggcag gaggacacgg gcagcctgga  10320
ggcaacccta aactacctgc tgaccaaccg gcggcagaag atcccctcgt tgcacagttt  10380
aaacagcgag gaggagcgca ttttgcgcta cgtgcagcag agcgtgagcc ttaacctgat  10440
gcgcgacggg gtaacgccca gcgtggcgct ggacatgacc gcgcgcaaca tggaaccggg  10500
catgtatgcc tcaaaccggc cgtttatcaa ccgcctaatg gactacttgc atcgcgcggc  10560
cgccgtgaac cccagtatt tcaccaatgc catcttgaac ccgcactggc taccgccccc  10620
tggtttctac accgggggat tcgaggtgcc cgagggtaac gatggattcc tctgggacga  10680
catagacgac agcgtgtttt ccccgcaacc gcagaccctg ctagagttgc aacagcgcga  10740
gcaggcagag gcggcgctgc gaaaggaaag cttccgcagg ccaagcagct tgtccgatct  10800
aggcgctgcg gccccgcggt cagatgctag tagcccattt ccaagcttga tagggtctct  10860
taccagcact cgcaccaccc gcccgcgcct gctgggcgag gaggagtacc taaacaactc  10920
gctgctgcag ccgcagcgcg aaaaaaacct gcctccggca tttcccaaca acgggataga  10980
gagcctagtg gacaagatga gtagatggaa gacgtacgcg caggagcaca gggacgtgcc  11040
aggcccgcgc ccgcccaccc gtcgtcaaag gcacgaccgt cagcggggtc tggtgtggga  11100
ggacgatgac tcggcagacg acagcagcgt cctggatttg gagggagtg gcaacccgtt  11160
tgcgcacctt cgccccaggc tggggagaat gttttaaaaa aaaaaagca tgatgcaaaa  11220
taaaaaactc accaaggcca tggcaccgag cgttggtttt cttgtattcc ccttagtatg  11280
cggcgcgcgg cgatgtatga ggaaggtcct cctccctcct acgagagtgt ggtgagcgcg  11340
gcgcagtgg cggcggcgct gggttctccc ttcgatgctc ccctggaccc gccgtttgtg  11400
cctccgcggt acctgcggcc taccgggggg agaaacagca tccgttactc tgagttggca  11460
```

```
cccctattcg acaccacccg tgtgtacctg gtggacaaca agtcaacgga tgtggcatcc  11520
ctgaactacc agaacgacca cagcaacttt ctgaccacgg tcattcaaaa caatgactac  11580
agcccggggg aggcaagcac acagaccatc aatcttgacg accggtcgca ctggggcggc  11640
gacctgaaaa ccatcctgca taccaacatg ccaaatgtga acgagttcat gtttaccaat  11700
aagtttaagg cgcgggtgat ggtgtcgcgc ttgcctacta aggacaatca ggtggagctg  11760
aaatacgagt gggtggagtt cacgctgccc gagggcaact actccgagac catgaccata  11820
gaccttatga caacgcgat cgtggagcac tacttgaaag tgggcagaca gaacggggtt  11880
```

(Note: line at 11880 reads: gaccttatga caacgcgat cgtggagcac tacttgaaag tgggcagaca gaacggggtt)

```
ctggaaagcg catcgggt aaagtttgac accgcaact tcagactggg gtttgacccc  11940
gtcactggtc ttgtcatgcc tggggtatat acaaacgaag ccttccatcc agacatcatt  12000
ttgctgccag gatgcgggt ggacttcacc cacagccgcc tgagcaactt gttgggcatc  12060
cgcaagcggc aacccttcca ggagggcttt aggatcacct acgatgatct ggagggtggt  12120
aacattcccg cactgttgga tgtggacgcc taccaggcga gcttgaaaga tgacaccgaa  12180
cagggcgggg gtggcgcagg cggcagcaac agcagtggca gcggcgcgga agagaactcc  12240
aacgcggcag ccgcggcaat gcagccggtg gaggacatga acgatcatgc cattcgcggc  12300
gacacctttg ccacacgggc tgaggagaag cgcgctgagg ccgaagcagc ggccgaagct  12360
gccgcccccg ctgcgcaacc cgaggtcgag aagcctcaga gaaaccggt gatcaaaccc  12420 ctgacagagg acagcaagaa acgcagttac aacctaataa gcaatgacag caccttcacc  12480
cagtaccgca gctggtacct tgcatacaac tacggcgacc ctcagaccgg aatccgctca  12540
tggaccctgc tttgcactcc tgacgtaacc tgcggctcgg agcaggtcta ctggtcgttg  12600
ccagacatga tgcaagaccc cgtgaccttc cgctccacgc gccagatcag caactttccg  12660
gtggtgggcg ccgagctgtt gcccgtgcac tccaagagct ctacaacga ccaggccgtc  12720 tactcccaac tcatccgcca gtttacctct ctgacccacg tgttcaatcg cttttcccgag  12780 aaccagattt tggcgcgccc gccagccccc accatcacca ccgtcagtga aaacgttcct  12840
gctctcacag atcacgggac gctaccgctg cgcaacagca tcggaggagt ccagcgagtg  12900
accattactg acgccagacg ccgcacctgc ccctacgttt acaaggccct gggcatagtc  12960
tcgccgcgcg tcctatcgag ccgcactttt tgagcaagca tgtccatcct tatatcgccc  13020
agcaataaca caggctgggg cctgcgcttc ccaagcaaga tgtttggcgg ggccaagaag  13080
cgctccgacc aacacccagt gcgcgtgcgc gggcactacc gcgcgccctg gggcgcgcac  13140
aaacgcggcc gcactgggcg caccaccgtc gatgacgcca tcgacgcggt ggtggaggag  13200
gcgcgcaact acacgcccac gccgccacca gtgtccacag tggacgcggc cattcagacc  13260
gtggtgcgcg gagcccggcg ctatgctaaa atgaagagac ggcggaggcg cgtagcacgt  13320
cgccaccgcc gccgacccgg cactgccgcc aacgcgcgg cggcggccct gcttaaccgc  13380
gcacgtcgca ccggccgacg ggcggccatg cgggccgctc gaaggctggc cgcgggtatt  13440
gtcactgtgc cccccaggtc caggcgacga gcggccgccg cagcagccgc ggccattagt  13500
gctatgactc agggtcgcag gggcaacgtg tattgggtgc gcgactcggt tagcggcctg  13560
cgcgtgcccg tgcgcacccg cccccgcgcg aactagattg caagaaaaaa ctacttagac  13620
tcgtactgtt gtatgtatcc agcggcggcg gcgcgcaacg aagctatgtc caagcgcaaa  13680
atcaaagaag agatgctcca ggtcatcgcg ccggagatct atggcccccc gaagaaggaa  13740
gagcaggatt acaagccccg aaagctaaag cgggtcaaaa agaaaagaa agatgatgat  13800
```

```
gatgaacttg acgacgaggt ggaactgctg cacgctaccg cgcccaggcg acgggtacag   13860
tggaaaggtc gacgcgtaaa acgtgttttg cgacccggca ccaccgtagt ctttacgccc   13920
ggtgagcgct ccacccgcac ctacaagcgc gtgtatgatg aggtgtacgg cgacgaggac   13980
ctgcttgagc aggccaacga gcgcctcggg gagtttgcct acggaaagcg gcataaggac   14040
atgctggcgt tgccgctgga cgagggcaac ccaacaccta gcctaaagcc cgtaacactg   14100
cagcaggtgc tgcccgcgct tgcaccgtcc gaagaaaagc gcggcctaaa gcgcgagtct   14160
ggtgacttgg cacccaccgt gcagctgatg gtacccaagc gccagcgact ggaagatgtc   14220
ttggaaaaaa tgaccgtgga acctgggctg gagcccgagg tccgcgtgcg gccaatcaag   14280
caggtggcgc cgggactggg cgtgcagacc gtggacgttc agatacccac taccagtagc   14340
accagtattg ccaccgccac agagggcatg gagacacaaa cgtccccggt tgcctcagcg   14400
gtggcggatg ccgcggtgca ggcggtcgct gcggccgcgt ccaagacctc tacggaggtg   14460 caaacgga cc cgtggatgtt tcgcgtttca gccccccggc gcccgcgcgg ttcgaggaag   14520
tacggcgccg ccagcgcgct actgcccgaa tatgccctac atccttccat tgcgcctacc   14580
cccggctatc gtggctacac ctaccgcccc agaagacgag caactacccg acgccgaacc   14640
accactggaa cccgccgccg ccgtcgccgt cgccagcccg tgctggcccc gatttccgtg   14700
cgcagggtgg ctcgcgaagg aggcaggacc ctggtgctgc caacagcgcg ctaccacccc   14760
agcatcgttt aaaagccggt ctttgtggtt cttgcagata tggccctcac ctgccgcctc   14820
cgtttcccgg tgccgggatt ccgaggaaga atgcaccgta ggaggggcat ggccggccac   14880
ggcctgacgg gcggcatgcg tcgtgcgcac caccggcggc ggcgcgcgtc gcaccgtcgc   14940
atgcgcggcg gtatcctgcc cctccttatt ccactgatcg ccgcggcgat tggcgccgtg   15000
cccggaattg catccgtggc cttgcaggcg cagagacact gattaaaaac aagttgcatg   15060
tggaaaaatc aaaataaaaa gtctggactc tcacgctcgc ttggtcctgt aactattttg   15120
tagaatggaa gacatcaact ttgcgtctct ggccccgcga cacggctcgc gcccgttcat   15180
gggaaactgg caagatatcg gcaccagcaa tatgagcggt ggcgccttca gctgggctc   15240 gctgtggagc ggcattaaaa atttcggttc caccgttaag aactatggca gcaaggcctg   15300
gaacagcagc acaggccaga tgctgaggga taagttgaaa gagcaaaatt ccaacaaaa   15360 ggtggtagat ggcctggcct ctggcattag cggggtggtg gacctggcca accaggcagt   15420 gcaaataag attaacagta agcttgatcc ccgccctccc gtagaggagc ctccaccggc   15480
cgtggagaca gtgtctccag aggggcgtgg cgaaaagcgt ccgcgccccg acagggaaga   15540
aactctggtg acgcaaatag acgagcctcc ctcgtacgag gaggcactaa agcaaggcct   15600
gcccaccacc cgtcccatcg cgcccatggc taccggagtg ctgggccagc acacaccgt   15660 aacgctggac ctgcctcccc ccgccgacac ccagcagaaa cctgtgctgc caggcccgac   15720
cgccgttgtt gtaacccgtc ctagccgcgc gtccctgcgc cgcccgcca gcggtccgcg   15780 atcgttgcgg cccgtagcca gtggcaactg gcaaagcaca ctgaacagca tcgtgggtct   15840
gggggtgcaa tccctgaagc gccgacgatg cttctgaata gctaacgtgt cgtatgtgtg   15900
tcatgtatgc gtccatgtcg ccgccagagg agctgctgag ccgccgcgcg cccgctttcc   15960
aagatggcta cccccttcgat gatgccgcag tggtcttaca tgcacatctc gggccaggac   16020
gcctcggagt acctgagccc cggggctggtg cagtttgccc gcgccaccga gacgtacttc   16080
agcctgaata acaagtttag aaacccccacg gtggcgccta cgcacgacgt gaccacagac   16140
cggtcccagc gtttgacgct gcggttcatc cctgtggacc gtgaggatac tgcgtactcg   16200
```

```
tacaaggcgc ggttcaccct agctgtgggt gataaccgtg tgctggacat ggcttccacg  16260
tactttgaca tccgcggcgt gctggacagg ggccctactt ttaagcccta ctctggcact  16320
gcctacaacg ccctggctcc caaggggtgcc ccaaatcctt gcgaatggga tgaagctgct  16380
actgctcttg aaataaacct agaagaagag gacgatgaca acgaagacga agtagacgag  16440
caagctgagc agcaaaaaac tcacgtattt gggcaggcgc cttattctgg tataaatatt  16500 acaaggagg gtattcaaat aggtgtcgaa ggtcaaacac ctaaatatgc cgataaaaca  16560
tttcaacctg aacctcaaat aggagaatct cagtggtacg aaactgaaat taatcatgca  16620
gctgggagag tccttaaaaa gactacccca atgaaaccat gttacggttc atatgcaaaa  16680
cccacaaatg aaaatggagg gcaaggcatt cttgtaaagc aacaaaatgg aaagctagaa  16740
agtcaagtgg aaatgcaatt tttctcaact actgaggcga ccgcaggcaa tggtgataac  16800
ttgactccta aagtggtatt gtacagtgaa gatgtagata tagaaacccc agacactcat  16860
atttcttaca tgcccactat taaggaaggt aactcacgag aactaatggg ccaacaatct  16920
atgcccaaca ggcctaatta cattgctttt agggacaatt ttattggtct aatgtattac  16980
aacagcacgg gtaatatggg tgttctggcg ggccaagcat cgcagttgaa tgctgttgta  17040
gatttgcaag acagaaacac agagcttttca taccagcttt tgcttgattc cattggtgat  17100
agaaccaggt acttttctat gtggaatcag gctgttgaca gctatgatcc agatgttaga  17160
attattgaaa atcatggaac tgaagatgaa cttccaaatt actgctttcc actgggaggt  17220
gtgattaata cagagactct taccaaggta aaacctaaaa caggtcagga aaatggatgg  17280
gaaaaagatg ctacagaatt ttcagataaa atgaaataa gagttggaaa taattttgcc  17340
atggaaatca atctaaatgc caacctgtgg agaaattcc tgtactccaa catagcgctg  17400
tatttgcccg acaagctaaa gtacagtcct tccaacgtaa aaatttctga taacccaaac  17460
acctacgact acatgaacaa gcgagtggtg gctcccgggt tagtggactg ctacattaac  17520
cttggagcac gctggtccct tgactatatg gacaacgtca acccatttaa ccaccaccgc  17580
aatgctggcc tgcgctaccg ctcaatgttg ctgggcaatg gtcgctatgt gcccttccac  17640
atccaggtgc ctcagaagtt cttttgccatt aaaaaacctcc ttctcctgcc gggctcatac  17700
acctacgagt ggaacttcag gaaggatgtt aacatggttc tgcagagctc cctaggaaat  17760
gacctaaggg ttgacggagc cagcattaag tttgatagca tttgccttta cgccaccttc  17820
ttccccatgg cccacaacac cgcctccacg cttgaggcca tgcttagaaa cgacaccaac  17880
gaccagtcct ttaacgacta tctctccgcc gccaacatgc tctaccctat acccgccaac  17940
gctaccaacg tgcccatatc catccccctcc cgcaactggg cggctttccg cggctgggcc  18000
ttcacgcgcc ttaagactaa ggaaaccccca tcactgggct cgggctacga cccttattac  18060
acctactctg gctctatacc ctacctagat ggaaccttttt acctcaacca cacctttaag  18120
aaggtggcca ttacctttga ctcttctgtc agctggcctg gcaatgaccg cctgcttacc  18180
cccaacgagt ttgaaattaa gcgctcagtt gacggggagg gttacaacgt tgcccagtgt  18240
aacatgacca aagactggtt cctggtacaa atgctagcta actacaacat tggctaccag  18300
ggcttctata tcccagagag ctacaaggac cgcatgtact ccttctttag aaacttccag  18360
cccatgagcc gtcaggtggt ggatgatact aaatacaagg actaccaaca ggtgggcatc  18420
ctacaccaac acaacaactc tggatttgtt ggctaccttg cccccaccat gcgcgaagga  18480
caggcctacc ctgctaactt cccctatccg cttataggca agaccgcagt tgacagcatt  18540
```

```
acccagaaaa agtttctttg cgatcgcacc ctttggcgca tcccattctc cagtaacttt   18600
atgtccatgg gcgcactcac agacctgggc caaaaccttc tctacgccaa ctccgcccac   18660
gcgctagaca tgacttttga ggtggatccc atggacgagc ccaccttct ttatgttttg    18720
tttgaagtct ttgacgtggt ccgtgtgcac cggccgcacc gcggcgtcat cgaaaccgtg   18780
tacctgcgca cgcccttctc ggccggcaac gccacaacat aaagaagcaa gcaacatcaa   18840
caacagctgc cgccatgggc tccagtgagc aggaactgaa agccattgtc aaagatcttg   18900
gttgtgggcc atattttttg ggcacctatg acaagcgctt ccaggctttt gtttctccac   18960
acaagctcgc ctgcgccata gtcaatacgg ccggtcgcga gactgggggc gtacactgga   19020
tggcctttgc ctggaacccg cactcaaaaa catgctacct ctttgagccc tttggctttt   19080
ctgaccagcg actcaagcag gtttaccagt ttgagtacga gtcactcctg cgccgtagcg   19140
ccattgcttc ttcccccgac cgctgtataa cgctggaaaa gtccacccaa agcgtacagg   19200
ggcccaactc ggccgcctgt ggactattct gctgcatgtt tctccacgcc tttgccaact   19260
ggccccaaac tcccatggat cacaacccca ccatgaacct tattaccggg gtacccaact   19320
ccatgctcaa cagtccccag gtacagccca ccctgcgtcg caaccaggaa cagctctaca   19380
gcttcctgga gcgccactcg ccctacttcc gcagccacag tgcgcagatt aggagcgcca   19440
cttcttttg tcacttgaaa aacatgtaaa aataatgtac tagagacact ttcaataaag    19500
gcaaatgctt ttatttgtac actctcgggt gattatttac ccccacccctt gccgtctgcg   19560
ccgtttaaaa atcaaagggg ttctgccgcg catcgctatg cgccactggc agggacacgt   19620
tgcgatactg gtgtttagtg ctccacttaa actcaggcac aaccatccgc ggcagctcgg   19680
tgaagttttc actccacagg ctgcgcacca tcaccaacgc gtttagcagg tcgggcgccg   19740
atatcttgaa gtcgcagttg gggcctccgc cctgcgcgcg cgagttgcga tacacagggt   19800
tgcagcactg gaacactatc agcgccgggt ggtgcacgct ggccagcacg ctcttgtcgg   19860
agatcagatc cgcgtccagg tcctccgcgt tgctcagggc gaacggagtc aactttggta   19920
gctgccttcc caaaaagggc gcgtgccag gctttgagtt gcactcgcac cgtagtggca   19980
tcaaaaggtg accgtgcccg gtctgggcgt taggatacag cgcctgcata aaagccttga   20040
tctgcttaaa agccacctga gccttgtcgc cttcagagaa gaacatgccg caagacttgc   20100
cggaaaactg attggccgga caggccgcgt cgtgcacgca gcaccttgcg tcggtgttgg   20160
agatctgcac cacatttcgg ccccaccggt tcttcacgat cttggccttg ctagactgct   20220
ccttcagcgc gcgctgcccg ttttcgctcg tcacatccat ttcaatcacg tgctccttat   20280
ttatcataat gcttccgtgt agacacttaa gctcgccttc gatctcagcg cagcggtgca   20340
gccacaacgc gcagccgtg ggctcgtgat gcttgtaggt cacctctgca aacgactgca    20400
ggtacgcctg caggaatcgc cccatcatcg tcacaaaggt cttgttgctg gtgaaggtca   20460
gctgcaaccc gcggtgctcc tcgttcagcc aggtcttgca tacggccgcc agagcttcca   20520
cttggtcagg cagtagtttg aagttcgcct ttagatcgtt atccacgtgg tacttgtcca   20580
tcagcgcgcg cgcagcctcc atgcccttct cccacgcaga cacgatcggc acactcagcg   20640
ggttcatcac cgtaatttca ctttccgctt cgctgggctc ttcctcttcc tcttgcgtcc   20700
gcataccacg cgccactggg tcgtcttcat tcagccgccg cactgtgcgc ttacctcctt   20760
tgccatgctt gattagcacc ggtgggttgc tgaaacccac catttgtagc gccacatctt   20820
ctctttcttc ctcgctgtcc acgattacct ctggtgatgg cggcgctcg ggcttgggag    20880
aagggcgctt ctttttcttc ttgggcgcaa tggccaaatc cgccgccgag gtcgatggcc   20940
```

```
gcgggctggg tgtgcgcggc accagcgcgt cttgtgatga gtcttcctcg tcctcggact   21000
cgatacgccg cctcatccgc tttttgggg gcgcccgggg aggcggcggc gacggggacg   21060
gggacgacac gtcctccatg gttggggac gtcgcgccgc accgcgtccg cgctcggggg   21120
tggtttcgcg ctgctcctct tcccgactgg ccatttcctt ctcctatagg cagaaaaaga   21180
tcatggagtc agtcgagaag aaggacagcc taaccgcccc ctctgagttc gccaccaccg   21240
cctccaccga tgccgccaac gcgcctacca ccttccccgt cgaggcaccc ccgcttgagg   21300
aggaggaagt gattatcgag caggacccag gttttgtaag cgaagacgac gaggaccgct   21360
cagtaccaac agaggataaa aagcaagacc aggacaacgc agaggcaaac gaggaacaag   21420
tcgggcgggg ggacgaaagg catggcgact acctagatgt gggagacgac gtgctgttga   21480
agcatctgca gcgccagtgc gccattatct gcgacgcgtt gcaagagcgc agcgatgtgc   21540
ccctcgccat agcggatgtc agccttgcct acgaacgcca cctattctca ccgcgcgtac   21600
cccccaaacg ccaagaaaac ggcacatgcg agcccaaccc gcgcctcaac ttctaccccg   21660
tatttgccgt gccagaggtg cttgccacct atcacatctt tttccaaaac tgcaagatac   21720
ccctatcctg ccgtgccaac cgcagccgag cggacaagca gctggccttg cggcagggcg   21780
ctgtcatacc tgatatcgcc tcgctcaacg aagtgccaaa aatctttgag ggtcttggac   21840
gcgacgagaa gcgcgcggca aacgctctgc aacaggaaaa cagcgaaaat gaaagtcact   21900
ctggagtgtt ggtggaactc gagggtgaca acgcgcgcct agccgtacta aaacgcagca   21960
tcgaggtcac ccactttgcc tacccggcac ttaacctacc ccccaaggtc atgagcacag   22020
tcatgagtga gctgatcgtg cgccgtgcgc agccctgga gagggatgca aatttgcaag   22080
aacaaacaga ggagggccta cccgcagttg gcgacgagca gctagcgcgc tggcttcaaa   22140
cgcgcgagcc tgccgacttg gaggagcgac gcaaactaat gatggccgca gtgctcgtta   22200
ccgtggagct tgagtgcatg cagcggttct ttgctgaccc ggagatgcag cgcaagctag   22260
aggaaacatt gcactacacc tttcgacagg gctacgtacg ccaggcctgc aagatctcca   22320
acgtggagct ctgcaacctg gtctcctacc ttggaatttt gcacgaaaac cgccttgggc   22380
aaaacgtgct tcattccacg ctcaagggcg aggcgcgccg cgactacgtc cgcgactgcg   22440
tttacttatt tctatgctac acctggcaga cggccatggg cgtttggcag cagtgcttgg   22500
aggagtgcaa cctcaaggag ctgcagaaac tgctaaagca aaacttgaag gacctatgga   22560
cggccttcaa cgagcgctcc gtggccgcgc acctggcgga catcattttc cccgaacgcc   22620
tgcttaaaac cctgcaacag ggtctgccag acttcaccag tcaaagcatg ttgcagaact   22680
ttaggaacttt tatcctagag cgctcaggaa tcttgcccgc cacctgctgt gcacttccta   22740
gcgactttgt gccattaag taccgcgaat gccctccgcc gctttggggc cactgctacc   22800
ttctgcagct agccaactac cttgcctacc actctgacat aatggaagac gtgagcggtg   22860
acggtctact ggagtgtcac tgtcgctgca acctatgcac cccgcaccgc tccctggttt   22920
gcaattcgca gctgcttaac gaaagtcaaa ttatcggtac ctttgagctg cagggtccct   22980
cgcctgacga aaagtccgcg gctccggggt tgaaactcac tccggggctg tggacgtcgg   23040
cttaccttcg caaatttgta cctgaggact accacgccca cgagattagg ttctacgaag   23100
accaatcccg cccgccaaat gcggagctta ccgcctgcgt cattacccag gccacattc   23160
ttggccaatt gcaagccatc aacaaagccc gccaagagtt tctgctacga aagggacggg   23220
gggtttactt ggaccccag tccggcgagg agctcaaccc aatcccccg ccgccgcagc   23280
```

```
cctatcagca gcagccgcgg gcccttgctt cccaggatgg cacccaaaaa gaagctgcag    23340
ctgccgccgc cacccacgga cgaggaggaa tactgggaca gtcaggcaga ggaggttttg    23400
gacgaggagg aggaggacat gatggaagac tgggagagcc tagacgagga agcttccgag    23460
gtcgaagagg tgtcagacga aacaccgtca ccctcggtcg cattcccctc gccggcgccc    23520
cagaaatcgg caaccggttc cagcatggct acaacctccg ctcctcaggc gccgccggca    23580
ctgcccgttc gccgacccaa ccgtagatgg gacaccactg gaaccagggc cggtaagtcc    23640
aagcagccgc cgccgttagc ccaagagcaa caacagcgcc aaggctaccg ctcatggcgc    23700
gggcacaaga acgccatagt tgcttgcttg caagactgtg ggggcaacat ctccttcgcc    23760
cgccgctttc ttctctacca tcacggcgtg gccttccccc gtaacatcct gcattactac    23820
cgtcatctct acagcccata ctgcaccggc ggcagcggca gcggcagcaa cagcagcggc    23880
cacacagaag caaaggcgac cggatagcaa gactctgaca aagcccaaga aatccacagc    23940
ggcggcagca gcaggaggag gagcgctgcg tctggcgccc aacgaacccg tatcgacccg    24000
cgagcttaga aacaggattt ttcccactct gtatgctata tttcaacaga gcaggggcca    24060
agaacaagag ctgaaaataa aaaacaggtc tctgcgatcc ctcacccgca gctgcctgta    24120
tcacaaaagc gaagatcagc ttcggcgcac gctggaagac gcggaggctc tcttcagtaa    24180
atactgcgcg ctgactctta aggactagtt tcgcgccctt tctcaaattt aagcgcgaaa    24240
actacgtcat ctccagcggc cacacccggc gccagcacct gtcgtcagcg ccattatgag    24300
caaggaaatt cccacgccct acatgtggag ttaccagcca caaatgggac ttgcggctgg    24360
agctgcccaa gactactcaa cccgaataaa ctacatgagc gcgggacccc acatgatatc    24420
ccgggtcaac ggaatccgcg cccaccgaaa ccgaattctc ttggaacagg cggctattac    24480
caccacacct cgtaataacc ttaatccccg tagttggccc gctgccctgg tgtaccagga    24540
aagtcccgct cccaccactg tggtacttcc cagagacgcc caggccgaag ttcagatgac    24600
taactcaggg gcgcagcttg cgggcggctt tcgtcacagg gtgcggtcgc ccgggcaggg    24660
tataactcac ctgacaatca gagggcgagg tattcagctc aacgacgagt cggtgagctc    24720
ctcgcttggt ctccgtccgg acgggacatt tcagatcggc ggcgccggcc gtccttcatt    24780
cacgcctcgt caggcaatcc taactctgca gacctcgtcc tctgagccgc gctctggagg    24840
cattggaact ctgcaattta ttgaggagtt tgtgccatcg gtctacttta accccttctc    24900
gggacctccc ggccactatc cggatcaatt tattcctaac tttgacgcgg taaaggactc    24960
ggcggacggc tacgactgaa tgttaagtgg agaggcagag caactgcgcc tgaaacacct    25020
ggtccactgt cgccgccaca agtgctttgc ccgcgactcc ggtgagtttt gctactttga    25080
attgcccgag gatcatatcg agggcccggc gcacggcgtc cggcttaccg cccagggaga    25140
gcttgcccgt agcctgattc gggagtttac ccagcgcccc ctgctagttg agcgggacag    25200
gggaccctgt gttctcactg tgatttgcaa ctgtcctaac cttggattac atcaagatcc    25260
tctagttaat taacagcttg catgcctgca ggtcgacgga tcgggagatc tcggccgcat    25320
attaagtgca ttgttctcga taccgctaag tgcattgttc tcgttagctc gatggacaag    25380
tgcattgttc tcttgctgaa agctcgatgg acaagtgcat tgttctcttg ctgaaagctc    25440
gatggacaag tgcattgttc tcttgctgaa agctcagtac ccgggagtac cctcgaccgc    25500
cggagtataa atagaggcgc ttcgtctacg gagcgacaat tcaattcaaa caagcaaagt    25560
gaacacgtcg ctaagcgaaa gctaagcaaa taaacaagcg cagctgaaca agctaaacaa    25620
tctgcagtaa agtgcaagtt aaagtgaatc aattaaaagt aaccagcaac caagtaaatc    25680
```

```
aactgcaact actgaaatct gccaagaagt aattattgaa tacaagaaga gaactctgaa    25740
tactttcaac aagttaccga gaaagaagaa ctcacacaca gctagcgttt aaacttaagc    25800
ttcaccatgg tggggccctg catgctgctg ctgctgctgc tgctgggcct gaggctacag    25860
ctctccctgg gcatcatcct agttgaggag gagaacccgg acttctggaa ccgcgaggca    25920
gccgaggccc tggtgccgc caagaagctg cagcctgcac agacagccgc caagaacctc    25980
atcatcttcc tgggcgatgg ggtgggggtg tctacggtga cagctgccag gatcctaaaa    26040
gggcagaaga aggacaaact ggggcctgag atacccctgg ccatggaccg cttcccatat    26100
gtggctctgt ccaagacata caatgtagac aaacatgtgc cagacagtgg agccacagcc    26160
acggcctacc tgtgcgggt caagggcaac ttccagacca ttggcttgag tgcagccgcc    26220
cgctttaacc agtgcaacac gacacgcggc aacgaggtca tctccgtgat gaatcgggcc    26280
aagaaagcag ggaagtcagt gggagtggta accaccacac gagtgcagca cgcctcgcca    26340
gccggcacct acgcccacac ggtgaaccgc aactggtact cggacgccga cgtgcctgcc    26400
tcggcccgcc aggaggggtg ccaggacatc gctacgcagc tcatctccaa catggacatt    26460
gacgtgatcc taggtggggg ccgaaagtac atgtttcgca tgggaacccc agaccctgag    26520
tacccagatg actacagcca aggtgggacc aggctggacg ggaagaatct ggtgcaggaa    26580
tggctggcga agcaccaggg tgcccggtac gtgtggaacc gcactgagct catgcgggct    26640
tccctggacc cgtctgtggc ccatctcatg ggtctctttg agcctggaga catgaaatac    26700
gagatccacc gagactccac actggacccc tccctgatgg agatgacaga ggctgccctg    26760
cgcctgctga gcaggaaccc ccgcggcttc ttcctcttcg tggagggtgg tcgcatcgac    26820
catggtcatc atgaaagcag ggcttaccgg gcactgactg agacgatcat gttcgacgac    26880
gccattgaga gggcgggcca gctcaccagc gaggaggaca cgctgagcct cgtcactgcc    26940
gaccactccc acgtcttctc cttcggaggc tgccccctgc gaggggctc catcttcggg    27000 ctggcccctg gcaaggcccg ggacaggaag gcctacacgg tcctcctata cggaaacggt    27060
ccaggctatg tgctcaagga cggcgcccgg ccggatgtta ccgagagcga gagcgggagc    27120
cccgagtatc ggcagcagtc agcagtgccc ctggacgaag agacccacgc aggcgaggac    27180
gtggcggtgt tcgcgcgcgg cccgcaggcg cacctggttc acggcgtgca ggagcagacc    27240
ttcatagcgc acgtcatggc cttcgccgcc tgcctggagc cctacaccgc ctgcgacctg    27300
gcgccccccg ccggcaccac cgacgccgcg caccggggc ggtccgtggt ccccgcgttg    27360
cttcctctgc tggccgggac cctgctgctg ctggagacgg ccactgctcc ctgagtgtcc    27420
cgtccctggg gctcctgctt ccccatcccg gagttctcct gctccccgcc tcctgtcgtc    27480
ctgcctggcc tccagcccga gtcgtcatcc ccggagtccc tatacagagg tcctgccatg    27540
gaaccttccc ctccccgtgc gctctgggga ctgagcccat gacaccaaac ctgccccttg    27600
gctgctctcg gactccctac cccaaccca gggacagatc tggccagatt tgtaaaacaa    27660
atagatttta ggcccaaaga ttatttaaag cattgcctgg aacgcagtga gttttttgtta    27720 gaaaagagaa taattcaaag tggcattgct ttgcttctta tgttaatttg gtacagacct    27780
gtggctgagt ttgctcaaag tattcagagc agaattgtgg agtggaaaga gagattggac    27840
aaagagttta gtttgtcagt gtatcaaaaa atgaagttta atgtggctat gggaattgga    27900
gttttagatt ggctaagaaa cagtgatgat gatgatgaag acagccagga aaatgctgat    27960
aaaaatgaag atggtgggga gaagaacatg gaagactcag ggcatgaaac aggcattgat    28020
```

```
tcacagtccc aaggctcatt tcaggcccct cagtcctcac agtctgttca tgatcataat    28080
cagccatacc acatttgtag aggttttact tgctttaaaa aacctccac acctcccct      28140
gaacctgaaa cataaaatga atgcaattgt tgttgttaac ttgtttattg cagcttataa    28200
tggttacaaa taaagcaata gcatcacaaa tttcacaaat aaagcatttt tttcactgca    28260
ttctagttgt ggtttgtcca aactcatcaa tgtatcttat catgtctgga tccccaggaa    28320
gctcctctgt gtcctcataa accctaacct cctctacttg agaggacatt ccaatcatag    28380
gctgcccatc caccctctgt gtcctcctgt taattaggtc acttaacaaa aaggaaattg    28440
ggtaggggtt tttcacagac cgctttctaa gggtaatttt aaaatatctg ggaagtccct    28500
tccactgctg tgttccagaa gtgttggtaa acagcccaca aatgtcaaca gcagaaacat    28560
acaagctgtc agctttgcac aagggcccaa caccctgctc atcaagaagc actgtggttg    28620
ctgtgttagt aatgtgcaaa acaggaggca catttttcccc acctgtgtag gttccaaaat    28680
atctagtgtt ttcattttta cttggatcag gaacccagca ctccactgga taagcattat    28740
ccttatccaa aacagccttg tggtcagtgt tcatctgctg actgtcaact gtagcatttt    28800
ttggggttac agtttgagca ggatatttgg tcctgtagtt tgctaacaca ccctgcagct    28860
ccaaaggttc cccaccaaca gcaaaaaaat gaaaatttga cccttgaatg ggttttccag    28920
caccatttc atgagttttt tgtgtccctg aatgcaagtt taacatagca gttaccccaa    28980
taacctcagt tttaacagta acagcttccc acatcaaaat atttccacag gttaagtcct    29040
catttaaatt aggcaaagga attccacttc ccactgcctt gcttccgtct cccattcaaa    29100
cttttatcaa ctgacattat tctaagtaaa atcctcttca ttatgttgtc agcaatccat    29160
tgcttgaagg cctggctccc cagaacccct cgactggtat gtcttctcct agaatactcc    29220
agaagaaaag gagtgtatga agatagtgac tgcacattaa aatgactgaa accatagtaa    29280
attaggatga gattctgggc agataaacag acagctggct aggatcattt ttttatgcct    29340
tggacttctt tggcaatctg ttgaagcctg acattcctca gaataatgtt ttaaagccca    29400
acaataagac cctgtagcac atataataag tactgcagtt ttgaagtagt gataagcata    29460
aatgatattt tgatatattt attataactg taatgagatg tgtacatatc tgtgacttca    29520
taggtactga ttgtactact gtgatttttt tgcctacttt caaaatgaaa aggaatgctt    29580
aatttcagtt agaggttagt aaagacaaat aggtaatttt cttctccagt gaagagcatg    29640
gcgccccttg ctattcatgg acgcttgctt aaagacttgt acacaggctt gctttgtatc    29700
aacctatgac ttcccttac agccgatgat aggtttttat ttgcacctcc ttcgtgtaca    29760
aagacagttt tggtggctac gccatcatta aactcattat tatcatgctt aagcctatag    29820
atgtatccag ttcttctgtt acataattga agctgtagtg aattgtctat cttaaactgc    29880
atcgctaact gactacattt cacacttcat ttgcttccaa catagactaa ccttcttgga    29940
tgtccactat tatttgaact tttgagattt tttttcctat ttctaatatc ttaaaatttc    30000
agaagactta agttttgca actacagggc tccatataga catctagctt gaatttatac     30060
actttctttc attgatgtcc ctggactaaa aaatgttaaa tatttctaac cgctgtactt    30120
aaagtccatt acaaacgaag actactgttg ttaagttgaa taggcatctt atatattttt    30180
caccggtgca ataataact tctattccct tctaacatct gcttgcgttg cactgagagt     30240
acactattga ttagcaatag gttcgtgatt acagcccttc tataattaat gttaggtta     30300
acatattatt cataaaatat tattttatta atttttactt gatttgctac tggatgctta    30360
gaaatagcta tgagtatatt ggtagaacca gtacttatat tttattacat ttttacattt    30420
```

```
cataaaattt aagtgatata aaaatcctga ggaagtatgc cacaaaagtg gtctcagtgg     30480
aaatttaaat atgttaacat ttatttttaa aatgtagcgt gaaatagaca acttttaaag     30540
ctcagcttaa aaaaaaaact caaggaagct gaacttgact ttttaaagca ctgaagtgca     30600
atatttaatg taggtcaaca tgtttaaatg ggaaaatttt tttcctaatt acagccaaat     30660
ccctagctgt aattaactta aaatttgtat actatttcac aacagagtca gcatatacca     30720 cttcttata aaattagaaa gatctaaaat tttagagctt atttggtgaa acaggcatat       30780
tgctacatct ttgtttataa attataatgt gcctttagag cccaataaca gataacaaga     30840
ttttgaaaat tcaggtgaat tagagttatc agagggaatg ttaatacact ctattcaaat     30900
actatatgag taagacattt aaaataggaa acaatacttt atatattaaa aaaaattaat     30960
cttccagtcg atttaatcca ctttatgaat tcatttaaat cgatttaaat tcgaattaat     31020
taactagagt acccggggat cttattccct ttaactaata aaaaaaaata ataaagcatc     31080
acttacttaa aatcagttag caaatttctg tccagtttat tcagcagcac ctccttgccc     31140
tcctcccagc tctggtattg cagcttcctc ctggctgcaa actttctcca caatctaaat     31200
ggaatgtcag tttcctcctg ttcctgtcca tccgcaccca ctatcttcat gttgttgcag     31260
atgaagcgcg caagaccgtc tgaagatacc ttcaaccccg tgtatccata tgacacggaa     31320
accggtcctc caactgtgcc ttttcttact cctcccttg  tatcccccaa tgggtttcaa      31380
gagagtcccc ctggggtact ctctttgcgc ctatccgaac ctctagttac ctccaatggc     31440
atgcttgcgc tcaaaatggg caacggcctc tctctggacg aggccggcaa ccttacctcc     31500
caaaatgtaa ccactgtgag cccacctctc aaaaaaacca agtcaaacat aaacctggaa     31560
atatctgcac ccctcacagt tacctcagaa gccctaactg tggctgccgc cgcacctcta     31620
atggtcgcgg gcaacacact caccatgcaa tcacaggccc cgctaaccgt gcacgactcc     31680
aaacttagca ttgccaccca aggacccctc acagtgtcag aaggaaagct agccctgcaa     31740
acatcaggcc ccctcaccac caccgatagc agtaccctta ctatcactgc ctcacccct      31800 ctaactactg ccactggtag cttgggcatt gacttgaaag agcccatttta tacacaaaat    31860 ggaaaactag gactaaagta cgggctcct ttgcatgtaa cagacgacct aaacactttg     31920
accgtagcaa ctggtccagg tgtgactatt aataatactt ccttgcaaac taagttact     31980 ggagccttgg gttttgattc acaaggcaat atgcaactta atgtagcagg aggactaagg     32040
attgattctc aaaacagacg ccttatactt gatgttagtt atccgtttga tgctcaaaac     32100
caactaaatc taagactagg acagggccct ctttttataa actcagccca caacttggat     32160
attaactaca acaaaggcct ttacttgttt acagcttcaa acaattccaa aaagcttgag     32220
gttaacctaa gcactgccaa ggggttgatg tttgacgcta cagccatagc cattaatgca     32280
ggagatgggc ttgaatttgg ttcacctaat gcaccaaaca caatcccct caaaacaaaa     32340 attggccatg gcctagaatt tgattcaaac aaggctatgg ttcctaaact aggaactggc     32400
cttagttttg acagcacagg tgccattaca gtaggaaaca aaaataatga taagctaact     32460
ttgtggacca caccagctcc atctcctaac tgtagactaa atgcagagaa agatgctaaa     32520
ctcactttgg tcttaacaaa atgtggcagt caaatacttg ctacagtttc agttttggct     32580
gttaaaggca gtttggctcc aatatctgga acagttcaaa gtgctcatct tattataaga     32640
tttgacgaaa atggagtgct actaaacaat tccttcctgg acccagaata ttggaacttt     32700
agaaatggag atcttactga aggcacagcc tatacaaacg ctgttggatt tatgcctaac     32760
```

```
ctatcagctt atccaaaatc tcacggtaaa actgccaaaa gtaacattgt cagtcaagtt   32820
tacttaaacg gagacaaaac taaacctgta acactaacca ttacactaaa cggtacacag   32880
gaaacaggag acacaactcc aagtgcatac tctatgtcat tttcatggga ctggtctggc   32940
cacaactaca ttaatgaaat atttgccaca tcctcttaca ctttttcata cattgcccaa   33000
gaataaagaa tcgtttgtgt tatgtttcaa cgtgtttatt tttcaattgc agaaaatttc   33060
aagtcatttt tcattcagta gtatagcccc accaccacat agcttataca gatcaccgta   33120
ccttaatcaa actcacagaa ccctagtatt caacctgcca cctccctccc aacacacaga   33180
gtacacagtc ctttctcccc ggctggcctt aaaaagcatc atatcatggg taacagacat   33240
attcttaggt gttatattcc acacggtttc ctgtcgagcc aaacgctcat cagtgatatt   33300
aataaactcc ccgggcagct cacttaagtt catgtcgctg tccagctgct gagccacagg   33360
ctgctgtcca acttgcggtt gcttaacggg cggcgaagga gaagtccacg cctacatggg   33420
ggtagagtca taatcgtgca tcaggatagg gcggtggtgc tgcagcagcg cgcgaataaa   33480
ctgctgccgc cgccgctccg tcctgcagga atacaacatg gcagtggtct cctcagcgat   33540
gattcgcacc gcccgcagca taaggcgcct tgtcctccgg gcacagcagc gcaccctgat   33600
ctcacttaaa tcagcacagt aactgcagca cagcaccaca atattgttca aaatcccaca   33660
gtgcaaggcg ctgtatccaa agctcatggc ggggaccaca gaaccacgt ggccatcata   33720 ccacaagcgc aggtagatta agtggcgacc cctcataaac acgctggaca taaacattac   33780
ctcttttggc atgttgtaat tcaccacctc ccggtaccat ataaacctct gattaaacat   33840
ggcgccatcc accaccatcc taaaccagct ggccaaaacc tgcccgccgg ctatacactg   33900
cagggaaccg ggactggaac aatgacagtg gagagcccag gactcgtaac catggatcat   33960
catgctcgtc atgatatcaa tgttggcaca acacaggcac acgtgcatac acttcctcag   34020
gattacaagc tcctcccgcg ttagaaccat atcccaggga acaacccatt cctgaatcag   34080
cgtaaatccc acactgcagg gaagacctcg cacgtaactc acgttgtgca ttgtcaaagt   34140
gttacattcg ggcagcagcg gatgatcctc cagtatggta gcgcgggttt ctgtctcaaa   34200
aggaggtaga cgatccctac tgtacggagt gcgccgagac aaccgagatc gtgttggtcg   34260
tagtgtcatg ccaaatggaa cgccggacgt agtcatattt cctgaagcaa accaggtgc   34320 gggcgtgaca aacagatctg cgtctccggt ctcgccgctt agatcgctct gtgtagtagt   34380
tgtagtatat ccactctctc aaagcatcca ggcgcccccct ggcttcgggt tctatgtaaa   34440
ctccttcatg cgccgctgcc ctgataacat ccaccaccgc agaataagcc acacccagcc   34500
aacctacaca ttcgttctgc gagtcacaca cgggaggagc gggaagagct ggaagaacca   34560 tgttttttt tttattccaa aagattatcc aaaacctcaa aatgaagatc tattaagtga   34620
acgcgctccc ctccggtggc gtggtcaaac tctacagcca agaacagat aatggcattt   34680 gtaagatgtt gcaaatggc ttccaaaagg caaacgccc tcacgtccaa gtggacgtaa   34740
aggctaaacc cttcagggtg aatctcctct ataaacattc cagcaccttc aaccatgccc   34800
aaataattct catctcgcca ccttctcaat atatctctaa gcaaatcccg aatattaagt   34860
ccggccattg taaaaatctg ctccagagcg ccctccacct tcagcctcaa gcagcgaatc   34920
atgattgcaa aaattcaggt tcctcacaga cctgtataag attcaaaagc ggaacattaa   34980
caaaaatacc gcgatcccgt aggtcccttc gcagggccag ctgaacataa tcgtgcaggt   35040
ctgcacggac cagcgcggcc acttcccgc caggaaccttgacaaaagaa cccacactga   35100 ttatgacacg catactcgga gctatgctaa ccagcgtagc cccgatgtaa gctttgttgc   35160
```

| | |
|---|---|
| atgggcggcg atataaaatg caaggtgctg ctcaaaaaat caggcaaagc ctcgcgcaaa | 35220 |
| aaagaaagca catcgtagtc atgctcatgc agataaaggc aggtaagctc cggaaccacc | 35280 |
| acagaaaaag acaccatttt tctctcaaac atgtctgcgg gtttctgcat aaacacaaaa | 35340 |
| taaaataaca aaaaacatt taaacattag aagcctgtct tacaacagga aaaacaaccc | 35400 |
| ttataagcat aagacggact acggccatgc cggcgtgacc gtaaaaaaac tggtcaccgt | 35460 |
| gattaaaaag caccaccgac agctcctcgg tcatgtccgg agtcataatg taagactcgg | 35520 |
| taaacacatc aggttgattc atcggtcagt gctaaaaagc gaccgaaata gcccggggga | 35580 |
| atacataccc gcaggcgtag agacaacatt acagccccca taggaggtat aacaaaatta | 35640 |
| ataggagaga aaacacata aacacctgaa aaaccctcct gcctaggcaa aatagcaccc | 35700 |
| tcccgctcca gaacaacata cagcgcttca cagcggcagc ctaacagtca gccttaccag | 35760 |
| taaaaagaa aacctattaa aaaaacacca ctcgacacgg caccagctca atcagtcaca | 35820 |
| gtgtaaaaaa gggccaagtg cagagcgagt atatatagga ctaaaaatg acgtaacggt | 35880 |
| taaagtccac aaaaaacacc cagaaaaccg cacgcgaacc tacgcccaga acgaaagcc | 35940 |
| aaaaaaccca caacttcctc aaatcgtcac ttccgttttc ccacgttacg tcacttccca | 36000 |
| tttttaagaaa actacaattc ccaacacata caagttactc cgccctaaaa cctacgtcac | 36060 |
| ccgccccgtt cccacgcccc gcgccacgtc acaaactcca cccctcatt atcatattgg | 36120 |
| cttcaatcca aaataaggta tattattgat gatg | 36154 |

```
<210> SEQ ID NO 2
<211> LENGTH: 31
<212> TYPE: DNA
<213> ORGANISM: Artificial Sequence
<220> FEATURE:
<223> OTHER INFORMATION: Synthetic

<400> SEQUENCE: 2
```

| | |
|---|---|
| cggaattcgg atccagcgac cgcgagctga t | 31 |

```
<210> SEQ ID NO 3
<211> LENGTH: 33
<212> TYPE: DNA
<213> ORGANISM: Artificial Sequence
<220> FEATURE:
<223> OTHER INFORMATION: Synthetic

<400> SEQUENCE: 3
```

| | |
|---|---|
| cggaattcag ccggcttcgt cgggccggat ggc | 33 |

```
<210> SEQ ID NO 4
<211> LENGTH: 32
<212> TYPE: DNA
<213> ORGANISM: Artificial Sequence
<220> FEATURE:
<223> OTHER INFORMATION: Synthetic

<400> SEQUENCE: 4
```

| | |
|---|---|
| cgcggatccg ccggctacgg cctgacgggc gg | 32 |

```
<210> SEQ ID NO 5
<211> LENGTH: 28
<212> TYPE: DNA
<213> ORGANISM: Artificial Sequence
<220> FEATURE:
<223> OTHER INFORMATION: Synthetic
```

<400> SEQUENCE: 5
cggaattcac acacatacga cacgttag                                28

<210> SEQ ID NO 6
<211> LENGTH: 32
<212> TYPE: DNA
<213> ORGANISM: Artificial Sequence
<220> FEATURE:
<223> OTHER INFORMATION: Synthetic

<400> SEQUENCE: 6
cggaattcgg ccggccatca tcaataatat ac                           32

<210> SEQ ID NO 7
<211> LENGTH: 43
<212> TYPE: DNA
<213> ORGANISM: Artificial Sequence
<220> FEATURE:
<223> OTHER INFORMATION: Synthetic

<400> SEQUENCE: 7
cggtcgattc aattgctggc aagcttcggc cctagacaaa tat               43

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
ctatgctaac cagcgtagc                                          19

<210> SEQ ID NO 9
<211> LENGTH: 36154
<212> TYPE: DNA
<213> ORGANISM: Artificial Sequence
<220> FEATURE:
<223> OTHER INFORMATION: Synthetic

<400> SEQUENCE: 9
catcatcaat aatataccttt attttggatt gaagccaata tgataatgag ggggtggagt    60
ttgtgacgtg gcgcggggcg tgggaacggg gcgggtgacg tagtagtgtg gcggaagtgt   120
gatgttgcaa gtgtggcgga acacatgtat aacttcgtat aatgtatgct atacgaagtt   180
atacatgtaa gcgacggatg tggcaaaagt gacgttttttg gtgtgcgccg gtgtacacag   240
gaagtgacaa ttttcgcgcg gttttaggcg gatgttgtag taaatttggg cgtaaccgag   300
taagatttgg ccattttcgc gggaaaactg aataagagga agtgaaatct gaataatttt   360
gtgttactca tagcgcgtaa tatttgtcta gggagatcta taacttcgta taatgtatgc   420
tatacgaagt tattaccgaa gaaatggctc gagatctgga aggtgctgag gtacgatgag   480
acccgcacca ggtgcagacc ctgcgagtgt ggcggtaaac atattaggaa ccagcctgtg   540
atgctggatg tgaccgagga gctgaggccc gatcacttgg tgctggcctg cacccgcgct   600
gagtttggct ctagcgatga agatacagat tgaggtactg aaatgtgtgg gcgtggctta   660
agggtgggaa agaatatata aggtgggggt cttatgtagt tttgtatctg ttttgcagca   720
gccgccgccg ccatgagcac caactcgttt gatggaagca ttgtgagctc atatttgaca   780
acgcgcatgc ccccatgggc cggggtgcgt cagaatgtga tgggctccag cattgatggt   840
cgccccgtcc tgcccgcaaa ctctactacc ttgacctacg agaccgtgtc tggaacgccg   900

```
ttggagactg cagcctccgc cgccgcttca gccgctgcag ccaccgcccg cgggattgtg    960
actgactttg ctttcctgag cccgcttgca agcagtgcag cttcccgttc atccgcccgc   1020
gatgacaagt tgacggctct tttggcacaa ttggattctt tgacccggga acttaatgtc   1080
gtttctcagc agctgttgga tctgcgccag caggtttctg ccctgaaggc ttcctcccct   1140
cccaatgcgg tttaaaacat aaataaaaaa ccagactctg tttggatttg gatcaagcaa   1200
gtgtcttgct gtctttattt aggggttttg cgcgcgcggt aggcccggga ccagcggtct   1260
cggtcgttga gggtcctgtg tattttttcc aggacgtggt aaaggtgact ctggatgttc   1320
agatacatgg gcataagccc gtctctgggg tggaggtagc accactgcag agcttcatgc   1380
tgcggggtgt tgttgtagat gatccagtcg tagcaggagc gctgggcgtg gtgcctaaaa   1440
atgtctttca gtagcaagct gattgccagg gcaggccct  tggtgtaagt gtttacaaag   1500
cggttaagct gggatgggtg catacgtggg gatatgagat gcatcttgga ctgtatttt   1560
aggttggcta tgttcccagc catatccctc cggggattca tgttgtgcag aaccaccagc   1620
acagtgtatc cggtgcactt gggaaatttg tcatgtagct tagaaggaaa tgcgtggaag   1680
aacttggaga cgcccttgtg acctccaaga ttttccatgc attcgtccat aatgatggca   1740
atgggcccac gggcggcggc ctgggcgaag atatttctgg gatcactaac gtcatagttg   1800
tgttccagga tgagatcgtc ataggccatt tttacaaagc gcgggcggag ggtgccagac   1860
tgcggtataa tggttccatc cggcccaggg gcgtagttac cctcacagat ttgcatttcc   1920
cacgctttga gttcagatgg ggggatcatg tctacctgcg gggcgatgaa gaaaacggtt   1980
tccggggtag gggagatcag ctgggaagaa agcaggttcc tgagcagctg cgacttaccg   2040
cagccggtgg gcccgtaaat cacacctatt accgggtgca actggtagtt aagagagctg   2100
cagctgccgt catccctgag cagggggggcc acttcgttaa gcatgtccct gactcgcatg   2160
ttttcccctga ccaaatccgc cagaaggcgc tcgccgccca gcgatagcag ttcttgcaag   2220
gaagcaaagt ttttcaacgg tttgagaccg tccgccgtag gcatgctttt gagcgtttga   2280
ccaagcagtt ccaggcggtc ccacagctcg gtcacctgct ctacggcatc tcgatccagc   2340
atatctcctc gtttcgcggg ttggggcggc tttcgctgta cggcagtagt cggtgctcgt   2400
ccagacgggc cagggtcatg tcttttccacg ggcgcagggt cctcgtcagc gtagtctggg   2460
tcacggtgaa ggggtgcgct ccgggctgcg cgctggccag ggtgcgcttg aggctggtcc   2520
tgctggtgct gaagcgctgc cggtcttcgc cctgcgcgtc ggccaggtag catttgacca   2580
tggtgtcata gtccagcccc tccgcggcgt ggcccttggc gcgcagcttg cccttggagg   2640
aggcgccgca cgaggggcag tgcagacttt tgagggcgta gagcttgggc gcgagaaata   2700
ccgattccgg ggagtaggca tccgcgccgc aggccccgca gacggtctcg cattccacga   2760
gccaggtgag ctctggccgt tcgggtcaa  aaaccaggtt tcccccatgc ttttttgatgc   2820
gtttcttacc tctggtttcc atgagccggt gtccacgctc ggtgacgaaa aggctgtccg   2880
tgtccccgta tacagacttg agaggcctgt cctcgagcgg tgttccgcgg tcctcctcgt   2940
atagaaactc ggaccactct gagacaaagg ctcgcgtcca ggccagcacg aaggaggcta   3000
agtgggaggg gtagcggtcg ttgtccacta gggggtccac tcgctccagg gtgtgaagac   3060
acatgtcgcc ctcttcggca tcaaggaagg tgattggttt gtaggtgtag gccacgtgac   3120
cgggtgttcc tgaaggggg  ctataaaagg gggtggggc  gcgttcgtcc tcactctctt   3180
ccgcatcgct gtctgcgagg gccagctgtt ggggtgagta ctccctctga aaagcgggca   3240
```

```
tgacttctgc gctaagattg tcagtttcca aaaacgagga ggatttgata ttcacctggc   3300
ccgcggtgat gcctttgagg gtggccgcat ccatctggtc agaaaagaca atcttttttgt  3360
tgtcaagctt ggtggcaaac gacccgtaga gggcgttgga cagcaacttg gcgatggagc   3420
gcagggtttg gttttttgtcg cgatcggcgc gctccttggc cgcgatgttt agctgcacgt  3480
attcgcgcgc aacgcaccgc cattcggaa agacggtggt gcgctcgtcg gcaccaggt    3540
gcacgcgcca accgcggttg tgcagggtga caaggtcaac gctggtggct acctctccgc   3600
gtaggcgctc gttggtccag cagaggcggc cgcccttgcg cgagcagaat ggcggtaggg   3660
ggtctagctg cgtctcgtcc gggggtctg cgtccacggt aaagaccccg ggcagcaggc    3720
gcgcgtcgaa gtagtctatc ttgcatcctt gcaagtctag cgcctgctgc catgcgcggg   3780
cggcaagcgc gcgctcgtat gggttgagtg ggggacccca tggcatgggg tgggtgagcg   3840
cggaggcgta catgccgcaa atgtcgtaaa cgtagagggg ctctctgagt attcaagat    3900
atgtagggta gcatcttcca ccgcggatgc tggcgcgcac gtaatcgtat agttcgtgcg   3960
agggagcgag gaggtcggga ccgaggttgc tacgggcggg ctgctctgct cggaagacta   4020
tctgcctgaa gatggcatgt gagttggatg atatggttgg acgctggaag acgttgaagc   4080
tggcgtctgt gagacctacc gcgtcacgca cgaaggaggc gtaggagtcg cgcagcttgt   4140
tgaccagctc ggcggtgacc tgcacgtcta gggcgcagta gtccagggtt tccttgatga   4200
tgtcatactt atcctgtccc ttttttttcc acagctcgcg gttgaggaca aactcttcgc   4260
ggtctttcca gtactcttgg atcggaaacc cgtcggcctc cgaacggtaa gagcctagca   4320
tgtagaactg gttgacggcc tggtaggcgc agcatccctt ttctacgggt agcgcgtatg   4380
cctgcgcggc cttccggagc gaggtgtggg tgagcgcaaa ggtgtccctg accatgactt   4440
tgaggtactg gtatttgaag tcagtgtcgt cgcatccgcc ctgctcccag agcaaaaagt   4500
ccgtgcgctt tttggaacgc ggatttggca gggcgaaggt gacatcgttg aagagtatct   4560
ttcccgcgcg aggcataaag ttgcgtgtga tgcggaaggg tcccggcacc tcggaacggt   4620
tgttaattac ctgggcggcg agcacgatct cgtcaaagcc gttgatgttg tggcccacaa   4680
tgtaaagttc caagaagcgc gggatgccct tgatggaagg caatttttta agttcctcgt   4740
aggtgagctc ttcaggggag ctgagcccgt gctctgaaag ggcccagtct gcaagatgag   4800
ggttggaagc gacgaatgag ctccacaggt cacgggccat tagcatttgc aggtggtcgc   4860
gaaaggtcct aaactggcga cctatggcca tttttttctgg ggtgatgcag tagaaggtaa   4920
gcgggtcttg ttcccagcgg tcccatccaa ggttcgcggc taggtctcgc gcggcagtca   4980
ctagaggctc atctccgccg aacttcatga ccagcatgaa gggcacgagc tgcttcccaa   5040
aggcccccat ccaagtatag gtctctacat cgtaggtgac aaagagacgc tcggtgcgag   5100
gatgcgagcc gatcgggaag aactggatct cccgccacca attggaggag tggctattga   5160
tgtggtgaaa gtagaagtcc ctgcgacggg ccgaacactc gtgctggctt ttgtaaaaac   5220
gtgcgcagta ctggcagcgg tgcacgggct gtacatcctg cacgaggttg acctgacgac   5280
cgcgcacaag gaagcagagt gggaatttga gcccctcgcc tggcgggttt ggctggtggt   5340
cttctacttc ggctgcttgt ccttgaccgt ctggctgctc gagggagtt acggtggatc   5400
ggaccaccac gccgcgcgag cccaaagtcc agatgtccgc gcgcggcggt cggagcttga   5460
tgacaacatc gcgcagatgg gagctgtcca tggtctggag ctcccgcggc gtcaggtcag   5520
gcgggagctc ctgcaggttt acctcgcata gacgggtcag ggcgcgggct agatccaggt   5580
gataccctaat ttccagggggc tggttggtgg cggcgtcgat ggcttgcaag aggccgcatc   5640
```

```
cccgcggcgc gactacggta ccgcgcggcg ggcggtgggc cgcggggtg tccttggatg    5700 atgcatctaa aagcggtgac gcgggcgagc ccccggaggt aggggggct ccggacccgc    5760 cgggagaggg ggcaggggca cgtcggcgcc gcgcgcgggc aggagctggt gctgcgcgcg    5820
taggttgctg gcgaacgcga cgacgcggcg gttgatctcc tgaatctggc gcctctgcgt    5880
gaagacgacg ggcccggtga gcttgagcct gaaagagagt tcgacagaat caatttcggt    5940
gtcgttgacg gcggcctggc gcaaaatctc ctgcacgtct cctgagttgt cttgataggc    6000
gatctcggcc atgaactgct cgatctcttc ctcctggaga tctccgcgtc cggctcgctc    6060
cacggtggcg gcgaggtcgt tggaaatgcg ggccatgagc tgcgagaagg cgttgaggcc    6120
tccctcgttc cagacgcggc tgtagaccac gccccttcg gcatcgcggg cgcgcatgac    6180
cacctgcgcg agattgagct ccacgtgccg ggcgaagacg gcgtagtttc gcaggcgctg    6240
aaagaggtag ttgagggtgg tggcggtgtg ttctgccacg aagaagtaca taacccagcg    6300
tcgcaacgtg gattcgttga tatcccccaa ggcctcaagg cgctccatgg cctcgtagaa    6360
gtccacggcg aagttgaaaa actgggagtt gcgcgccgac acggttaact cctcctccag    6420
aagacggatg agctcggcga cagtgtcgcg cacctcgcgc tcaaaggcta caggggcctc    6480
ttcttcttct tcaatctcct cttccataag ggcctcccct tcttcttctt ctggcggcgg    6540
tgggggaggg gggacacggc ggcgacgacg gcgcaccggg aggcggtcga caaagcgctc    6600
gatcatctcc ccgcggcgac ggcgcatggt ctcggtgacg gcgcggccgt tctcgcgggg    6660
gcgcagttgg aagacgccgc ccgtcatgtc ccggttatgg gttggcgggg ggctgccatg    6720
cggcagggat acggcgctaa cgatgcatct caacaattgt tgtgtaggta ctccgccgcc    6780
gagggacctg agcgagtccg catcgaccgg atcggaaaac ctctcgagaa aggcgtctaa    6840
ccagtcacag tcgcaaggta ggctgagcac cgtggcgggc ggcagcgggc ggcggtcggg    6900
gttgtttctg gcgaggtgc tgctgatgat gtaattaaag taggcggtct tgagacggcg    6960
gatggtcgac agaagcacca tgtccttggg tccggcctgc tgaatgcgca ggcggtcggc    7020
catgccccag gcttcgtttt gacatcggcg caggtctttg tagtagtctt gcatgagcct    7080
ttctaccggc acttcttctt ctccttcctc ttgtcctgca tctcttgcat ctatcgctgc    7140
ggcggcggcg gagtttggcc gtaggtggcg ccctcttcct cccatgcgtg tgaccccgaa    7200
gcccctcatc ggctgaagca gggctaggtc ggcgacaacg cgctcggcta atatggcctg    7260
ctgcacctgc gtgagggtag actggaagtc atccatgtcc acaaagcggt ggtatgcgcc    7320
cgtgttgatg gtgtaagtgc agttggccat aacggaccag ttaacggtct ggtgacccgg    7380
ctgcgagagc tcggtgtacc tgagacgcga gtaagccctc gagtcaaata cgtagtcgtt    7440
gcaagtccgc accaggtact ggtatcccac caaaaagtgc ggcggcggct ggcggtagag    7500
gggccagcgt agggtggccg gggctccggg ggcgagatct ccaacataa ggcgatgata    7560 tccgtagatg tacctggaca tccaggtgat gccggcggcg gtggtggagg cgcgcggaaa    7620
gtcgcggacg cggttccaga tgttgcgcag cggcaaaaag tgctccatgg tcgggacgct    7680
ctggccggtc aggcgcgcgc aatcgttgac gctctaccgt gcaaaggag agcctgtaag    7740 cgggcactct tccgtggtct ggtggataaa ttcgcaaggg tatcatgcg gacgaccggg    7800 gttcgagccc cgtatccggc cgtccgccgt gatccatgcg gttaccgccc gcgtgtcgaa    7860
cccaggtgtg cgacgtcaga caacggggga gtgctccttt tggcttcctt ccaggcgcgg    7920
cggctgctgc gctagctttt ttggccactg gccgcgcgca gcgtaagcgg ttaggctgga    7980
```

```
aagcgaaagc attaagtggc tcgctccctg tagccggagg gttattttcc aagggttgag   8040
tcgcgggacc cccggttcga gtctcggacc ggccggactg cggcgaacgg gggtttgcct   8100
ccccgtcatg caagaccccg cttgcaaatt cctccggaaa cagggacgag cccctttttt   8160
gcttttccca gatgcatccg gtgctgcggc agatgcgccc ccctcctcag cagcggcaag   8220
agcaagagca gcggcagaca tgcagggcac cctcccctcc tcctaccgcg tcaggagggg   8280
cgacatccgc ggttgacgcg gcagcagatg gtgattacga accccgcgg cgccgggccc    8340
ggcactacct ggacttggag gagggcgagg gcctggcgcg gctaggagcg ccctctcctg   8400
agcggtaccc aagggtgcag ctgaagcgtg atacgcgtga ggcgtacgtg ccgcggcaga   8460
acctgtttcg cgaccgcgag ggagaggagc ccgaggagat gcgggatcga aagttccacg   8520
cagggcgcga gctgcggcat ggcctgaatc gcgagcggtt gctgcgcgag gaggactttg   8580
agcccgacgc gcgaaccggg attagtcccg cgcgcgcaca cgtggcggcc gccgacctgg   8640
taaccgcata cgagcagacg gtgaaccagg agattaactt tcaaaaaagc tttaacaacc   8700
acgtgcgtac gcttgtggcg cgcgaggagg tggctatagg actgatgcat ctgtgggact   8760
tgtaagcgc gctggagcaa aacccaaata gcaagccgct catggcgcag ctgttcctta    8820
tagtgcagca cagcagggac aacgaggcat tcagggatgc gctgctaaac atagtagagc   8880
ccgagggccg ctggctgctc gatttgataa acatcctgca gagcatagtg gtgcaggagc   8940
gcagcttgag cctggctgac aaggtggccg ccatcaacta ttccatgctt agcctgggca   9000
agttttacgc ccgcaagata taccataccc cttacgttcc catagacaag gaggtaaaga   9060
tcgagggtt ctacatgcgc atggcgctga aggtgcttac cttgagcgac gacctgggcg    9120
tttatcgcaa cgagcgcatc cacaaggccg tgagcgtgag ccggcggcgc gagctcagcg   9180
accgcgagct gatgcacagc ctgcaaaggg ccctggctgg cacgggcagc ggcgatagag   9240
aggccgagtc ctactttgac gcgggcgctg acctgcgctg gccccaagcc cgacgcgccc   9300
tggaggcagc tggggccgga cctgggctgg cggtggcacc cgcgcgcgct ggcaacgtcg   9360
gcggcgtgga ggaatatgac gaggacgatg agtacgagcc agaggacggc gagtactaag   9420
cggtgatgtt tctgatcaga tgatgcaaga cgcaacggac ccggcggtgc gggcggcgct   9480
gcagagccag ccgtccggcc ttaactccac ggacgactgg cgccaggtca tggaccgcat   9540
catgtcgctg actgcgcgca atcctgacgc gttccggcag cagccgcagg ccaaccggct   9600
ctccgcaatt ctggaagcgg tggtcccggc gcgcgcaaac cccacgcacg agaaggtgct   9660
ggcgatcgta aacgcgctgg ccgaaaacag ggccatccgg cccgacgaag ccggcctggt   9720
ctacgacgcg ctgcttcagc gcgtggctcg ttacaacagc ggcaacgtgc agaccaacct   9780
ggaccggctg gtgggggatg tgcgcgaggc cgtggcgcag cgtgagcgcg cgcagcagca   9840
gggcaacctg ggctccatgg ttgcactaaa cgccttcctg agtacacagc ccgccaacgt   9900
gccgcgggga caggaggact acaccaactt tgtgagcgca ctgcgggtaa tggtgactga   9960
gacaccgcaa agtgaggtgt accagtctgg gccagactat tttttccaga ccagtagaca  10020
aggcctgcag accgtaaacc tgagccaggc tttcaaaaac ttgcagggc tgtgggggt    10080
gcgggctccc acaggcgacc gcgcgaccgt gtctagcttg ctgacgccca actcgcgcct  10140
gttgctgctg ctaatagcgc ccttcacgga cagtggcagc gtgtcccggg acacataccct 10200
aggtcacttg ctgacactgt accgcgaggc cataggtcag gcgcatgtgg acgagcatac  10260
tttccaggag attacaagtg tcagccgcgc gctggggcag gaggacacgg gcagcctgga  10320
ggcaacccta aactacctgc tgaccaaccg gcggcagaag atcccctcgt tgcacagttt  10380
```

```
aaacagcgag gaggagcgca ttttgcgcta cgtgcagcag agcgtgagcc ttaacctgat    10440
gcgcgacggg gtaacgccca gcgtggcgct ggacatgacc gcgcgcaaca tggaaccggg    10500
catgtatgcc tcaaaccggc cgtttatcaa ccgcctaatg gactacttgc atcgcgcggc    10560
cgccgtgaac cccgagtatt tcaccaatgc catcttgaac ccgcactggc taccgccccc    10620
tggtttctac accgggggat tcgaggtgcc cgagggtaac gatggattcc tctgggacga    10680
catagacgac agcgtgtttt ccccgcaacc gcagaccctg ctagagttgc aacagcgcga    10740
gcaggcagag gcgcgcgctg cgaaggaaag cttccgcagg ccaagcagct tgtccgatct    10800
aggcgctgcg gccccgcggt cagatgctag tagcccattt ccaagcttga tagggtctct    10860
taccagcact cgcaccaccc gcccgcgcct gctgggcgag gaggagtacc taaacaactc    10920
gctgctgcag ccgcagcgcg aaaaaaacct gcctccggca tttcccaaca acgggataga    10980
gagcctagtg gacaagatga gtagatggaa gacgtacgcg caggagcaca gggacgtgcc    11040
aggcccgcgc ccgcccaccc gtcgtcaaag gcacgaccgt cagcggggtc tggtgtggga    11100
ggacgatgac tcggcagacg acagcagcgt cctggatttg ggagggagtg gcaacccgtt    11160
tgcgcacctt cgccccaggc tggggagaat gttttaaaaa aaaaaagca tgatgcaaaa    11220 taaaaaactc accaaggcca tggcaccgag cgttggtttt cttgtattcc ccttagtatg    11280
cggcgcgcgg cgatgtatga ggaaggtcct cctccctcct acgagagtgt ggtgagcgcg    11340 gcgcagtgg cggcggcgct gggttctccc ttcgatgctc ccctggaccc gccgtttgtg    11400
cctccgcggt acctgcggcc taccgggggg agaaacagca tccgttactc tgagttggca    11460
cccctattcg acaccacccg tgtgtacctg gtggacaaca agtcaacgga tgtggcatcc    11520
ctgaactacc agaacgacca cagcaacttt ctgaccacgg tcattcaaaa caatgactac    11580
agcccggggg aggcaagcac acagaccatc aatcttgacg accggtcgca ctggggcggc    11640
gacctgaaaa ccatcctgca taccaacatg ccaaatgtga acgagttcat gtttaccaat    11700
aagtttaagg cgcgggtgat ggtgtcgcgc ttgcctacta aggacaatca ggtggagctg    11760
aaatacgagt gggtggagtt cacgctgccc gagggcaact actccgagac catgaccata    11820
gaccttatga acaacgcgat cgtggagcac tacttgaaag tgggcagaca gaacggggtt    11880
ctggaaagcg acatcgggt aaagtttgac acccgcaact tcagactggg gtttgacccc    11940
gtcactggtc ttgtcatgcc tgggtatat acaaacgaag ccttccatcc agacatcatt    12000
ttgctgccag gatgcgggt ggacttcacc cacagccgcc tgagcaactt gttgggcatc    12060
cgcaagcggc aaccctccca ggagggcttt aggatcacct acgatgatct ggagggtggt    12120
aacattcccg cactgttgga tgtggacgcc taccaggcga gcttgaaaga tgacaccgaa    12180
cagggcgggg gtggcgcagg cggcagcaac agcagtggca gcggcgcgga agagaactcc    12240
aacgcggcag ccgcggcaat gcagccggtg gaggacatga acgatcatgc cattcgcggc    12300
gacacctttg ccacacgggc tgaggagaag cgcgctgagg ccgaagcagc ggccgaagct    12360 gccgccccg ctgcgcaacc cgaggtcgag aagcctcaga agaaaccggt gatcaaaccc    12420
ctgacagagg acagcaagaa acgcagttac aacctaataa gcaatgacag cacccttcacc    12480 cagtaccgca gctggtacct tgcatacaac tacggcgacc ctcagaccgg aatccgctca    12540
tggaccctgc tttgcactcc tgacgtaacc tgcggctcgg agcaggtcta ctggtcgttg    12600
ccagacatga tgcaagaccc cgtgaccttc cgctccacgc gccagatcag caactttccg    12660
gtggtgggcg ccgagctgtt gcccgtgcac tccaagagct tctacaacga ccaggccgtc    12720
```

```
tactcccaac tcatccgcca gtttacctct ctgacccacg tgttcaatcg ctttcccgag    12780
aaccagattt tggcgcgccc gccagccccc accatcacca ccgtcagtga aaacgttcct    12840
gctctcacag atcacgggac gctaccgctg cgcaacagca tcggaggagt ccagcgagtg    12900
accattactg acgccagacg ccgcacctgc ccctacgttt acaaggccct gggcatagtc    12960
tcgccgcgcg tcctatcgag ccgcactttt tgagcaagca tgtccatcct tatatcgccc    13020
agcaataaca caggctgggg cctgcgcttc caagcaaga tgtttggcgg ggccaagaag    13080
cgctccgacc aacacccagt gcgcgtgcgc gggcactacc gcgcgccctg gggcgcgcac    13140
aaacgcggcc gcactgggcg caccaccgtc gatgacgcca tcgacgcggt ggtggaggag    13200
gcgcgcaact acacgcccac gccgccacca gtgtccacag tggacgcggc cattcagacc    13260
gtggtgcgcg gagcccggcg ctatgctaaa atgaagagac ggcggaggcg cgtagcacgt    13320
cgccaccgcc gccgacccgg cactgccgcc caacgcgcgg cggcggccct gcttaaccgc    13380
gcacgtcgca ccgccgacg ggcggccatg cgggccgctc gaaggctggc cgcgggtatt    13440
gtcactgtgc cccccaggtc caggcgacga gcggccgccg cagcagccgc ggccattagt    13500
gctatgactc agggtcgcag gggcaacgtg tattgggtgc gcgactcggt tagcggcctg    13560
cgcgtgcccg tgcgcacccg ccccccgcgc aactagattg caagaaaaaa ctacttagac    13620
tcgtactgtt gtatgtatcc agcggcggcg gcgcgcaacg aagctatgtc caagcgcaaa    13680
atcaaagaag agatgctcca ggtcatcgcg ccggagatct atggcccccc gaagaaggaa    13740
gagcaggatt acaagcccg aaagctaaag cgggtcaaaa agaaaaagaa agatgatgat    13800
gatgaacttg acgacgaggt ggaactgctg cacgctaccg cgcccaggcg acgggtacag    13860
tggaaaggtc gacgcgtaaa acgtgttttg cgacccggca ccaccgtagt ctttacgccc    13920
ggtgagcgct ccacccgcac ctacaagcgc gtgtatgatg aggtgtacgg cgacgaggac    13980
ctgcttgagc aggccaacga gcgcctcggg gagtttgcct acggaaagcg gcataaggac    14040
atgctggcgt tgccgctgga cgagggcaac ccaacaccta gcctaaagcc cgtaacactg    14100
cagcaggtgc tgcccgcgct tgcaccgtcc gaagaaaagc gcggcctaaa gcgcgagtct    14160
ggtgacttgg cacccaccgt gcagctgatg gtacccaagc gccagcgact ggaagatgtc    14220
ttggaaaaaa tgaccgtgga acctgggctg gagcccgagg tccgcgtgcg gccaatcaag    14280
caggtggcgc cgggactggg cgtgcagacc gtggacgttc agatacccac taccagtagc    14340
accagtattg ccaccgccac agagggcatg gagacacaaa cgtccccggt tgcctcagcg    14400
gtggcggatg ccgcggtgca ggcggtcgct gcggccgcgt ccaagacctc tacggaggtg    14460
caaacggacc cgtggatgtt tcgcgtttca gcccccggc gcccgcgcgg ttcgaggaag    14520
tacggcgccc ccagcgcgct actgcccgaa tatgccctac atccttccat tgcgcctacc    14580
cccggctatc gtggctacac ctaccgcccc agaagacgag caactacccg acgccgaacc    14640
accactggaa cccgccgccg ccgtcgccgt cgccagcccg tgctggcccc gatttccgtg    14700
cgcagggtgg ctcgcgaagg aggcaggacc ctggtgctgc aacagcgcg ctaccacccc    14760 agcatcgttt aaaagccggt cttttgtggtt cttgcagata tggccctcac ctgccgcctc    14820
cgtttcccgg tgccgggatt ccgaggaaga atgcaccgta ggagggcat ggccggctac    14880 ggcctgacgg gcggcatgcg tcgtgcgcac caccggcggc ggcgcgcgtc gcaccgtcgc    14940
atgcgcggcg gtatcctgcc cctccttatt ccactgatcg ccgcggcgat tggcgccgtg    15000
cccggaattg catccgtggc cttgcaggcg cagagacact gattaaaaac aagttgcatg    15060
tggaaaaatc aaaataaaaa gtctggactc tcacgctcgc ttggtcctgt aactattttg    15120
```

```
tagaatggaa gacatcaact ttgcgtctct ggccccgcga cacggctcgc gcccgttcat   15180
gggaaactgg caagatatcg gcaccagcaa tatgagcggt ggcgccttca gctggggctc   15240
gctgtggagc ggcattaaaa atttcggttc caccgttaag aactatggca gcaaggcctg   15300
gaacagcagc acaggccaga tgctgaggga taagttgaaa gagcaaaatt ccaacaaaa    15360
ggtggtagat ggcctggcct ctggcattag cggggtggtg gacctggcca accaggcagt   15420
gcaaaataag attaacagta agcttgatcc ccgccctccc gtagaggagc ctccaccggc   15480
cgtggagaca gtgtctccag aggggcgtgg cgaaaagcgt ccgcgcccg acagggaaga    15540
aactctggtg acgcaaatag acgagcctcc ctcgtacgag gaggcactaa agcaaggcct   15600
gcccaccacc cgtcccatcg cgcccatggc taccggagtg ctgggccagc acacacccgt   15660
aacgctggac ctgcctcccc ccgccgacac ccagcagaaa cctgtgctgc aggcccgac    15720
cgccgttgtt gtaacccgtc ctagccgcgc gtccctgcgc cgcgccgcca gcggtccgcg   15780
atcgttgcgg cccgtagcca gtggcaactg gcaaagcaca ctgaacagca tcgtgggtct   15840
gggggtgcaa tccctgaagc gccgacgatg cttctgaata gctaacgtgt cgtatgtgtg   15900
tcatgtatgc gtccatgtcg ccgccagagg agctgctgag ccgccgcgcg cccgctttcc   15960
aagatggcta ccccttcgat gatgccgcag tggtcttaca tgcacatctc gggccaggac   16020
gcctcggagt acctgagccc cgggctggtg cagtttgccc gcgccaccga cgtacttc     16080
agcctgaata caagtttag aaaccccacg gtggcgccta cgcacgacgt gaccacagac    16140
cggtcccagc gtttgacgct gcggttcatc cctgtggacc gtgaggatac tgcgtactcg   16200
tacaaggcgc ggttcaccct agctgtgggt gataaccgtg tgctggacat ggcttccacg   16260
tactttgaca tccgcggcgt gctggacagg ggccctactt ttaagcccta ctctggcact   16320
gcctacaacg ccctggctcc caagggtgcc ccaaatcctt gcgaatggga tgaagctgct   16380
actgctcttg aaataaacct agaagaagag gacgatgaca acgaagacga agtagacgag   16440
caagctgagc agcaaaaaac tcacgtattt gggcaggcgc cttattctgg tataaatatt   16500
acaaggagg tattcaaat aggtgtcgaa ggtcaaacac ctaaatatgc cgataaaaca    16560
tttcaacctg aacctcaaat aggagaatct cagtggtacg aaactgaaat taatcatgca   16620
gctgggagag tccttaaaaa gactacccca atgaaaccat gttacggttc atatgcaaaa   16680
cccacaaatg aaaatggagg gcaaggcatt cttgtaaagc aacaaatgg aaagctagaa    16740
agtcaagtgg aaatgcaatt tttctcaact actgaggcga ccgcaggcaa tggtgataac   16800
ttgactccta aagtggtatt gtacagtgaa gatgtagata tagaaacccc agacactcat   16860
atttcttaca tgcccactat taaggaaggt aactcacgag aactaatggg ccaacaatct   16920
atgcccaaca ggcctaatta cattgctttt agggacaatt ttattggtct aatgtattac   16980
aacagcacgg gtaatatggg tgttctggcg ggccaagcat cgcagttgaa tgctgttgta   17040
gatttgcaag acagaaacac agagctttca taccagcttt tgcttgattc cattggtgat   17100
agaaccaggt acttttctat gtggaatcag gctgttgaca gctatgatcc agatgttaga   17160
attattgaaa atcatggaac tgaagatgaa cttccaaatt actgctttcc actgggaggt   17220
gtgattaata cagagactct taccaaggta aaacctaaaa caggtcagga aaatggatgg   17280
gaaaagatg ctacagaatt ttcagataaa aatgaaataa gagttggaaa taattttgcc    17340
atggaaatca atctaaatgc caacctgtgg agaaatttcc tgtactccaa catagcgctg   17400
tatttgcccg acaagctaaa gtacagtcct tccaacgtaa aaatttctga taacccaaac   17460
```

```
acctacgact acatgaacaa gcgagtggtg gctcccgggt tagtggactg ctacattaac  17520
cttggagcac gctggtccct tgactatatg gacaacgtca acccatttaa ccaccaccgc  17580
aatgctggcc tgcgctaccg ctcaatgttg ctgggcaatg gtcgctatgt gcccttccac  17640
atccaggtgc ctcagaagtt ctttgccatt aaaaacctcc ttctcctgcc gggctcatac  17700
acctacgagt ggaacttcag gaaggatgtt aacatggttc tgcagagctc cctaggaaat  17760
gacctaaggg ttgacggagc cagcattaag tttgatagca tttgccttta cgccaccttc  17820
ttccccatgg cccacaacac cgcctccacg cttgaggcca tgcttagaaa cgacaccaac  17880
gaccagtcct ttaacgacta tctctccgcc gccaacatgc tctaccctat acccgccaac  17940
gctaccaacg tgcccatatc catcccctcc cgcaactggg cggctttccg cggctgggcc  18000
ttcacgcgcc ttaagactaa ggaaacccca tcactgggct cgggctacga cccttattac  18060
acctactctg gctctatacc ctacctagat ggaacctttt acctcaacca caccctttaag  18120 aaggtggcca ttacctttga ctcttctgtc agctggcctg gcaatgaccg cctgcttacc  18180
cccaacgagt ttgaaattaa gcgctcagtt gacggggagg gttacaacgt tgcccagtgt  18240
aacatgacca aagactggtt cctggtacaa atgctagcta actacaacat tggctaccag  18300
ggcttctata tcccagagag ctacaaggac cgcatgtact ccttctttag aaacttccag  18360
cccatgagcc gtcaggtggt ggatgatact aaatacaagg actaccaaca ggtgggcatc  18420
ctacaccaac acaacaactc tggatttgtt ggctaccttg cccccaccat gcgcgaagga  18480
caggcctacc ctgctaactt cccctatccg cttataggca agaccgcagt tgacagcatt  18540
acccagaaaa agtttctttg cgatcgcacc cttggcgca tcccattctc cagtaacttt  18600
atgtccatgg gcgcactcac agacctgggc caaaaccttc tctacgccaa ctccgcccac  18660
gcgctagaca tgacttttga ggtggatccc atggacgagc ccacccttct ttatgttttg  18720
tttgaagtct ttgacgtggt ccgtgtgcac cggccgcacc gcggcgtcat cgaaaccgtg  18780
tacctgcgca cgcccttctc ggccggcaac gccacaacat aaagaagcaa gcaacatcaa  18840
caacagctgc cgccatgggc tccagtgagc aggaactgaa agccattgtc aaagatcttg  18900
gttgtgggcc atattttttg ggcacctatg acaagcgctt ccaggctttt gtttctccac  18960
acaagctcgc ctgcgccata gtcaatacgg ccggtcgcga gactgggggc gtacactgga  19020
tggcctttgc ctggaacccg cactcaaaaa catgctacct ctttgagccc tttggctttt  19080
ctgaccagcg actcaagcag gtttaccagt ttgagtacga gtcactcctg cgccgtagcg  19140
ccattgcttc ttccccgac cgctgtataa cgctggaaaa gtccacccaa agcgtacagg  19200
ggcccaactc ggccgcctgt ggactattct gctgcatgtt tctccacgcc tttgccaact  19260
ggccccaaac tcccatggat cacaaccccc ccatgaacct tattaccggg gtacccaact  19320
ccatgctcaa cagtccccag gtacagccca ccctgcgtcg caaccaggaa cagctctaca  19380
gcttcctgga gcgccactcg ccctacttcc gcagccacag tgcgcagatt aggagcgcca  19440 cttcttttg tcacttgaaa aacatgtaaa aataatgtac tagagacact ttcaataaag  19500
gcaaatgctt ttatttgtac actctcgggt gattatttac ccccacccct gccgtctgcg  19560
ccgtttaaaa atcaaagggg ttctgccgcg catcgctatg cgccactggc agggacacgt  19620
tgcgatactg gtgtttagtg ctccacttaa actcaggcac aaccatccgc ggcagctcgg  19680
tgaagttttc actccacagg ctgcgcacca tcaccaacgc gtttagcagg tcgggcgccg  19740
atatcttgaa gtcgcagttg gggcctccgc cctgcgcgcg cgagttgcga tacacagggt  19800
tgcagcactg gaacactatc agcgccgggt ggtgcacgct ggccagcacg ctcttgtcgg  19860
```

-continued

```
agatcagatc cgcgtccagg tcctccgcgt tgctcagggc gaacggagtc aactttggta  19920
gctgccttcc caaaaagggc gcgtgcccag gctttgagtt gcactcgcac cgtagtggca  19980
tcaaaaggtg accgtgcccg gtctgggcgt taggatacag cgcctgcata aaagccttga  20040
tctgcttaaa agccacctga gcctttgcgc cttcagagaa gaacatgccg caagacttgc  20100
cggaaaactg attggccgga caggccgcgt cgtgcacgca gcaccttgcg tcggtgttgg  20160
agatctgcac cacatttcgg ccccaccggt tcttcacgat cttggccttg ctagactgct  20220
ccttcagcgc gcgctgcccg ttttcgctcg tcacatccat ttcaatcacg tgctccttat  20280
ttatcataat gcttccgtgt agacacttaa gctcgccttc gatctcagcg cagcggtgca  20340
gccacaacgc gcagcccgtg ggctcgtgat gcttgtaggt cacctctgca aacgactgca  20400
ggtacgcctg caggaatcgc cccatcatcg tcacaaaggt cttgttgctg gtgaaggtca  20460
gctgcaaccc gcggtgctcc tcgttcagcc aggtcttgca tacggccgcc agagcttcca  20520
cttggtcagg cagtagtttg aagttcgcct ttagatcgtt atccacgtgg tacttgtcca  20580
tcagcgcgcg cgcagcctcc atgcccttct cccacgcaga cacgatcggc acactcagcg  20640
ggttcatcac cgtaatttca ctttccgctt cgctgggctc ttcctcttcc tcttgcgtcc  20700
gcataccacg cgccactggg tcgtcttcat tcagccgccg cactgtgcgc ttacctcctt  20760
tgccatgctt gattagcacc ggtgggttgc tgaaacccac catttgtagc gccacatctt  20820
ctctttcttc ctcgctgtcc acgattacct ctggtgatgg cgggcgctcg ggcttgggag  20880
aagggcgctt ctttttcttc ttgggcgcaa tggccaaatc cgccgccgag gtcgatggcc  20940
gcgggctggg tgtgcgcggc accagcgcgt cttgtgatga gtcttcctcg tcctcggact  21000
cgatacgccg cctcatccgc ttttttgggg gcgcccgggg aggcggcggc gacggggacg  21060
gggacgacac gtcctccatg gttggggac gtcgcgccgc accgcgtccg cgctcggggg  21120
tggtttcgcg ctgctcctct tcccgactgg ccatttcctt ctcctatagg cagaaaaaga  21180
tcatggagtc agtcgagaag aaggacagcc taaccgcccc ctctgagttc gccaccaccg  21240
cctccaccga tgccgccaac gcgcctacca ccttccccgt cgaggcaccc ccgcttgagg  21300
aggaggaagt gattatcgag caggacccag gttttgtaag cgaagacgac gaggaccgct  21360
cagtaccaac agaggataaa aagcaagacc aggacaacgc agaggcaaac gaggaacaag  21420
tcgggcgggg ggacgaaagg catggcgact acctagatgt gggagacgac gtgctgttga  21480
agcatctgca gcgccagtgc gccattatct gcgacgcgtt gcaagagcgc agcgatgtgc  21540
ccctcgccat agcggatgtc agccttgcct acgaacgcca cctattctca ccgcgcgtac  21600
cccccaaacg ccaagaaaac ggcacatgcg agcccaaccc gcgcctcaac ttctaccccg  21660
tatttgccgt gccagaggtg cttgccacct atcacatctt tttccaaaac tgcaagatac  21720
ccctatcctg ccgtgccaac cgcagccgag cggacaagca gctggccttg cggcagggcg  21780
ctgtcatacc tgatatcgcc tcgctcaacg aagtgccaaa aatctttgag ggtcttggac  21840
gcgacgagaa gcgcgcggca aacgctctgc aacaggaaaa cagcgaaaat gaaagtcact  21900
ctggagtgtt ggtggaactc gagggtgaca acgcgcgcct agccgtacta aaacgcagca  21960
tcgaggtcac ccactttgcc tacccggcac ttaacctacc ccccaaggtc atgagcacag  22020
tcatgagtga gctgatcgtg cgccgtgcgc agcccctgga gagggatgca aatttgcaag  22080
aacaaacaga ggagggccta cccgcagttg gcgacgagca gctagcgcgc tggcttcaaa  22140
cgcgcgagcc tgccgacttg gaggagcgac gcaaactaat gatggccgca gtgctcgtta  22200
```

```
ccgtggagct tgagtgcatg cagcggttct ttgctgaccc ggagatgcag cgcaagctag   22260
aggaaacatt gcactacacc tttcgacagg gctacgtacg ccaggcctgc aagatctcca   22320
acgtggagct ctgcaacctg gtctcctacc ttggaattt  gcacgaaaac cgccttgggc   22380
aaaacgtgct tcattccacg ctcaagggcg aggcgcgccg cgactacgtc cgcgactgcg   22440
tttacttatt tctatgctac acctggcaga cggccatggg cgtttggcag cagtgcttgg   22500
aggagtgcaa cctcaaggag ctgcagaaac tgctaaagca aaacttgaag gacctatgga   22560
cggccttcaa cgagcgctcc gtggccgcgc acctggcgga catcattttc cccgaacgcc   22620
tgcttaaaac cctgcaacag ggtctgccag acttcaccag tcaaagcatg ttgcagaact   22680
ttaggaactt tatcctagag cgctcaggaa tcttgcccgc cacctgctgt gcacttccta   22740
gcgactttgt gccattaag  taccgcgaat gccctccgcc gctttgggc  cactgctacc   22800 ttctgcagct agccaactac cttgcctacc actctgacat aatggaagac gtgagcggtg   22860
acggtctact ggagtgtcac tgtcgctgca acctatgcac cccgcaccgc tccctggttt   22920
gcaattcgca gctgcttaac gaaagtcaaa ttatcggtac ctttgagctg cagggtccct   22980
cgcctgacga aaagtccgcg gctccggggt tgaaactcac tccggggctg tggacgtcgg   23040
cttaccttcg caaatttgta cctgaggact accacgccca cgagattagg ttctacgaag   23100
accaatcccg cccgccaaat gcggagctta ccgcctgcgt cattacccag gccacattc   23160 ttggccaatt gcaagccatc aacaaagccc gccaagagtt tctgctacga aagggacggg   23220
gggtttactt ggaccccag  tccggcgagg agctcaaccc aatccccccg ccgccgcagc   23280
cctatcagca gcagccgcgg gcccttgctt cccaggatgg cacccaaaaa gaagctgcag   23340
ctgccgccgc cacccacgga cgaggaggaa tactgggaca gtcaggcaga ggaggttttg   23400
gacgaggagg aggaggacat gatggaagac tgggagagcc tagacgagga agcttccgag   23460
gtcgaagagg tgtcagacga aacaccgtca ccctcggtcg cattcccctc gccggcgccc   23520
cagaaatcgg caaccggttc cagcatggct acaacctccg ctcctcaggc gccgccggca   23580
ctgcccgttc gccgacccaa ccgtagatgg gacaccactg gaaccagggc cggtaagtcc   23640
aagcagccgc cgccgttagc ccaagagcaa caacagcgcc aaggctaccg ctcatggcgc   23700
gggcacaaga acgccatagt tgcttgcttg caagactgtg ggggcaacat ctccttcgcc   23760
cgccgctttc ttctctacca tcacggcgtg gccttcccc  gtaacatcct gcattactac   23820
cgtcatctct acagcccata ctgcaccggc ggcagcggca gcggcagcaa cagcagcggc   23880
cacacagaag caaaggcgac cggatagcaa gactctgaca aagcccaaga atccacagc   23940 ggcggcagca gcaggaggag gagcgctgcg tctggcgccc aacgaacccg tatcgacccg   24000
cgagcttaga aacaggattt ttcccactct gtatgctata tttcaacaga gcaggggcca   24060
agaacaagag ctgaaaataa aaaacaggtc tctgcgatcc ctcacccgca gctgcctgta   24120
tcacaaaagc gaagatcagc ttcggcgcac gctggaagac gcggaggctc tcttcagtaa   24180
atactgcgcg ctgactctta aggactagtt tcgcgccctt tctcaaattt aagcgcgaaa   24240
actacgtcat ctccagcggc cacacccggc gccagcacct gtcgtcagcg ccattatgag   24300
caaggaaatt cccacgccct acatgtggag ttaccagcca caaatgggac ttgcggctgg   24360
agctgcccaa gactactcaa cccgaataaa ctacatgagc gcgggacccc acatgatatc   24420
ccgggtcaac ggaatccgcg cccaccgaaa ccgaattctc ttggaacagg cggctattac   24480
caccacacct cgtaataacc ttaatcccg  tagttggccc gctgccctgg tgtaccagga   24540
aagtcccgct cccaccactg tggtacttcc cagagacgcc caggccgaag ttcagatgac   24600
```

```
taactcaggg gcgcagcttg cgggcggctt tcgtcacagg gtgcggtcgc ccgggcaggg       24660
tataactcac ctgacaatca gagggcgagg tattcagctc aacgacgagt cggtgagctc       24720
ctcgcttggt ctccgtccgg acgggacatt tcagatcggc ggcgccggcc gtccttcatt       24780
cacgcctcgt caggcaatcc taactctgca gacctcgtcc tctgagccgc gctctggagg       24840
cattggaact ctgcaatttta ttgaggagtt tgtgccatcg gtctacttta accccttctc      24900
gggacctccc ggccactatc cggatcaatt tattcctaac tttgacgcgg taaaggactc       24960
ggcggacggc tacgactgaa tgttaagtgg agaggcagag caactgcgcc tgaaacacct       25020
ggtccactgt cgccgccaca agtgctttgc ccgcgactcc ggtgagtttt gctactttga       25080
attgcccgag gatcatatcg agggcccggc gcacggcgtc cggcttaccg cccagggaga       25140
gcttgcccgt agcctgattc gggagtttac ccagcgcccc ctgctagttg agcgggacag       25200
gggaccctgt gttctcactg tgatttgcaa ctgtcctaac cttggattac atcaagatcc       25260
tctagttaat taacagcttg catgcctgca ggtcgacgga tcgggagatc tcggccgcat       25320
attaagtgca ttgttctcga taccgctaag tgcattgttc tcgttagctc gatggacaag       25380
tgcattgttc tcttgctgaa agctcgatgg acaagtgcat tgttctcttg ctgaaagctc       25440
gatggacaag tgcattgttc tcttgctgaa agctcgagtac ccgggagtac cctcgaccgc      25500
cggagtataa atagaggcgc ttcgtctacg gagcgacaat tcaattcaaa caagcaaagt       25560
gaacacgtcg ctaagcgaaa gctaagcaaa taaacaagcg cagctgaaca agctaaacaa       25620
tctgcagtaa agtgcaagtt aaagtgaatc aattaaaagt aaccagcaac caagtaaatc       25680
aactgcaact actgaaatct gccaagaagt aattattgaa tacaagaaga gaactctgaa       25740
tactttcaac aagttaccga gaaagaagaa ctcacacaca gctagcgttt aaacttaagc       25800
ttcaccatgg tggggccctg catgctgctg ctgctgctgc tgctgggcct gaggctacag       25860 ctctcccctgg gcatcatcct agttgaggag gagaacccgg acttctggaa ccgcgaggca      25920
gccgaggccc tgggtgccgc caagaagctg cagcctgcac agacagccgc caagaacctc       25980
atcatcttcc tgggcgatgg ggtgggggtg tctacggtga cagctgccag gatcctaaaa       26040
gggcagaaga aggacaaact ggggcctgag atacccctgg ccatggaccg cttcccatat       26100
gtggctctgt ccaagacata caatgtagac aaacatgtgc cagacagtgg agccacagcc       26160
acggcctacc tgtgcgggt caagggcaac ttccagacca ttggcttgag tgcagccgcc       26220
cgctttaacc agtgcaacac gacacgcggc aacgaggtca tctccgtgat gaatcgggcc       26280
aagaaagcag ggaagtcagt gggagtggta accaccacac gagtgcagca cgcctcgcca       26340 gccggcaccgt acgcccacac ggtgaaccgc aactggtact cggacgccga cgtgcctgcc       26400
tcggcccgcc aggagggggtg ccaggacatc gctacgcagc tcatctccaa catggacatt       26460
gacgtgatcc taggtgggggg ccgaaagtac atgtttcgca tgggaacccc agaccctgag       26520
tacccagatg actacagcca aggtgggacc aggctggacg ggaagaatct ggtgcaggaa       26580
tggctggcga agcaccaggg tgcccggtac gtgtggaacc gcactgagct catgcgggct       26640
tccctggacc cgtctgtggc ccatctcatg ggtctctttg agcctggaga catgaaatac       26700
gagatccacc gagactccac actgaccccc tccctgatgg agatgacaga ggctgccctg       26760
cgcctgctga gcaggaaccc ccgcggcttc ttcctcttcg tggagggtgg tcgcatcgac       26820
catggtcatc atgaaagcag ggcttaccgg gcactgactg agacgatcat gttcgacgac       26880
gccattgaga gggcgggcca gctcaccagc gaggaggaca cgctgagcct cgtcactgcc       26940
```

```
gaccactccc acgtcttctc cttcggaggc tgcccctgc aggggggctc catcttcggg    27000
ctggcccctg gcaaggcccg ggacaggaag gcctacacgg tcctcctata cggaaacggt    27060
ccaggctatg tgctcaagga cggcgcccgg ccggatgtta ccgagagcga gagcgggagc    27120
cccgagtatc ggcagcagtc agcagtgccc ctggacgaag agacccacgc aggcgaggac    27180
gtggcggtgt tcgcgcgcgg cccgcaggcg cacctggttc acggcgtgca ggagcagacc    27240
ttcatagcgc acgtcatggc cttcgccgcc tgcctggagc cctacaccgc ctgcgacctg    27300
gcgcccccg ccggcaccac cgacgccgcg caccggggc ggtccgtggt ccccgcgttg      27360
cttcctctgc tggccgggac cctgctgctg ctggagacgg ccactgctcc ctgagtgtcc    27420
cgtccctggg gctcctgctt ccccatcccg gagttctcct gctccccgcc tcctgtcgtc    27480
ctgcctggcc tccagcccga gtcgtcatcc ccggagtccc tatacagagg tcctgccatg    27540
gaaccttccc ctccccgtgc gctctgggga ctgagcccat gacaccaaac ctgcccttg     27600
gctgctctcg gactccctac cccaaccca gggacagatc tggccagatt tgtaaaacaa     27660
atagatttta ggcccaaaga ttatttaaag cattgcctgg aacgcagtga gttttgtta    27720
gaaaagagaa taattcaaag tggcattgct ttgcttctta tgttaatttg gtacagacct    27780
gtggctgagt ttgctcaaag tattcagagc agaattgtgg agtggaaaga gagattggac    27840
aaagagttta gtttgtcagt gtatcaaaaa atgaagttta atgtggctat gggaattgga    27900
gttttagatt ggctaagaaa cagtgatgat gatgatgaag acagccagga aaatgctgat    27960
aaaaatgaag atggtgggga gaagaacatg gaagactcag ggcatgaaac aggcattgat    28020
tcacagtccc aaggctcatt tcaggcccct cagtcctcac agtctgttca tgatcataat    28080
cagccatacc acatttgtag aggttttact tgctttaaaa aacctcccac acctccccct    28140
gaacctgaaa cataaaatga atgcaattgt tgttgttaac ttgtttattg cagcttataa    28200
tggttacaaa taaagcaata gcatcacaaa tttcacaaat aaagcatttt tttcactgca    28260
ttctagttgt ggtttgtcca aactcatcaa tgtatcttat catgtctgga tccccaggaa    28320
gctcctctgt gtcctcataa accctaacct cctctacttg agaggacatt ccaatcatag    28380
gctgcccatc caccctctgt gtcctcctgt taattaggtc acttaacaaa aaggaaattg    28440
ggtaggggtt tttcacagac cgcttttctaa gggtaatttt aaaatatctg ggaagtccct    28500
tccactgctg tgttccagaa gtgttggtaa acagcccaca aatgtcaaca gcagaaacat    28560
acaagctgtc agctttgcac aagggcccaa caccctgctc atcaagaagc actgtggttg    28620
ctgtgttagt aatgtgcaaa acaggaggca cattttcccc acctgtgtag gttccaaaat    28680
atctagtgtt ttcattttta cttggatcag gaacccagca ctccactgga taagcattat    28740
ccttatccaa aacagccttg tggtcagtgt tcatctgctg actgtcaact gtagcatttt    28800
ttggggttac agtttgagca ggatatttgg tcctgtagtt tgctaacaca ccctgcagct    28860
ccaaggttc cccaccaaca gcaaaaaat gaaaatttga cccttgaatg ggttttccag      28920
caccattttc atgagttttt tgtgtccctg aatgcaagtt taacatagca gttaccccaa    28980
taacctcagt tttaacagta acagcttccc acatcaaaat atttccacag gttaagtcct    29040
catttaaatt aggcaaagga attccacttc ccactgcctt gcttccgtct cccattcaaa    29100
cttttatcaa ctgacattat tctaagtaaa atcctcttca ttatgttgtc agcaatccat    29160
tgcttgaagg cctggctccc cagaaccct cgactggtat gtcttctcct agaatactcc     29220
agaagaaaag gagtgtatga agatagtgac tgcacattaa aatgactgaa accatagtaa    29280
attaggatga gattctgggc agataaacag acagctggct aggatcattt ttttatgcct    29340
```

```
tggacttctt tggcaatctg ttgaagcctg acattcctca gaataatgtt ttaaagccca    29400
acaataagac cctgtagcac atataataag tactgcagtt ttgaagtagt gataagcata    29460
aatgatattt tgatatattt attataactg taatgagatg tgtacatatc tgtgacttca    29520
taggtactga ttgtactact gtgattttt tgcctacttt caaaatgaaa aggaatgctt     29580
aatttcagtt agaggttagt aaagacaaat aggtaatttt cttctccagt gaagagcatg    29640
gcgccccttg ctattcatgg acgcttgctt aaagacttgt acacaggctt gctttgtatc    29700
aacctatgac ttccccttac agccgatgat aggttttat ttgcacctcc ttcgtgtaca     29760
aagacagttt tggtggctac gccatcatta aactcattat tatcatgctt aagcctatag    29820
atgtatccag ttcttctgtt acataattga agctgtagtg aattgtctat cttaaactgc    29880
atcgctaact gactacattt cacacttcat ttgcttccaa catagactaa ccttcttgga    29940
tgtccactat tatttgaact tttgagattt ttttcctat ttctaatatc ttaaaatttc     30000
agaagactta agttttgca actacagggc tccatataga catctagctt gaatttatac     30060
actttctttc attgatgtcc ctggactaaa aaatgttaaa tatttctaac cgctgtactt    30120
aaagtccatt acaaacgaag actactgttg ttaagttgaa taggcatctt atatatttt     30180 caccggtgca ataaataact tctattccct tctaacatct gcttgcgttg cactgagagt    30240
acactattga ttagcaatag gttcgtgatt acagcccttc tataattaat tgttaggtta    30300
acatattatt cataaaatat tattttatta atttttactt gatttgctac tggatgctta    30360
gaaatagcta tgagtatatt ggtagaacca gtacttatat tttattacat ttttacattt    30420
cataaaattt aagtgatata aaatcctga ggaagtatgc cacaaaagtg gtctcagtgg     30480
aaatttaaat atgttaacat ttattttaa aatgtagcgt gaaatagaca actttaaaag     30540
ctcagcttaa aaaaaaaact caaggaagct gaacttgact ttttaaagca ctgaagtgca    30600
atatttaatg taggtcaaca tgtttaaatg ggaaaatttt tttcctaatt acagccaaat    30660
ccctagctgt aattaactta aaatttgtat actatttcac aacagagtca gcatatacca    30720 cttttcttata aaattagaaa gatctaaaat tttagagctt atttggtgaa acaggcatat    30780
tgctacatct ttgtttataa attataatgt gcctttagag cccaataaca gataacaaga    30840
ttttgaaaat tcaggtgaat tagagttatc agagggaatg ttaatacact ctattcaaat    30900
actatatgag taagacattt aaaataggaa acaatacttt atatattaaa aaaaattaat    30960
cttccagtcg atttaatcca ctttatgaat tcatttaaat cgatttaaat tcgaattaat    31020
taactagagt acccggggat cttattccct ttaactaata aaaaaaaata ataaagcatc    31080
acttacttaa aatcagttag caaatttctg tccagtttat tcagcagcac tccttgccc     31140 tcctcccagc tctggtattg cagcttcctc ctggctgcaa actttctcca caatctaaat    31200
ggaatgtcag tttcctcctg ttcctgtcca tccgcaccca ctatcttcat gttgttgcag    31260
atgaagcgcg caagaccgtc tgaagatacc ttcaaccccg tgtatccata tgacacggaa    31320
accggtcctc caactgtgcc ttttcttact cctccctttg tatcccccaa tgggtttcaa    31380
gagagtcccc ctggggtact ctctttgcgc ctatccgaac ctctagttac ctccaatggc    31440
atgcttgcgc tcaaaatggg caacggcctc tctctggacg aggccggcaa ccttacctcc    31500
caaaatgtaa ccactgtgag cccacctctc aaaaaaacca agtcaaacat aaacctgaa     31560 atatctgcac ccctcacagt tacctcagaa gccctaactg tggctgccgc cgcacctcta    31620
atggtcgcgg gcaacacact caccatgcaa tcacaggccc cgctaaccgt gcacgactcc    31680
```

```
aaacttagca ttgccaccca aggacccctc acagtgtcag aaggaaagct agccctgcaa    31740
acatcaggcc ccctcaccac caccgatagc agtaccctta ctatcactgc ctcacccct     31800 ctaactactg ccactggtag cttgggcatt gacttgaaag agcccattta tacacaaaat    31860
ggaaaactag gactaaagta cggggctcct ttgcatgtaa cagacgacct aaacactttg    31920
accgtagcaa ctggtccagg tgtgactatt aataatactt ccttgcaaac taaagttact    31980
ggagccttgg gttttgattc acaaggcaat atgcaactta atgtagcagg aggactaagg    32040
attgattctc aaaacagacg cctatactt gatgttagtt atccgtttga tgctcaaaac     32100
caactaaatc taagactagg acagggccct cttttatataa actcagccca caacttggat   32160
attaactaca acaaaggcct ttacttgttt acagcttcaa acaattccaa aaagcttgag    32220
gttaacctaa gcactgccaa ggggttgatg tttgacgcta cagccatagc cattaatgca    32280
ggagatgggc ttgaatttgg ttcacctaat gcaccaaaca caaatcccct caaaacaaaa    32340
attggccatg gcctagaatt tgattcaaac aaggctatgg ttcctaaact aggaactggc    32400
cttagttttg acagcacagg tgccattaca gtaggaaaca aaaataatga taagctaact   32460
ttgtggacca caccagctcc atctcctaac tgtagactaa atgcagagaa agatgctaaa    32520
ctcactttgg tcttaacaaa atgtggcagt caaatacttg ctacagtttc agttttggct    32580
gttaaaggca gtttggctcc aatatctgga acagttcaaa gtgctcatct tattataaga    32640
tttgacgaaa atggagtgct actaaacaat tccttcctgg acccagaata ttggaacttt    32700
agaaatggag atcttactga aggcacagcc tatacaaacg ctgttggatt tatgcctaac    32760
ctatcagctt atccaaaatc tcacggtaaa actgccaaaa gtaacattgt cagtcaagtt    32820
tacttaaacg gagacaaaac taaacctgta acactaacca ttacactaaa cggtacacag    32880
gaaacaggag acacaactcc aagtgcatac tctatgtcat tttcatggga ctggtctggc    32940
cacaactaca ttaatgaaat atttgccaca tcctcttaca ctttttcata cattgcccaa    33000
gaataaagaa tcgtttgtgt tatgtttcaa cgtgtttatt tttcaattgc agaaaatttc    33060
aagtcatttt tcattcagta gtatagcccc accaccacat agcttataca gatcaccgta    33120
ccttaatcaa actcacagaa ccctagtatt caacctgcca cctccctccc aacacacaga    33180
gtacacagtc ctttctcccc ggctggcctt aaaaagcatc atatcatggg taacagacat    33240
attcttaggt gttatattcc acacggtttc ctgtcgagcc aaacgctcat cagtgatatt    33300
aataaactcc ccgggcagct cacttaagtt catgtcgctg tccagctgct gagccacagg    33360
ctgctgtcca acttgcggtt gcttaacggg cggcgaagga gaagtccacg cctacatggg    33420
ggtagagtca taatcgtgca tcaggatagg gcggtggtgc tgcagcagcg cgcgaataaa    33480
ctgctgccgc cgccgctccg tcctgcagga atacaacatg gcagtggtct cctcagcgat    33540
gattcgcacc gcccgcagca taaggcgcct tgtcctccgg gcacagcagc gcaccctgat    33600
ctcacttaaa tcagcacagt aactgcagca cagcaccaca atattgttca aaatcccaca    33660
gtgcaaggcg ctgtatccaa agctcatggc ggggaccaca gaacccacgt ggccatcata    33720
ccacaagcgc aggtagatta agtggcgacc cctcataaac acgctggaca taaacattac    33780
ctcttttggc atgttgtaat tcaccacctc ccggtaccat ataaacctct gattaaacat    33840
ggcgccatcc accaccatcc taaaccagct ggccaaaacc tgcccgccgg ctatacactg    33900
cagggaaccg ggactggaac aatgacagtg gagagcccag gactcgtaac catggatcat    33960
catgctcgtc atgatatcaa tgttggcaca acacaggcac acgtgcatac acttcctcag    34020
gattacaagc tcctcccgcg ttagaaccat atcccaggga acaacccatt cctgaatcag    34080
```

```
cgtaaatccc acactgcagg gaagacctcg cacgtaactc acgttgtgca ttgtcaaagt    34140
gttacattcg ggcagcagcg gatgatcctc cagtatggta gcgcgggttt ctgtctcaaa    34200
aggaggtaga cgatccctac tgtacggagt gcgccgagac aaccgagatc gtgttggtcg    34260
tagtgtcatg ccaaatggaa cgccggacgt agtcatattt cctgaagcaa aaccaggtgc    34320
gggcgtgaca aacagatctg cgtctccggt ctcgccgctt agatcgctct gtgtagtagt    34380
tgtagtatat ccactctctc aaagcatcca ggcgccccct ggcttcgggt tctatgtaaa    34440
ctccttcatg cgccgctgcc ctgataacat ccaccaccgc agaataagcc acacccagcc    34500
aacctacaca ttcgttctgc gagtcacaca cgggaggagc gggaagagct ggaagaacca    34560
tgtttttttt tttattccaa aagattatcc aaaacctcaa aatgaagatc tattaagtga    34620
acgcgctccc ctccggtggc gtggtcaaac tctacagcca aagaacagat aatggcattt    34680
gtaagatgtt gcacaatggc ttccaaaagg caaacggccc tcacgtccaa gtggacgtaa    34740
aggctaaacc cttcagggtg aatctcctct ataaacattc cagcaccttc aaccatgccc    34800
aaataattct catctcgcca ccttctcaat atatctctaa gcaaatcccg aatattaagt    34860
ccggccattg taaaaatctg ctccagagcg ccctccacct tcagcctcaa gcagcgaatc    34920
atgattgcaa aaattcaggt tcctcacaga cctgtataag attcaaaagc ggaacattaa    34980
caaaaatacc gcgatcccgt aggtcccttc gcagggccag ctgaacataa tcgtgcaggt    35040
ctgcacggac cagcgcggcc acttccccgc caggaacctt gacaaaagaa cccacactga    35100
ttatgacacg catactcgga gctatgctaa ccagcgtagc cccgatgtaa gctttgttgc    35160
atgggcggcg atataaaatg caaggtgctg ctcaaaaaat caggcaaagc ctcgcgcaaa    35220
aaagaaagca catcgtagtc atgctcatgc agataaaggc aggtaagctc cggaaccacc    35280
acagaaaaag acaccatttt tctctcaaac atgtctgcgg gtttctgcat aaacacaaaa    35340
taaaataaca aaaaaacatt taaacattag aagcctgtct tacaacagga aaaacaaccc    35400
ttataagcat aagacggact acggccatgc cggcgtgacc gtaaaaaaac tggtcaccgt    35460
gattaaaaag caccaccgac agctcctcgg tcatgtccgg agtcataatg taagactcgg    35520
taaacacatc aggttgattc atcggtcagt gctaaaaagc gaccgaaata gcccggggga    35580
atacataccc gcaggcgtag agacaacatt acagccccca taggaggtat aacaaaatta    35640
ataggagaga aaacacata aacacctgaa aaaccctcct gcctaggcaa aatagcaccc    35700
tcccgctcca gaacaacata cagcgcttca cagcggcagc ctaacagtca gccttaccag    35760 taaaaagaa aacctattaa aaaaacacca ctcgacacgg caccagctca atcagtcaca    35820
gtgtaaaaaa gggccaagtg cagagcgagt atatatagga ctaaaaaatg acgtaacggt    35880
taaagtccac aaaaaacacc cagaaaaccg cacgcgaacc tacgcccaga aacgaaagcc    35940
aaaaaaccca caacttcctc aaatcgtcac ttccgttttc ccacgttacg taacttccca    36000
ttttaagaaa actacaattc ccaacacata caagttactc cgccctaaaa cctacgtcac    36060 ccgcccccgtt cccacgcccc gcgccacgtc acaaactcca ccccctcatt atcatattgg    36120
cttcaatcca aaataaggta tattattgat gatg                                36154
```

<210> SEQ ID NO 10
<211> LENGTH: 103
<212> TYPE: DNA
<213> ORGANISM: Artificial Sequence
<220> FEATURE:
<223> OTHER INFORMATION: Synthetic

```
<400> SEQUENCE: 10
catcatcaat aatataccttt attttggatt gaagccaata tgataatgag ggggtggagt      60
ttgtgacgtg gcgcggggcg tgggaacggg gcgggtgacg tag                        103

<210> SEQ ID NO 11
<211> LENGTH: 73
<212> TYPE: DNA
<213> ORGANISM: Artificial Sequence
<220> FEATURE:
<223> OTHER INFORMATION: Synthetic

<400> SEQUENCE: 11
catcatcaat aatataccttt attttggatt gaagccaata tgataatgag ggggtggagt      60
ttgtgacgtg gcg                                                         73

<210> SEQ ID NO 12
<211> LENGTH: 2989
<212> TYPE: DNA
<213> ORGANISM: Artificial Sequence
<220> FEATURE:
<223> OTHER INFORMATION: Synthetic

<400> SEQUENCE: 12
ctaaattgta agcgttaata ttttgttaaa attcgcgtta aattttttgtt aaatcagctc      60 attttttaac caataggccg aaatcggcaa atcccttat aaatcaaaag aatagaccga      120
gatagggttg agtgttgttc cagtttggaa caagagtcca ctattaaaga acgtggactc      180
caacgtcaaa gggcgaaaaa ccgtctatca gggcgatggc ccactacgtg aaccatcacc      240
ctaatcaagt ttttgggggt cgaggtgccg taaagcacta aatcggaacc ctaaagggag      300
cccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac      420
cacacccgcc gcgcttaatg cgccgctaca gggcgcgtcc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgagc gcgcgtaata cgactcacta tagggcgaat tggagcttac      660
gtattaatta aggcgccgcg gtggcggccg ctctagaact agtggatccc ccgggctgca      720
ggaattcggc cgcctaggcc acgcgtaagc ttatcgatac cgtcgacctc gagggggggc      780
ccggtaccca gcttttgttc cctttagtga gggttaattg cgcgcttggc gtaatcatgg      840
tcatagctgt ttcctgtgtg aaattgttat ccgctcacaa ttccacacaa catacgagcc      900
ggaagcataa agtgtaaagc ctggggtgcc taatgagtga gctaactcac attaattgcg      960
ttgcgctcac tgcccgcttt ccagtcggga aacctgtcgt gccagctgca ttaatgaatc    1020
ggccaacgcg cggggagagg cggtttgcgt attgggcgct cttccgcttc ctcgctcact    1080
gactcgctgc gctcggtcgt tcggctgcgg cgagcggtat cagctcactc aaaggcggta    1140
atacggttat ccacagaatc aggggataac gcaggaaaga acatgtgagc aaaaggccag    1200
caaaaggcca ggaaccgtaa aaaggccgcg ttgctggcgt ttttccatag gctccgcccc    1260
cctgacgagc atcacaaaaa tcgacgctca agtcagaggt ggcgaaaccc gacaggacta    1320
taaagatacc aggcgtttcc ccctggaagc tccctcgtgc gctctcctgt tccgaccctg    1380
ccgcttaccg gatacctgtc cgcctttctc ccttcgggaa gcgtggcgct ttctcatagc    1440
tcacgctgta ggtatctcag ttcggtgtag gtcgttcgct ccaagctggg ctgtgtgcac    1500
```

| | |
|---|---|
| gaaccccccg ttcagcccga ccgctgcgcc ttatccggta actatcgtct tgagtccaac | 1560 |
| ccggtaagac acgacttatc gccactggca gcagccactg gtaacaggat tagcagagcg | 1620 |
| aggtatgtag gcggtgctac agagttcttg aagtggtggc ctaactacgg ctacactaga | 1680 |
| aggacagtat ttggtatctg cgctctgctg aagccagtta ccttcggaaa aagagttggt | 1740 |
| agctcttgat ccggcaaaca aaccaccgct ggtagcggtg ttttttttgt ttgcaagcag | 1800 |
| cagattacgc gcagaaaaaa aggatctcaa gaagatcctt tgatcttttc tacggggtct | 1860 |
| gacgctcagt ggaacgaaaa ctcacgttaa gggattttgg tcatgagatt atcaaaaagg | 1920 |
| atcttcacct agatcctttt aaattaaaaa tgaagtttta atcaatcta aagtatatat | 1980 |
| gagtaaactt ggtctgacag ttaccaatgc ttaatcagtg aggcacctat ctcagcgatc | 2040 |
| tgtctatttc gttcatccat agttgcctga ctccccgtcg tgtagataac tacgatacgg | 2100 |
| gagggcttac catctggccc cagtgctgca atgataccgc gagacccacg ctcaccggct | 2160 |
| ccagatttat cagcaataaa ccagccagcc ggaagggccg agcgcagaag tggtcctgca | 2220 |
| actttatccg cctccatcca gtctattaat tgttgccggg aagctagagt aagtagttcg | 2280 |
| ccagttaata gtttgcgcaa cgttgttgcc attgctacag gcatcgtggt gtcacgctcg | 2340 |
| tcgtttggta tggcttcatt cagctccggt tcccaacgat caaggcgagt tacatgatcc | 2400 |
| cccatgttgt gcaaaaaagc ggttagctcc ttcggtcctc cgatcgttgt cagaagtaag | 2460 |
| ttggccgcag tgttatcact catggttatg gcagcactgc ataattctct tactgtcatg | 2520 |
| ccatccgtaa gatgcttttc tgtgactggt gagtactcaa ccaagtcatt ctgagaatag | 2580 |
| tgtatgcggc gaccgagttg ctcttgcccg gcgtcaatac gggataatac cgcgccacat | 2640 |
| agcagaactt taaaagtgct catcattgga aaacgttctt cggggcgaaa actctcaagg | 2700 |
| atcttaccgc tgttgagatc cagttcgatg taacccactc gtgcacccaa ctgatcttca | 2760 |
| gcatctttta ctttcaccag cgtttctggg tgagcaaaaa caggaaggca aaatgccgca | 2820 |
| aaaaagggaa taagggcgac acggaaatgt tgaatactca tactcttcct ttttcaatat | 2880 |
| tattgaagca tttatcaggg ttattgtctc atgagcggat acatatttga atgtatttag | 2940 |
| aaaaataaac aaatagggggt tccgcgcaca tttccccgaa aagtgccac | 2989 |

<210> SEQ ID NO 13
<211> LENGTH: 38041
<212> TYPE: DNA
<213> ORGANISM: Artificial Sequence
<220> FEATURE:
<223> OTHER INFORMATION: Synthetic

<400> SEQUENCE: 13

| | |
|---|---|
| ctaaattgta agcgttaata ttttgttaaa attcggccgg ccatcatcaa taatatacct | 60 |
| tattttggat tgaagccaat atgataatga ggggtggag tttgtgacgt ggcgcggggc | 120 |
| gtgggaacgg ggcgggtgac gtagtagtgt ggcggaagtg tgatgttgca agtgtggcgg | 180 |
| aacacatgta taacttcgta taatgtatgc tatacgaagt tatacatgta agcgacggat | 240 |
| gtggcaaaag tgacgttttt ggtgtgcgcc ggtgtacaca ggaagtgaca attttcgcgc | 300 |
| ggttttaggc ggatgttgta gtaaatttgg gcgtaaccga gtaagatttg gccattttcg | 360 |
| cgggaaaact gaataagagg aagtgaaatc tgaataattt tgtgttactc atagcgcgta | 420 |
| atatttgtct aggagatct ataacttcgt ataatgtatg ctatacgaag ttattaccga | 480 |
| agaaatggct cgagatctgg aaggtgctga ggtacgatga gacccgcacc aggtgcagac | 540 |

```
cctgcgagtg tggcggtaaa catattagga accagcctgt gatgctggat gtgaccgagg    600
agctgaggcc cgatcacttg gtgctggcct gcacccgcgc tgagtttggc tctagcgatg    660
aagatacaga ttgaggtact gaaatgtgtg ggcgtggctt aagggtggga aagaatatat    720
aaggtggggg tcttatgtag ttttgtatct gttttgcagc agccgccgcc gccatgagca    780
ccaactcgtt tgatggaagc attgtgagct catatttgac aacgcgcatg cccccatggg    840
ccggggtgcg tcagaatgtg atgggctcca gcattgatgg tcgccccgtc ctgcccgcaa    900
actctactac cttgacctac gagaccgtgt ctggaacgcc gttggagact gcagcctccg    960
ccgccgcttc agccgctgca gccaccgccc gcgggattgt gactgacttt gctttcctga   1020
gcccgcttgc aagcagtgca gcttcccgtt catccgcccg cgatgacaag ttgacggctc   1080
ttttggcaca attggattct ttgacccggg aacttaatgt cgtttctcag cagctgttgg   1140
atctgcgcca gcaggtttct gccctgaagg cttcctcccc tcccaatgcg gtttaaaaca   1200
taaataaaaa accagactct gtttggattt ggatcaagca agtgtcttgc tgtctttatt   1260
tagggttttt gcgcgcgcgg taggcccggg accagcggtc tcggtcgttg agggtcctgt   1320
gtattttttc caggacgtgg taaaggtgac tctggatgtt cagatacatg ggcataagcc   1380
cgtctctggg gtggaggtag caccactgca gagcttcatg ctgcggggtg gtgttgtaga   1440
tgatccagtc gtagcaggag cgctgggcgt ggtgcctaaa aatgtctttc agtagcaagc   1500
tgattgccag gggcaggccc ttggtgtaag tgtttacaaa gcggttaagc tgggatgggt   1560
gcatacgtgg ggatatgaga tgcatcttgg actgtatttt taggttggct atgttcccag   1620
ccatatccct ccggggattc atgttgtgca gaaccaccag cacagtgtat ccggtgcact   1680
tgggaaattt gtcatgtagc ttagaaggaa atgcgtggaa gaacttggag acgcccttgt   1740
gacctccaag attttccatg cattcgtcca taatgatggc aatgggccca cgggcggcgg   1800
cctgggcgaa gatatttctg ggatcactaa cgtcatagtt gtgttccagg atgagatcgt   1860
cataggccat ttttacaaag cgcgggcgga gggtgccaga ctgcggtata atggttccat   1920
ccggcccagg ggcgtagtta ccctcacaga tttgcatttc ccacgctttg agttcagatg   1980
ggggggatcat gtctacctgc ggggcgatga agaaaacggt ttccggggta ggggagatca   2040
gctgggaaga aagcaggttc ctgagcagct gcgacttacc gcagccggtg ggcccgtaaa   2100
tcacacctat taccgggtgc aactggtagt taagagagct gcagctgccg tcatccctga   2160
gcagggggggc cacttcgtta agcatgtccc tgactcgcat gttttccctg accaaatccg   2220
ccagaaggcg ctcgccgccc agcgatagca gttcttgcaa ggaagcaaag tttttcaacg   2280
gtttgagacc gtccgccgta ggcatgcttt tgagcgtttg accaagcagt tccaggcggt   2340
cccacagctc ggtcacctgc tctacggcat ctcgatccag catatctcct cgtttcgcgg   2400
gttgggcgg ctttcgctgt acggcagtag tcggtgctcg tccagacggg ccagggtcat   2460
gtctttccac gggcgcaggg tcctcgtcag cgtagtctgg gtcacggtga gggggtgcgc   2520
tccgggctgc gcgctggcca gggtgcgctt gaggctggtc ctgctggtgc tgaagcgctg   2580
ccggtcttcg ccctgcgcgt cggccaggta gcatttgacc atggtgtcat agtccagccc   2640
ctccgcggcg tggcccttgg cgcgcagctt gcccttggag gaggcgccgc acgaggggca   2700
gtgcagactt tgagggcgt agagcttggg cgcgagaaat accgattccg gggagtaggc   2760
atccgcgccg caggcccgc agacggtctc gcattccacg agccaggtga gctctggccg   2820
ttcggggtca aaaaccaggt ttcccccatg cttttttgatg cgtttcttac ctctggtttc   2880
catgagccgg tgtccacgct cggtgacgaa aaggctgtcc gtgtccccgt atacagactt   2940
```

```
gagaggcctg tcctcgagcg gtgttccgcg gtcctcctcg tatagaaact cggaccactc    3000
tgagacaaag gctcgcgtcc aggccagcac gaaggaggct aagtgggagg ggtagcggtc    3060
gttgtccact agggggtcca ctcgctccag ggtgtgaaga cacatgtcgc cctcttcggc    3120
atcaaggaag gtgattggtt tgtaggtgta ggccacgtga ccgggtgttc ctgaaggggg    3180
gctataaaag ggggtggggg cgcgttcgtc ctcactctct tccgcatcgc tgtctgcgag    3240
ggccagctgt tggggtgagt actccctctg aaaagcgggc atgacttctg cgctaagatt    3300 gtcagttttcc aaaaacgagg aggatttgat attcacctgg cccgcggtga tgcctttgag    3360
ggtggccgca tccatctggt cagaaaagac aatctttttg ttgtcaagct tggtggcaaa    3420
cgacccgtag agggcgttgg acagcaactt ggcgatggag cgcagggttt ggttttttgtc    3480 gcgatcggcg cgctccttgg ccgcgatgtt tagctgcacg tattcgcgcg caacgcaccg    3540
ccattcggga aagacggtgg tgcgctcgtc gggcaccagg tgcacgcgcc aaccgcggtt    3600
gtgcagggtg acaaggtcaa cgctggtggc tacctctccg cgtaggcgct cgttggtcca    3660
gcagaggcgg ccgcccttgc gcgagcagaa tggcggtagg gggtctagct gcgtctcgtc    3720 cgggggtct gcgtccacgg taaagacccc gggcagcagg cgcgcgtcga agtagtctat    3780
cttgcatcct tgcaagtcta gcgcctgctg ccatgcgcgg gcggcaagcg cgcgctcgta    3840
tgggttgagt gggggacccc atggcatggg gtgggtgagc gcggaggcgt acatgccgca    3900
aatgtcgtaa acgtagaggg gctctctgag tattccaaga tatgtagggt agcatcttcc    3960
accgcggatg ctggcgcgca cgtaatcgta tagttcgtgc gagggagcga ggaggtcggg    4020
accgaggttg ctacgggcgg gctgctctgc tcggaagact atctgcctga agatggcatg    4080
tgagttggat gatatggttg gacgctggaa gacgttgaag ctggcgtctg tgagacctac    4140
cgcgtcacgc acgaaggagg cgtaggagtc gcgcagcttg ttgaccagct cggcggtgac    4200
ctgcacgtct agggcgcagt agtccagggt ttccttgatg atgtcatact tatcctgtcc    4260 ctttttttc cacagctcgc ggttgaggac aaactcttcg cggtctttcc agtactcttg    4320
gatcggaaac ccgtcggcct ccgaacggta agagcctagc atgtagaact ggttgacggc    4380
ctggtaggcg cagcatccct tttctacggg tagcgcgtat gcctgcgcgg ccttccggag    4440
cgaggtgtgg gtgagcgcaa aggtgtccct gaccatgact ttgaggtact ggtatttgaa    4500
gtcagtgtcg tcgcatccgc cctgctccca gagcaaaaag tccgtgcgct ttttggaacg    4560
cggatttggc agggcgaagg tgacatcgtt gaagagtatc tttcccgcgc gaggcataaa    4620
gttgcgtgtg atgcggaagg gtcccggcac ctcggaacgg ttgttaatta cctgggcggc    4680
gagcacgatc tcgtcaaagc cgttgatgtt gtggcccaca atgtaaagtt ccaagaagcg    4740
cgggatgccc ttgatggaag gcaattttttt aagttcctcg taggtgagct cttcagggga    4800
gctgagcccg tgctctgaaa gggcccagtc tgcaagatga gggttggaag cgacgaatga    4860
gctccacagg tcacgggcca ttagcatttg caggtggtcg cgaaaggtcc taaactggcg    4920
acctatggcc attttttctg gggtgatgca gtagaaggta agcgggtctt gttcccagcg    4980
gtcccatcca aggttcgcgg ctaggtctcg cgcggcagtc actagaggct catctccgcc    5040
gaacttcatg accagcatga agggcacgag ctgcttccca aaggccccca tccaagtata    5100
ggtctctaca tcgtaggtga caaagagacg ctcggtgcga ggatgcgagc cgatcgggaa    5160 gaactgatc tcccgccacc aattggagga gtggctattg atgtggtgaa agtagaagtc    5220
cctgcgacgg gccgaacact cgtgctggct tttgtaaaaa cgtgcgcagt actggcagcg    5280
```

```
gtgcacgggc tgtacatcct gcacgaggtt gacctgacga ccgcgcacaa ggaagcagag    5340
tgggaatttg agcccctcgc ctggcgggtt tggctggtgg tcttctactt cggctgcttg    5400
tccttgaccg tctggctgct cgaggggagt tacggtggat cggaccacca cgccgcgcga    5460
gcccaaagtc cagatgtccg cgcgcggcgg tcggagcttg atgacaacat cgcgcagatg    5520
ggagctgtcc atggtctgga gctcccgcgg cgtcaggtca ggcggagct cctgcaggtt     5580
tacctcgcat agacgggtca gggcgcgggc tagatccagg tgatacctaa tttccagggg    5640
ctggttggtg gcggcgtcga tggcttgcaa gaggccgcat cccgcggcg cgactacggt     5700
accgcgcggc gggcggtggg ccgcggggt gtccttggat gatgcatcta aaagcggtga     5760
cgcgggcgag ccccggagg taggggggc tccggacccg ccgggagagg gggcaggggc      5820
acgtcggcgc cgcgcgcggg caggagctgg tgctgcgcgc gtaggttgct ggcgaacgcg    5880
acgacgcggc ggttgatctc ctgaatctgg cgcctctgcg tgaagacgac gggcccggtg    5940
agcttgagcc tgaaagagag ttcgacagaa tcaatttcgg tgtcgttgac ggcggcctgg    6000
cgcaaaatct cctgcacgtc tcctgagttg tcttgatagg cgatctcggc catgaactgc    6060
tcgatctctt cctcctggag atctccgcgt ccggctcgct ccacggtggc ggcgaggtcg    6120
ttggaaatgc gggccatgag ctgcgagaag gcgttgaggc ctccctcgtt ccagacgcgg    6180
ctgtagacca cgcccccttc ggcatcgcgg gcgcgcatga ccacctgcgc gagattgagc    6240
tccacgtgcc gggcgaagac ggcgtagttt cgcaggcgct gaaagaggta gttgagggtg    6300
gtggcggtgt gttctgccac gaagaagtac ataacccagc gtcgcaacgt ggattcgttg    6360
atatccccca aggcctcaag gcgctccatg gcctcgtaga agtccacggc gaagttgaaa    6420
aactgggagt tgcgcgccga cacggttaac tcctcctcca gaagacggat gagctcggcg    6480
acagtgtcgc gcacctcgcg ctcaaaggct acaggggcct cttcttcttc ttcaatctcc    6540
tcttccataa gggcctcccc ttcttcttct tctggcggcg gtggggggagg ggggacacgg   6600
cggcgacgac ggcgcaccgg gaggcggtcg acaaagcgct cgatcatctc cccgcggcga    6660
cggcgcatgg tctcggtgac ggcgcggccg ttctcgcggg ggcgcagttg gaagacgccg    6720
cccgtcatgt cccggttatg ggttggcggg gggctgccat gcggcaggga tacggcgcta    6780
acgatgcatc tcaacaattg ttgtgtaggt actccgccgc cgagggacct gagcgagtcc    6840
gcatcgaccg gatcggaaaa cctctcgaga aaggcgtcta accagtcaca gtcgcaaggt    6900
aggctgagca ccgtggcggg cggcagcggg cggcggtcgg ggttgtttct ggcggaggtg    6960
ctgctgatga tgtaattaaa gtaggcggtc ttgagacggc ggatggtcga cagaagcacc    7020
atgtccttgg gtccggcctg ctgaatgcgc aggcggtcgg ccatgcccca ggcttcgttt    7080
tgacatcggc gcaggtcttt gtagtagtct tgcatgagcc tttctaccgg cacttcttct    7140
tctccttcct cttgtcctgc atctcttgca tctatcgctg cggcggcggc ggagtttggc    7200
cgtaggtggc gccctcttcc tcccatgcgt gtgaccccga agccctcat cggctgaagc     7260
agggctaggt cggcgacaac gcgctcggct aatatggcct gctgcacctg cgtgagggta    7320
gactggaagt catccatgtc cacaaagcgg tggtatcgcg ccgtgttgat ggtgtaagtg    7380
cagttggcca taacggacca gttaacggtc tggtgacccg gctgcgagag ctcggtgtac    7440
ctgagacgcg agtaagccct cgagtcaaat acgtagtcgt tgcaagtccg caccaggtac    7500
tggtatccca ccaaaaagtg cggcggcggc tggcggtaga ggggccagcg tagggtggcc    7560
ggggctccgg gggcgagatc ttccaacata aggcgatgat atccgtagat gtacctggac    7620
atccaggtga tgccggcggc ggtggtggag gcgcgcggaa agtcgcggac gcggttccag    7680
```

-continued

```
atgttgcgca gcggcaaaaa gtgctccatg gtcgggacgc tctggccggt caggcgcgcg     7740
caatcgttga cgctctaccg tgcaaaagga gagcctgtaa gcgggcactc ttccgtggtc     7800
tggtggataa attcgcaagg gtatcatggc ggacgaccgg ggttcgagcc ccgtatccgg     7860
ccgtccgccg tgatccatgc ggttaccgcc cgcgtgtcga acccaggtgt gcgacgtcag     7920
acaacggggg agtgctcctt ttggcttcct tccaggcgcg gcggctgctg cgctagcttt     7980
tttggccact ggccgcgcgc agcgtaagcg gttaggctgg aaagcgaaag cattaagtgg     8040
ctcgctccct gtagccggag ggttattttc caagggttga gtcgcgggac ccccggttcg     8100
agtctcggac cggccggact gcggcgaacg ggggtttgcc tccccgtcat gcaagacccc     8160
gcttgcaaat tcctccggaa acagggacga gcccctttt tgcttttccc agatgcatcc     8220
ggtgctgcgg cagatgcgcc cccctcctca gcagcggcaa gagcaagagc agcggcagac     8280
atgcagggca ccctcccctc ctcctaccgc gtcaggaggg gcgacatccg cggttgacgc     8340
ggcagcagat ggtgattacg aaccccccgcg gcgccgggcc cggcactacc tggacttgga     8400
ggagggcgag ggcctggcgc ggctaggagc gccctctcct gagcggtacc caagggtgca     8460
gctgaagcgt gatacgcgtg aggcgtacgt gccgcggcag aacctgtttc gcgaccgcga     8520
gggagaggag cccgaggaga tgcgggatcg aaagttccac gcagggcgcg agctgccggca     8580 tggcctgaat cgcgagcggt tgctgcgcga ggaggacttt gagcccgacg cgcgaaccgg     8640
gattagtccc gcgcgcgcac acgtggcggc cgccgacctg gtaaccgcat acgagcagac     8700
ggtgaaccag gagattaact ttcaaaaaag ctttaacaac cacgtgcgta cgcttgtggc     8760
gcgcgaggag gtggctatag gactgatgca tctgtgggac tttgtaagcg cgctggagca     8820
aaacccaaat agcaagccgc tcatggcgca gctgttcctt atagtgcagc acagcaggga     8880
caacgaggca ttcagggatg cgctgctaaa catagtagag cccgagggcc gctggctgct     8940
cgatttgata aacatcctgc agagcatagt ggtgcaggag cgcagcttga gcctggctga     9000
caaggtggcc gccatcaact attccatgct tagcctgggc aagttttacg cccgcaagat     9060
ataccatacc ccttacgttc ccatagacaa ggaggtaaag atcgaggggt tctacatgcg     9120
catggcgctg aaggtgctta ccttgagcga cgacctgggc gtttatcgca cgagcgcat     9180 ccacaaggcc gtgagcgtga ccggcgcgcg cgagctcagc gaccgcgagc tgatgcacag     9240
cctgcaaagg gccctggctg gcacgggcag cggcgataga gaggccgagt cctactttga     9300
cgcgggcgct gacctgcgct gggccccaag ccgacgcgcc ctggaggcag ctggggccgg     9360
acctgggctg gcggtggcac ccgcgcgcgc tggcaacgtc ggcggcgtgg aggaatatga     9420
cgaggacgat gagtacgagc cagaggacgg cgagtactaa gcggtgatgt ttctgatcag     9480
atgatgcaag acgcaacgga cccggcggtg cgggcggcgc tgcagagcca gccgtccggc     9540
cttaactcca cggacgactg gcgccaggtc atggaccgca tcatgtcgct gactgcgcgc     9600
aatcctgacg cgttccggca gcagccgcag gccaaccggc tctccgcaat tctggaagcg     9660
gtggtcccgg cgcgcgcaaa ccccacgcac gagaaggtgc tggcgatcgt aaacgcgctg     9720
gccgaaaaca gggccatccg gccgacgaa gccggcctgg tctacgacgc gctgcttcag     9780
cgcgtggctc gttacaacag cggcaacgtg cagaccaacc tggaccggct ggtgggggat     9840
gtgcgcgagg ccgtggcgca gcgtgagcgc gcgcagcagc agggcaacct gggctccatg     9900
gttgcactaa acgccttcct gagtacacag cccgccaacg tgccgcgggg acaggaggac     9960
tacaccaact ttgtgagcgc actgcggcta atggtgactg agacaccgca aagtgaggtg    10020
```

```
taccagtctg ggccagacta ttttttccag accagtagac aaggcctgca gaccgtaaac    10080
ctgagccagg ctttcaaaaa cttgcagggg ctgtgggggg tgcgggctcc cacaggcgac    10140
cgcgcgaccg tgtctagctt gctgacgccc aactcgcgcc tgttgctgct gctaatagcg    10200
cccttcacgg acagtggcag cgtgtcccgg acacatacc taggtcactt gctgacactg    10260
taccgcgagg ccataggtca ggcgcatgtg gacgagcata ctttccagga gattacaagt    10320
gtcagccgcg cgctggggca ggaggacacg ggcagcctgg aggcaaccct aaactacctg    10380
ctgaccaacc ggcggcagaa gatccctcg ttgcacagtt taaacagcga ggaggagcgc    10440
attttgcgct acgtgcagca gagcgtgagc cttaacctga tgcgcgacgg ggtaacgccc    10500
agcgtggcgc tggacatgac cgcgcgcaac atggaaccgg gcatgtatgc ctcaaaccgg    10560
ccgtttatca accgcctaat ggactacttg catcgcgcgg ccgccgtgaa ccccgagtat    10620
ttcaccaatg ccatcttgaa cccgcactgg ctaccgcccc ctggtttcta caccggggga    10680
ttcgaggtgc ccgagggtaa cgatggattc ctctgggacg acatagacga cagcgtgttt    10740
tccccgcaac cgcagaccct gctagagttg caacagcgcg agcaggcaga ggcggcgctg    10800
cgaaaggaaa gcttccgcag gccaagcagc ttgtccgatc taggcgctgc ggccccgcgg    10860
tcagatgcta gtagcccatt tccaagcttg ataggggtctc ttaccagcac tcgcaccacc    10920
cgcccgcgcc tgctgggcga ggaggagtac ctaaacaact cgctgctgca gccgcagcgc    10980
gaaaaaaacc tgcctccggc atttcccaac aacgggatag agagcctagt ggacaagatg    11040
agtagatgga agacgtacgc gcaggagcac agggacgtgc caggcccgcg cccgcccacc    11100
cgtcgtcaaa ggcacgaccg tcagcggggt ctggtgtggg aggacgatga ctcggcagac    11160
gacagcagcg tcctggattt gggagggagt ggcaacccgt ttgcgcacct tcgccccagg    11220
ctggggagaa tgtttaaaa aaaaaaaagc atgatgcaaa ataaaaaact caccaaggcc    11280
atggcaccga gcgttggttt tcttgtattc cccttagtat gcggcgcgcg gcgatgtatg    11340
aggaaggtcc tcctccctcc tacgagagtg tggtgagcgc ggcgccagtg gcggcggcgc    11400
tgggttctcc cttcgatgct cccctggacc cgccgtttgt gcctccgcgg tacctgcggc    11460
ctaccggggg gagaaacagc atccgttact ctgagttggc accccctattc gacaccaccc    11520 gtgtgtacct ggtggacaac aagtcaacgg atgtggcatc cctgaactac cagaacgacc    11580
acagcaactt tctgaccacg gtcattcaaa acaatgacta cagcccgggg gaggcaagca    11640
cacagaccat caatcttgac gaccggtcgc actgggcgg cgacctgaaa accatcctgc    11700
ataccaacat gccaaatgtg aacgagttca tgtttaccaa taagtttaag gcgcgggtga    11760
tggtgtcgcg cttgcctact aaggacaatc aggtggagct gaaatacgag tgggtggagt    11820
tcacgctgcc cgagggcaac tactccgaga ccatgaccat agaccttatg aacaacgcga    11880
tcgtggagca ctacttgaaa gtgggcagac agaacggggt tctggaaagc gacatcgggg    11940
taaagtttga caccccgcaac ttcagactgg ggtttgaccc cgtcactggt cttgtcatgc    12000 ctgggggtata tacaaacgaa gccttccatc cagacatcat tttgctgcca ggatgcgggg    12060
tggacttcac ccacagccgc ctgagcaact tgttgggcat ccgcaagcgg caacccttcc    12120
aggagggctt taggatcacc tacgatgatc tggagggtgg taacattccc gcactgttgg    12180
atgtggacgc ctaccaggcg agcttgaaag atgacaccga acaggcgggg ggtgcgcag    12240 gcggcagcaa cagcagtggc agcggcgcgg aagagaactc caacgcggca gccgcggcaa    12300
tgcagccggt ggaggacatg aacgatcatg ccattcgcgg cgacaccttt gccacacggg    12360
ctgaggagaa gcgcgctgag gccgaagcag cggccgaagc tgccgccccc gctgcgcaac    12420
```

```
ccgaggtcga gaagcctcag agaaaccgg tgatcaaacc cctgacagag gacagcaaga   12480
aacgcagtta caacctaata agcaatgaca gcaccttcac ccagtaccgc agctggtacc   12540
ttgcatacaa ctacggcgac cctcagaccg gaatccgctc atggaccctg ctttgcactc   12600
ctgacgtaac ctgcggctcg gagcaggtct actggtcgtt gccagacatg atgcaagacc   12660
ccgtgacctt ccgctccacg cgccagatca gcaactttcc ggtggtgggc gccgagctgt   12720
tgcccgtgca ctccaagagc ttctacaacg accaggccgt ctactcccaa ctcatccgcc   12780
agtttacctc tctgacccac gtgttcaatc gctttcccga aaccagatt ttggcgcgcc   12840 cgccagcccc caccatcacc accgtcagtg aaaacgttcc tgctctcaca gatcacggga   12900
cgctaccgct gcgcaacagc atcggaggag tccagcgagt gaccattact gacgccagac   12960
gccgcacctg cccctacgtt tacaaggccc tgggcatagt ctcgccgcgc gtcctatcga   13020
gccgcacttt ttgagcaagc atgtccatcc ttatatcgcc cagcaataac acaggctggg   13080
gcctgcgctt cccaagcaag atgtttggcg gggccaagaa gcgctccgac caacacccag   13140
tgcgcgtgcg cgggcactac cgcgcgccct ggggcgcgca caaacgcggc cgcactgggc   13200
gcaccaccgt cgatgacgcc atcgacgcgg tggtggagga ggcgcgcaac tacacgccca   13260
cgccgccacc agtgtccaca gtggacgcgg ccattcagac cgtggtgcgc ggagcccggc   13320
gctatgctaa aatgaagaga cggcggaggc gcgtagcacg tcgccaccgc cgccgacccg   13380
gcactgccgc ccaacgcgcg gcggcggccc tgcttaaccg cgcacgtcgc accggccgac   13440
gggcggccat gcgggccgct cgaaggctgg ccgcgggtat tgtcactgtg ccccccaggt   13500
ccaggcgacg agcggccgcc gcagcagccg cggccattag tgctatgact cagggtcgca   13560
ggggcaacgt gtattgggtg cgcgactcgg ttagcggcct gcgcgtgccc gtgcgcaccc   13620 gcccccccgcg caactagatt gcaagaaaaa actacttaga ctcgtactgt tgtatgtatc   13680
cagcggcggc ggcgcgcaac gaagcgtatgt ccaagcgcaa aatcaaagaa gagatgctcc   13740
aggtcatcgc gccggagatc tatggccccc cgaagaagga agagcaggat tacaagcccc   13800
gaaagctaaa gcgggtcaaa aagaaaaaga aagatgatga tgatgaactt gacgacgagg   13860
tggaactgct gcacgctacc gcgcccaggc gacgggtaca gtggaaaggt cgacgcgtaa   13920
aacgtgtttt gcgaccccggc accaccgtag tctttacgcc cggtgagcgc tccaccccgca   13980 cctacaagcg cgtgtatgat gaggtgtacg gcgacgagga cctgcttgag caggccaacg   14040
agcgcctcgg ggagtttgcc tacgaaagc ggcataagga catgctggcg ttgccgctgg   14100
acgagggcaa cccaacacct agcctaaagc ccgtaacact gcagcaggtg ctgcccgcgc   14160
ttgcaccgtc cgaagaaaag cgcggcctaa agcgcgagtc tggtgacttg gcacccaccg   14220
tgcagctgat ggtacccaag cgccagcgac tggaagatgt cttggaaaaa atgaccgtgg   14280
aacctgggct ggagcccgag gtccgcgtgc ggccaatcaa gcaggtggcg ccgggactgg   14340
gcgtgcagac cgtggacgtt cagatacccca ctaccagtag caccagtatt gccaccgcca   14400
cagagggcat ggagacacaa acgtccccgg ttgcctcagc ggtggcggat gccgcggtgc   14460
aggcggtcgc tgcggccgcg tccaagacct ctacggaggt gcaaacggac ccgtggatgt   14520
ttcgcgtttc agcccccgg cgccgcgcg gttcgaggaa gtacggcgcc gcagcgcgc   14580 tactgcccga atatgcccta catccttcca ttgcgcctac ccccggctat cgtggctaca   14640
cctaccgccc cagaagacga gcaactaccc gacgccgaac caccactgga acccgccgcc   14700
gccgtcgccg tcgccagccc gtgctggccc cgatttccgt gcgcagggtg gctcgcgaag   14760
```

```
gaggcaggac cctggtgctg ccaacagcgc gctaccaccc cagcatcgtt taaaagccgg   14820
tctttgtggt tcttgcagat atggccctca cctgccgcct ccgtttcccg gtgccgggat   14880
tccgaggaag aatgcaccgt aggagggca tggccggcta cggcctgacg ggcggcatgc   14940
gtcgtgcgca ccaccggcgg cggcgcgcgt cgcaccgtcg catgcgcggc ggtatcctgc   15000
ccctccttat tccactgatc gccgcggcga ttggcgccgt gcccggaatt gcatccgtgg   15060
ccttgcaggc gcagagacac tgattaaaaa caagttgcat gtggaaaaat caaaataaaa   15120
agtctggact ctcacgctcg cttggtcctg taactatttt gtagaatgga agacatcaac   15180
tttgcgtctc tggccccgcg acacggctcg cgcccgttca tgggaaactg gcaagatatc   15240
ggcaccagca atatgagcgg tggcgccttc agctggggct cgctgtggag cggcattaaa   15300
aatttcggtt ccaccgttaa gaactatggc agcaaggcct ggaacagcag cacaggccag   15360
atgctgaggg ataagttgaa agagcaaaat tccaacaaa aggtggtaga tggcctggcc   15420
tctggcatta gcggggtggt ggacctggcc aaccaggcag tgcaaaataa gattaacagt   15480
aagcttgatc ccgccctcc cgtagaggag cctccaccgg ccgtggagac agtgtctcca   15540
gaggggcgtg gcgaaaagcg tccgcgcccc gacaggaag aaactctggt gacgcaaata   15600
gacgagcctc cctcgtacga ggaggcacta aagcaaggcc tgcccaccac ccgtcccatc   15660
gcgcccatgg ctaccggagt gctgggccag cacacacccg taacgctgga cctgcctccc   15720
cccgccgaca cccagcagaa acctgtgctg ccaggcccga ccgccgttgt tgtaacccgt   15780
cctagccgcg cgtccctgcg ccgcgccgcc agcggtccgc gatcgttgcg gcccgtagcc   15840
agtggcaact ggcaaagcac actgaacagc atcgtgggtc tgggggtgca atccctgaag   15900
cgccgacgat gcttctgaat agctaacgtg tcgtatgtgt gtcatgtatg cgtccatgtc   15960
gccgccagag gagctgctga ccgccgcgc gcccgctttc caagatggct accccttcga   16020
tgatgccgca gtggtcttac atgcacatct cgggccagga cgcctcggag tacctgagcc   16080
ccgggctggt gcagtttgcc cgcgccaccg agacgtactt cagcctgaat aacaagttta   16140
gaaaccccac ggtggcgcct acgcacgacg tgaccacaga ccggtcccag cgtttgacgc   16200
tgcggttcat ccctgtggac cgtgaggata ctgcgtactc gtacaaggcg cggttcaccc   16260
tagctgtggg tgataaccgt gtgctggaca tggcttccac gtactttgac atccgcggcg   16320
tgctggacag gggccctact tttaagccct actctggcac tgcctacaac gccctggctc   16380
ccaagggtgc cccaaatcct tgcgaatggg atgaagctgc tactgctctt gaaataaacc   16440
tagaagaaga ggacgatgac aacgaagacg aagtagacga gcaagctgag cagcaaaaaa   16500
ctcacgtatt tgggcaggcg ccttattctg gtataaatat tacaaaggag ggtattcaaa   16560
taggtgtcga aggtcaaaca cctaaatatg ccgataaaac atttcaacct gaacctcaaa   16620
taggagaatc tcagtggtac gaaactgaaa ttaatcatgc agctgggaga gtccttaaaa   16680
agactacccc aatgaaacca tgttacggtt catatgcaaa acccacaaat gaaaatggag   16740
ggcaaggcat tcttgtaaag caacaaaatg gaaagctaga aagtcaagtg gaaatgcaat   16800
ttttctcaac tactgaggcg accgcaggca atggtgataa cttgactcct aaagtggtat   16860
tgtacagtga agatgtagat atagaaaccc cagacactca tatttcttac atgcccacta   16920
ttaaggaagg taactcacga gaactaatgg ccaacaatc tatgcccaac aggcctaatt   16980
acattgcttt tagggacaat tttattggtc taatgtatta caacagcacg ggtaatatgg   17040
gtgttctggc gggccaagca tcgcagttga atgctgttgt agatttgcaa gacagaaaca   17100
cagagctttc ataccagctt ttgcttgatt ccattggtga tagaaccagg tactttttcta   17160
```

```
tgtggaatca ggctgttgac agctatgatc cagatgttag aattattgaa aatcatggaa    17220
ctgaagatga acttccaaat tactgctttc cactgggagg tgtgattaat acagagactc    17280
ttaccaaggt aaaacctaaa acaggtcagg aaaatggatg ggaaaaagat gctacagaat    17340
tttcagataa aaatgaaata agagttggaa ataattttgc catggaaatc aatctaaatg    17400
ccaacctgtg gagaaattte ctgtactcca acatagcgct gtatttgccc gacaagctaa    17460
agtacagtcc ttccaacgta aaaatttctg ataacccaaa cacctacgac tacatgaaca    17520
agcgagtggt ggctcccggg ttagtggact gctacattaa ccttggagca cgctggtccc    17580
ttgactatat ggacaacgtc aacccattta accaccaccg caatgctggc ctgcgctacc    17640
gctcaatgtt gctgggcaat ggtcgctatg tgcccttcca catccaggtg cctcagaagt    17700
tctttgccat taaaaacctc cttctcctgc cgggctcata cacctacgag tggaacttca    17760
ggaaggatgt taacatggtt ctgcagagct ccctaggaaa tgacctaagg gttgacggag    17820
ccagcattaa gtttgatagc atttgccttt acgccaccct cttccccatg cccacaaca    17880
ccgcctccac gcttgaggcc atgcttagaa acgacaccaa cgaccagtcc tttaacgact    17940
atctctccgc cgccaacatg ctctacccta tacccgccaa cgctaccaac gtgcccatat    18000
ccatcccctc ccgcaactgg gcggcttttcc gcggctgggc cttcacgcgc cttaagacta    18060
aggaaacccc atcactgggc tcgggctacg acccttatta cacctactct ggctctatac    18120
cctacctaga tggaaccttt tacctcaacc acacctttaa gaaggtggcc attaccttttg    18180
actcttctgt cagctggcct ggcaatgacc gcctgcttac ccccaacgag tttgaaatta    18240
agcgctcagt tgacggggag ggttacaacg ttgcccagtg taacatgacc aaagactggt    18300
tcctggtaca aatgctagct aactacaaca ttggctacca gggcttctat atcccagaga    18360
gctacaagga ccgcatgtac tccttcttta gaaacttcca gcccatgagc cgtcaggtgg    18420
tggatgatac taaatacaag gactaccaac aggtgggcat cctacaccaa cacaacaact    18480
ctggatttgt tggctacctt gcccccacca tgcgcgaagg acaggcctac cctgctaact    18540
tcccctatcc gctataggc aagaccgcag ttgacagcat tacccagaaa aagtttctttt    18600
gcgatcgcac cctttggcgc atcccattct ccagtaactt tatgtccatg gcgcactca    18660
cagacctggg ccaaaacctt ctctacgcca actccgccca cgcgctagac atgacttttg    18720
aggtggatcc catggacgag cccacccttc tttatgtttt gtttgaagtc tttgacgtgg    18780
tccgtgtgca ccggccgcac cgcggcgtca tcgaaaccgt gtacctgcgc acgcccttct    18840
cggccggcaa cgccacaaca taaagaagca agcaacatca acaacagctg ccgccatggg    18900
ctccagtgag caggaactga aagccattgt caaagatctt ggttgtgggc catattttt    18960
gggcacctat gacaagcgct ttccaggctt tgttctcca cacaagctcg cctgcgccat    19020
agtcaatacg gccggtcgcg agactggggg cgtacactgg atggcctttg cctggaaccc    19080
gcactcaaaa acatgctacc tctttgagcc ctttggcttt tctgaccagc gactcaagca    19140
ggtttaccag tttgagtacg agtcactcct gcgccgtagc gccattgctt cttccccgga    19200
ccgctgtata acgctggaaa agtccaccca aagcgtacag gggcccaact cggccgcctg    19260
tggactattc tgctgcatgt ttctccacgc ctttgccaac tggcccccaaa ctcccatgga    19320
tcacaacccc accatgaacc ttattaccgg ggtacccaac tccatgctca acagtcccca    19380
ggtacagccc acccctgcgtc gcaaccagga acagctctac agcttcctgg agcgccactc    19440
gccctacttc cgcagccaca gtgcgcagat taggagcgcc acttctttt gtcacttgaa    19500
```

```
aaacatgtaa aaataatgta ctagagacac tttcaataaa ggcaaatgct tttatttgta    19560
cactctcggg tgattattta cccccaccct tgccgtctgc gccgtttaaa aatcaaaggg    19620
gttctgccgc gcatcgctat gcgccactgg cagggacacg ttgcgatact ggtgtttagt    19680
gctccactta aactcaggca caaccatccg cggcagctcg gtgaagtttt cactccacag    19740
gctgcgcacc atcaccaacg cgtttagcag gtcgggcgcc gatatcttga agtcgcagtt    19800
ggggcctccg ccctgcgcgc gcgagttgcg atacacaggg ttgcagcact ggaacactat    19860
cagcgccggg tggtgcacgc tggccagcac gctcttgtcg gagatcagat ccgcgtccag    19920
gtcctccgcg ttgctcaggg cgaacggagt caactttggt agctgccttc ccaaaaaggg    19980
cgcgtgccca ggctttgagt tgcactcgca ccgtagtggc atcaaaaggt gaccgtgccc    20040
ggtctgggcg ttaggataca gcgcctgcat aaaagccttg atctgcttaa aagccacctg    20100
agcctttgcg ccttcagaga agaacatgcc gcaagacttg ccggaaaact gattggccgg    20160
acaggccgcg tcgtgcacgc agcaccttgc gtcggtgttg gagatctgca ccacatttcg    20220
gccccaccgg ttcttcacga tcttggcctt gctagactgc tccttcagcg cgcgctgccc    20280
gttttcgctc gtcacatcca tttcaatcac gtgctcctta tttatcataa tgcttccgtg    20340
tagacactta agctcgcctt cgatctcagc gcagcggtgc agccacaacg cgcagcccgt    20400
gggctcgtga tgcttgtagg tcacctctgc aaacgactgc aggtacgcct gcaggaatcg    20460
ccccatcatc gtcacaaagg tcttgttgct ggtgaaggtc agctgcaacc cgcggtgctc    20520
ctcgttcagc caggtcttgc atacggccgc cagagcttcc acttggtcag gcagtagttt    20580
gaagttcgcc tttagatcgt tatccacgtg gtacttgtcc atcagcgcgc gcgcagcctc    20640
catgcccttc tcccacgcag acacgatcgg cacactcagc gggttcatca ccgtaatttc    20700
actttccgct tcgctgggct cttcctcttc ctcttgcgtc cgcataccac gcgccactgg    20760
gtcgtcttca ttcagccgcc gcactgtgcg cttacctcct ttgccatgct tgattagcac    20820
cggtgggttg ctgaaaccca ccatttgtag cgccacatct tctctttctt cctcgctgtc    20880
cacgattacc tctggtgatg gcgggcgctc gggcttggga aagggcgct tcttttcctt    20940 cttgggcgca atggccaaat ccgccgccga ggtcgatggc cgcgggctgg gtgtgcgcgg    21000
caccagcgcg tcttgtgatg agtcttcctc gtcctcggac tcgatacgcc gcctcatccg    21060
cttttttggg ggcgcccggg gaggcggcgg cgacggggac ggggacgaca cgtcctccat    21120
ggttggggga cgtcgcgccg caccgcgtcc gcgctcgggg gtggtttcgc gctgctcctc    21180
ttcccgactg gccatttcct tctcctatag gcagaaaaag atcatggagt cagtcgagaa    21240
gaaggacagc ctaaccgccc cctctgagtt cgccaccacc gcctccaccg atgccgccaa    21300
cgcgcctacc accttccccg tcgaggcacc cccgcttgag gaggaggaag tgattatcga    21360
gcaggaccca ggttttgtaa gcgaagacga cgaggaccgc tcagtaccaa cagaggataa    21420
aaagcaagac caggacaacg cagaggcaaa cgaggaacaa gtcgggcggg gggacgaaag    21480
gcatggcgac tacctagatg tgggagacga cgtgctgttg aagcatctgc agcgccagtg    21540
cgccattatc tgcgacgcgt tgcaagacgc cagcgatgtg cccctcgcca tagcggatgt    21600
cagccttgcc tacgaacgcc acctattctc accgcgcgta ccccccaaac gccaagaaaa    21660
cggcacatgc gagcccaacc cgcgcctcaa cttctacccc gtatttgccg tgccagaggt    21720
gcttgccacc tatcacatct ttttccaaaa ctgcaagata cccctatcct gccgtgccaa    21780
ccgcagccga gcgacaagc agctggcctt gcggcagggc gctgtcatac ctgatatcgc    21840
ctcgctcaac gaagtgccaa aaatctttga gggtcttgga cgcgacgaga agcgcgcggc    21900
```

```
aaacgctctg caacaggaaa acagcgaaaa tgaaagtcac tctggagtgt tggtggaact    21960
cgagggtgac aacgcgcgcc tagccgtact aaaacgcagc atcgaggtca cccactttgc    22020
ctacccggca cttaacctac cccccaaggt catgagcaca gtcatgagtg agctgatcgt    22080
gcgccgtgcg cagcccctgg agagggatgc aaatttgcaa gaacaaacag aggagggcct    22140
acccgcagtt ggcgacgagc agctagcgcg ctggcttcaa acgcgcgagc ctgccgactt    22200
ggaggagcga cgcaaactaa tgatggccgc agtgctcgtt accgtggagc ttgagtgcat    22260
gcagcggttc tttgctgacc cggagatgca gcgcaagcta gaggaaacat tgcactacac    22320 cttttcgacag ggctacgtac gccaggcctg caagatctcc aacgtggagc tctgcaacct    22380
ggtctcctac cttggaattt tgcacgaaaa ccgccttggg caaaacgtgc ttcattccac    22440
gctcaagggc gaggcgcgcc gcgactacgt ccgcgactgc gtttacttat ttctatgcta    22500
cacctggcag acggccatgg gcgtttggca gcagtgcttg gaggagtgca acctcaagga    22560
gctgcagaaa ctgctaaagc aaaacttgaa ggacctatgg acggccttca acgagcgctc    22620
cgtggccgcg cacctggcgg acatcatttt ccccgaacgc ctgcttaaaa ccctgcaaca    22680
gggtctgcca gacttcacca gtcaaagcat gttgcagaac tttaggaact ttatcctaga    22740
gcgctcagga atcttgcccg ccacctgctg tgcacttcct agcgactttg tgcccattaa    22800
gtaccgcgaa tgccctccgc cgctttgggg ccactgctac cttctgcagc tagccaacta    22860
ccttgcctac cactctgaca taatggaaga cgtgagcggt gacggtctac tggagtgtca    22920
ctgtcgctgc aacctatgca ccccgcaccg ctccctggtt tgcaattcgc agctgcttaa    22980
cgaaagtcaa attatcggta cctttgagct gcagggtccc tcgcctgacg aaaagtccgc    23040
ggctccgggg ttgaaactca ctccggggct gtggacgtcg gcttaccttc gcaaatttgt    23100
acctgaggac taccacgccc acgagattag gttctacgaa gaccaatccc gcccgccaaa    23160
tgcggagctt accgcctgcg tcattaccca gggccacatt cttggccaat gcaagccat    23220 caacaaagcc cgccaagagt ttctgctacg aaagggacgg ggggtttact tggacccccca    23280 gtccggcgag gagctcaacc caatccccc gccgccgcag ccctatcagc agcagccgcg    23340
ggcccttgct tcccaggatg gcacccaaaa agaagctgca gctgccgccg ccaccacgg    23400 acgaggagga atactgggac agtcaggcag aggaggtttt ggacgaggag gaggaggaca    23460
tgatggaaga ctgggagagc ctagacgagg aagcttccga ggtcgaagag gtgtcagacg    23520
aaacaccgtc accctcggtc gcattcccct cgccggcgcc ccagaaatcg gcaaccggtt    23580
ccagcatggc tacaacctcc gctcctcagg cgccgccggc actgcccgtt cgccgaccca    23640
accgtagatg ggacaccact ggaaccaggg ccggtaagtc caagcagccg ccgccgttag    23700
cccaagagca acaacagcgc caaggctacc gctcatggcg cgggcacaag aacgccatag    23760
ttgcttgctt gcaagactgt gggggcaaca tctccttcgc ccgccgcttt cttctctacc    23820
atcacggcgt ggccttcccc cgtaacatcc tgcattacta ccgtcatctc tacagcccat    23880
actgcaccgg cggcagcggc agcggcagca acagcagcgg ccacacagaa gcaaaggcga    23940
ccggatagca agactctgac aaagcccaag aaatccacag cggcggcagc agcaggagga    24000
ggagcgctgc gtctggcgcc caacgaaccc gtatcgaccc gcgagcttag aaacaggatt    24060
tttcccactc tgtatgctat atttcaacag agcaggggcc aagaacaaga gctgaaaata    24120
aaaaacaggt ctctgcgatc cctcacccgc agctgcctgt atcacaaaag cgaagatcag    24180
cttcggcgca cgctggaaga cgcggaggct ctcttcagta aatactgcgc gctgactctt    24240
```

```
aaggactagt ttcgcgccct ttctcaaatt taagcgcgaa aactacgtca tctccagcgg   24300
ccacacccgg cgccagcacc tgtcgtcagc gccattatga gcaaggaaat tcccacgccc   24360
tacatgtgga gttaccagcc acaaatggga cttgcggctg gagctgccca agactactca   24420
acccgaataa actacatgag cgcgggaccc cacatgatat cccgggtcaa cggaatccgc   24480
gcccaccgaa accgaattct cttggaacag gcggctatta ccaccacacc tcgtaataac   24540
cttaatcccc gtagttggcc cgctgccctg gtgtaccagg aaagtcccgc tcccaccact   24600
gtggtacttc ccagagacgc ccaggccgaa gttcagatga ctaactcagg ggcgcagctt   24660
gcgggcggct ttcgtcacag ggtgcggtcg cccgggcagg gtataactca cctgacaatc   24720
agagggcgag gtattcagct caacgacgag tcggtgagct cctcgcttgg tctccgtccg   24780
gacgggacat ttcagatcgg cggcgccggc cgtccttcat tcacgcctcg tcaggcaatc   24840
ctaactctgc agacctcgtc tctgagccg cgctctggag gcattggaac tctgcaattt   24900
attgaggagt ttgtgccatc ggtctacttt aaccccttct cgggacctcc cggccactat   24960
ccggatcaat ttattcctaa ctttgacgcg gtaaaggact cggcggacgg ctacgactga   25020
atgttaagtg gagaggcaga gcaactgcgc ctgaaacacc tggtccactg tcgccgccac   25080
aagtgctttg cccgcgactc cggtgagttt tgctactttg aattgcccga ggatcatatc   25140
gagggcccgg cgcacggcgt ccggcttacc gcccagggag agcttgcccg tagcctgatt   25200
cgggagttta cccagcgccc cctgctagtt gagcgggaca ggggaccctg tgttctcact   25260
gtgatttgca actgtcctaa ccttggatta catcaagatc tctagttaa ttaacagctt   25320 gcatgcctgc aggtcgacgg atcgggagat ctcggccgca tattaagtgc attgttctcg   25380
ataccgctaa gtgcattgtt ctcgttagct cgatggacaa gtgcattgtt ctcttgctga   25440
aagctcgatg gacaagtgca ttgttctctt gctgaaagct cgatggacaa gtgcattgtt   25500
ctcttgctga aagctcagta cccgggagta ccctcgaccg ccggagtata aatagaggcg   25560
cttcgtctac ggagcgacaa ttcaattcaa acaagcaaag tgaacacgtc gctaagcgaa   25620
agctaagcaa ataaacaagc gcagctgaac aagctaaaca atctgcagta aagtgcaagt   25680
taaagtgaat caattaaaag taaccagcaa ccaagtaaat caactgcaac tactgaaatc   25740
tgccaagaag taattattga atacaagaag agaactctga atactttcaa caagttaccg   25800
agaaagaaga actcacacac agctagcgtt taaacttaag cttcaccatg gtggggccct   25860
gcatgctgct gctgctgctg ctgctgggcc tgaggctaca gctctccctg ggcatcatcc   25920
tagttgagga ggagaacccg gacttctgga accgcgaggc agccgaggcc ctgggtgccg   25980
ccaagaagct gcagcctgca cagacagccg ccaagaacct catcatcttc ctgggcgatg   26040
gggtgggggt gtctacggtg acagctgcca ggatcctaaa agggcagaag aaggacaaac   26100 tgggggcctga gataccctg gccatggacc gcttcccata tgtggctctg tccaagacat   26160
acaatgtaga caaacatgtg ccagacagtg gagccacagc cacggcctac ctgtgcgggg   26220
tcaagggcaa cttccagacc attggcttga gtgcagccgc ccgctttaac cagtgcaaca   26280
cgacacgcgg caacgaggtc atctccgtga tgaatcgggc caagaaagca gggaagtcag   26340
tgggagtggt aaccaccaca cgagtgcagc acgcctcgcc agccggcacc tacgcccaca   26400
cggtgaaccg caactggtac tcggacgccg acgtgcctgc ctcggccgc caggaggggt   26460 gccaggacat cgctacgcag ctcatctcca acatggacat tgacgtgatc ctaggtgggg   26520
gccgaaagta catgtttcgc atgggaaccc cagaccctga gtaccagat gactacagcc   26580 aaggtgggac caggctggac gggaagaatc tggtgcagga atggctggcg aagcaccagg   26640
```

```
gtgcccggta cgtgtggaac cgcactgagc tcatgcgggc ttccctggac ccgtctgtgg   26700
cccatctcat gggtctcttt gagcctggag acatgaaata cgagatccac cgagactcca   26760
cactggaccc ctccctgatg gagatgacag aggctgccct gcgcctgctg agcaggaacc   26820
cccgcggctt cttcctcttc gtggagggtg gtcgcatcga ccatggtcat catgaaagca   26880
gggcttaccg ggcactgact gagacgatca tgttcgacga cgccattgag agggcgggcc   26940
agctcaccag cgaggaggac acgctgagcc tcgtcactgc cgaccactcc cacgtcttct   27000
ccttcggagg ctgcccsctg cgaggggct ccatcttcgg gctggcccct ggcaaggccc   27060
gggacaggaa ggcctacacg gtcctcctat acggaaacgg tccaggctat gtgctcaagg   27120
acggcgcccg gccggatgtt accgagagcg agagcgggag cccgagtat cggcagcagt   27180 cagcagtgcc cctggacgaa gagacccacg caggcgagga cgtggcggtg ttcgcgcgcg   27240
gcccgcaggc gcacctggtt cacggcgtgc aggagcagac cttcatagcg cacgtcatgg   27300
ccttcgccgc ctgcctggag ccctacaccg cctgcgacct ggcgcccccc gccggcacca   27360
ccgacgccgc gcaccggggg cggtccgtgg tccccgcgtt gcttcctctg ctggccggga   27420
ccctgctgct gctggagacg gccactgctc cctgagtgtc ccgtccctgg ggctcctgct   27480
tccccatccc ggagttctcc tgctccccgc ctcctgtcgt cctgcctggc ctccagcccg   27540
agtcgtcatc cccggagtcc ctatacagag gtcctgccat ggaaccttcc cctccccgtg   27600
cgctctgggg actgagccca tgacaccaaa cctgccccct tggctgctctc ggactcccta   27660 ccccaacccc agggacagat ctggccagat ttgtaaaaca aatagatttt aggcccaaag   27720
attatttaaa gcattgcctg gaacgcagtg agttttgtt agaaaagaga ataattcaaa   27780
gtggcattgc tttgcttctt atgttaattt ggtacagacc tgtggctgag tttgctcaaa   27840
gtattcagag cagaattgtg gagtggaaag agagattgga caaagagttt agtttgtcag   27900
tgtatcaaaa aatgaagttt aatgtggcta tgggaattgg agttttagat tggctaagaa   27960
acagtgatga tgatgatgaa gacagccagg aaaatgctga taaaaatgaa gatggtgggg   28020
agaagaacat ggaagactca gggcatgaaa caggcattga ttcacagtcc caaggctcat   28080
ttcaggcccc tcagtcctca cagtctgttc atgatcataa tcagccatac cacatttgta   28140
gaggttttac ttgctttaaa aaacctccca cacctccccc tgaacctgaa acataaaatg   28200
aatgcaattg ttgttgttaa cttgtttatt gcagcttata atggttacaa ataaagcaat   28260
agcatcacaa atttcacaaa taagcatttt ttttcactgc attctagttg tggtttgtcc   28320
aaactcatca atgtatctta tcatgtctgg atccccagga agctcctctg tgtcctcata   28380
aaccctaacc tcctctactt gagaggacat tccaatcata ggctgcccat ccaccctctg   28440
tgtcctcctg ttaattaggt cacttaacaa aaaggaaatt gggtaggggt ttttcacaga   28500
ccgcttccta agggtaattt taaaatatct gggaagtccc ttccactgct gtgttccaga   28560
agtgttggta aacagcccac aaatgtcaac agcagaaaca tacaagctgt cagctttgca   28620
caagggccca cacccctgct catcaagaag cactgtggtt gctgtgttag taatgtgcaa   28680
aacaggaggc acattttccc cacctgtgta ggttccaaaa tatctagtgt tttcatttt   28740 acttggatca ggaacccagc actccactgg ataagcatta tccttatcca aaacagcctt   28800
gtggtcagtg ttcatctgct gactgtcaac tgtagcattt tttggggtta cagtttgagc   28860
aggatatttg gtcctgtagt ttgctaacac accctgcagc tccaaaggtt ccccaccaac   28920
agcaaaaaaa tgaaaatttg acccttgaat gggttttcca gcaccatttt catgagtttt   28980
```

```
ttgtgtccct gaatgcaagt ttaacatagc agttacccca ataacctcag ttttaacagt   29040
aacagcttcc cacatcaaaa tatttccaca ggttaagtcc tcatttaaat taggcaaagg   29100
aattccactt cccactgcct tgcttccgtc tcccattcaa acttttatca actgacatta   29160
ttctaagtaa aatcctcttc attatgttgt cagcaatcca ttgcttgaag gcctggctcc   29220
ccagaacccc tcgactggta tgtcttctcc tagaatactc cagaagaaaa ggagtgtatg   29280
aagatagtga ctgcacatta aaatgactga aaccatagta aattaggatg agattctggg   29340
cagataaaca gacagctggc taggatcatt tttttatgcc ttggacttct ttggcaatct   29400
gttgaagcct gacattcctc agaataatgt tttaaagccc aacaataaga ccctgtagca   29460
catataataa gtactgcagt tttgaagtag tgataagcat aaatgatatt ttgatatatt   29520
tattataact gtaatgagat gtgtacatat ctgtgacttc ataggtactg attgtactac   29580
tgtgattttt ttgcctactt tcaaaatgaa aaggaatgct taatttcagt tagaggttag   29640
taaagacaaa taggtaattt tcttctccag tgaagagcat ggcgcccctt gctattcatg   29700
gacgcttgct taaagacttg tacacaggct tgctttgtat caacctatga cttcccctta   29760
cagccgatga taggttttta tttgcacctc cttcgtgtac aaagacagtt ttggtggcta   29820
cgccatcatt aaactcatta ttatcatgct taagcctata gatgtatcca gttcttctgt   29880
tacataattg aagctgtagt gaattgtcta tcttaaactg catcgctaac tgactacatt   29940
tcacacttca tttgcttcca acatagacta accttcttgg atgtccacta ttatttgaac   30000
ttttgagatt tttttttccta tttctaatat cttaaaattt cagaagactt aaagttttgc   30060
aactacaggg ctccatatag acatctagct tgaatttata cactttcttt cattgatgtc   30120
cctggactaa aaaatgttaa atatttctaa ccgctgtact taaagtccat tacaaacgaa   30180
gactactgtt gttaagttga ataggcatct tatatatttt tcaccggtgc aataaataac   30240
ttctattccc ttctaacatc tgcttgcgtt gcactgagag tacactattg attagcaata   30300
ggttcgtgat tacagcccct ctataattaa ttgttaggtt aacatattat tcataaaata   30360
ttattttatt aatttttact tgatttgcta ctggatgctt agaaatagct atgagtatat   30420
tggtagaacc agtacttata ttttattaca tttttacatt tcataaaatt taagtgatat   30480
aaaaatcctg aggaagtatg ccacaaaagt ggtctcagtg gaaatttaaa tatgttaaca   30540
tttattttta aaatgtagcg tgaaatagac aactttaaaa gctcagctta aaaaaaaaac   30600
tcaaggaagc tgaacttgac ttttaaagc actgaagtgc aatatttaat gtaggtcaac   30660
atgtttaaat gggaaaattt ttttcctaat tacagccaaa tccctagctg taattaactt   30720
aaaatttgta tactatttca caacagagtc agcatatacc actttcttat aaaattagaa   30780
agatctaaaa ttttagagct tatttggtga aacaggcata ttgctacatc tttgttttata   30840
aattataatg tgcctttaga gcccaataac agataacaag attttgaaaa ttcaggtgaa   30900
ttagagttat cagagggaat gttaatacac tctattcaaa tactatatga gtaagacatt   30960
taaaatagga aacaatactt tatatattaa aaaaaattaa tcttccagtc gatttaatcc   31020
actttatgaa ttcatttaaa tcgatttaaa ttcgaattaa ttaactagag tacccgggga   31080
tcttattccc tttaactaat aaaaaaaaat aataaagcat cacttactta aaatcagtta   31140
gcaaatttct gtccagttta ttcagcagca cctccttgcc ctcctcccag ctctggtatt   31200
gcagcttcct cctggctgca aactttctcc acaatctaaa tggaatgtca gtttcctcct   31260
gttcctgtcc atccgcaccc actatcttca tgttgttgca gatgaagcgc gcaagaccgt   31320
ctgaagatac cttcaacccc gtgtatccat atgacacgga aaccggtcct ccaactgtgc   31380
```

```
cttttcttac tcctcccttt gtatccccca atgggtttca agagagtccc cctggggtac    31440
tctctttgcg cctatccgaa cctctagtta cctccaatgg catgcttgcg ctcaaaatgg    31500
gcaacggcct ctctctggac gaggccggca accttacctc ccaaaatgta accactgtga    31560
gcccacctct caaaaaaacc aagtcaaaca taaacctgga aatatctgca cccctcacag    31620
ttacctcaga agccctaact gtggctgccg ccgcacctct aatggtcgcg ggcaacacac    31680
tcaccatgca atcacaggcc ccgctaaccg tgcacgactc caaacttagc attgccaccc    31740
aaggacccct cacagtgtca gaaggaaagc tagccctgca aacatcaggc cccctcacca    31800
ccaccgatag cagtacccct actatcactg cctcaccccc tctaactact gccactggta    31860
gcttgggcat tgacttgaaa gagcccattt atacacaaaa tggaaaacta ggactaaagt    31920
acggggctcc tttgcatgta acagacgacc taaacacttt gaccgtagca actggtccag    31980
gtgtgactat taataatact tccttgcaaa ctaaagttac tggagccttg ggttttgatt    32040
cacaaggcaa tatgcaactt aatgtagcag gaggactaag gattgattct caaaacagac    32100
gccttatact tgatgttagt tatccgtttg atgctcaaaa ccaactaaat ctaagactag    32160
gacagggccc tcttttata aactcagccc acaacttgga tattaactac aacaaaggcc    32220
tttacttgtt tacagcttca aacaattcca aaaagcttga ggttaaccta agcactgcca    32280
aggggttgat gtttgacgct acagccatag ccattaatgc aggagatggg cttgaatttg    32340
gttcacctaa tgcaccaaac acaaatcccc tcaaaacaaa aattggccat ggcctagaat    32400
ttgattcaaa caaggctatg gttcctaaac taggaactgg ccttagttt  tgacagcacag    32460
gtgccattac agtaggaaac aaaaataatg ataagctaac tttgtggacc acaccagctc    32520
catctcctaa ctgtagacta aatgcagaga agatgctaa actcactttg gtcttaacaa    32580
aatgtggcag tcaaatactt gctacagttt cagttttggc tgttaaaggc agtttggctc    32640
caatatctgg aacagttcaa agtgctcatc ttattataag atttgacgaa aatggagtgc    32700
tactaaacaa ttccttcctg acccagaat attggaactt tagaaatgga gatcttactg    32760
aaggcacagc ctatacaaac gctgttggat ttatgcctaa cctatcagct tatccaaaat    32820
ctcacggtaa aactgccaaa agtaacattg tcagtcaagt ttacttaaac ggagacaaaa    32880
ctaaacctgt aacactaacc attacactaa acggtacaca ggaaacagga gacacaactc    32940
caagtgcata ctctatgtca tttttcatgg gactggtctgg ccacaactac attaatgaaa    33000
tatttgccac atcctcttac acttttttcat acattgccca agaataaaga atcgtttgtg    33060
ttatgtttca acgtgtttat ttttcaattg cagaaaattt caagtcattt ttcattcagt    33120
agtatagccc caccaccaca tagcttatac agatcaccgt accttaatca aactcacaga    33180
accctagtat tcaacctgcc acctccctcc caacacacag agtacacagt cctttctccc    33240
cggctggcct taaaaagcat catatcatgg gtaacagaca tattcttagg tgttatattc    33300
cacacggttt cctgtcgagc caaacgctca tcagtgatat taataaactc cccgggcagc    33360
tcacttaagt tcatgtcgct gtccagctgc tgagccacag gctgctgtcc aacttgcggt    33420
tgcttaacgg gcggcgaagg agaagtccac gcctacatgg gggtagagtc ataatcgtgc    33480
atcaggatag ggcggtggtg ctgcagcagc gcgcgaataa actgctgccg ccgccgctcc    33540
gtcctgcagg aatacaacat ggcagtggtc tcctcagcga tgattcgcac cgcccgcagc    33600
ataaggcgcc ttgtcctccg ggcacagcag cgcaccctga tctcacttaa atcagcacag    33660
taactgcagc acagcaccac aatattgttc aaaatcccac agtgcaaggc gctgtatcca    33720
```

```
aagctcatgg cggggaccac agaacccacg tggccatcat accacaagcg caggtagatt   33780
aagtggcgac ccctcataaa cacgctggac ataaacatta cctcttttgg catgttgtaa   33840
ttcaccacct cccggtacca tataaacctc tgattaaaca tggcgccatc caccaccatc   33900
ctaaaccagc tggccaaaac ctgcccgccg gctatacact gcagggaacc gggactggaa   33960
caatgacagt ggagagccca ggactcgtaa ccatggatca tcatgctcgt catgatatca   34020
atgttggcac aacacaggca cacttcctca ggattacaag ctcctcccgc              34080
gttagaacca tatcccaggg aacaacccat tcctgaatca gcgtaaatcc cacactgcag   34140
ggaagacctc gcacgtaact cacgttgtgc attgtcaaag tgttacattc gggcagcagc   34200
ggatgatcct ccagtatggt agcgcgggtt tctgtctcaa aaggaggtag acgatcccta   34260
ctgtacggag tgcgccgaga caaccgagat cgtgttggtc gtagtgtcat gccaaatgga   34320
acgccggacg tagtcatatt tcctgaagca aaaccaggtg cgggcgtgac aaacagatct   34380
gcgtctccgg tctcgccgct tagatcgctc tgtgtagtag ttgtagtata tccactctct   34440
caaagcatcc aggcgccccc tggcttcggg ttctatgtaa actccttcat gcgccgctgc   34500
cctgataaca tccaccaccg cagaataagc cacacccagc caacctacac attcgttctg   34560
cgagtcacac acgggaggag cgggaagagc tggaagaacc atgttttttt ttttattcca   34620
aaagattatc caaaacctca aaatgaagat ctattaagtg aacgcgctcc cctccggtgg   34680
cgtggtcaaa ctctacagcc aaagaacaga taatggcatt tgtaagatgt tgcacaatgg   34740
cttccaaaag gcaaacggcc ctcacgtcca agtggacgta aaggctaaac ccttcagggt   34800
gaatctcctc tataaacatt ccagcacctt caaccatgcc caaataattc tcatctcgcc   34860
accttctcaa tatatctcta agcaaatccc gaatattaag tccggccatt gtaaaaatct   34920
gctccagagc gccctccacc ttcagcctca agcagcgaat catgattgca aaaattcagg   34980
ttcctcacag acctgtataa gattcaaaag cggaacatta acaaaaatac cgcgatcccg   35040
taggtccctt cgcagggcca gctgaacata atcgtgcagg tctgcacgga ccagcgcggc   35100
cacttccccg ccaggaacct tgacaaaaga acccacactg attatgacac gcatactcgg   35160
agctatgcta accagcgtag ccccgatgta agctttgttg catgggcggc gatataaaat   35220
gcaaggtgct gctcaaaaaa tcaggcaaag cctcgcgcaa aaaagaaagc acatcgtagt   35280
catgctcatg cagataaagg caggtaagct ccggaaccac cacagaaaaa gacaccattt   35340
ttctctcaaa catgtctgcg ggtttctgca taaacacaaa ataaataac aaaaaaacat    35400
ttaaacatta gaagcctgtc ttacaacagg aaaacaacc cttataagca taagacggac    35460
tacggccatg ccggcgtgac cgtaaaaaaa ctggtcaccg tgattaaaaa gcaccaccga   35520
cagctcctcg gtcatgtccg gagtcataat gtaagactcg gtaaacacat caggttgatt   35580
catcggtcag tgctaaaaag cgaccgaaat agcccggggg aatacatacc cgcaggcgta   35640
gagacaacat tacagccccc ataggaggta taacaaaatt aataggagag aaaaacacat   35700
aaacacctga aaaccctcc tgcctaggca aaatagcacc ctcccgctcc agaacaacat    35760
acagcgcttc acagcggcag cctaacagtc agccttacca gtaaaaaaga aaacctatta   35820
aaaaaacacc actcgacacg gcaccagctc aatcagtcac agtgtaaaaa agggccaagt   35880
gcagagcgag tatatatagg actaaaaaat gacgtaacgg ttaaagtcca caaaaaacac   35940
ccagaaaacc gcacgcgaac ctacgcccag aaacgaaagc caaaaaaccc acaacttcct   36000
caaatcgtca cttccgtttt cccacgttac gtaacttccc attttaagaa aactacaatt   36060
cccaacacat acaagttact ccgccctaaa acctacgtca cccgccccgt tcccacgccc   36120
```

```
cgcgccacgt cacaaactcc accccctcat tatcatattg gcttcaatcc aaaataaggt    36180
atattattga tgatggccgg ccgaattgaa tcagggdata acgcaggaaa gaacatgtga    36240
gcaaaaggcc agcaaaaggc caggaaccgt aaaaaggccg cgttgctggc gttttttccat   36300 aggctccgcc cccctgacga gcatcacaaa aatcgacgct caagtcagag gtggcgaaac    36360
ccgacaggac tataaagata ccaggcgttt ccccctggaa gctccctcgt gcgctctcct    36420
gttccgaccc tgccgcttac cggatacctg tccgcctttc tcccttcggg aagcgtggcg    36480
ctttctcata gctcacgctg taggtatctc agttcggtgt aggtcgttcg ctccaagctg    36540
ggctgtgtgc acgaaccccc cgttcagccc gaccgctgcg ccttatccgg taactatcgt    36600
cttgagtcca acccggtaag acacgactta tcgccactgg cagcagccac tggtaacagg    36660
attagcagag cgaggtatgt aggcggtgct acagagttct tgaagtggtg cctaactac     36720 ggctacacta aaggacagt atttggtatc tgcgctctgc tgaagccagt taccttcgga    36780
aaaagagttg gtagctcttg atccggcaaa caaaccaccg ctggtagcgg tggtttttt     36840 gtttgcaagc agcagattac gcgcagaaaa aaaggatctc aagaagatcc tttgatcttt    36900
tctacggggt ctgacgctca gtggaacgaa aactcacgtt aagggatttt ggtcatgaga    36960
ttatcaaaaa ggatcttcac ctagatcctt ttaaattaaa aatgaagttt taaatcaatc    37020
taaagtatat atgagtaaac ttggtctgac agttaccaat gcttaatcag tgaggcacct    37080
atctcagcga tctgtctatt tcgttcatcc atagttgcct gactccccgt cgtgtagata    37140
actacgatac gggagggctt accatctggc cccagtgctg caatgatacc gcgagaccca    37200
cgctcaccgg ctccagattt atcagcaata aaccagccag ccggaagggc cgagcgcaga    37260
agtggtcctg caactttatc cgcctccatc cagtctatta attgttgccg ggaagctaga    37320
gtaagtagtt cgccagttaa tagtttgcgc aacgttgttg ccattgctac aggcatcgtg    37380
gtgtcacgct cgtcgtttgg tatggcttca ttcagctccg gttcccaacg atcaaggcga    37440
gttacatgat cccccatgtt gtgcaaaaaa gcggttagct ccttcggtcc tccgatcgtt    37500
gtcagaagta agttggccgc agtgttatca ctcatggtta tggcagcact gcataattct    37560
cttactgtca tgccatccgt aagatgcttt tctgtgactg gtgagtactc aaccaagtca    37620
ttctgagaat agtgtatgcg gcgaccgagt tgctcttgcc cggcgtcaat acgggataat    37680
accgcgccac atagcagaac tttaaaagtg ctcatcattg gaaaacgttc ttcggggcga    37740
aaactctcaa ggatcttacc gctgttgaga tccagttcga tgtaacccac tcgtgcaccc    37800
aactgatctt cagcatcttt tactttcacc agcgtttctg ggtgagcaaa aacaggaagg    37860
caaaatgccg caaaaaaggg aataagggcg acacggaaat gttgaatact catactcttc    37920 cttttcaat attattgaag catttatcag ggttattgtc tcatgagcgg atacatattt     37980
gaatgtattt agaaaaataa acaaataggg gttccgcgca catttccccg aaaagtgcca    38040
c                                                                   38041
```

<210> SEQ ID NO 14
<211> LENGTH: 7180
<212> TYPE: DNA
<213> ORGANISM: Artificial Sequence
<220> FEATURE:
<223> OTHER INFORMATION: Synthetic

<400> SEQUENCE: 14

```
tctagagtcg accggtcatg gctgcgcccc gacacccgcc aacacccgct gacgcgccct    60
```

```
gacgggcttg tctgctcccg gcatccgctt acagacaagc tgtgaccgtc tccgggagct    120
gcatgtgtca gaggttttca ccgtcatcac cgaaacgcgc gaggcagccg gatcataatc    180
agccatacca catttgtaga ggttttactt gctttaaaaa acctccccac ctccccctga    240
acctgaaaca taaaatgaat gcaattgttg ttgttaactt gtttattgca gcttataatg    300
gttacaaata aagcaatagc atcacaaatt tcacaaataa agcattttt tcactgcatt    360 ctagttgtgg tttgtccaaa ctcatcaatg tatcttatca tgtctggatc cagttcgatg    420
taacccactc gtgcacccaa ctgatcttca gcatcttta ctttcaccag cgtttctggg    480
tgagcaaaaa caggaaggca aaatgccgca aaaagggaa taagggcgac acggaaatgt    540
tgaatactca tactcttcct ttttcaatat tattgaagca tttatcaggg ttattgtctc    600
atgagcggat acatatttga atgtatttag aaaataaac aaatagggt tccgcgcaca    660 tttccccgaa aagtgccacc tgacgtccat tgttcattcc acggacaaaa acagagaaag    720
gaaacgacag aggccaaaaa gcctcgcttt cagcacctgt cgtttccttt cttttcagag    780
ggtattttaa ataaaaacat taagttatga cgaagaagaa cggaaacgcc ttaaaccgga    840
aaattttcat aaatagcgaa aacccgcgag gtcgccgccc cgtaacctgt cggatcaccg    900
gaaaggaccc gtaaagtgat aatgattatc atctagacta catcgatggg tcgtgcgctc    960
ctttcggtcg ggcgctgcgg gtcgtggggc gggcgtcagg caccgggctt gcgggtcatg   1020
caccaggtcg cgcggtcctt cgggcactcg acgtcggcgg tgacggtgaa gccgagccgc   1080
tcgtagaagg ggaggttgcg gggcgcggag gtctccagga aggcgggcac cccggcgcgc   1140
tcggccgcct ccactccggg gagcacgacg gcgctgccca gacccttgcc ctggtggtcg   1200
ggcgagacgc cgacggtggc caggaaccac gcgggctcct tgggccggtg cggcgccagg   1260
aggccttcca tctgttgctg cgcggccagc cgggaaccgc tcaactcggc catgcgcggg   1320
ccgatctcgg cgaacaccgc ccccgcttcg acgctctccg gcgtggtcca gaccgccacc   1380
gcggcgccgt cgtccgcgac ccacaccttg ccgatgtcga gcccgacgcg cgtgaggaag   1440
agttcttgca gctcggtgac ccgctcgatg tggcggtccg gatcgacggt gtggcgcgtg   1500
gcggggtagt cggcgaacgc ggcggcgagg gtgcgtacgg ccctggggac gtcgtcgcgg   1560
gtggcgaggc gcaccgtggg cttgtactcg gtcatggtaa gcttgctagc agctggtacc   1620
cagcttctag agatctgacg gttcactaaa cgagctctgc ttatatagac ctcccaccgt   1680
acacgcctac cgcccatttg cgtcaacggg gcggggttat tacgacattt tggaaagtcc   1740
cgttgatttt ggtgccaaaa caaactccca ttgacgtcaa tggggtggag acttggaaat   1800
ccccgtgagt caaaccgcta tccacgccca ttggtgtact gccaaaaccg catcaccatg   1860
gtaatagcga tgactaatac gtagatgtac tgccaagtag gaaagtcccg taaggtcatg   1920
tactgggcat aatgccaggc gggccattta ccgtcattga cgtcaatagg gggcggactt   1980
ggcatatgat acacttgatg tactgccaag tgggcagttt accgtaaata ctccacccat   2040
tgacgtcaat ggaaagtccc tattggcgtt actatgggaa catacgtcat tattgacgtc   2100
aatgggcggg ggtcgttggg cggtcagcca ggcgggccat ttaccgtaag ttatgtaacg   2160
cggaactcca tatatgggct atgaactaat gaccccgtaa ttgattacta ttaataacta   2220
gtcaataatc aatgtcaaca tggcggtcat attggacatg agccaatata aatgtacata   2280
ttatgatata gatacaacgt atgcaatggc caatagccaa tattgattta tgctatataa   2340
ccaatgacta atatggctaa ttgccaatat tgattcaatg tatagatctt ccatacctac   2400
cagttctgcg cctgcagcaa tgcaacaacg ttgcccggat ctgcgatgat aagctgtcaa   2460
```

```
acatgagaat tggtcgacta gcttggcacg ccagaaatcc gcgcggtggt ttttgggggt    2520
cgggggtgtt tggcagccac agacgcccgg tgttcgtgtc gcgccagtac atgcggtcca    2580
tgcccaggcc atccaaaaac catgggtctg tctgctcagt ccagtcgtgg accagacccc    2640
acgcaacgcc caaaataata acccccacga accataaacc attccccatg ggggaccccg    2700
tccctaaccc acggggccag tggctatggc agggcctgcc gccccgacgt tggctgcgag    2760
ccctgggcct tcacccgaac ttgggggtg gggtgggaa aaggaagaaa cgcgggcgta     2820
ttggccccaa tggggtctcg gtggggtatc gacagagtgc cagccctggg accgaacccc    2880
gcgtttatga acaaacgacc caacacccgt gcgttttatt ctgtcttttt attgccgtca    2940
tagcgcgggt tccttccggt attgtctcct tccgtgtttc agttagcctc cccatctcc     3000 cctattcctt tgccctcgga cgagtgctgg ggcgtcggtt tccactatcg gcgagtactt    3060
ctacacagcc atcggtccag acggccgcgc ttctgcgggc gatttgtgta cgcccgacag    3120
tcccggctcc ggatcggacg attgcgtcgc atcgaccctg cgcccaagct gcatcatcga    3180
aattgccgtc aaccaagctc tgatagagtt ggtcaagacc aatgcggagc atatacgccc    3240
ggagccgcgg cgatcctgca agctccggat gcctccgctc gaagtagcgc gtctgctgct    3300
ccatacaagc caaccacggc ctccagaaga agatgttggc gacctcgtat tgggaatccc    3360
cgaacatcgc ctcgctccag tcaatgaccg ctgttatgcg ccattgtcc gtcaggacat     3420 tgttggagcc gaaatccgcg tgcacgaggt gccggacttc ggggcagtcc tcggcccaaa    3480
gcatcagctc atcgagagcc tgcgcgacgg acgcactgac ggtgtcgtcc atcacagttt    3540
gccagtgata cacatgggga tcagcaatcg cgcatatgaa atcacgccat gtagtgtatt    3600
gaccgattcc ttgcggtccg aatgggccga acccgctcgt ctggctaaga tcggccgcag    3660
cgcgcgcaaa acccctaaat aaagacagca agacacttgc ttgatccaaa tccaaacaga    3720
gtctggtttt ttatttatgt tttaaaccgc attgggaggg gaggaagcct tcagggcaga    3780
aacctgctgg cgcagatcca acagctgctg agaaacgaca ttaagttccc gggtcaaaga    3840
atccaattgt gccaaaagag ccgtcaactt gtcatcgcgg gcggatgaac gggaagctgc    3900
actgcttgca agcgggctca ggaaagcaaa gtcagtcaca atcccgcggg cggtggctgc    3960
agcggctgaa gcggcggcgg aggctgcagt ctccaacggc gttccagaca cggtctcgta    4020
ggtcaaggta gtagagtttg cgggcaggac ggggcgacca tcaatgctgg agcccatcac    4080
attctgacgc accccggccc atgggggcat gcgcgttgtc aaatatgagc tcacaatgct    4140
tccatcaaac gagttggtgc tcatggcggc ggcggctgct gcaaaacaga tacaaaacta    4200
cataagaccc ccaccttata tattctttcc cacccgggat ctgcggcacg ctgttgacgc    4260
tgttaagcgg gtcgctgcag ggtcgctcgg tgttcgaggc cacacgcgtc accttaatat    4320
gcgaagtgga cctgggaccg cgccgccccg actgcatctg cgtgttcgaa ttcgccaatg    4380
acaagacgct gggcggggtt tgtgtcatca tagaactaaa gacatgcaaa tatatttctt    4440
ccggggacac cgccagcaaa cgcgagcaac gggccacggg gatgaagcag gcatggcgg     4500 ccgacgcgct gggctacgtc ttgctggcgt tcgcgacgcg aggctggatg gccttcccca    4560
ttatgattct tctcgcttcc ggcggcatcg ggatgcccgc gttgcaggcc atgctgtcca    4620
ggcaggtaga tgacgaccat cagggacagc ttcaaggatc gctcgcggct cttaccagcc    4680
taacttcgat cactgaccg ctgatcgtca cggcgattta tgccgcctcg gcagcacat     4740 ggaacgggtt ggcatggatt gtaggcgccg ccctatacct tgtctgcctc cccgcgttgc    4800
```

```
gtcgcggtgc atggagccgg gccacctcga cctgaatgga agccggcggc acctcgctaa    4860
cggattcacc actccaagaa ttggagccaa tcaattcttg cggagaactg tgaatgcgca    4920
aaccaaccct tggcagaaca tatccatcgc gtccgccatc tccagcagcc gcacgcggcg    4980
cagcaaaagg ccaggaaccg taaaaaggcc gcgttgctgg cgttttttcca taggctccgc    5040
ccccctgacg agcatcacaa aaatcgacgc tcaagtcaga ggtggcgaaa cccgacagga    5100
ctataaagat accaggcgtt ccccctgga agctccctcg tgcgctctcc tgttccgacc    5160
ctgccgctta ccggatacct gtccgccttt ctcccttcgg aagcgtggc gctttctcat    5220
agctcacgct gtaggtatct cagttcggtg taggtcgttc gctccaagct gggctgtgtg    5280
cacgaacccc ccgttcagcc cgaccgctgc gccttatccg gtaactatcg tcttgagtcc    5340
aacccggtaa gacacgactt atcgccactg gcagcagcca ctggtaacag gattagcaga    5400
gcgaggtatg taggcggtgc tacagagttc ttgaagtggt ggcctaacta cggctacact    5460
agaaggacag tatttggtat ctgcgctctg ctgaagccag ttaccttcgg aaaaagagtt    5520
ggtagctctt gatccggcaa acaaaccacc gctggtagcg gtggtttttt tgtttgcaag    5580
cagcagatta cgcgcagaaa aaaggatct caagaagatc ctttgatctt ttctacgggg    5640
tctgacgctc agtggaacga aaactcacgt taagggattt tggtcatgag attatcaaaa    5700
aggatcttca cctagatcct tttaaattaa aaatgaagtt ttaaatcaat ctaaagtata    5760
tatgagtaaa cttggtctga cagttaccaa tgcttaatca gtgaggcacc tatctcagcg    5820
atctgtctat ttcgttcatc catagttgcc tgactccccg tcgtgtagat aactacgata    5880
cgggagggct taccatctgg ccccagtgct gcaatgatac cgcgagaccc acgctcaccg    5940
gctccagatt tatcagcaat aaaccagcca gccggaaggg ccgagcgcag aagtggtcct    6000
gcaactttat ccgcctccat ccagtctatt aattgttgcc gggaagctag agtaagtagt    6060
tcgccagtta atagtttgcg caacgttgtt gccattgctg caggcatcgt ggtgtcacgc    6120
tcgtcgtttg gtatggcttc attcagctcc ggttcccaac gatcaaggcg agttacatga    6180
tcccccatgt tgtgcaaaaa agcggttagc tccttcggtc ctccgatcgt tgtcagaagt    6240
aagttggccg cagtgttatc actcatggtt atggcagcac tgcataattc tcttactgtc    6300
atgccatccg taagatgctt ttctgtgact ggtgagtact caaccaagtc attctgagaa    6360
tagtgtatgc ggcgaccgag ttgctcttgc ccggcgtcaa cacgggataa taccgcgcca    6420
catagcagaa ctttaaaagt gctcatcatt ggaaaacgtt cttcggggcg aaaactctca    6480
aggatcttac cgctgttgag atccagttcg atgtaaccca ctcgtgcacc caactgatct    6540
tcagcatctt ttactttcac cagcgtttct gggtgagcaa aaacaggaag gcaaaatgcc    6600
gcaaaaaagg aataagggc gacacggaaa tgttgaatac tcatactctt ccttttcaa    6660
tattattgaa gcatttatca gggttattgt ctcatgagcg gatacatatt tgaatgtatt    6720
tagaaaaata aacaaatagg ggttccgcgc acatttcccc gaaaagtgcc acctgacgtc    6780
taagaaacca ttattatcat gacattaacc tataaaaata ggcgtatcac gaggcccttc    6840
ccgtagtctt cctgggcccc tgggaggtac atgtccccca gcattggtgt aagagcttca    6900
gccaagagtt acacataaag gcaatgttgt gttgcagtcc acagactgca aagtctgctc    6960
caggatgaaa gccactcagt gttggcaaat gtgcacatcc atttataagg atgtcaacta    7020
cagtcagaga accccttgt gtttggtccc ccccgtgtc acatgtggaa cagggcccag    7080
ttggcaagtt gtaccaacca actgaaggga ttacatgcac tgccccgcga agaagggca    7140
gagatgccgt agtcaggttt agttcgtccg gcggcggggc                          7180
```

<210> SEQ ID NO 15
<211> LENGTH: 37391
<212> TYPE: DNA
<213> ORGANISM: Artificial Sequence
<220> FEATURE:
<223> OTHER INFORMATION: Synthetic

<400> SEQUENCE: 15

```
ctaaattgta agcgttaata ttttgttaaa attcggccgg ccatcatcaa taatatacct      60
tattttggat tgaagccaat atgataatga ggggtggag tttgtgacgt ggcgcggggc      120
gtgggaacgg ggcgggtgac gtagtagtgt ggcggaagtg tgatgttgca agtgtggcgg     180
aacacatgta taacttcgta taatgtatgc tatacgaagt tatacatgta agcgacggat     240
gtggcaaaag tgacgttttt ggtgtgcgcc ggtgtacaca ggaagtgaca attttcgcgc     300
ggttttaggc ggatgttgta gtaaatttgg gcgtaaccga gtaagatttg gccattttcg     360
cgggaaaact gaataagagg aagtgaaatc tgaataattt tgtgttactc atagcgcgta     420
atatttgtct agggagatca attggattct ttgacccggg aacttaatgt cgtttctcag     480
cagctgttgg atctgcgcca gcaggtttct gccctgaagg cttcctcccc tcccaatgcg     540
gtttaaaaca taaataaaaa accagactct gtttggattt ggatcaagca agtgtcttgc     600
tgtctttatt taggggtttt gcgcgcgcgg taggcccggg accagcggtc tcggtcgttg     660
agggtcctgt gtatttttc caggacgtgg taaaggtgac tctggatgtt cagatacatg     720
ggcataagcc cgtctctggg gtggaggtag caccactgca gagcttcatg ctgcggggtg     780
gtgttgtaga tgatccagtc gtagcaggag cgctgggcgt ggtgcctaaa aatgtctttc     840
agtagcaagc tgattgccag gggcaggccc ttggtgtaag tgtttacaaa gcggttaagc     900
tgggatgggt gcatacgtgg ggatatgaga tgcatcttgg actgtatttt taggttggct     960
atgttcccag ccatatccct ccggggattc atgttgtgca gaaccaccag cacagtgtat     1020
ccggtgcact tgggaaattt gtcatgtagc ttagaaggaa atgcgtggaa gaacttggag     1080
acgcccttgt gacctccaag attttccatg cattcgtcca taatgatggc aatgggccca     1140
cgggcggcgg cctgggcgaa gatatttctg ggatcactaa cgtcatagtt gtgttccagg     1200
atgagatcgt cataggccat ttttacaaag cgcgggcga gggtgccaga ctgcggtata     1260
atggttccat ccggcccagg ggcgtagtta ccctcacaga tttgcatttc ccacgctttg     1320
agttcagatg gggggatcat gtctacctgc ggggcgatga agaaaacggt tccggggta     1380
ggggagatca gctgggaaga aagcaggttc ctgagcagct gcgacttacc gcagccggtg     1440
ggcccgtaaa tcacacctat taccgggtgc aactggtagt taagagagct gcagctgccg     1500
tcatccctga gcagggggc cacttcgtta agcatgtccc tgactcgcat gttttccctg     1560
accaaatccg ccagaaggcg ctccgccgcc agcgatagca gttcttgcaa ggaagcaaag     1620
tttttcaacg gtttgagacc gtccgccgta ggcatgcttt tgagcgtttg accaagcagt     1680
tccaggcggt cccacagctc ggtcacctgc tctacggcat ctcgatccag catatctcct     1740
cgtttcgcgg gttggggcgg ctttcgctgt acggcagtag tcggtgctcg tccagacggg     1800
ccagggtcat gtcttccac gggcgcaggg tcctcgtcag cgtagtctgg gtcacggtga     1860
aggggtgcgc tccgggctgc gcgctggcca gggtgcgctt gaggctggtc ctgctggtgc     1920
tgaagcgctg ccggtcttcg ccctgcgcgt cggccaggta gcatttgacc atggtgtcat     1980
agtccagccc ctccgcggcg tggccttggg cgcgcagctt gcccttggag gaggcgccgc     2040
```

```
acgaggggca gtgcagactt ttgagggcgt agagcttggg cgcgagaaat accgattccg   2100
gggagtaggc atccgcgccg caggccccgc agacggtctc gcattccacg agccaggtga   2160
gctctggccg ttcggggtca aaaccaggt ttcccccatg cttttgatg cgtttcttac    2220
ctctggtttc catgagccgg tgtccacgct cggtgacgaa aaggctgtcc gtgtcccgt    2280
atacagactt gagaggcctg tcctcgagcg gtgttccgcg gtcctcctcg tatagaaact   2340
cggaccactc tgagacaaag gctcgcgtcc aggccagcac gaaggaggct aagtgggagg   2400
ggtagcggtc gttgtccact agggggtcca ctcgctccag ggtgtgaaga cacatgtcgc   2460
cctcttcggc atcaaggaag gtgattggtt tgtaggtgta ggccacgtga ccgggtgttc   2520
ctgaaggggg gctataaaag ggggtggggg cgcgttcgtc ctcactctct tccgcatcgc   2580
tgtctgcgag ggccagctgt tggggtgagt actccctctg aaaagcgggc atgacttctg   2640
cgctaagatt gtcagtttcc aaaaacgagg aggatttgat attcacctgg cccgcggtga   2700
tgcctttgag ggtggccgca tccatctggt cagaaaagac aatcttttg ttgtcaagct    2760
tggtggcaaa cgacccgtag agggcgttgg acagcaactt ggcgatggag cgcagggttt   2820
ggttttgtc gcgatcggcg cgctcctttgg ccgcgatgtt tagctgcacg tattcgcgcg   2880
caacgcaccg ccattcggga aagacggtgg tgcgctcgtc gggcaccagg tgcacgcgcc   2940
aaccgcggtt gtgcagggtg acaaggtcaa cgctggtggc tacctctccg cgtaggcgct   3000
cgttggtcca gcagaggcgg ccgcccttgc gcgagcagaa tggcggtagg gggtctagct   3060
gcgtctcgtc cgggggtct gcgtccacgg taaagacccc gggcagcagg cgcgcgtcga    3120
agtagtctat cttgcatcct tgcaagtcta gcgcctgctg ccatgcgcgg gcggcaagcg   3180
cgcgctcgta tgggttgagt ggggggacccc atggcatggg gtgggtgagc gcggaggcgt   3240
acatgccgca aatgtcgtaa acgtagaggg gctctctgag tattccaaga tatgtagggt   3300
agcatcttcc accgcggatg ctggcgcgca cgtaatcgta tagttcgtgc gagggagcga   3360
ggaggtcggg accgaggttg ctacgggcgg gctgctctgc tcggaagact atctgcctga   3420
agatggcatg tgagttggat gatatggttg gacgctggaa gacgttgaag ctggcgtctg   3480
tgagacctac cgcgtcacgc acgaaggagg cgtaggagtc gcgcagcttg ttgaccagct   3540
cggcggtgac ctgcacgtct agggcgcagt agtccagggt ttccttgatg atgtcatact   3600
tatcctgtcc cttttttttc cacagctcgc ggttgaggac aaactcttcg cggtctttcc   3660
agtactcttg gatcggaaac ccgtcggcct ccgaacggta agagcctagc atgtagaact   3720
ggttgacggc ctggtaggcg cagcatccct tttctacggg tagcgcgtat gcctgcgcgg   3780
ccttccggag cgaggtgtgg gtgagcgcaa aggtgtccct gaccatgact ttgaggtact   3840
ggtatttgaa gtcagtgtcg tcgcatccgc cctgctccca gagcaaaaag tccgtgcgct   3900
ttttggaacg cggatttggc agggcgaagg tgacatcgtt gaagagtatc tttcccgcgc   3960
gaggcataaa gttgcgtgtg atgcggaagg gtcccgcgca ctcggaacgg ttgttaatta   4020
cctgggcggc gagcacgatc tcgtcaaagc cgttgatgtt gtggcccaca atgtaaagtt   4080
ccaagaagcg cgggatgccc ttgatggaag gcaattttt aagttcctcg taggtgagct    4140
cttcagggga gctgagcccg tgctctgaaa gggcccagtc tgcaagatga gggttggaag   4200
cgacgaatga gctccacagg tcacgggcca ttagcatttg caggtggtcg cgaaaggtcc   4260
taaactggcg acctatggcc atttttttctg gggtgatgca gtagaaggta agcgggtctt   4320
gttcccagcg gtcccatcca aggttcgcgg ctaggtctcg cgcggcagtc actagaggct   4380
catctccgcc gaacttcatg accagcatga agggcacgag ctgcttccca aaggccccca   4440
```

```
tccaagtata ggtctctaca tcgtaggtga caaagagacg ctcggtgcga ggatgcgagc   4500
cgatcgggaa gaactggatc tcccgccacc aattggagga gtggctattg atgtggtgaa   4560
agtagaagtc cctgcgacgg gccgaacact cgtgctggct tttgtaaaaa cgtgcgcagt   4620
actggcagcg gtgcacgggc tgtacatcct gcacgaggtt gacctgacga ccgcgcacaa   4680
ggaagcagag tgggaatttg agcccctcgc ctggcgggtt tggctggtgg tcttctactt   4740
cggctgcttg tccttgaccg tctggctgct cgagggagt tacggtggat cggaccacca    4800
cgccgcgcga gcccaaagtc cagatgtccg cgcgcggcgg tcggagcttg atgacaacat   4860
cgcgcagatg ggagctgtcc atggtctgga gctcccgcgg cgtcaggtca ggcgggagct   4920
cctgcaggtt tacctcgcat agacgggtca gggcgcgggc tagatccagg tgatacctaa   4980
tttccagggg ctggttggtg gcggcgtcga tggcttgcaa gaggccgcat ccccgcggcg   5040
cgactacggt accgcgcggc gggcggtggg ccgcgggggg gtccttggat gatgcatcta   5100
aaagcggtga cgcgggcgag cccccggagg tagggggggc tccggacccg ccgggagagg   5160
gggcaggggc acgtcggcgc cgcgcgcggg caggagctgg tgctgcgcgc gtaggttgct   5220
ggcgaacgcg acgacgcggc ggttgatctc ctgaatctgg cgcctctgcg tgaagacgac   5280
gggcccggtg agcttgagcc tgaaagagag ttcgacagaa tcaatttcgg tgtcgttgac   5340
ggcggcctgg cgcaaaatct cctgcacgtc tcctgagttg tcttgatagg cgatctcggc   5400
catgaactgc tcgatctctt cctcctggag atctccgcgt ccggctcgct ccacggtggc   5460
ggcgaggtcg ttggaaatgc gggccatgag ctgcgagaag gcgttgaggc ctccctcgtt   5520
ccagacgcgg ctgtagacca cgccccctcc ggcatcgcgg gcgcgcatga ccacctgcgc   5580
gagattgagc tccacgtgcc gggcgaagac ggcgtagttt cgcaggcgct gaaagaggta   5640
gttgagggtg gtggcggtgt gttctgccac gaagaagtac ataacccagc gtcgcaacgt   5700
ggattcgttg atatccccca aggcctcaag gcgctccatg gcctcgtaga agtccacggc   5760
gaagttgaaa aactgggagt gcgcgccga cacggttaac tcctcctcca gaagacggat    5820
gagctcggcg acagtgtcgc gcacctcgcg ctcaaaggct acaggggcct cttcttcttc   5880
ttcaatctcc tcttccataa gggcctcccc ttcttcttct tctggcggcg gtggggagg    5940 ggggacacgg cggcgacgac ggcgcaccgg gaggcggtcg acaaagcgct cgatcatctc   6000
cccgcggcga cggcgcatgg tctcggtgac ggcgcggccg ttctcgcggg ggcgcagttg   6060
gaagacgccg cccgtcatgt cccggttatg ggttggcggg gggctgccat gcggcaggga   6120
tacggcgcta acgatgcatc tcaacaattg ttgtgtaggt actccgccgc cgagggacct   6180
gagcgagtcc gcatcgaccg gatcggaaaa cctctcgaga aaggcgtcta accagtcaca   6240
gtcgcaaggt aggctgagca ccgtggcggg cggcagcggg cggcggtcgg ggttgtttct   6300
ggcggaggtc ctgctgatga tgtaattaaa gtaggcggtc ttgagacggc ggatggtcga   6360
cagaagcacc atgtccttgg gtccggcctg ctgaatgcgc aggcggtcgg ccatgcccca   6420
ggcttcgttt tgacatcggc gcaggtcttt gtagtagtct tgcatgagcc tttctaccgg   6480
cacttcttct tctccttcct cttgtcctgc atctcttgca tctatcgctg cggcggcggc   6540
ggagtttggc cgtaggtggc gccctcttcc tcccatgcgt gtgacccga agcccctcat    6600 cggctgaagc agggctaggt cggcgacaac gcgctcggct aatatggcct gctgcacctg   6660
cgtgagggta gactgaagt catccatgtc cacaaagcgg tggtatgcgc ccgtgttgat    6720
ggtgtaagtg cagttggcca taacggacca gttaacggtc tggtgacccg gctgcgagag   6780
```

```
ctcggtgtac ctgagacgcg agtaagccct cgagtcaaat acgtagtcgt tgcaagtccg    6840
caccaggtac tggtatccca ccaaaaagtg cggcggcggc tggcggtaga ggggccagcg    6900
tagggtggcc ggggctccgg gggcgagatc ttccaacata aggcgatgat atccgtagat    6960
gtacctggac atccaggtga tgccggcggc ggtggtggag gcgcgcggaa agtcgcggac    7020
gcggttccag atgttgcgca gcggcaaaaa gtgctccatg gtcgggacgc tctggccggt    7080
caggcgcgcg caatcgttga cgctctaccg tgcaaaagga gagcctgtaa gcgggcactc    7140
ttccgtggtc tggtggataa attcgcaagg gtatcatggc ggacgaccgg ggttcgagcc    7200
ccgtatccgg ccgtccgccg tgatccatgc ggttaccgcc cgcgtgtcga acccaggtgt    7260
gcgacgtcag acaacggggg agtgctcctt ttggcttcct tccaggcgcg cggctgctg    7320 cgctagcttt tttggccact ggccgcgcgc agcgtaagcg gttaggctgg aaagcgaaag    7380
cattaagtgg ctcgctccct gtagccggag ggttattttc caagggttga gtcgcgggac    7440
ccccggttcg agtctcggac cggccggact gcggcgaacg ggggtttgcc tccccgtcat    7500
gcaagacccc gcttgcaaat tcctccggaa acagggacga gccccttttt tgcttttccc    7560
agatgcatcc ggtgctgcgg cagatgcgcc cccctcctca gcagcggcaa gagcaagagc    7620
agcggcagac atgcagggca ccctcccctc ctcctaccgc gtcaggaggg gcgacatccg    7680
cggttgacgc ggcagcagat ggtgattacg aaccccgcg gcgccgggcc cggcactacc    7740
tggacttgga ggagggcgag ggcctggcgc ggctaggagc gccctctcct gagcggtacc    7800
caagggtgca gctgaagcgt gatacgcgtg aggcgtacgt gccgcggcag aacctgtttc    7860
gcgaccgcga gggagaggag cccgaggaga tgcgggatcg aaagttccac gcagggcgcg    7920
agctgcggca tggcctgaat cgcgagcggt tgctgcgcga ggaggacttt gagcccgacg    7980
cgcgaaccgg gattagtccc gcgcgcgcac acgtggcggc cgccgacctg gtaaccgcat    8040
acgagcagac ggtgaaccag gagattaact ttcaaaaaag ctttaacaac cacgtgcgta    8100
cgcttgtggc gcgcgaggag gtggctatag gactgatgca tctgtgggac tttgtaagcg    8160
cgctggagca aaacccaaat agcaagccgc tcatggcgca gctgttcctt atagtgcagc    8220
acagcaggga caacgaggca ttcagggatg cgctgctaaa catagtagag cccgagggcc    8280
gctggctgct cgatttgata aacatcctgc agagcatagt ggtgcaggag cgcagcttga    8340
gcctggctga caaggtggcc gccatcaact attccatgct tagcctgggc aagttttacg    8400
cccgcaagat ataccatacc ccttacgttc ccatagacaa ggaggtaaag atcgaggggt    8460
tctacatgcg catggcgctg aaggtgctta ccttgagcga cgacctgggc gtttatcgca    8520
acgagcgcat ccacaaggcc gtgagcgtga gccggcggcg cgagctcagc gaccgcgagc    8580
tgatgcacag cctgcaaagg gccctggctg cacgggcag cggcgataga gaggccgagt    8640
cctactttga cgcgggcgct gacctgcgct gggccccaag ccgacgcgcc ctggaggcag    8700
ctggggccga acctgggctg gcggtggcac ccgcgcgcg tggcaacgtc ggcggcgtgg    8760
aggaatatga cgaggacgat gagtacgagc cagaggacgg cgagtactaa gcggtgatgt    8820
ttctgatcag atgatgcaag acgcaacgga cccggcggtg cggcggcgc tgcagagcca    8880 gccgtccggc cttaactcca cggacgactg cgccaggtc atggaccgca tcatgtcgct    8940
gactgcgcgc aatcctgacg cgttccgca gcagccgcag gccaaccggc tctccgcaat    9000
tctggaagcg gtggtccggg cgcgcgcaaa ccccacgcac gagaaggtgc tggcgatcgt    9060
aaacgcgctg gccgaaaaca gggccatccg gcccgacgaa gccggcctgg tctacgacgc    9120
gctgcttcag cgcgtggctc gttacaacag cggcaacgtg cagaccaacc tggaccggct    9180
```

```
ggtgggggat gtgcgcgagg ccgtggcgca gcgtgagcgc gcgcagcagc agggcaacct    9240
gggctccatg gttgcactaa acgccttcct gagtacacag cccgccaacg tgccgcgggg    9300
acaggaggac tacaccaact tgtgagcgc actgcggcta atggtgactg agacaccgca    9360
aagtgaggtg taccagtctg gccagacta ttttttccag accagtagac aaggcctgca    9420
gaccgtaaac ctgagccagg cttcaaaaa cttgcagggg ctgtgggggg tgcgggctcc    9480
cacaggcgac cgcgcgaccg tgtctagctt gctgacgccc aactcgcgcc tgttgctgct    9540
gctaatagcg cccttcacgg acagtggcag cgtgtcccgg dacacatacc taggtcactt    9600
gctgacactg taccgcgagg ccataggtca ggcgcatgtg gacgagcata ctttccagga    9660
gattacaagt gtcagccgcg cgctggggca ggaggacacg ggcagcctgg aggcaaccct    9720
aaactacctg ctgaccaacc ggcggcagaa gatccctcg ttgcacagtt taaacagcga    9780
ggaggagcgc attttgcgct acgtgcagca gagcgtgagc cttaacctga tgcgcgacgg    9840
ggtaacgccc agcgtggcgc tggacatgac cgcgcgcaac atggaaccgg gcatgtatgc    9900
ctcaaaccgg ccgtttatca accgcctaat ggactacttg catcgcgcgg ccgccgtgaa    9960
ccccgagtat ttcaccaatg ccatcttgaa cccgcactgg ctaccgcccc ctggttttcta   10020 caccggggga ttcgaggtgc ccgagggtaa cgatggattc ctctgggacg acatagacga   10080
cagcgtgttt tcccccgcaac cgcagaccct gctagagttg caacagcgcg agcaggcaga   10140
ggcggcgctg cgaaaggaaa gcttccgcag gccaagcagc ttgtccgatc taggcgctgc   10200 ggcccccgcgg tcagatgcta gtagcccatt tccaagcttg ataggtctc ttaccagcac   10260 tcgcaccacc cgcccgcgcc tgctgggcga ggaggagtac ctaaacaact cgctgctgca   10320
gccgcagcgc gaaaaaaacc tgcctccggc atttcccaac aacgggatag agagcctagt   10380
ggacaagatg agtagatgga agacgtacgc gcaggagcac agggacgtgc caggcccgcg   10440
cccgcccacc cgtcgtcaaa ggcacgaccg tcagcggggt ctggtgtggg aggacgatga   10500
ctcggcagac gacagcagcg tcctggattt gggagggagt ggcaacccgt tgcgcacct    10560 tcgcccccagg ctggggagaa tgttttaaaa aaaaaaagc atgatgcaaa ataaaaaact   10620
caccaaggcc atggcaccga gcgttggttt tcttgtattc cccttagtat gcggcgcgcg   10680
gcgatgtatg aggaaggtcc tcctccctcc tacgagagtg tggtgagcgc ggcgccagtg   10740
gcggcggcgc tgggttctcc cttcgatgct ccctggacc cgccgtttgt gcctccgcgg   10800
tacctgcggc ctaccggggg gagaaacagc atccgttact ctgagttggc acccctattc   10860
gacaccaccc gtgtgtacct ggtggacaac aagtcaacgg atgtggcatc cctgaactac   10920
cagaacgacc acagcaactt tctgaccacg gtcattcaaa acaatgacta cagcccgggg   10980
gaggcaagca cacagaccat caatcttgac gaccggtcgc actgggcgg cgacctgaaa   11040 accatcctgc ataccaacat gccaaatgtg aacgagttca tgtttaccaa taagtttaag   11100
gcgcgggtga tggtgtcgcg cttgcctact aaggacaatc aggtggagct gaaatacgag   11160
tgggtggagt tcacgctgcc cgagggcaac tactccgaga ccatgaccat agaccttatg   11220
aacaacgcga tcgtggagca ctacttgaaa gtgggcagac agaacggggt tctggaaagc   11280
gacatcgggg taaagttga cacccgcaac ttcagactgg ggtttgaccc cgtcactggt   11340
cttgtcatgc ctgggtata tacaaacgaa gccttccatc cagacatcat tttgctgcca   11400
ggatgcgggg tggacttcac ccacagccgc ctgagcaact tgttgggcat ccgcaagcgg   11460
caacccttcc aggagggctt taggatcacc tacgatgatc tggagggtgg taacattccc   11520
```

```
gcactgttgg atgtggacgc ctaccaggcg agcttgaaag atgacaccga acagggcggg   11580
ggtggcgcag gcggcagcaa cagcagtggc agcggcgcgg aagagaactc caacgcggca   11640
gccgcggcaa tgcagccggt ggaggacatg aacgatcatg ccattcgcgg cgacaccttt   11700
gccacacggg ctgaggagaa gcgcgctgag gccgaagcag cggccgaagc tgccgccccc   11760
gctgcgcaac ccgaggtcga gaagcctcag aagaaaccgg tgatcaaacc cctgacagag   11820
gacagcaaga aacgcagtta caacctaata agcaatgaca gcaccttcac ccagtaccgc   11880
agctggtacc ttgcatacaa ctacggcgac cctcagaccg gaatccgctc atggaccctg   11940
ctttgcactc ctgacgtaac ctgcggctcg gagcaggtct actggtcgtt gccagacatg   12000
atgcaagacc ccgtgacctt ccgctccacg cgccagatca gcaactttcc ggtggtgggc   12060
gccgagctgt tgcccgtgca ctccaagagc ttctacaacg accaggccgt ctactcccaa   12120
ctcatccgcc agtttacctc tctgacccac gtgttcaatc gctttcccga gaaccagatt   12180
ttggcgcgcc cgccagcccc caccatcacc accgtcagtg aaaacgttcc tgctctcaca   12240
gatcacggga cgctaccgct gcgcaacagc atcggaggag tccagcgagt gaccattact   12300
gacgccagac gccgcacctg cccctacgtt tacaaggccc tgggcatagt ctcgccgcgc   12360
gtcctatcga gccgcacttt ttgagcaagc atgtccatcc ttatatcgcc cagcaataac   12420
acaggctggg gcctgcgctt cccaagcaag atgtttggcg gggccaagaa gcgctccgac   12480
caacacccag tgcgcgtgcg cgggcactac cgcgcgccct ggggcgcgca caaacgcggc   12540
cgcactgggc gcaccaccgt cgatgacgcc atcgacgcgg tggtggagga ggcgcgcaac   12600
tacacgccca cgccgccacc agtgtccaca gtggacgcgg ccattcagac cgtggtgcgc   12660
ggagcccggc gctatgctaa aatgaagaga cggcggaggc gcgtagcacg tcgccaccgc   12720
cgccgacccg gcactgccgc ccaacgcgcg gcggcggccc tgcttaaccg cgcacgtcgc   12780
accggccgac gggcggccat gcgggccgct cgaaggctgg ccgcgggtat tgtcactgtg   12840 cccccccaggt ccaggcgacg agcggccgcc gcagcagccg cggccattag tgctatgact   12900
cagggtcgca ggggcaacgt gtattgggtg cgcgactcgg ttagcggcct gcgcgtgccc   12960
gtgcgcaccc gccccccgcg caactagatt gcaagaaaaa actacttaga ctcgtactgt   13020
tgtatgtatc cagcggcggc ggcgcgcaac gaagctatgt ccaagcgcaa aatcaaagaa   13080
gagatgctcc aggtcatcgc gccggagatc tatggccccc cgaagaagga agagcaggat   13140
tacaagcccc gaaagctaaa gcgggtcaaa aagaaaaaga aagatgatga tgatgaactt   13200
gacgacgagg tggaactgct gcacgctacc gcgcccaggc gacgggtaca gtggaaaggt   13260
cgacgcgtaa aacgtgtttt gcgacccggc accaccgtag tctttacgcc cggtgagcgc   13320
tccacccgca cctacaagcg cgtgtatgat gaggtgtacg gcgacgagga cctgcttgag   13380
caggccaacg agcgcctcgg ggagtttgcc tacggaaagc ggcataagga catgctggcg   13440
ttgccgctgg acgagggcaa cccaacacct agcctaaagc ccgtaacact gcagcaggtg   13500
ctgcccgcgc ttgcaccgtc cgaagaaaag cgcggcctaa agcgcgagtc tggtgacttg   13560
gcacccaccg tgcagctgat ggtacccaag cgccagcgac tggaagatgt cttggaaaaa   13620
atgaccgtgg aacctgggct ggagcccgag gtccgcgtgc ggccaatcaa gcaggtggcg   13680
ccgggactgg gcgtgcagac cgtggacgtt cagataccca ctaccagtag caccagtatt   13740
gccaccgcca cagagggcat ggagacacaa acgtccccgg ttgcctcagc ggtggcggat   13800
gccgcggtgc aggcggtcgc tgcggccgcg tccaagacct ctacgaggt gcaaacggac   13860 ccgtggatgt ttcgcgtttc agccccccgg cgcccgcgcg gttcgaggaa gtacggcgcc   13920
```

```
gccagcgcgc tactgcccga atatgccta catccttcca ttgcgcctac ccccggctat   13980
cgtggctaca cctaccgccc cagaagacga gcaactaccc gacgccgaac caccactgga   14040
acccgccgcc gccgtcgccg tcgccagccc gtgctggccc cgatttccgt gcgcagggtg   14100
gctcgcgaag gaggcaggac cctggtgctg ccaacagcgc gctaccaccc cagcatcgtt   14160
taaaagccgg tctttgtggt tcttgcagat atggccctca cctgccgcct ccgtttcccg   14220
gtgccgggat tccgaggaag aatgcaccgt aggaggggca tggccggcta cggcctgacg   14280
ggcggcatgc gtcgtgcgca ccaccggcgg cggcgcgcgt cgcaccgtcg catgcgcggc   14340
ggtatcctgc ccctccttat tccactgatc gccgcggcga ttggcgccgt gcccggaatt   14400
gcatccgtgg ccttgcaggc gcagagacac tgattaaaaa caagttgcat gtggaaaaat   14460
caaaataaaa agtctggact ctcacgctcg cttggtcctg taactatttt gtagaatgga   14520
agacatcaac tttgcgtctc tggccccgcg acacggctcg cgcccgttca tgggaaactg   14580
gcaagatatc ggcaccagca atatgagcgg tggcgccttc agctggggct cgctgtggag   14640
cggcattaaa aatttcggtt ccaccgttaa gaactatggc agcaaggcct ggaacagcag   14700
cacaggccag atgctgaggg ataagttgaa agagcaaaat ttccaacaaa aggtggtaga   14760
tggcctggcc tctggcatta gcggggtggt ggacctggcc aaccaggcag tgcaaaataa   14820
gattaacagt aagcttgatc cccgcccctcc cgtagaggag cctccaccgg ccgtggagac   14880
agtgtctcca gaggggcgtg gcgaaaagcg tccgcgcccc gacagggaag aaactctggt   14940
gacgcaaata gacgagcctc cctcgtacga ggaggcacta agcaaggcc tgcccaccac   15000
ccgtcccatc gcgcccatgg ctaccggagt gctgggccag cacacacccg taacgctgga   15060
cctgcctccc cccgccgaca cccagcagaa acctgtgctg ccaggcccga ccgccgttgt   15120
tgtaacccgt cctagccgcg cgtccctgcg ccgcgccgcc agcggtccgc gatcgttgcg   15180
gcccgtagcc agtggcaact ggcaaagcac actgaacagc atcgtgggtc tggggtgca   15240
atccctgaag cgccgacgat gcttctgaat agctaacgtg tcgtatgtgt gtcatgtatg   15300
cgtccatgtc gccgccagag gagctgctga gccgccgcgc gcccgctttc caagatggct   15360
acccccttcga tgatgccgca gtggtcttac atgcacatct cgggccagga cgcctcggag   15420
tacctgagcc ccgggctggt gcagtttgcc cgcgccaccg agacgtactt cagcctgaat   15480
aacaagttta gaaaccccac ggtggcgcct acgcacgacg tgaccacaga ccggtcccag   15540
cgtttgacgc tgcggttcat ccctgtggac cgtgaggata ctgcgtactc gtacaaggcg   15600
cggttcaccc tagctgtggg tgataaccgt gtgctggaca tggcttccac gtactttgac   15660
atccgcggcg tgctggacag gggccctact tttaagccct actctggcac tgcctacaac   15720
gccctggctc ccaagggtgc cccaaatcct tgcgaatggg atgaagctgc tactgctctt   15780
gaaataaacc tagaagaaga ggacgatgac aacgaagacg aagtagacga gcaagctgag   15840
cagcaaaaaa ctcacgtatt tgggcaggcg ccttattctg gtataaatat tacaaaggag   15900
ggtattcaaa taggtgtcga aggtcaaaca cctaaatatg ccgataaaac atttcaacct   15960
gaacctcaaa taggagaatc tcagtggtac gaaactgaaa ttaatcatgc agctgggaga   16020
gtccttaaaa agactacccc aatgaaacca tgttacggtt catatgcaaa acccacaaat   16080
gaaaatggag ggcaaggcat tcttgtaaag caacaaaatg gaaagctaga aagtcaagtg   16140
gaaatgcaat ttttctcaac tactgaggcg accgcaggca atggtgataa cttgactcct   16200
aaagtggtat tgtacagtga agatgtagat atagaaaccc cagacactca tatttcttac   16260
```

```
atgcccacta ttaaggaagg taactcacga gaactaatgg gccaacaatc tatgcccaac    16320
aggcctaatt acattgcttt tagggacaat tttattggtc taatgtatta caacagcacg    16380
ggtaatatgg gtgttctggc gggccaagca tcgcagttga atgctgttgt agatttgcaa    16440
gacagaaaca cagagctttc ataccagctt ttgcttgatt ccattggtga tagaaccagg    16500
tactttctta tgtggaatca ggctgttgac agctatgatc cagatgttag aattattgaa    16560
aatcatggaa ctgaagatga acttccaaat tactgctttc cactgggagg tgtgattaat    16620
acagagactc ttaccaaggt aaaacctaaa acaggtcagg aaaatggatg ggaaaaagat    16680
gctacagaat tttcagataa aaatgaaata agagttggaa ataattttgc catggaaatc    16740
aatctaaatg ccaacctgtg gagaaatttc ctgtactcca acatagcgct gtatttgccc    16800
gacaagctaa agtacagtcc ttccaacgta aaaattctg ataacccaaa cacctacgac     16860
tacatgaaca agcgagtggt ggctcccggg ttagtggact gctacattaa ccttggagca    16920
cgctggtccc ttgactatat ggacaacgtc aacccattta ccaccaccg caatgctggc     16980
ctgcgctacc gctcaatgtt gctgggcaat ggtcgctatg tgcccttcca catccaggtg    17040
cctcagaagt tctttgccat taaaaacctc cttctcctgc cgggctcata cacctacgag    17100
tggaacttca ggaaggatgt taacatggtt ctgcagagct ccctaggaaa tgacctaagg    17160
gttgacggag ccagcattaa gtttgatagc atttgccttt acgccacctt cttccccatg    17220
gcccacaaca ccgcctccac gcttgaggcc atgcttagaa acgacaccaa cgaccagtcc    17280
tttaacgact atctctccgc cgccaacatg ctctaccct acccgccaa cgctaccaac      17340
gtgcccatat ccatcccctc ccgcaactgg gcggctttcc gcggctgggc cttcacgcgc    17400
cttaagacta aggaaacccc atcactgggc tcgggctacg acccttatta cacctactct    17460
ggctctatac cctacctaga tggaaccttt tacctcaacc acacctttaa gaaggtggcc    17520
attaccttg actcttctgt cagctggcct ggcaatgacc gcctgcttac ccccaacgag     17580
tttgaaatta agcgctcagt tgacggggag ggttacaacg ttgcccagtg taacatgacc    17640
aaagactggt tcctggtaca aatgctagct aactacaaca ttggctacca gggcttctat    17700
atcccagaga gctacaagga ccgcatgtac tccttcttta gaaacttcca gcccatgagc    17760
cgtcaggtgg tggatgatac taaatacaag gactaccaac aggtgggcat cctacaccaa    17820
cacaacaact ctggatttgt tggctacctt gcccccacca tgcgcgaagg acaggcctac    17880
cctgctaact tccctatcc gcttataggc aagaccgcag ttgacagcat tacccagaaa     17940
aagtttcttt gcgatcgcac ccttgggcgc atcccattct ccagtaactt tatgtccatg    18000
ggcgcactca cagacctggg ccaaaacctt ctctacgcca actccgccca cgcgctagac    18060
atgacttttg aggtggatcc catggacgag cccacccttc tttatgtttt gtttgaagtc    18120
tttgacgtgg tccgtgtgca ccggccgcac cgcggcgtca tcgaaaccgt gtacctgcgc    18180
acgcccttct cggccggcaa cgccacaaca taaagaagca agcaacatca acaacagctg    18240
ccgccatggg ctccagtgag caggaactga aagccattgt caaagatctt ggttgtgggc    18300
catatttttt gggcacctat gacaagcgct ttccaggctt tgtttctcca cacaagctcg    18360
cctgcgccat agtcaatacg gccggtcgcg agactggggg cgtacactgg atggcctttg    18420
cctggaaccc gcactcaaaa acatgctacc tctttgagcc ctttggcttt tctgaccagc    18480
gactcaagca ggtttaccag tttgagtacg agtcactcct gcgccgtagc gccattgctt    18540
cttcccccga ccgctgtata acgctggaaa agtccaccca aagcgtacag ggcccaact     18600
cggccgcctg tggactattc tgctgcatgt ttctccacgc cttgccaac tggccccaaa     18660
```

```
ctcccatgga tcacaacccc accatgaacc ttattaccgg ggtacccaac tccatgctca   18720
acagtcccca ggtacagccc accctgcgtc gcaaccagga acagtctac agcttcctgg    18780 agcgccactc gccctacttc cgcagccaca gtgcgcagat taggagcgcc acttcttttt   18840
gtcacttgaa aaacatgtaa aaataatgta ctagagacac tttcaataaa ggcaaatgct   18900
tttatttgta cactctcggg tgattattta cccccaccct tgccgtctgc gccgtttaaa   18960
aatcaaaggg gttctgccgc gcatcgctat gcgccactgg cagggacacg ttgcgatact   19020
ggtgtttagt gctccactta aactcaggca caaccatccg cggcagctcg gtgaagtttt   19080
cactccacag gctgcgcacc atcaccaacg cgtttagcag gtcgggcgcc gatatcttga   19140
agtcgcagtt ggggcctccg ccctgcgcgc gcgagttgcg atacacaggg ttgcagcact   19200
ggaacactat cagcgccggg tggtgcacgc tggccagcac gctcttgtcg gagatcagat   19260
ccgcgtccag gtcctccgcg ttgctcaggg cgaacggagt caactttggt agctgccttc   19320
ccaaaaaggg cgcgtgccca ggctttgagt tgcactcgca ccgtagtggc atcaaaaggt   19380
gaccgtgccc ggtctgggcg ttaggataca gcgcctgcat aaaagccttg atctgcttaa   19440
aagccacctg agcctttgcg ccttcagaga agaacatgcc gcaagacttg ccggaaaact   19500
gattggccgg acaggccgcg tcgtgcacgc agcaccttgc gtcggtgttg gagatctgca   19560
ccacatttcg gccccaccgg ttcttcacga tcttggcctt gctagactgc tccttcagcg   19620
cgcgctgccc gttttcgctc gtcacatcca tttcaatcac gtgctcctta tttatcataa   19680
tgcttccgtg tagacactta agctcgcctt cgatctcagc gcagcggtgc agccacaacg   19740
cgcagcccgt gggctcgtga tgcttgtagg tcacctctgc aaacgactgc aggtacgcct   19800
gcaggaatcg ccccatcatc gtcacaaagg tcttgttgct ggtgaaggtc agctgcaacc   19860
cgcggtgctc ctcgttcagc caggtcttgc atacggccgc cagagcttcc acttggtcag   19920
gcagtagttt gaagttcgcc tttagatcgt tatccacgtg gtacttgtcc atcagcgcgc   19980
gcgcagcctc catgcccttc tcccacgcag acacgatcgg cacactcagc gggttcatca   20040
ccgtaatttc actttccgct tcgctgggct cttcctcttc ctcttgcgtc cgcataccac   20100
gcgccactgg gtcgtcttca ttcagccgcc gcactgtgcg cttacctcct ttgccatgct   20160
tgattagcac cggtggggttg ctgaaaccca ccatttgtag cgccacatct tctctttctt   20220
cctcgctgtc cacgattacc tctggtgatg gcgggcgctc gggcttggga aagggcgct    20280 tcttttttctt cttgggcgca atggccaaat ccgccgccga ggtcgatggc cgcgggctgg   20340
gtgtgcgcgg caccagcgcg tcttgtgatg agtcttcctc gtcctcggac tcgatacgcc   20400
gcctcatccg cttttttggg ggcgcccggg gaggcggcgg cgacggggac ggggacgaca   20460
cgtcctccat ggttggggga cgtcgcgccg caccgcgtcc gcgctcgggg gtggtttcgc    20520
gctgctcctc ttcccgactg gccatttcct tctcctatag gcagaaaaag atcatggagt   20580
cagtcgagaa gaaggacagc ctaaccgccc cctctgagtt cgccaccacc gcctccaccg   20640
atgccgccaa cgcgcctacc accttcccg tcgaggcacc cccgcttgag gaggaggaag    20700
tgattatcga gcaggaccca ggttttgtaa gcgaagacga cgaggaccgc tcagtaccaa   20760
cagaggataa aaagcaagac caggacaacg cagaggcaaa cgaggaacaa gtcgggcggg   20820
gggacgaaag gcatggcgac tacctagatg tgggagacga cgtgctgttg aagcatctgc   20880
agcgccagtg cgccattatc tgcgacgcgt tgcaagagcg cagcgatgtg cccctcgcca   20940
tagcggatgt cagccttgcc tacgaacgcc acctattctc accgcgcgta cccccccaaac  21000
```

```
gccaagaaaa cggcacatgc gagcccaacc cgcgcctcaa cttctacccc gtatttgccg   21060
tgccagaggt gcttgccacc tatcacatct ttttccaaaa ctgcaagata ccctatcct    21120 gccgtgccaa ccgcagccga gcggacaagc agctggcctt gcggcagggc gctgtcatac   21180
ctgatatcgc ctcgctcaac gaagtgccaa aaatctttga gggtcttgga cgcgacgaga   21240
agcgcgcggc aaacgctctg caacaggaaa acagcgaaaa tgaaagtcac tctggagtgt   21300
tggtggaact cgagggtgac aacgcgcgcc tagccgtact aaaacgcagc atcgaggtca   21360
cccactttgc ctaccggca cttaacctac cccccaaggt catgagcaca gtcatgagtg    21420
agctgatcgt gcgccgtgcg cagccctgg agggatgc aaatttgcaa gaacaaacag      21480
aggagggcct acccgcagtt ggcgacgagc agctagcgcg ctggcttcaa acgcgcgagc   21540
ctgccgactt ggaggagcga cgcaaactaa tgatggccgc agtgctcgtt accgtggagc   21600
ttgagtgcat gcagcggttc tttgctgacc cggagatgca gcgcaagcta gaggaaacat   21660
tgcactacac ctttcgacag ggctacgtac gccaggcctg caagatctcc aacgtggagc   21720
tctgcaacct ggtctcctac cttggaattt tgcacgaaaa ccgccttggg caaaacgtgc   21780
ttcattccac gctcaagggc gaggcgcgcc gcgactacgt ccgcgactgc gtttacttat   21840
ttctatgcta cacctggcag acggccatgg gcgtttggca gcagtgcttg gaggagtgca   21900
acctcaagga gctgcagaaa ctgctaaagc aaaacttgaa ggacctatgg acggccttca   21960
acgagcgctc cgtggccgcg cacctggcgg acatcatttt ccccgaacgc ctgcttaaaa   22020
ccctgcaaca gggtctgcca gacttcacca gtcaaagcat gttgcagaac tttaggaact   22080
ttatcctaga gcgctcagga atcttgcccg ccacctgctg tgcacttcct agcgactttg   22140
tgcccattaa gtaccgcgaa tgccctccgc cgctttgggg ccactgctac cttctgcagc   22200
tagccaacta ccttgcctac cactctgaca taatggaaga cgtgagcggt gacggtctac   22260
tggagtgtca ctgtcgctgc aacctatgca ccccgcaccg ctccctggtt tgcaattcgc   22320
agctgcttaa cgaaagtcaa attatcggta cctttgagct gcagggtccc tcgcctgacg   22380
aaaagtccgc ggctccgggg ttgaaactca ctccggggct gtggacgtcg gcttaccttc   22440
gcaaatttgt acctgaggac taccacgccc acgagattag gttctacgaa gaccaatccc   22500
gcccgccaaa tgcggagctt accgcctgcg tcattaccca gggccacatt cttggccaat   22560
tgcaagccat caacaaagcc cgccaagagt ttctgctacg aaagggacgg ggggtttact   22620
tggaccccca gtccggcgag gagctcaacc caatccccc gccgccgcag ccctatcagc    22680
agcagccgcg ggcccttgct tcccaggatg gcacccaaaa agaagctgca gctgccgccg   22740
ccacccacgg acgaggagga atactgggac agtcaggcag aggaggtttt ggacgaggag   22800
gaggaggaca tgatgaaga ctgggagagc ctagacgagg aagcttccga ggtcgaagag   22860
gtgtcagacg aaacaccgtc accctcggtc gcattcccct cgccggcgcc cagaaatcg    22920 gcaaccggtt ccagcatggc tacaacctcc gctcctcagg cgccgccggc actgcccgtt   22980
cgccgaccca accgtagatg ggacaccact ggaaccaggg ccggtaagtc caagcagccg   23040
ccgccgttag cccaagagca acaacagcgc caaggctacc gctcatggcg cgggcacaag   23100
aacgccatag ttgcttgctt gcaagactgt ggggcaaca tctccttcgc ccgccgcttt     23160
cttctctacc atcacggcgt ggccttcccc cgtaacatcc tgcattacta ccgtcatctc   23220
tacagcccat actgcaccgg cggcagcggc agcggcagca acagcagcgg ccacacagaa   23280
gcaaaggcga ccgatagca agactctgac aaagcccaag aaatccacag cggcggcagc    23340
agcaggagga ggagcgctgc gtctggcgcc caacgaaccc gtatcgaccc gcgagcttag   23400
```

```
aaacaggatt tttcccactc tgtatgctat atttcaacag agcaggggcc aagaacaaga    23460
gctgaaaata aaaacaggt ctctgcgatc cctcacccgc agctgcctgt atcacaaaag    23520
cgaagatcag cttcggcgca cgctggaaga cgcggaggct ctcttcagta aatactgcgc    23580
gctgactctt aaggactagt ttcgcgccct ttctcaaatt taagcgcgaa aactacgtca    23640
tctccagcgg ccacacccgg cgccagcacc tgtcgtcagc gccattatga gcaaggaaat    23700
tcccacgccc tacatgtgga gttaccagcc acaaatggga cttgcggctg agctgccca    23760 agactactca acccgaataa actacatgag cgcgggaccc cacatgatat cccgggtcaa    23820
cggaatccgc gcccaccgaa accgaattct cttggaacag gcggctatta ccaccacacc    23880
tcgtaataac cttaatcccc gtagttggcc cgctgccctg tgtaccagg aaagtcccgc    23940 tcccaccact gtggtacttc ccagagacgc ccaggccgaa gttcagatga ctaactcagg    24000
ggcgcagctt gcgggcggct ttcgtcacag ggtgcggtcg cccggcagg gtataactca    24060 cctgacaatc agagggcgag gtattcagct caacgacgag tcggtgagct cctcgcttgg    24120
tctccgtccg gacgggacat ttcagatcgg cggcgccggc cgtccttcat tcacgcctcg    24180
tcaggcaatc ctaactctgc agacctcgtc tctgagccg cgctctggag gcattggaac    24240
tctgcaattt attgaggagt ttgtgccatc ggtctacttt aaccccttct cgggacctcc    24300
cggccactat ccggatcaat ttattcctaa cttttgacgcg gtaaaggact cggcggacgg    24360
ctacgactga atgttaagtg gagaggcaga gcaactgcgc ctgaaacacc tggtccactg    24420
tcgccgccac aagtgctttg cccgcgactc cggtgagttt tgctactttg aattgcccga    24480
ggatcatatc gagggcccgg cgcacggcgt ccggcttacc gcccagggag agcttgcccg    24540
tagcctgatt cgggagtttta cccagcgccc cctgctagtt gagcgggaca ggggaccctg    24600
tgttctcact gtgatttgca actgtcctaa ccttggatta catcaagatc ctctagttaa    24660
ttaacagctt gcatgcctgc aggtcgacgg atcgggagat ctcggccgca tattaagtgc    24720
attgttctcg ataccgctaa gtgcattgtt ctcgttagct cgatggacaa gtgcattgtt    24780
ctcttgctga aagctcgatg gacaagtgca ttgttctctt gctgaaagct cgatggacaa    24840
gtgcattgtt ctcttgctga aagctcagta cccgggagta ccctcgaccg ccggagtata    24900
aatagaggcg cttcgtctac ggagcgacaa ttcaattcaa acaagcaaag tgaacacgtc    24960
gctaagcgaa agctaagcaa ataaacaagc gcagctgaac aagctaaaca atctgcagta    25020
aagtgcaagt taaagtgaat caattaaaag taaccagcaa ccaagtaaat caactgcaac    25080
tactgaaatc tgccaagaag taattattga atacaagaag agaactctga atactttcaa    25140
caagttaccg agaaagaaga actcacacac agctagcgtt taaacttaag cttcaccatg    25200
gtggggccct gcatgctgct gctgctgctg ctgctgggcc tgaggctaca gctctccctg    25260
ggcatcatcc tagttgagga ggagaacccc gacttctgga accgcgaggc agccgaggcc    25320
ctgggtgccg ccaagaagct gcagcctgca cagacagccg ccaagaacct catcatcttc    25380
ctgggcgatg gggtggggt gtctacggtg acagctgcca ggatcctaaa agggcagaag    25440
aaggacaaac tggggcctga gataccctg gccatggacc gcttcccata tgtggctctg    25500
tccaagacat acaatgtaga caaacatgtg ccagacagtg gagccacagc cacggcctac    25560
ctgtgcgggg tcaagggcaa cttccagacc attggcttga gtgcagccgc ccgctttaac    25620
cagtgcaaca cgacacgcgg caacgaggtc atctccgtga tgaatcgggc caagaaagca    25680
gggaagtcag tgggagtggt aaccaccaca cgagtgcagc acgcctcgcc agccggcacc    25740
```

```
tacgcccaca cggtgaaccg caactggtac tcggacgccg acgtgcctgc ctcggcccgc   25800
caggaggggt gccaggacat cgctacgcag ctcatctcca acatggacat tgacgtgatc   25860
ctaggtgggg gccgaaagta catgtttcgc atgggaaccc cagaccctga gtacccagat   25920
gactacagcc aaggtgggac caggctggac gggaagaatc tggtgcagga atggctggcg   25980
aagcaccagg gtgcccggta cgtgtggaac cgcactgagc tcatgcgggc ttccctggac   26040
ccgtctgtgg cccatctcat gggtctcttt gagcctggag acatgaaata cgagatccac   26100
cgagactcca cactggaccc ctccctgatg gagatgacag aggctgccct gcgcctgctg   26160
agcaggaacc cccgcggctt cttcctcttc gtggagggtg gtcgcatcga ccatggtcat   26220
catgaaagca gggcttaccg ggcactgact gagacgatca tgttcgacga cgccattgag   26280
agggcgggcc agctcaccag cgaggaggac acgctgagcc tcgtcactgc cgaccactcc   26340
cacgtcttct ccttcggagg ctgcccctg cgagggggct ccatcttcgg ctggcccct    26400 ggcaaggccc gggacaggaa ggcctacacg gtcctcctat acggaaacgg tccaggctat   26460
gtgctcaagg acggcgcccg gccggatgtt accgagagcg agagcgggag ccccgagtat   26520
cggcagcagt cagcagtgcc cctggacgaa gagacccacg caggcgagga cgtggcggtg   26580
ttcgcgcgcg gcccgcaggc gcacctggtt cacggcgtgc aggagcagac cttcatagcg   26640
cacgtcatgg ccttcgccgc ctgcctggag ccctacaccg cctgcgacct ggcgcccccc   26700
gccggcacca ccgacgccgc gcacccgggg cggtccgtgg tccccgcgtt gcttcctctg   26760
ctggccggga ccctgctgct gctggagacg gccactgctc cctgagtgtc ccgtccctgg   26820
ggctcctgct tccccatccc ggagttctcc tgctccccgc ctcctgtcgt cctgcctggc   26880
ctccagcccg agtcgtcatc cccggagtcc ctatacagag gtcctgccat ggaaccttcc   26940
cctccccgtg cgctctgggg actgagccca tgacaccaaa cctgcccctt ggctgctctc   27000
ggactcccta ccccaacccc agggacagat ctggccagat ttgtaaaaca aatagatttt   27060
aggcccaaag attatttaaa gcattgcctg gaacgcagtg agttttttgtt agaaaagaga   27120 ataattcaaa gtggcattgc tttgcttctt atgttaattt ggtacagacc tgtggctgag   27180
tttgctcaaa gtattcagag cagaattgtg gagtggaaag agagattgga caaagagttt   27240
agtttgtcag tgtatcaaaa aatgaagttt aatgtggcta tgggaattgg agttttagat   27300
tggctaagaa acagtgatga tgatgatgaa gacagccagg aaaatgctga taaaaatgaa   27360
gatggtgggg agaagaacat ggaagactca gggcatgaaa caggcattga ttcacagtcc   27420
caaggctcat ttcaggcccc tcagtcctca cagtctgttc atgatcataa tcagccatac   27480
cacatttgta gaggttttac ttgctttaaa aaacctccca cacctccccc tgaacctgaa   27540
acataaaatg aatgcaattg ttgttgttaa cttgtttatt gcagcttata atggttacaa   27600
ataaagcaat agcatcacaa atttcacaaa taaagcattt ttttcactgc attctagttg   27660
tggtttgtcc aaaactcatca atgtatctta tcatgtctgg atcccaggaa gctcctctg    27720 tgtcctcata aaccctaacc tcctctactt gagaggacat tccaatcata ggctgcccat   27780
ccaccctctg tgtcctcctg ttaattaggt cacttaacaa aaaggaaatt gggtaggggt   27840
ttttcacaga ccgctttcta agggtaattt taaaatatct gggaagtccc ttccactgct   27900
gtgttccaga agtgttggta aacagcccac aaatgtcaac agcagaaaca tacaagctgt   27960
cagctttgca caagggccca acaccctgct catcaagaag cactgtggtt gctgtgttag   28020
taatgtgcaa aacaggaggc acattttccc cacctgtgta ggttccaaaa tatctagtgt   28080 tttcatttt acttggatca ggaacccagc actccactgg ataagcatta tccttatcca    28140
```

```
aaacagcctt gtggtcagtg ttcatctgct gactgtcaac tgtagcattt tttggggtta    28200
cagtttgagc aggatatttg gtcctgtagt ttgctaacac accctgcagc tccaaaggtt    28260
ccccaccaac agcaaaaaaa tgaaaatttg acccttgaat gggttttcca gcaccatttt    28320
catgagtttt ttgtgtccct gaatgcaagt ttaacatagc agttacccca ataacctcag    28380
ttttaacagt aacagcttcc cacatcaaaa tatttccaca ggttaagtcc tcatttaaat    28440
taggcaaagg aattccactt cccactgcct tgcttccgtc tcccattcaa acttttatca    28500
actgacatta ttctaagtaa aatcctcttc attatgttgt cagcaatcca ttgcttgaag    28560
gcctggctcc ccagaacccc tcgactggta tgtcttctcc tagaatactc cagaagaaaa    28620
ggagtgtatg aagatagtga ctgcacatta aaatgactga aaccatagta aattaggatg    28680
agattctggg cagataaaca gacagctggc taggatcatt ttttatgcc ttggacttct    28740 ttggcaatct gttgaagcct gacattcctc agaataatgt tttaaagccc aacaataaga    28800
ccctgtagca catataataa gtactgcagt tttgaagtag tgataagcat aaatgatatt    28860
ttgatatatt tattataact gtaatgagat gtgtacatat ctgtgacttc ataggtactg    28920
attgtactac tgtgattttt ttgcctactt tcaaaatgaa aaggaatgct taatttcagt    28980
tagaggttag taaagacaaa taggtaattt cttctccag tgaagagcat ggcgcccctt    29040
gctattcatg gacgcttgct taaagacttg tacacaggct tgctttgtat caacctatga    29100 cttccccta cagccgatga taggttttta tttgcacctc cttcgtgtac aaagacagtt    29160
ttggtggcta cgccatcatt aaactcatta ttatcatgct taagcctata gatgtatcca    29220
gttcttctgt tacataattg aagctgtagt gaattgtcta tcttaaactg catcgctaac    29280
tgactacatt tcacacttca tttgcttcca acatagacta accttcttgg atgtccacta    29340
ttatttgaac ttttgagatt ttttttccta tttctaatat cttaaaattt cagaagactt    29400
aaagttttgc aactacaggg ctccatatag acatctagct tgaatttata cactttcttt    29460
cattgatgtc cctggactaa aaaatgttaa atatttctaa ccgctgtact aaagtccat    29520 tacaaacgaa gactactgtt gttaagttga ataggcatct tatatatttt tcaccggtgc    29580
aataaataac ttctattccc ttctaacatc tgcttgcgtt gcactgagag tacactattg    29640
attagcaata ggttcgtgat tacagcccct ctataattaa ttgttaggtt aacatatat    29700 tcataaaata ttatttttatt aatttttact tgatttgcta ctggatgctt agaaatagct    29760
atgagtatat tggtagaacc agtacttata ttttattaca tttttacatt tcataaaatt    29820
taagtgatat aaaaatcctg aggaagtatg ccacaaaagt ggtctcagtg gaaatttaaa    29880
tatgttaaca tttattttta aaatgtagcg tgaaatagac aactttaaaa gctcagctta    29940 aaaaaaaac tcaaggaagc tgaacttgac ttttaaagc actgaagtgc aatatttaat    30000
gtaggtcaac atgtttaaat gggaaaattt ttttcctaat tacagccaaa tccctagctg    30060
taattaactt aaaatttgta tactatttca caacagagtc agcatatacc actttcttat    30120
aaaattagaa agatctaaaa ttttagagct tatttggtga aacaggcata ttgctacatc    30180
tttgtttata aattataatg tgcctttaga gcccaataac agataacaag atttgaaaa    30240 ttcaggtgaa ttagagttat cagagggaat gttaatacac tctattcaaa tactatatga    30300
gtaagacatt taaaatagga aacaatactt tatatattaa aaaaaattaa tcttccagtc    30360
gatttaatcc actttatgaa ttcatttaaa tcgatttaaa ttcgaattaa ttaactagag    30420
tacccgggga tcttattccc tttaactaat aaaaaaaaat aataaagcat cacttactta    30480
```

```
aaatcagtta gcaaatttct gtccagttta ttcagcagca cctccttgcc ctcctcccag   30540
ctctggtatt gcagcttcct cctggctgca aactttctcc acaatctaaa tggaatgtca   30600
gtttcctcct gttcctgtcc atccgcaccc actatcttca tgttgttgca gatgaagcgc   30660
gcaagaccgt ctgaagatac cttcaacccc gtgtatccat atgacacgga aaccggtcct   30720
ccaactgtgc cttttcttac tcctcccttt gtatcccccca atgggtttca agagagtccc   30780
cctggggtac tctctttgcg cctatccgaa cctctagtta cctccaatgg catgcttgcg   30840
ctcaaaatgg gcaacggcct ctctctggac gaggccggca accttacctc ccaaaatgta   30900
accactgtga gcccacctct caaaaaaacc aagtcaaaca taaacctgga aatatctgca   30960
cccctcacag ttacctcaga agccctaact gtggctgccg ccgcacctct aatggtcgcg   31020
ggcaacacac tcaccatgca atcacaggcc ccgctaaccg tgcacgactc caacttagc   31080 attgccaccc aaggacccct cacagtgtca gaaggaaagc tagccctgca acatcaggc   31140 cccctcacca ccaccgatag cagtaccctt actatcactg cctcaccccc tctaactact   31200
gccactggta gcttgggcat tgacttgaaa gagcccattt atacacaaaa tggaaaacta   31260
ggactaaagt acggggctcc tttgcatgta acagacgacc taaacacttt gaccgtagca   31320
actggtccag gtgtgactat taataatact tccttgcaaa ctaaagttac tggagccttg   31380
ggttttgatt cacaaggcaa tatgcaactt aatgtagcag gaggactaag gattgattct   31440
caaaacagac gccttatact tgatgttagt tatccgtttg atgctcaaaa ccaactaaat   31500
ctaagactag gacagggccc tcttttttata aactcagccc acaacttgga tattaactac   31560
aacaaaggcc tttacttgtt tacagcttca acaattcca aaaagcttga ggttaaccta   31620
agcactgcca aggggttgat gtttgacgct acagccatag ccattaatgc aggagatggg   31680
cttgaatttg gttcacctaa tgcaccaaac acaaatcccc tcaaaacaaa aattggccat   31740
ggcctagaat ttgattcaaa caaggctatg gttcctaaac taggaactgg ccttagtttt   31800
gacagcacag gtgccattac agtaggaaac aaaaataatg ataagctaac tttgtggacc   31860
acaccagctc catctcctaa ctgtagacta aatgcagaga aagatgctaa actcactttg   31920
gtcttaacaa aatgtggcag tcaaatactt gctacagttt cagttttggc tgttaaaggc   31980
agtttggctc caatatctgg aacagttcaa agtgctcatc ttattataag atttgacgaa   32040
aatggagtgc tactaaacaa ttccttcctg gacccagaat attggaactt tagaaatgga   32100
gatcttactg aaggcacagc ctatacaaac gctgttggat ttatgcctaa cctatcagct   32160
tatccaaaat ctcacggtaa aactgccaaa agtaacattg tcagtcaagt ttacttaaac   32220
ggagacaaaa ctaaacctgt aacactaacc attacactaa acggtacaca ggaaacagga   32280
gacacaactc caagtgcata ctctatgtca tttttcatggg actggtctgg ccacaactac   32340
attaatgaaa tatttgccac atcctcttac acttttttcat acattgccca agaataaaga   32400
atcgtttgtg ttatgtttca acgtgtttat ttttcaattg cagaaaattt caagtcattt   32460
ttcattcagt agtatagccc caccaccaca tagcttatac agatcaccgt accttaatca   32520
aactcacaga accctagtat tcaacctgcc acctccctcc caaacacacag agtacacagt   32580 cctttctccc cggctggcct taaaagcat catatcatgg gtaacagaca tattcttagg   32640
tgttatattc cacacggttt cctgtcgagc caaacgctca tcagtgatat taataaactc   32700
cccgggcagc tcacttaagt tcatgtcgct gtccagctgc tgagccacag gctgctgtcc   32760
aacttgcggt tgcttaacgg gcggcgaagg agaagtccac gcctacatgg gggtagagtc   32820
ataatcgtgc atcaggatag ggcggtggtg ctgcagcagc gcgcgaataa actgctgccg   32880
```

```
ccgccgctcc gtcctgcagg aatacaacat ggcagtggtc tcctcagcga tgattcgcac   32940
cgcccgcagc ataaggcgcc ttgtcctccg ggcacagcag cgcaccctga tctcacttaa   33000
atcagcacag taactgcagc acagcaccac aatattgttc aaaatcccac agtgcaaggc   33060
gctgtatcca aagctcatgg cggggaccac agaacccacg tggccatcat accacaagcg   33120
caggtagatt aagtggcgac ccctcataaa cacgctggac ataaacatta cctcttttgg   33180
catgttgtaa ttcaccacct cccggtacca tataaacctc tgattaaaca tggcgccatc   33240
caccaccatc ctaaaccagc tggccaaaac ctgcccgccg gctatacact gcagggaacc   33300
gggactggaa caatgacagt ggagagccca ggactcgtaa ccatggatca tcatgctcgt   33360
catgatatca atgttggcac aacacaggca cacgtgcata cacttcctca ggattacaag   33420
ctcctcccgc gttagaacca tatcccaggg aacaacccat tcctgaatca gcgtaaatcc   33480
cacactgcag ggaagacctc gcacgtaact cacgttgtgc attgtcaaag tgttacattc   33540
gggcagcagc ggatgatcct ccagtatggt agcgcgggtt tctgtctcaa aaggaggtag   33600
acgatcccta ctgtacggag tgcgccgaga caaccgagat cgtgttggtc gtagtgtcat   33660
gccaaatgga acgccggacg tagtcatatt tcctgaagca aaaccaggtg cgggcgtgac   33720
aaacagatct gcgtctccgg tctcgccgct tagatcgctc tgtgtagtag ttgtagtata   33780
tccactctct caaagcatcc aggcgccccc tggcttcggg ttctatgtaa actccttcat   33840
gcgccgctgc cctgataaca tccaccaccg cagaataagc cacacccagc caacctacac   33900
attcgttctg cgagtcacac acgggaggag cgggaagagc tggaagaacc atgtttttt   33960
ttttattcca aaagattatc caaaacctca aaatgaagat ctattaagtg aacgcgctcc   34020
cctccggtgg cgtggtcaaa ctctacagcc aaagaacaga taatggcatt tgtaagatgt   34080
tgcacaatgg cttccaaaag gcaaacggcc ctcacgtcca agtggacgta aaggctaaac   34140
ccttcagggt gaatctcctc tataaacatt ccagcacctt caaccatgcc caaataattc   34200
tcatctcgcc accttctcaa tatatctcta agcaaatccc gaatattaag tccggccatt   34260
gtaaaaatct gctccagagc gccctccacc ttcagcctca agcagcgaat catgattgca   34320
aaaattcagg ttcctcacag acctgtataa gattcaaaag cggaacatta acaaaaatac   34380
cgcgatcccg taggtccctt cgcagggcca gctgaacata atcgtgcagg tctgcacgga   34440
ccagcgcggc cacttccccg ccaggaacct tgacaaaaga acccacactg attatgacac   34500
gcatactcgg agctatgcta accagcgtag ccccgatgta agctttgttg catgggcggc   34560
gatataaaat gcaaggtgct gctcaaaaaa tcaggcaaag cctcgcgcaa aaaagaaagc   34620
acatcgtagt catgctcatg cagataaagg caggtaagct ccggaaccac cacagaaaaa   34680
gacaccattt ttctctcaaa catgtctgcg ggtttctgca taaacacaaa ataaaataac   34740
aaaaaaacat ttaaacatta gaagcctgtc ttacaacagg aaaaacaacc cttataagca   34800
taagacggac tacggccatg ccggcgtgac cgtaaaaaaa ctggtcaccg tgattaaaaa   34860
gcaccaccga cagctcctcg gtcatgtccg gagtcataat gtaagactcg gtaaacacat   34920
caggttgatt catcggtcag tgctaaaaag cgaccgaaat agcccggggg aatacatacc   34980
cgcaggcgta gagacaacat tacagccccc ataggaggta taacaaaatt aataggagag   35040
aaaaacacat aaacacctga aaaccctcc tgcctaggca aaatagcacc ctcccgctcc   35100
agaacaacat acagcgcttc acagcggcag cctaacagtc agccttacca gtaaaaaaga   35160
aaacctatta aaaaaacacc actcgacacg gcaccagctc aatcagtcac agtgtaaaaa   35220
```

```
agggccaagt gcagagcgag tatatatagg actaaaaaat gacgtaacgg ttaaagtcca    35280
caaaaaacac ccagaaaacc gcacgcgaac ctacgcccag aaacgaaagc caaaaaaccc    35340
acaacttcct caaatcgtca cttccgtttt cccacgttac gtaacttccc attttaagaa    35400
aactacaatt cccaacacat acaagttact ccgccctaaa acctacgtca cccgccccgt    35460
tcccacgccc cgcgccacgt cacaaactcc acccctcat tatcatattg gcttcaatcc    35520
aaaataaggt atattattga tgatggccgg ccgaattgaa tcagggata acgcaggaaa    35580 gaacatgtga gcaaaaggcc agcaaaaggc caggaaccgt aaaaaggccg cgttgctggc    35640 gttttttccat aggctccgcc ccctgacga gcatcacaaa aatcgacgct caagtcagag    35700
gtggcgaaac ccgacaggac tataaagata ccaggcgttt ccccctggaa gctccctcgt    35760
gcgctctcct gttccgaccc tgccgcttac cggatacctg tccgccttc tcccttcggg    35820 aagcgtggcg ctttctcata gctcacgctg taggtatctc agttcggtgt aggtcgttcg    35880
ctccaagctg ggctgtgtgc acgaaccccc cgttcagccc gaccgctgcg ccttatccgg    35940
taactatcgt cttgagtcca acccggtaag acacgactta tcgccactgg cagcagccac    36000
tggtaacagg attagcagag cgaggtatgt aggcggtgct acagagttct tgaagtggtg    36060
gcctaactac ggctacacta aaggacagt atttggtatc tgcgctctgc tgaagccagt    36120
taccttcgga aaaagagttg gtagctcttg atccggcaaa caaaccaccg ctggtagcgg    36180
tggttttttt gtttgcaagc agcagattac gcgcagaaaa aaaggatctc aagaagatcc    36240
tttgatcttt tctacggggt ctgacgctca gtggaacgaa aactcacgtt aagggatttt    36300
ggtcatgaga ttatcaaaaa ggatcttcac ctagatcctt ttaaattaaa aatgaagttt    36360
taaatcaatc taaagtatat atgagtaaac ttggtctgac agttaccaat gcttaatcag    36420
tgaggcacct atctcagcga tctgtctatt tcgttcatcc atagttgcct gactccccgt    36480
cgtgtagata actacgatac gggagggctt accatctggc cccagtgctg caatgatacc    36540
gcgagaccca cgctcaccgg ctccagattt atcagcaata accagccag ccggaagggc    36600 cgagcgcaga gtggtcctg caactttatc cgcctccatc cagtctatta attgttgccg    36660
ggaagctaga gtaagtagtt cgccagttaa tagtttgcgc aacgttgttg ccattgctac    36720
aggcatcgtg gtgtcacgct cgtcgtttgg tatggcttca ttcagctccg gttcccaacg    36780
atcaaggcga gttacatgat cccccatgtt gtgcaaaaaa gcggttagct ccttcggtcc    36840
tccgatcgtt gtcagaagta agttggccgc agtgttatca ctcatggtta tggcagcact    36900
gcataattct cttactgtca tgccatccgt aagatgcttt tctgtgactg gtgagtactc    36960
aaccaagtca ttctgagaat agtgtatgcg gcgaccgagt tgctcttgcc cggcgtcaat    37020
acgggataat accgcgccac atagcagaac tttaaaagtg ctcatcattg gaaaacgttc    37080
ttcggggcga aaactctcaa ggatcttacc gctgttgaga tccagttcga tgtaacccac    37140
tcgtgcaccc aactgatctt cagcatcttt tactttcacc agcgtttctg ggtgagcaaa    37200
aacaggaagg caaaatgccg caaaaaaggg aataagggcg acacggaaat gttgaatact    37260
catactcttc ctttttcaat attattgaag catttatcag ggttattgtc tcatgagcgg    37320
atacatattt gaatgtattt agaaaaataa acaaataggg gttccgcgca catttccccg    37380
aaaagtgcca c                                                        37391

<210> SEQ ID NO 16

<400> SEQUENCE: 16
```

```
<210> SEQ ID NO 17
<211> LENGTH: 671
<212> TYPE: PRT
<213> ORGANISM: Homo sapiens

<400> SEQUENCE: 17

Met Ala Leu Ser Val Asn Asp Cys Ala Arg Leu Thr Gly Gln Ser Val
1               5                   10                  15

Pro Thr Met Glu His Phe Leu Pro Leu Arg Asn Ile Trp Asn Arg Val
            20                  25                  30

Arg Asp Phe Pro Arg Ala Ser Thr Ala Ala Gly Ile Thr Trp Met
        35                  40                  45

Ser Arg Tyr Ile Tyr Gly Tyr His Arg Leu Met Leu Glu Asp Leu Ala
    50                  55                  60

Pro Gly Ala Pro Ala Thr Leu Arg Trp Pro Leu Tyr Arg Gln Pro Pro
65                  70                  75                  80

Pro His Phe Leu Val Gly Tyr Gln Tyr Leu Val Arg Thr Cys Asn Asp
                85                  90                  95

Tyr Val Phe Asp Ser Arg Ala Tyr Ser Arg Leu Arg Tyr Thr Glu Leu
                100                 105                 110

Ser Gln Pro Gly His Gln Thr Val Asn Trp Ser Val Met Ala Asn Cys
            115                 120                 125

Thr Tyr Thr Ile Asn Thr Gly Ala Tyr His Arg Phe Val Asp Met Asp
130                 135                 140

Asp Phe Gln Ser Thr Leu Thr Gln Val Gln Gln Ala Ile Leu Ala Glu
145                 150                 155                 160

Arg Val Val Ala Asp Leu Ala Leu Leu Gln Pro Met Arg Gly Phe Gly
                165                 170                 175

Val Thr Arg Met Gly Gly Arg Gly Arg His Leu Arg Pro Asn Ser Ala
            180                 185                 190

Ala Ala Val Ala Ile Asp Ala Arg Asp Ala Gly Gln Glu Glu Gly Glu
        195                 200                 205

Glu Glu Val Pro Val Glu Arg Leu Met Gln Asp Tyr Tyr Lys Asp Leu
    210                 215                 220

Arg Arg Cys Gln Asn Glu Ala Trp Gly Met Ala Asp Arg Leu Arg Ile
225                 230                 235                 240

Gln Gln Ala Gly Pro Lys Asp Met Val Leu Leu Ser Thr Ile Arg Arg
                245                 250                 255

Leu Lys Thr Ala Tyr Phe Asn Tyr Ile Ile Ser Ser Thr Ser Ala Arg
            260                 265                 270

Asn Asn Pro Asp Arg His Pro Leu Pro Pro Ala Thr Val Leu Ser Leu
        275                 280                 285

Pro Cys Asp Cys Asp Trp Leu Asp Ala Phe Leu Glu Arg Phe Ser Asp
    290                 295                 300

Pro Val Asp Ala Asp Ser Leu Arg Ser Leu Gly Gly Val Pro Thr
305                 310                 315                 320

Gln Gln Leu Leu Arg Cys Ile Val Ser Ala Val Ser Leu Pro His Gly
                325                 330                 335

Ser Pro Pro Pro Thr His Asn Arg Asp Met Thr Gly Gly Val Phe Gln
            340                 345                 350

Leu Arg Pro Arg Glu Asn Gly Arg Ala Val Thr Glu Thr Met Arg Arg
        355                 360                 365
```

```
Arg Arg Gly Glu Met Ile Glu Arg Phe Val Asp Arg Leu Pro Val Arg
    370                 375                 380

Arg Arg Arg Arg Arg Val Pro Pro Pro Pro Pro Pro Glu Glu Glu
385                 390                 395                 400

Glu Glu Gly Glu Ala Leu Met Glu Glu Ile Glu Glu Glu Ala
                405                 410                 415

Pro Val Ala Phe Glu Arg Glu Val Arg Asp Thr Val Ala Glu Leu Ile
                420                 425                 430

Arg Leu Leu Glu Glu Leu Thr Val Ser Ala Arg Asn Ser Gln Phe
            435                 440                 445

Phe Asn Phe Ala Val Asp Phe Tyr Glu Ala Met Glu Arg Leu Glu Ala
    450                 455                 460

Leu Gly Asp Ile Asn Glu Ser Thr Leu Arg Arg Trp Val Met Tyr Phe
465                 470                 475                 480

Phe Val Ala Glu His Thr Ala Thr Thr Leu Asn Tyr Leu Phe Gln Arg
                485                 490                 495

Leu Arg Asn Tyr Ala Val Phe Ala Arg His Val Glu Leu Asn Leu Ala
                500                 505                 510

Gln Val Val Met Arg Ala Arg Asp Ala Glu Gly Gly Val Val Tyr Ser
            515                 520                 525

Arg Val Trp Asn Glu Gly Gly Leu Asn Ala Phe Ser Gln Leu Met Ala
530                 535                 540

Arg Ile Ser Asn Asp Leu Ala Ala Thr Val Glu Arg Ala Gly Arg Gly
545                 550                 555                 560

Asp Leu Gln Glu Glu Ile Glu Gln Phe Met Ala Glu Ile Ala Tyr
                565                 570                 575

Gln Asp Asn Ser Gly Asp Val Gln Glu Ile Leu Arg Gln Ala Ala Val
            580                 585                 590

Asn Asp Thr Glu Ile Asp Ser Val Glu Leu Ser Phe Arg Phe Lys Leu
            595                 600                 605

Thr Gly Pro Val Val Phe Thr Gln Arg Arg Gln Ile Gln Glu Ile Asn
    610                 615                 620

Arg Arg Val Val Ala Phe Ala Ser Asn Leu Arg Ala Gln His Gln Leu
625                 630                 635                 640

Leu Pro Ala Arg Gly Ala Asp Val Pro Leu Pro Leu Pro Ala Gly
                645                 650                 655

Pro Glu Pro Pro Leu Pro Pro Gly Ala Arg Pro Arg His Arg Phe
            660                 665                 670

<210> SEQ ID NO 18
<211> LENGTH: 322
<212> TYPE: PRT
<213> ORGANISM: Homo sapiens

<400> SEQUENCE: 18

Val Phe Gln Leu Arg Pro Arg Glu Asn Gly Arg Ala Val Thr Glu Thr
1               5                   10                  15

Met Arg Arg Arg Arg Gly Glu Met Ile Glu Arg Phe Val Asp Arg Leu
                20                  25                  30

Pro Val Arg Arg Arg Arg Arg Val Pro Pro Pro Pro Pro Pro Pro
                35                  40                  45

Glu Glu Glu Glu Glu Gly Glu Ala Leu Met Glu Glu Ile Glu Glu
            50                  55                  60

Glu Glu Ala Pro Val Ala Phe Glu Arg Glu Val Arg Asp Thr Val Ala
65                  70                  75                  80
```

```
Glu Leu Ile Arg Leu Leu Glu Glu Leu Thr Val Ser Ala Arg Asn
                85                  90                  95

Ser Gln Phe Phe Asn Phe Ala Val Asp Phe Tyr Glu Ala Met Glu Arg
                100                 105                 110

Leu Glu Ala Leu Gly Asp Ile Asn Glu Ser Thr Leu Arg Arg Trp Val
                115                 120                 125

Met Tyr Phe Phe Val Ala Glu His Thr Ala Thr Leu Asn Tyr Leu
    130                 135                 140

Phe Gln Arg Leu Arg Asn Tyr Ala Val Phe Ala Arg His Val Glu Leu
145                 150                 155                 160

Asn Leu Ala Gln Val Val Met Arg Ala Arg Asp Ala Glu Gly Gly Val
                165                 170                 175

Val Tyr Ser Arg Val Trp Asn Glu Gly Leu Asn Ala Phe Ser Gln
                180                 185                 190

Leu Met Ala Arg Ile Ser Asn Asp Leu Ala Ala Thr Val Glu Arg Ala
                195                 200                 205

Gly Arg Gly Asp Leu Gln Glu Glu Ile Glu Gln Phe Met Ala Glu
    210                 215                 220

Ile Ala Tyr Gln Asp Asn Ser Gly Asp Val Gln Glu Ile Leu Arg Gln
225                 230                 235                 240

Ala Ala Val Asn Asp Thr Glu Ile Asp Ser Val Glu Leu Ser Phe Arg
                245                 250                 255

Phe Lys Leu Thr Gly Pro Val Val Phe Thr Gln Arg Arg Gln Ile Gln
                260                 265                 270

Glu Ile Asn Arg Arg Val Val Ala Phe Ala Ser Asn Leu Arg Ala Gln
                275                 280                 285

His Gln Leu Leu Pro Ala Arg Gly Ala Asp Val Pro Leu Pro Pro Leu
                290                 295                 300

Pro Ala Gly Pro Glu Pro Pro Leu Pro Pro Gly Ala Arg Pro Arg His
305                 310                 315                 320

Arg Phe

<210> SEQ ID NO 19
<211> LENGTH: 671
<212> TYPE: PRT
<213> ORGANISM: Homo sapiens

<400> SEQUENCE: 19

Met Ala Leu Ser Val Asn Asp Cys Ala Arg Leu Thr Gly Gln Ser Val
1               5                   10                  15

Pro Thr Met Glu His Phe Leu Pro Leu Arg Asn Ile Trp Asn Arg Val
                20                  25                  30

Arg Asp Phe Pro Arg Ala Ser Thr Thr Ala Ala Gly Ile Thr Trp Met
                35                  40                  45

Ser Arg Tyr Ile Tyr Gly Tyr His Arg Leu Met Leu Glu Asp Leu Ala
            50                  55                  60

Pro Gly Ala Pro Ala Thr Leu Arg Trp Pro Leu Tyr Arg Gln Pro Pro
65                  70                  75                  80

Pro His Phe Leu Val Gly Tyr Gln Tyr Leu Val Arg Thr Cys Asn Asp
                85                  90                  95

Tyr Val Phe Asp Ser Arg Ala Tyr Ser Arg Leu Arg Tyr Thr Glu Leu
                100                 105                 110

Ser Gln Pro Gly His Gln Thr Val Asn Trp Ser Val Met Ala Asn Cys
                115                 120                 125
```

```
Thr Tyr Thr Ile Asn Thr Gly Ala Tyr His Arg Phe Val Asp Met Asp
    130                 135                 140

Asp Phe Gln Ser Thr Leu Thr Gln Val Gln Gln Ala Ile Leu Ala Glu
145                 150                 155                 160

Arg Val Val Ala Asp Leu Ala Leu Leu Gln Pro Met Arg Gly Phe Gly
                165                 170                 175

Val Thr Arg Met Gly Gly Arg Gly Arg His Leu Arg Pro Asn Ser Ala
            180                 185                 190

Ala Ala Ala Ile Asp Ala Arg Asp Ala Gly Gln Glu Glu Gly Glu
        195                 200                 205

Glu Glu Val Pro Val Glu Arg Leu Met Gln Asp Tyr Tyr Lys Asp Leu
    210                 215                 220

Arg Arg Cys Gln Asn Glu Ala Trp Gly Met Ala Asp Arg Leu Arg Ile
225                 230                 235                 240

Gln Gln Ala Gly Pro Lys Asp Met Val Leu Leu Ser Thr Ile Arg Arg
                245                 250                 255

Leu Lys Thr Ala Tyr Phe Asn Tyr Ile Ile Ser Ser Thr Ser Ala Arg
            260                 265                 270

Asn Asn Pro Asp Arg Arg Pro Leu Pro Pro Ala Thr Val Leu Ser Leu
        275                 280                 285

Pro Cys Asp Cys Asp Trp Leu Asp Ala Phe Leu Glu Arg Phe Ser Asp
    290                 295                 300

Pro Val Asp Ala Asp Ser Leu Arg Ser Leu Gly Gly Val Pro Thr
305                 310                 315                 320

Gln Gln Leu Leu Arg Cys Ile Val Ser Ala Val Ser Leu Pro His Gly
                325                 330                 335

Ser Pro Pro Pro Thr His Asn Arg Asp Met Thr Gly Gly Val Phe Gln
            340                 345                 350

Leu Arg Pro Arg Glu Asn Gly Arg Ala Val Thr Glu Thr Met Arg Arg
        355                 360                 365

Arg Arg Gly Glu Met Ile Glu Arg Phe Val Asp Arg Leu Pro Val Arg
    370                 375                 380

Arg Arg Arg Arg Val Pro Pro Pro Pro Pro Glu Glu Glu
385                 390                 395                 400

Glu Gly Glu Ala Leu Met Glu Glu Ile Glu Glu Glu Glu Ala
                405                 410                 415

Pro Val Ala Phe Glu Arg Glu Val Arg Asp Thr Val Ala Glu Leu Ile
            420                 425                 430

Arg Leu Leu Glu Glu Glu Leu Thr Val Ser Ala Arg Asn Ser Gln Phe
        435                 440                 445

Phe Asn Phe Ala Val Asp Phe Tyr Glu Ala Met Glu Arg Leu Glu Ala
    450                 455                 460

Leu Gly Asp Ile Asn Glu Ser Thr Leu Arg Arg Trp Val Met Tyr Phe
465                 470                 475                 480

Phe Val Ala Glu His Thr Ala Thr Thr Leu Asn Tyr Leu Phe Gln Arg
                485                 490                 495

Leu Arg Asn Tyr Ala Val Phe Ala Arg His Val Glu Leu Asn Leu Ala
            500                 505                 510

Gln Val Val Met Arg Ala Arg Asp Ala Glu Gly Gly Val Val Tyr Ser
        515                 520                 525

Arg Val Trp Asn Glu Gly Gly Leu Asn Ala Phe Ser Gln Leu Met Ala
    530                 535                 540
```

```
Arg Ile Ser Asn Asp Leu Ala Ala Thr Val Glu Arg Ala Gly Arg Gly
545                 550                 555                 560

Asp Leu Gln Glu Glu Ile Glu Gln Phe Met Ala Glu Ile Ala Tyr
                565                 570                 575

Gln Asp Asn Ser Gly Asp Val Gln Glu Ile Leu Arg Gln Ala Ala Val
            580                 585                 590

Asn Asp Thr Glu Ile Asp Ser Val Glu Leu Ser Phe Arg Leu Lys Leu
                595                 600                 605

Thr Gly Pro Val Val Phe Thr Gln Arg Arg Gln Ile Gln Glu Ile Asn
            610                 615                 620

Arg Arg Val Val Ala Phe Ala Ser Asn Leu Arg Ala Gln His Gln Leu
625                 630                 635                 640

Leu Pro Ala Arg Gly Ala Asp Val Pro Leu Pro Pro Leu Pro Ala Gly
                645                 650                 655

Pro Glu Pro Pro Leu Pro Pro Gly Ala Arg Pro Arg His Arg Phe
                660                 665                 670
```

<210> SEQ ID NO 20
<211> LENGTH: 322
<212> TYPE: PRT
<213> ORGANISM: Homo sapiens

<400> SEQUENCE: 20

```
Val Phe Gln Leu Arg Pro Arg Glu Asn Gly Arg Ala Val Thr Glu Thr
1               5                   10                  15

Met Arg Arg Arg Gly Glu Met Ile Glu Arg Phe Val Asp Arg Leu
            20                  25                  30

Pro Val Arg Arg Arg Arg Arg Val Pro Pro Pro Pro Pro Pro
                35                  40                  45

Glu Glu Glu Glu Gly Glu Ala Leu Met Glu Glu Ile Glu Glu Glu
            50                  55                  60

Glu Glu Ala Pro Val Ala Phe Glu Arg Glu Val Arg Asp Thr Val Ala
65                  70                  75                  80

Glu Leu Ile Arg Leu Leu Glu Glu Glu Leu Thr Val Ser Ala Arg Asn
                85                  90                  95

Ser Gln Phe Phe Asn Phe Ala Val Asp Phe Tyr Glu Ala Met Glu Arg
                100                 105                 110

Leu Glu Ala Leu Gly Asp Ile Asn Glu Ser Thr Leu Arg Arg Trp Val
            115                 120                 125

Met Tyr Phe Phe Val Ala Glu His Thr Ala Thr Leu Asn Tyr Leu
            130                 135                 140

Phe Gln Arg Leu Arg Asn Tyr Ala Val Phe Ala Arg His Val Glu Leu
145                 150                 155                 160

Asn Leu Ala Gln Val Val Met Arg Ala Arg Asp Ala Glu Gly Gly Val
                165                 170                 175

Val Tyr Ser Arg Val Trp Asn Glu Gly Gly Leu Asn Ala Phe Ser Gln
            180                 185                 190

Leu Met Ala Arg Ile Ser Asn Asp Leu Ala Ala Thr Val Glu Arg Ala
            195                 200                 205

Gly Arg Gly Asp Leu Gln Glu Glu Ile Glu Gln Phe Met Ala Glu
            210                 215                 220

Ile Ala Tyr Gln Asp Asn Ser Gly Asp Val Gln Glu Ile Leu Arg Gln
225                 230                 235                 240

Ala Ala Val Asn Asp Thr Glu Ile Asp Ser Val Glu Leu Ser Phe Arg
                245                 250                 255
```

```
Leu Lys Leu Thr Gly Pro Val Val Phe Thr Gln Arg Arg Gln Ile Gln
            260                 265                 270

Glu Ile Asn Arg Arg Val Val Ala Phe Ala Ser Asn Leu Arg Ala Gln
        275                 280                 285

His Gln Leu Leu Pro Ala Arg Gly Ala Asp Val Pro Leu Pro Pro Leu
    290                 295                 300

Pro Ala Gly Pro Glu Pro Pro Leu Pro Pro Gly Ala Arg Pro Arg His
305                 310                 315                 320

Arg Phe

<210> SEQ ID NO 21
<211> LENGTH: 12
<212> TYPE: DNA
<213> ORGANISM: Artificial Sequence
<220> FEATURE:
<223> OTHER INFORMATION: Synthetic

<400> SEQUENCE: 21
catcatcaat aa                                                             12

<210> SEQ ID NO 22
<211> LENGTH: 12
<212> TYPE: DNA
<213> ORGANISM: Artificial Sequence
<220> FEATURE:
<223> OTHER INFORMATION: Synthetic

<400> SEQUENCE: 22
gtagtagtta tt                                                             12

<210> SEQ ID NO 23
<211> LENGTH: 15
<212> TYPE: DNA
<213> ORGANISM: Artificial Sequence
<220> FEATURE:
<223> OTHER INFORMATION: Synthetic

<400> SEQUENCE: 23
taacatcatc aataa                                                          15

<210> SEQ ID NO 24
<211> LENGTH: 17
<212> TYPE: DNA
<213> ORGANISM: Artificial Sequence
<220> FEATURE:
<223> OTHER INFORMATION: Synthetic

<400> SEQUENCE: 24
taattgtagt agttatt                                                        17

<210> SEQ ID NO 25
<211> LENGTH: 13
<212> TYPE: DNA
<213> ORGANISM: Artificial Sequence
<220> FEATURE:
<223> OTHER INFORMATION: Synthetic

<400> SEQUENCE: 25
ccatcatcaa taa                                                            13

<210> SEQ ID NO 26
<211> LENGTH: 17
<212> TYPE: DNA
```

```
<213> ORGANISM: Artificial Sequence
<220> FEATURE:
<223> OTHER INFORMATION: Synthetic

<400> SEQUENCE: 26
ggccggtagt agttatt                                                  17

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
gacgaggccg gcctggtc                                                 18

<210> SEQ ID NO 28
<211> LENGTH: 18
<212> TYPE: DNA
<213> ORGANISM: Artificial Sequence
<220> FEATURE:
<223> OTHER INFORMATION: Synthetic

<400> SEQUENCE: 28
ggcatggccg gccacggc                                                 18

<210> SEQ ID NO 29
<211> LENGTH: 18
<212> TYPE: DNA
<213> ORGANISM: Artificial Sequence
<220> FEATURE:
<223> OTHER INFORMATION: Synthetic

<400> SEQUENCE: 29
gacgaagccg gcctggtc                                                 18

<210> SEQ ID NO 30
<211> LENGTH: 18
<212> TYPE: DNA
<213> ORGANISM: Artificial Sequence
<220> FEATURE:
<223> OTHER INFORMATION: Synthetic

<400> SEQUENCE: 30
ggcatggccg gctacggc                                                 18

<210> SEQ ID NO 31
<211> LENGTH: 13
<212> TYPE: DNA
<213> ORGANISM: Artificial Sequence
<220> FEATURE:
<223> OTHER INFORMATION: Synthetic

<400> SEQUENCE: 31
ccatcatcaa taa                                                      13

<210> SEQ ID NO 32
<211> LENGTH: 17
<212> TYPE: DNA
<213> ORGANISM: Artificial Sequence
<220> FEATURE:
<223> OTHER INFORMATION: Synthetic

<400> SEQUENCE: 32
ggccggtagt agttatt                                                  17
```

```
<210> SEQ ID NO 33
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: n is a, c, g, or t

<400> SEQUENCE: 33
nnnnnggccg gtagtagtta tt                                              22

<210> SEQ ID NO 34
<211> LENGTH: 13
<212> TYPE: DNA
<213> ORGANISM: Artificial Sequence
<220> FEATURE:
<223> OTHER INFORMATION: Synthetic

<400> SEQUENCE: 34
ggtagtagtt att                                                        13
```

PRODUCTION OF VIRAL VECTORS

The present Application claims priority to U.S. Provisional Application Ser. No. 60/235,060, filed Sep. 25, 2000, hereby incorporated by reference.

This invention was made with Government support under contract NIH P01A6015434. The government has certain rights in this invention.

FIELD OF THE INVENTION

The present invention relates to methods and compositions for the production of viral vectors. In particular, the present invention provides methods and compositions for faster, higher titer and higher purity production of adenovirus vectors.

BACKGROUND OF THE INVENTION

Conventional adenovirus (Ad) gene-delivery vectors are based on replacement of early regions of the viral genome with an expression cassette coding for a gene of interest. Unfortunately, Ad vectors have drawbacks that limit their usefulness for many applications. First, the cloning capacity of these vectors is limited to 8-10 kb. Second, despite deletion of the E1 region, leaky expression of immunogenic viral proteins occurs in vivo, which leads to a host immune response and elimination of gene expression from transduced tissues. Gutted, or helper-dependent, adenoviral vectors may overcome these drawbacks. Gutted vectors contain cis-acting DNA sequences necessary for viral replication and packaging, but usually do not contain viral coding sequences (See U.S. Pat. No. 6,083,750, incorporated by reference). These vectors can accommodate up to 36 kb of exogenous DNA and are unable to express viral proteins. Gutted vectors are produced by replication in the presence of a helper virus, which provides all necessary viral proteins in trans. Since the viral proteins act to replicate both gutted and helper genomes, gutted adenovirus particles are prepared as a mixture with helper virions, though selection against helper virus packaging can reduce this contamination. Particles containing gutted viral genomes, rather than helper genomes, are subsequently purified on the basis of their lower density.

Generally, the starting point for production of a gutted virus is plasmid DNA. The plasmid contains the viral inverted terminal repeats (ITRs), the viral packaging signal, and exogenous DNA to be carried by the gutted virus. To increase production of gutted virus, most investigators linearize the gutted viral plasmid (some systems require the ligation of viral ITRs after linearization). The plasmid DNA is co-introduced with helper sequences into a cell line that can replicate the helper virus, normally 293 cells. Replication of the helper virus eventually causes lysis of the cells with the lysate containing a large number of helper virions and a comparatively small number of gutted virions.

To increase the number and proportion of gutted virions in the lysate, the initial mixture is generally serially passaged. Helper-dependent Ad vectors are usually propagated with constant selective pressure against helper virus packaging. During early passages, selection allows for gradual improvement in the ratio of gutted to helper virus. At the last passage selection removes the majority of helper virus before further purification. Unfortunately, growth of vector stocks under selective pressure can lead to rearrangement of helper and gutted viruses.

The production of gutted virus particles from plasmid DNA in the first step of gutted vector production is so inefficient that titers of less than 100 particles per milliliter have been reported. In some cases no gutted virions can be detected until at least one serial passage has been performed. What is needed is methods and compositions for faster, higher titer and higher purity production of adenovirus vectors.

SUMMARY OF THE INVENTION

The present invention relates to methods and compositions for the production of viral vectors. In particular, the present invention provides methods and compositions for faster, higher titer and higher purity production of viral vectors (e.g. adenoviral vectors). In some embodiments, the present invention provides gutted and helper viruses with corresponding termini. In other embodiments, the present invention provides terminal protein linked adenoviral DNA. In other embodiments, the present invention provides template extended adenoviral DNA (e.g. for increased viral production/recovery and plaquing efficiency). In additional embodiments, the present invention provides methods and compositions for culturing gutted and helper adenoviruses (e.g. with similar or identical termini). For example, the present invention provides compositions and methods for regulated expression of site specific recombinases. In another example, the present invention provides compositions (e.g. cell lines) and methods for culturing adenoviral vectors with adenoviral protein IX.

In some embodiments, the present invention provides methods for producing helper-dependent viral vectors comprising: a) providing; i) helper-dependent viral DNA comprising a first origin of replication, ii) helper viral DNA comprising a second origin of replication, wherein the second origin of replication has similar activity level in a replication assay as the first origin of replication, and iii) target cells; and b) transfecting the target cells with the helper-dependent viral DNA and the helper viral DNA under conditions such that helper-dependent viral vectors are produced. In particular embodiments, the present invention provides compositions comprising the helper-dependent viral vectors produced with the methods of the present invention. In certain embodiments, the helper-dependent viral DNA comprises adenoviral DNA. In particular embodiments, the helper-dependent viral DNA comprises a heterologous gene sequence. In some embodiments, the helper-dependent viral DNA comprises the left and right inverted terminal repeats (ITRs) of adenovirus, the adenoviral packaging sequence (e.g. linked to one of the ITRs), and a heterologous gene sequence.

In preferred embodiments, the first origin of replication and the second origin of replication have nucleic acid sequences that are identical. In some embodiments, the first and/or second origin of replication lie near the terminus of the viral DNA. In other embodiments, the helper-dependent viral DNA has been released from a plasmid backbone by restriction enzyme digestion. In some embodiments, the helper viral DNA has been released from a plasmid backbone. In preferred embodiments, the helper-dependent viral DNA is at least partially linear (in some cases, entirely linear). In other embodiments, the helper viral DNA is at least partially linear (in some cases, entirely linear). In certain embodiments, both the helper-viral DNA and the helper viral DNA lack internal FseI restriction sites (e.g. so plasmids containing both kinds of viral DNA may be digested with FseI to release the viral DNA without cutting viral coding sequences).

In certain embodiments, the first origin of replication and the second origin of replication have nucleic acid sequences that are similar (e.g. they differ by one base, two bases, or three bases). In additional embodiments, the origins are similar and one of the origins is the natural origin and the other is unnatural (e.g. it has additional sequences attached). In some embodiments, the helper viral DNA is adenoviral helper viral DNA. In preferred embodiments, the first origin of replication and the second origin of replication are not linked to terminal protein or any terminal protein remnant.

In some embodiments, the helper viral DNA comprises a crippling sequence. In preferred embodiments, the crippling sequence comprises recognition sites for site-specific recombinases (e.g. loxP and Frt). In some embodiments, the target cells express adenoviral DNA polymerase and preterminal protein. In other embodiments, the target cells express adenoviral factor IX.

In some embodiments, the present invention provides methods for producing helper-dependent viral vectors comprising: a) providing; i) helper-dependent viral DNA comprising a first origin of replication, ii) helper viral DNA comprising a crippling sequence and a second origin of replication, wherein the second origin of replication has similar activity level in a replication assay as the first origin of replication, iii) target cells, and iv) a vector encoding a site-specific recombinase; and b) transfecting the target cells with the helper-dependent viral DNA, the helper viral DNA, and the vector encoding a site-specific recombinase under conditions such that helper-dependent viral vectors are produced. In preferred embodiments, the transfection of the helper-dependent viral DNA, the helper viral DNA, and the vector encoding a site-specific recombinase all occur at approximately the same time. In particularly preferred embodiments, the transfection of the helper-dependent viral DNA, the helper viral DNA, and the vector encoding a site-specific recombinase all occur at approximately the same time such that the vector expresses the recombinase in a regulated manner (e.g. the amount of recombinase in the transfected cells builds up slowly over time). In some embodiments, the transfection of the helper-dependent viral DNA, the helper viral DNA, and the vector encoding a site-specific recombinase occur at different time (e.g. the helper-dependent viral DNA is transfected before the helper viral DNA, or vice versa). In particular embodiments, the transfecting is accomplished by a method selected from calcium phosphate-DNA co-precipitation, DEAE-dextran-mediated transfection, polybrene-mediated transfection, electroporation, microinjection, liposome fusion, lipofection, and biolistics.

In some embodiments, the present invention provides methods for producing helper-dependent viral vectors comprising: a) providing; i) helper-dependent viral DNA comprising a first origin of replication, ii) helper viral DNA comprising a second origin of replication, wherein the second origin of replication has a similar activity level in a replication assay as the first origin of replication, and iii) target cells; b) transfecting the target cells with the helper-dependent viral DNA and the helper viral DNA under conditions such that helper-dependent viral vectors are produced; and c) recovering the helper-dependent vectors. In preferred embodiments, the recovering step yields a helper-dependent titer of up to approximately 30 fold increase compared to transfection/infection protocols in cells expressing adenoviral DNA polymerase and preterminal protein (e.g., at least a 10 fold, at least a 15 fold, at least a 20 fold, or at least 25 fold increase). In particularly preferred embodiments, the recovering step yields a helper-dependent titer of up to approximately 60 fold increase compared to transfection/infection protocols in cells expressing adenoviral DNA polymerase and preterminal protein (e.g., at least 40 fold, at least 50 fold, or at least 55 fold increase).

In some embodiments, the present invention provides compositions comprising; a) helper-dependent viral DNA comprising a first origin of replication, and b) helper viral DNA comprising a second origin of replication, wherein the second origin of replication has a similar activity level in a replication assay as the first origin of replication. In certain embodiments, the helper-dependent viral DNA comprises adenoviral DNA. In particular embodiments, the helper-dependent viral DNA comprises a heterologous gene sequence. In some embodiments, the helper-dependent viral DNA comprises the left and right inverted terminal repeats (ITRs) of adenovirus, the adenoviral packaging sequence (e.g. linked to one of the ITRs), and a heterologous gene sequence. In preferred embodiments, the first origin of replication and the second origin of replication have nucleic acid sequences that are identical. In certain embodiments, the first origin of replication and the second origin of replication have nucleic acid sequences that are similar (e.g. they differ by one base, two bases, or three bases). In additional embodiments, the origins are similar and one of the origins is the natural origin and the other is unnatural (e.g. it has additional sequences attached). In some embodiments, the helper viral DNA is adenoviral helper viral DNA. In preferred embodiments, the first origin of replication and the second origin of replication are not linked to terminal protein or any terminal protein remnant.

In some embodiments, the present invention provides kits and systems comprising; i) helper-dependent viral DNA comprising a first origin of replication, and ii) helper viral DNA comprising a second origin of replication, wherein the second origin of replication has similar activity level in a replication assay as the first origin of replication. In preferred embodiments, the kits and systems of the present invention further comprise target cells (e.g., cells expressing adenoviral DNA polymerase and preterminal protein). In other embodiments, the kits and systems of the present invention comprise the helper-dependent viral vectors produced by the methods of the present invention, and one additional component (e.g., an insert component with written instructions for using the components of the kit and system). The kits and systems of the present invention may comprise any of the components listed herein (e.g., helper-dependent viral DNA, helper viral DNA, target cells, insert component, etc.). In particular embodiments, the kits and systems of the present invention comprise a host cell and one additional component, wherein the host cell comprises a) helper-dependent viral DNA comprising a first origin of replication, and b) helper viral DNA comprising a second origin of replication, wherein the second origin of replication has a similar activity level in a replication assay as the first origin of replication.

In some embodiments, the present invention provides methods for producing helper-dependent viral vectors comprising: a) providing; i) helper-dependent viral DNA comprising an origin of replication linked to a replication-promoting agent, and ii) target cells; and b) transfecting the target cells with the helper-dependent viral DNA under conditions such that helper-dependent viral vectors are produced. In particular embodiments, the present invention provides methods for producing helper-dependent viral vectors comprising: a) providing; i) helper-dependent viral DNA comprising an origin of replication linked to a replication-promoting agent, ii) helper viral DNA, and iii) target cells; and b) transfecting the target cells with the helper-dependent viral DNA and the helper viral DNA under conditions such that helper-dependent viral vectors are produced. In certain embodiments, the present invention provides compositions comprising the helper-dependent viral vectors produced with the methods of the present invention. In preferred embodiments, the replication-promoting agent is selected from Ad2 preterminal protein, Ad2 terminal protein, Ad5 preterminal protein, and Ad5 terminal protein. In other embodiments, replication-promoting agent is selected from at least a portion of Ad2 preterminal protein, Ad2 terminal protein, Ad5 preterminal protein, and Ad5 terminal protein. In preferred embodiments, the replication-promoting agent is Ad5 terminal protein.

In some embodiments, the helper-dependent viral DNA comprises adenoviral DNA. In other embodiments, the helper-dependent viral DNA comprises a heterologous gene sequence. In some embodiments, the helper-dependent viral DNA comprises the left and right inverted terminal repeats (ITRs) of adenovirus, the adenoviral packaging sequence (e.g. linked to one of the ITRs), and a heterologous gene sequence. In some embodiments, the helper viral DNA is linked to adenoviral terminal protein. In additional embodiments, the helper viral DNA is adenoviral helper viral DNA. In preferred embodiments, the helper viral DNA comprises a crippling sequence (e.g. loxP). In particular embodiments, the helper viral DNA comprises recognition sites for site-specific recombinases. In certain embodiments, the target cells express adenoviral DNA polymerase and preterminal protein. In other embodiments, the target cells express adenoviral protein IX. In certain embodiments, the target cells express adenoviral DNA polymerase, preterminal protein, and adenoviral protein IX. In some embodiments, the method further comprises recovering the helper-dependent vectors. In particular embodiments, the recovering yields a helper-dependent titer of up to approximately 85 fold increase compared to transfection/infection protocols in cells expressing adenoviral DNA polymerase and preterminal protein (e.g., at least a 40 fold, 55 fold, 70 fold, or 80 fold increase). In preferred embodiments, the recovering yields a helper-dependent titer of up to 170 fold increase compared to transfection/infection protocols in cells expressing adenoviral DNA polymerase and preterminal protein (e.g., at least 100 fold, 120 fold, 140 fold, 150 fold, or 160 fold increase).

In particular embodiments, the present invention provides methods for producing helper-dependent viral vectors comprising: a) providing; i) helper-dependent viral DNA comprising an origin of replication linked to a replication-promoting agent, ii) helper viral DNA comprising a crippling sequence, and iii) target cells; and b) transfecting the target cells with the helper-dependent viral DNA and the helper viral DNA under conditions such that helper-dependent viral vectors are produced. In preferred embodiments, the transfection of the helper-dependent viral DNA, the helper viral DNA, and the vector encoding a site-specific recombinase all occur at approximately the same time. In particularly preferred embodiments, the transfection of the helper-dependent viral DNA, the helper viral DNA, and the vector encoding a site-specific recombinase all occur at approximately the same time such that the vector expresses the recombinase in a regulated manner (e.g. the amount of recombinase in the transfected cells builds up slowly over time). In some embodiments, the transfection of the helper-dependent viral DNA, the helper viral DNA, and the vector encoding a site-specific recombinase occur at different time (e.g. the helper-dependent viral DNA is transfected before the helper viral DNA, or vice versa). In particular embodiments, the transfecting is accomplished by a method selected from calcium phosphate-DNA co-precipitation, DEAE-dextran-mediated transfection, polybrene-mediated transfection, electroporation, microinjection, liposome fusion, lipofection, and biolistics.

In some embodiments, the present invention provides compositions comprising helper-dependent viral DNA comprising an origin of replication linked a replication-promoting agent. In preferred embodiments, the replication-promoting agent is selected from Ad2 preterminal protein, Ad2 terminal protein, Ad5 preterminal protein, and Ad5 terminal protein. In other embodiments, replication-promoting agent is selected from at least a portion of Ad2 preterminal protein, Ad2 terminal protein, Ad5 preterminal protein, and Ad5 terminal protein. In preferred embodiments, the replication-promoting agent is Ad5 terminal protein.

In some embodiments, the present invention provides kits and systems comprising i) helper-dependent viral DNA comprising an origin of replication linked to a replication-promoting agent, and ii) target cells. In preferred embodiments, the kits and systems of the present invention further comprise helper viral DNA. In other embodiments, the kits and systems of the present invention comprise the helper-dependent viral vectors produced by the methods of the present invention, and one additional component (e.g., an insert component with written instructions). The kits and systems of the present invention may comprise any of the components listed herein (e.g., helper-dependent viral DNA, helper viral DNA, target cells, insert component, etc.).

In certain embodiments, the present invention provides methods comprising: a) providing; i) a first helper-dependent viral DNA comprising a first origin of replication capable of promoting a first activity level in a replication assay, ii) an agent capable of extending the first origin of replication, and b) contacting the helper-dependent viral DNA with the agent for a period of time sufficient to generate a second helper-dependent viral DNA with an second origin of replication capable of promoting a second activity level in a replication assay, wherein the second activity level in a replication assay is greater than the first activity level in a replication assay. In other embodiments, the present invention provides methods comprising: a) providing; i) a first helper-dependent viral DNA comprising a first origin of replication capable of promoting a first activity level in a replication assay, ii) an agent capable of extending the first origin of replication, iii) helper viral DNA, and iv) target cells; b) contacting the helper-dependent viral DNA with the agent for a period of time sufficient to generate a second helper-dependent viral DNA with an second origin of replication capable of promoting a second activity level in a replication assay, wherein the second activity level in a replication assay is greater than the first activity level in a replication assay; and c) transfecting the target cells with the second helper-dependent viral DNA and the helper viral DNA under conditions such that helper-dependent viral vectors are produced.

In certain embodiments, the first origin of replication is natural. In some embodiments, the first origin of replication is non-natural (e.g. it has one, two, or three bases added onto the natural origin of replication). In other embodiments, the agent is selected from the group of terminal transferase, T4 DNA ligase, and T4 RNA ligase. In preferred embodiments, the agent is terminal transferase. In some embodiments, the helper-dependent viral DNA comprises adenoviral DNA. In other embodiments, the helper-dependent viral DNA comprises a heterologous gene sequence. In still other embodiments, the helper-dependent viral DNA comprises the left and right inverted terminal repeats (ITRs) of adenovirus, the adenoviral packaging sequence (e.g. linked to of the ITRs), and a heterologous gene sequence. In particular embodiments, the helper viral DNA is adenoviral helper viral DNA. In preferred embodiments, the helper viral DNA comprises a crippling sequence (e.g. a site specific recombinase). In some embodiments, the crippling sequence is loxP. In some embodiments, the target cells express adenoviral DNA polymerase and preterminal protein. In other embodiments, the target cells express adenoviral factor IX. In certain embodiments, the method further comprises recovering the helper-dependent vectors. In preferred embodiments, the second activity level in a replication assay is approximately 2-2.5 fold greater than the first activity level in a replication assay.

In other embodiments, the present invention provides methods comprising: a) providing; i) a first helper-dependent viral DNA comprising a first origin of replication capable of promoting a first activity level in a replication assay, ii) an agent capable of extending the first origin of replication, iii) helper viral DNA, iv) target cells and v) a vector encoding a site-specific recombinase; b) contacting the helper-dependent viral DNA with the agent for a period of time sufficient to generate a second helper-dependent viral DNA with an second origin of replication capable of promoting a second activity level in a replication assay, wherein the second activity level in a replication assay is greater than the first activity level in a replication assay; and c) transfecting the target cells with the second helper-dependent viral DNA, the helper viral DNA, and the vector encoding a site-specific recombinase under conditions such that helper-dependent viral vectors are produced. In certain embodiments, the present invention provides compositions comprising the helper-dependent viral vectors produced with the methods of the present invention. In preferred embodiments, the transfection of the helper-dependent viral DNA, the helper viral DNA, and the vector encoding a site-specific recombinase all occur at approximately the same time. In particularly preferred embodiments, the transfection of the helper-dependent viral DNA, the helper viral DNA, and the vector encoding a site-specific recombinase all occur at approximately the same time such that the vector expresses the recombinase in a regulated manner (e.g. the amount of recombinase in the transfected cells builds up slowly over time). In some embodiments, the transfection of the helper-dependent viral DNA, the helper viral DNA, and the vector encoding a site-specific recombinase occur at different time (e.g. the helper-dependent viral DNA is transfected before the helper viral DNA, or vice versa). In particular embodiments, the transfecting is accomplished by a method selected from calcium phosphate-DNA co-precipitation, DEAE-dextran-mediated transfection, polybrene-mediated transfection, electroporation, microinjection, liposome fusion, lipofection, retroviral infection and biolistics.

In some embodiments, the present invention provides kits and systems comprising i) a first helper-dependent viral DNA comprising a first origin of replication capable of promoting a first activity level in a replication assay, and an agent capable of extending the first origin of replication. In other embodiments, the kits and systems further comprise helper viral DNA and/or target cells. In other embodiments, the kits and systems of the present invention comprise the helper-dependent viral vectors produced by the methods of the present invention, and one additional component (e.g., an insert component with written instructions). The kits and systems of the present invention may comprise any of the components listed herein (e.g., helper-dependent viral DNA, helper viral DNA, target cells, insert component, etc.). In particular embodiments, the kits and systems of the present invention comprise a host cell and one additional component, wherein the host cell (e.g., mammalian) stably and constitutively expresses adenovirus preterminal protein, adenovirus DNA polymerase, and adenovirus protein IX.

In some embodiments the present invention provides mammalian cell lines stably and constitutively expressing adenovirus preterminal protein, adenovirus DNA polymerase, and adenovirus protein IX. In some embodiments, the cell line is D2104#10.

DESCRIPTION OF THE FIGURES

FIG. 3 shows a method for conversion of plasmid-derived Ad origins to natural form (creating TP-primer and ligating it to plasmid derived viral DNA).

FIG. 4 shows that conversion of plasmid-derived gutted virus to a natural, TP-linked structure facilitates gutted virus rescue.

FIG. 8 shows the nucleic acid sequence of (+)lox(+)pol helper virus (SEQ ID NO:1).

FIG. 9 shows the nucleic acid sequence of pBSX (SEQ ID NO:12).

FIG. 11 shows the nucleic acid sequence of ΔFseI.4 helper virus (SEQ ID NO:9).

FIG. 13 shows TP-DNA complex from (+)lox(+)pol helper viral DNA; deproteinized Hirt prep DNA from ΔFseI.4; and pD1940#3 and pD1940#6.

FIG. 14 shows the nucleic acid sequence of pD1940 (SEQ ID NO:13).

FIG. 15 shows the nucleic acid sequence of pD1962delBbsI-pIX (SEQ ID NO:14).

FIG. 17 shows the nucleic acid sequence of ΔHIX#3 (SEQ ID NO:15).

FIG. 18 shows the nucleic acid sequence for: Ad2 preterminal protein (SEQ ID NO:17); Ad2 terminal protein (SEQ ID NO:18); Ad5 preterminal protein (SEQ ID NO:19); and Ad5 terminal protein (SEQ ID NO:20).

DEFINITIONS

Figure 1:
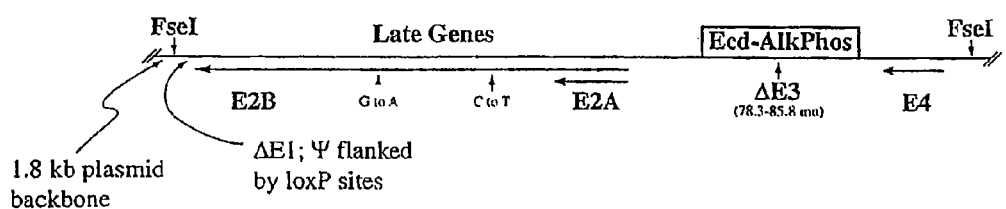
FIG. 1 shows: A) (SEQ ID NOS:21-26) the structure of viral origins of replication (both natural and non-natural origins that result when particular restriction enzymes are employed); B) (SEQ ID NOS:27-30) points where viral genome is mutated to remove FseI restriction sites; and C) partial structure of pD1940#3 and pD1940#6.

To facilitate an understanding of the present invention, a number of terms and phrases are defined below:

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. Oligonucleotide may be generated in any manner, including chemical synthesis, DNA replication, reverse transcription, or a combination thereof.

As used herein, the term "helper dependent viral DNA" or "gutted viral DNA" refers to viral DNA that codes for viral vectors that contain cis-acting DNA sequences necessary for viral replication and packaging, but generally no viral coding sequences (See U.S. Pat. No. 6,083,750, incorporated by reference). These vectors can accommodate up to about 36 kb of exogenous DNA and are unable to express viral proteins sufficient for replication. Helper-dependent viral vectors are produced by replication of the helper dependent viral DNA in the presence of a helper adenovirus, which alone or with a packaging cell line, supplies necessary viral proteins in trans such that the helper-dependent viral DNA is able to be replicated. Gutted vectors may be constructed as described in U.S. Pat. No. 6,083,750.

As used herein the term "helper viral DNA" refers to viral DNA encoding helper viral vectors, that are capable of providing, alone or with a packaging cell line, viral proteins in trans such that a gutted virus is able to replicate. A "helper adenovirus" or "helper virus" refers to an adenovirus which is replication-competent in a particular host cell. The host may provide, for example, Ad gene products such as E1 proteins. The 'helper virus' is used to supply in trans functions (e.g., proteins) which are lacking in a second replication-incompetent virus (e.g. a gutted viral vector). Therefore, the first replication-competent virus is said to "help" the second replication-incompetent virus thereby permitting the propagation of the second viral genome in the cell containing the helper and second viruses. Helper virus may include a sequence capable of crippling helper virus replication in the presence of certain crippling agents. An example of a helper virus with a crippling sequence is the (+)lox(+)pol helper virus (SEQ ID NO:1). The (+)lox(+)pol helper virus is an E1-, E3-deleted virus that can be negatively selected using Cre recombinase and carries an alkaline phosphatase reporter gene in its E3 region. The packaging signal, which consists of packaging elements I-V, is flanked by loxP sites in direct repeat orientation, allowing removal of the packaging signal in the presence of Cre (a crippling agent).

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery). Adenoviruses are double-stranded DNA viruses. The left and right inverted terminal repeats (ITRs) are short elements located at the 5' and 3' termini of the linear Ad genome, respectively, and are required for replication of the viral DNA. The left ITR is located between 1-130 bp in the Ad genome (also referred to as 0-0.5 mu). The right ITR is located from ~35,800 bp to the end of the genome (also referred to as 99.5-100 mu). The two ITRs are inverted repeats of each other.

The term "transfection" as used herein refers to the introduction of foreign DNA into eukaryotic cells. Transfection may be accomplished by a variety of means known to the art including, but not limited to, calcium phosphate-DNA co-precipitation, DEAE-dextran-mediated transfection, polybrene-mediated transfection, electroporation, microinjection, liposome fusion, lipofection and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

As used herein, the term "gene of interest" or "heterologous gene sequence" refers to a gene inserted into a vector or plasmid whose expression is desired in a host cell. Genes of interest include genes having therapeutic value as well as reporter genes. A variety of such genes are contemplated, including genes of interest encoding proteins which provide a therapeutic function (such as the dystrophin gene, which is capable of correcting the defect seen in the muscle of MD patients), the utrophin gene, the CFTR gene (capable of correcting the defect seen in cystic fibrosis patients), etc.

The term "reporter gene" indicates a gene sequence that encodes a reporter molecule (including an enzyme). A "reporter molecule" is detectable in detection systems, including, but not limited to enzyme (e.g., ELISA, as well as enzyme-based histochemical assays), fluorescent, radioactive, and luminescent systems. Examples of reporter molecules include, but are not limited to, beta-galactosidase gene (available from Pharmacia Biotech, Pistacataway, N.J.), green fluorescent protein (GFP) (commercially available from Clontech, Palo Alto, Calif.), the human placental alkaline phosphatase gene, and the chloramphenicol acetyltransferase (CAT) gene. Other reporter genes are known to the art and may be employed.

As used herein, the term "activity level in a replication assay" refers to the level of activity observed for a particular type of viral origin of replication as measured in a replication assay. Examples of replication assays include, but are not limited to, plaque assays, rate of initiation of DNA replication assays, and replication factor affinity assays.

As used herein, the term "plaque assay" refers to a means for measuring the frequency with which virus or viral DNA can replicate productively (See, Graham, F. L. and Prevec, L. *Manipulation of Adenovirus Vectors in Gene Transfer and Expression Protocols*, Clifton: The Humana Press, Inc., 1991, hereby incorporated by reference). The assay may be performed, for example, by using either virus (by infection) or viral DNA (by transfection). For purposes of measuring the activity of an origin of replication the assay is performed using viral DNA. When viral DNA is introduced into cells by transfection, some transfected cells allow replication of the genome and progeny virions are produced. If the cells have been overlayed with agarose, the progeny virions diffuse to and infect only nearby cells. Thus, after several rounds of replication, foci of dead cells are observed (e.g. their presence may be highlighted through use of dyes like neutral red). These foci of dead cells are referred to as "plaques". To measure the activity of an origin of replication in this assay, the origin is linked to helper-independent viral DNA and transfected into cells which support growth of the virus. The cells are overlayed with agarose, and the investigator waits for the appearance of plaques (e.g. 3-14 days). After plaques have appeared, their appearance may be highlighted with dye, and their number counted. The higher the number of plaques, the more often the viral DNA has been converted into replicating virus, and the higher the activity of the origin of replication is found to be. The number of plaques observed is also correlated with the amount of DNA transfected, so the results of a plaque assay may be expressed as "specific activity"; that is, the number of plaques observed per weight of DNA transfected. An origin of replication that is more active than a second origin will tend to display more plaques in the plaque assay.

As used herein, the term "rate of initiation of DNA replication assays" refers to methods for determining the rate of initiation of DNA replication on a given origin (See, Challberg M D., Rawlins Dr., *P.N.A.S.,* 81(1):100-4, 1984, herein incorporated by reference). The rate of initiation of DNA replication on a given origin may be measured, for example, by incubating the origin together with all the viral and cellular factors required for initiation, and then noting the rate with which new copies of the non-template strand appear. Generally, the steps in such an assay include: isolation of cellular and viral factors from infected cells; incubation of the isolated factors with origin fragments and radioactive nucleotides; observation of new DNA copies using an assay method such as gel electrophoresis followed by autoradiography. For each origin, the analysis is usually performed at several time points, so that the appearance of new DNA copies may be charted over time. Using this information, the rate of their appearance can be calculated. An origin of replication that is more active than a second origin will tend to cause the rate of appearance of new DNA copies to be more rapid in this assay.

As used herein, the term "replication factor affinity assays" refers to methods for determining the ability of viral DNA to attract viral replication factors (e.g. adenovirus DNA polymerase, adenovirus preterminal protein, NFI, and NFIII, See Pronk et al., *Nucleic Acids Research*, 25(10):2293-300, 1993, herein incorporated by reference). The affinity of a replication factor for an origin of replication may be measured, for example, by incubating the two together at a variety of concentrations and then determining, at each concentration, the amount of origin DNA that was bound by factor. One example of a method used to determine the amount of bound origin DNA is an "electrophoretic mobility shift assay" (EMSA). In this assay, the presence of factor bound to DNA causes the mobility of the origin-containing DNA to be reduced in polyacrylamide gels. Using radioactive origin DNA, the amount of DNA bound by factor can therefore be determined by measuring the amount of radioactivity found in an electrophoretic band of reduced mobility—the larger the amount of radioactivity, the larger the amount of DNA bound by factor. The affinity of an origin of replication for a replication factor is indicated by the concentration levels at which substantial binding can occur: the lower the concentration at which binding occurs, the higher the affinity is said to be. The relative affinities of two origins for a replication factor could be compared by incubating radioactive samples of each origin together with different concentrations of replication factor, usually in the presence of random DNA fragments to inhibit non-specific interactions. If the first origin has a higher affinity for factor than the second origin, a lesser concentration of factor will be required to bind a given amount of origin DNA. For example, a lesser concentration of factor will be required to retard the migration of a certain proportion of DNA sequences containing the first origin than DNA sequences containing the second, as determined by EMSA.

As used herein, the term "target cells" refers to any cells that may be transfected with viral DNA. Target cells include, but are not limited to, bacterial cells, mammalian cells, and insect cells. Target cells may from any source including, but not limited to, bacterial colonies, cell lines, tissue samples, and blood samples.

As used herein the term "expresses said recombinase in a regulated manner" refers to the expression of recombinase in a target cell such that the level of recombinase in the cell gradually increases over time. This gradual increase in expression allows the helper viral DNA to replicate at a greater rate initially after transfection (when the level of recombinase is lower), and slows the replication rate of the helper virus as the level of recombinase increases. One example expression of recombinase in a regulated manner is provided in Example 6.

As used herein, the term "similar activity level in a replication assay" refers to the situation where two origins of replication have about the same activity level in a replication assay (e.g. plaque assay, replication factor affinity assay, or rate of initiation of DNA replication assay). For example, similar activity level includes a difference of 20 fold or less, preferably 10 fold or less, more preferably 5 fold or less, and most preferably 2 fold or less.

As used herein, the phrase "wherein said second activity level in a replication assay is greater than said first activity level in a replication assay" refers to a second activity level of at least 5% greater, preferably 10%, more preferably 20% greater, most preferably 50% greater, than said first activity level.

As used herein the phrase "at about the same time" refers to transfection steps that occur within approximately one hour of each other.

As used herein, the term "under conditions such that helper-dependent viral vectors are produced" refers to conditions such that help dependent viral DNA is able to replicate inside a cell (e.g. may require helper viral DNA) such that helper-dependent viral vectors (particles) are produced.

As used herein, the term "origin of replication" refers to the DNA sequence elements that are necessary and sufficient to direct replication of a DNA molecule to which they are attached. Generally, the sequence elements include binding sites for replication factors and usually span the points at which the synthesis of new DNA strand begin. Origins of replication can often be identified by the fact that their mutation or removal prevents replication of DNA molecules to which they had been attached and which had formerly replicated in a given system. In addition, the attachment of an origin of replication to a formerly inert molecule should be sufficient to cause its replication in a given system. For example, the origin of replication for adenoviral DNA has been identified as including at least the first 50 base pairs of the adenoviral genome and commonly refers to approximately the first 100 base pairs of the adenoviral genome also known as the inverted terminal repeat (ITR). Removal of the ITRs from adenoviral genome prevents its replication; the addition of ITRs to most DNA molecules is sufficient to allow their replication in cells that have been infected by helper independent adenovirals, which provides viral replication factors.

As used herein the term "viral recovery" refers to collection and storage of progeny virions produced by cells (e.g. infected by helper-dependent and helper viral DNA). This can be accomplished with or without purification of the virions to remove cellular contaminants. For example, a simple method for viral recovery is to collect lysed cells and store them in the freezer. The presence of virions may be revealed through an examination of the lysate by any of several methods including, but not limited to, plaque assay, a transduction assay that reveals the presence of a marker genes like beta-galactosidase, or physical methods such as chromatography followed by spectroscopy.

As used herein, the term "transfection/infection protocol" refers to the standard protocol where helper-dependent viral DNA is introduced into cells by a transfection method at approximately the same time (e.g. plus or minus 24 hours) that intact helper independent viral particles (e.g. contain adenoviral terminal protein linked to the origin of replication) are allowed to contact the cells and infect them. After a variable period of time the cells lyse due to replication of the virus. At that point, the progeny viral particles are collected.

As used herein, the term "replication-promoting agent" refers to a compound or molecule that may be ligated to viral DNA terminus such that the activity level in a replication assay of such viral DNA is increased (compared to not having the replication-promoting agent ligated to the viral terminus). Examples of replication-promoting agents include, but are not limited to, Ad5 adnenoviral preterminal protein, Ad5 adenoviral protein, Ad2 preterminal protein, and Ad2 terminal protein.

As used herein, the term "agent capable of extending said first origin of replication" refers to any agent that is capable of adding single nucleotides, or oligonucleotides (e.g. 10 mers) to the terminal end of viral DNA. Examples of such agents include, but are not limited to, terminal transferase, T4 DNA ligase, and T4 RNA ligase.

As used herein, the phrase "contacting said helper-dependent viral DNA with said agent for a period of time sufficient to generate", in regards to time, refers to the length of time required to expose viral DNA origins (natural or un-natural) to an agent capable of extending such origins, such that the activity level in a replication assay of such extended origin is increased (as compared to not extended origins). This time period may vary according to the agent employed and other conditions (e.g. type and concentrations of nucleotides). One example of determining the appropriate length of time is provided in Example 5.

As used herein, the phrase "said first origin of replication and said second origin of replication have nucleic acid sequences that are substantially similar" refers to the situation where the first and second origins, while not identical, have origins of replication that are similar in nature (e.g. they both have additional nucleotides added to the natural origin of replication such that the ability). One example of substantially similar origins is provided in FIG. 1A, comparing the structure of the PacI digested viral DNA origin to the FseI digested viral DNA origin.

DESCRIPTION OF THE INVENTION

The present invention relates to methods and compositions for the production of viral vectors. In particular, the present invention provides methods and compositions for faster, higher titer and higher purity production of viral vectors (e.g. adenoviral vectors). In some embodiments, the present invention provides gutted and helper viruses with corresponding termini. In other embodiments, the present invention provides terminal protein linked adenoviral DNA. In other embodiments, the present invention provides template extended adenoviral DNA (e.g. for increased viral production/recovery and plaquing efficiency). In additional embodiments, the present invention provides methods and compositions for culturing gutted and helper adenoviruses (e.g. with similar or identical termini). For example, the present invention provides compositions and methods for regulated expression of site specific recombinases. In another example, the present invention provides compositions (e.g. cell lines) and methods for culturing adenoviral vectors with adenoviral protein IX.

I. Gutted and Helper Viruses with Similar or Identical Termini

In typical gutted virus-helper virus rescue production methods, the helper virus eventually comes to dominate the contents of the packaging cell (to the detriment of the gutted adenovirus). The number and proportion of gutted virions is small because plasmid DNA, whether circular (with fused ITRs) or linear, is a poor substrate for initiation of adenoviral DNA replication. As a result, replication of the helper virus occurs in many cells without concomitant production of gutted virus, despite the presence of gutted viral plasmid substrate.

As mentioned above, to increase the number and proportion of gutted virions in the lysate, the initial mixture is generally serially passaged. Helper-dependent Ad vectors are usually propagated with constant selective pressure against helper virus packaging. During early passages, selection allows for gradual improvement in the ratio of gutted to helper virus. Unfortunately, growth of vector stocks under selective pressure can lead to rearrangement of helper and gutted viruses. In addition, serial passage is time consuming.

Published protocols for rescue of helper-dependent Ad vectors employ gutted viral DNA derived from plasmids and helper viral DNA derived from replicating virus. Most investigators transfect gutted viral DNA and then infect with replication-competent helper virus the "transfection/infection" protocol. Others have compared transfection/infection to co-transfection of gutted viral DNA from plasmids and helper viral DNA prepared from replicating virus and found that co-transfection is more efficient. In these protocols, the helper and gutted viral DNAs have different structures at their origins of replication.

The present invention provides gutted and helper viral DNA with similar corresponding termini or linked to terminal protein, thus alleviating some of the problems of normal viral rescue protocols. While not limited to any mechanism, providing gutted and viral DNA that are substantially similar at the origin of replication allows parallel amplification of both types of vectors, thus preventing the helper viruses production from dominating over gutted virus production. Again, while not limited to any mechanism, it is believed that substantially similar termini or origins of replication (or identical termini or origins of replication) allow parallel amplification of both types of vectors because neither type of virus has a competitive advantage for attracting replication factors (such as adenoviral polymerase, transcription factors, etc.).

The present invention provides gutted and helper viruses with corresponding termini, and methods of employing such vectors for increased production yields (and faster production) of adenoviral vectors (which, may then be used, for example, for gene therapy applications). In some embodiments, gutted adenoviral DNA and helper adenoviral DNA (e.g. both located on plasmids) are released from their plasmids with the same restriction enzyme (cutting at the termini) such that the termini of the linearized DNA are the same (i.e. the gutted and helper adenoviral DNA have corresponding termini). Any type of restriction enzyme (or other enzyme that will cut DNA) may be used, as long as at least one viral terminus is released from its host vector or the ends of the DNA are able to be cut, leaving corresponding termini on both the gutted and helper DNA. In particular embodiments, different restriction enzymes are employed. In such embodiments, the ends of the viral DNA may not be identical, but the ability of the ends to promote replication in cells is approximately the same (e.g. neither type of DNA has a substantial competitive advantage after transfection, such that replication of both types of viruses proceeds at approximately the same pace). In preferred embodiments, the same restriction enzyme is used to generate the termini of both the gutted and helper viral DNA.

Preferably, restriction enzymes are employed that cut close to or at the termini of helper and gutted viral DNA. In some embodiments, creating gutted and helper adenoviral DNA with identical or similar termini requires that particular restriction sites be removed from one or both types of DNA (to prevent the digestion of the viral DNA). An example of removing unwanted restriction sites (FseI sites) from viral DNA (the Ad5 genome) is provided in Example 1. A similar procedure can be employed to remove other types of unwanted restriction sites from viral DNA. In this regard, any restriction enzyme could be employed to create identical (or similar) termini if the suitable modification are made (if necessary) in the viral DNA.

To confirm that the restriction enzyme employed is capable of releasing replication-competent viral DNA from flanking DNA sequences (e.g. plasmid DNA), an assay similar to Example 2 may be employed (transfecting gutted and helper DNA into cells known to replicate adenoviral DNA). Such a technique may also be employed to test the relative efficiency of production of viral particles from viral DNA with various termini.

In certain embodiments, neither the gutted or the helper viral DNA contain terminal protein, and both types are transfected into a cell line as DNA (e.g. the helper DNA is transfected as DNA, instead of a viral particle). In such embodiments, the identity of the termini of the helper and gutted viral DNA is not critical, as long as the termini both do not contain terminal protein or any terminal protein remnant (e.g. one serine residue). In certain embodiments, the gutted and helper viral DNA are co-transfected into a packaging cell line.

II. Replication-Promoting Agent Linked Adenoviral DNA

Another method for increasing viral production is linking gutted adenoviral DNA (e.g. the adenoviral origin) to a replication-promoting agent (e.g. adenoviral preterminal protein or adenoviral terminal protein). The normal substrate for initiation of adenoviral DNA replication is terminal protein-DNA complex. Plasmid-based substrates propagated in, for example, *E. coli*, normally lack terminal protein. As such, replication is greatly increased by linking gutted adenoviral DNA (and, in some embodiments, helper viral DNA) to adenoviral terminal protein.

In the transfection/infection protocol, or when helper virus terminal protein-DNA complex is used for co-transfection, the helper virus DNA is already attached to adenoviral terminal protein. While not limited to any mechanism, it is believed that linking the gutted adenoviral DNA termini to a replication-promoting agent (e.g. adenoviral terminal protein) reduces the competitive advantage helper virus has when supplied as viral particles (or DNA) that is already attached to terminal protein. In this regard, both types of viral DNA have a similar ability to attract replication factors and replicate into viral particles. Again, while not limited to any mechanism, it is believed that the presence of a replication-promoting agent (e.g. adenoviral preterminal protein) bound to the template confers higher affinity for incoming Ad polymerase-preterminal protein complex, an essential viral replication factor.

One method for preparing gutted viral genomes linked to adenoviral terminal protein (i.e. terminal protein serves as the replication-promoting agent) involves purifying terminal protein-containing fragments. Terminal protein-containing fragments (e.g. isolated from intact virus), can be purified away from other viral DNA fragments before ligation. It is desired that such purification be employed as the presence of other viral fragments would tend to inhibit the desired ligation reaction, since both partners in the desired ligation (gutted viral genomes and terminal protein-containing fragments) would likely be ligated to contaminating, more numerous random viral fragments in a mixed reaction. A second purification step may be performed after ligation, when unligated terminal protein-DNA fragments are removed. As these fragments contain natural Ad origins, failure to remove them could reduce the yield of gutted virus by inhibiting viral replication. Another method for obtaining terminal protein is purification of terminal protein-gutted genome complex from gutted virus preparations.

In a preferred embodiments, gutted Ad genomes are linked to normal Ad origins (FIG. 4). This method requires relatively small amounts of terminal protein DNA-complex (e.g. 2-4 moles of terminal protein-DNA complex are sufficient to convert approximately 1 mole of gutted viral genomes to the natural, terminal protein-containing form). Conveniently, the reaction can be performed without purification of the terminal protein-DNA reagent either before or after origin conversion (See Example 3).

In some embodiments, the compound used in the conversion process is terminal protein linked to single-stranded DNA (e.g. from the non-template strand of an Ad ITR). Another term for terminal protein linked to single-stranded DNA is "TP-primer". Example 3 provides one example of the preparation of TP-primer, employing a restriction enzyme digest of viral TP-DNA complex (employing Bsh1236I, AluI, and HinfI) followed by λ exonuclease treatment. Other restriction enzymes may be employed in this process. Preferably, restriction enzymes are chosen that leave a substantial length of nucleic acid (i.e. 'primer') on the TP-primer reagent. For example, Bsh1236I, employed in Example 3, is known to cut between base pairs 73 and 74 of the Ad5 ITR, so this type of digestion results in terminal protein linked to a 73-bp, double stranded DNA molecule. This method may also employ other exonucleases (i.e. besides λ exonuclease), preferably 5' to 3' exonucleases (e.g. T7 gene 6 exonuclease).

In some embodiments, the TP-primer reagent is purified after it is constructed (e.g. to remove any mononucleotides or oligonucleotides created as a result of the enzyme digests). For example, as the TP-primer contains single-stranded DNA, any type of solid-phase purification strategy may be used (e.g. paramagnetic beads linked to single-stranded DNA that is complementary to the DNA in the TP-primer reagent— after binding of TP-primer to the beads, the beads could be collected and the TP-primer reagent released through heating). Other suitable purification/collection techniques are known in the art.

TP-primer may also be constructed synthetically. Such a synthetic reagent would contain, for example, a peptide fragment (or entire protein) of the Ad terminal protein linked to any number of bases from an adenovirus ITR. Synthesis techniques for polypeptides and nucleic acid are well known in the art.

A natural or synthetic "primer" sequence, for generating a TP-primer molecule, is selected to be substantially or completely complementary to a strand of specific sequence of the gutted viral template. A primer must be sufficiently complementary to hybridize with a template strand (e.g. such that primer elongation can occur). A primer sequence need not reflect the exact sequence of the template. Non-complementary bases or longer sequences can be interspersed into the primer, provided that the primer sequence has sufficient complementarity with the sequence of the template to hybridize and thereby form a template primer complex. Complementarity need not be perfect, stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

TP-primer molecules (or similar molecules) are used to convert viral origins to "natural" viral origins of replication. In a preferred embodiment, TP-primer is used to convert plasmid derived gutted viral genomes to natural adenoviral origins by attaching TP-primer to the terminus of adenoviral DNA. Any type of method may be employed. For example, gutted viral genomic DNA (flanked by restriction enzyme sites) may be digested with the appropriate restriction enzyme to release the gutted viral DNA. The products of this are then subjected to limited digestion with a 5' to 3' exonuclease (limited digestion with this type of enzyme exposes single-stranded regions near the gutted vector genomic termini, see FIG. 3B). Any type of 5' to 3' exonuclease may be employed (e.g. T7-gene-6 exonuclease, λ exonuclease, etc.). Digestion with the 5' to 3' nuclease is for a limited time (e.g. about 1-2 minutes), such that enough single strand template is exposed to hybridize to the nucleic acid in the TP-primer, but not so much that the entire strand is digested. The longer the single-stranded nucleic acid is on the TP-primer compound, the more 5' to 3' digestion is needed to expose a single-stranded template for hybridization. The exonuclease is preferably inactivated (e.g. by heating) prior to the introduction of the TP-primer.

TP-primer is then added to the digested product that is created after exonuclease digestion. The nucleic acid portion of the TP-primer (i.e. the 'primer' portion) will hybridize to its complement on the partially digested viral DNA. In preferred embodiments, the nucleic acid portion of the TP-primer is relatively long (e.g. 25 or more bases) such that the TP-primer reagent can bind efficiently to the exonuclease digest gutted DNA, even at low molar ratios. However, any length of 'primer' nucleic acid capable of hybridizing to the exonuclease digested viral DNA may be employed (see discussion above). Once the TP-primer reagent is added to the digested viral DNA, the mixture may be subjected to conditions that promote rapid hybridization. For example, the temperature of the mixture may be raised (e.g. to 75° C.) and allowed to cool (e.g. the temperature is allowed to fall slowly over 2-3 hours to room temperature).

Hybridized TP-primer molecules are then extended (e.g. using T4 DNA polymerase, Taq polymerase, etc.) and nicks are repaired (e.g. using T4 DNA ligase) in the presence of dNTPs. In some embodiments, products of the extension and nick repair are incubated for a period of time (e.g. 5 minutes) at 0°, then a period of time (e.g. 5 minutes) at room temperature, and then a period of time (e.g. 2 hours) at 37° C. In certain embodiments, EDTA is then added to this mixture, and the mixture is stored on ice. In particular embodiments, the reaction products are dialyzed against transfection buffer before being used (e.g. before being used to transfect cells).

In particular embodiments, the successful addition of TP-primer to the origin of replication (e.g. of gutted adenoviral DNA) is confirmed. Confirmation may be performed by any method. For example, a restriction digestion may be performed on the TP-primer-viral DNA molecules followed by agarose gel electrophoresis (See FIG. 4A, and Example 3). Another example of a method that may be employed to confirm the successful addition of TP-primer to the origin of replication is determining if these molecules have increased specific activity of these molecules (e.g. Example 4).

Linking gutted viral DNA to adenoviral terminal protein (e.g. by attaching TP-primer) increased the yield of gutted virus produced in a gutted viral rescue procedure. In some embodiments, co-transfection of terminal protein linked gutted DNA with terminal protein DNA complex from helper virus results in an 85 fold increase in virus production, when compared to transfection/infection protocols using C7 cells without linking the gutted viral DNA to adenoviral terminal protein. In other embodiments, co-transfection of adenoviral terminal linked gutted and helper adenoviral DNA results in greater than a 2.5 fold increase in adenoviral production (e.g. 2.7 fold increase), compared to not linking either viral DNA to adenoviral terminal protein.

The replication-promoting agent may be adenoviral terminal protein. Viral DNA may also be linked to adenoviral preterminal protein. Any source of terminal or preterminal protein (e.g. natural or synthetic) from any type of adenovirus (e.g. Ad5 and Ad2). The terminal protein or preterminal protein may be made synthetically by, for example, transfecting cells with an expression vector (e.g. plasmid) with a gene sequence encoding a least a portion of adenoviral terminal, or preterminal, protein. Examples of such nucleic acid sequences that may be express in such a recombinant fashion include, but are not limited to, SEQ ID NO:18 (Ad2 terminal protein, FIG. 18) and SEQ ID NO:20 (Ad5 terminal protein, FIG. 18). Examples of preterminal protein nucleic acid sequences include, but are not limited to, SEQ ID NO:17 (Ad2 preterminal protein, FIG. 18) and SEQ ID NO:19 (Ad5 preterminal protein). The sequences, or portions thereof, may linked to viral DNA as described above. The present invention also contemplates other replication promoting agents, including lipids, other proteins, carbohydrates, and nucleic acids, as long as they are capable of promoting the replication of viral DNA when linked to the origin of the viral DNA.

Another method for creating terminal protein-linked viral DNA is by the use of Cre recombinase to transfer a segment of DNA linked to terminal protein. For example, gutted viral plasmid DNA containing a loxP site near at least one terminus is incubated with terminal protein-DNA complex from a helper virus whose genome contains a loxP site. Cre is then added to the reaction to facilitate intermolecular exchange.

The present invention contemplates terminal protein linked gutted adenoviral DNA that is transfected with helper viral DNA that is either linked to terminal protein (e.g. natural adenoviral DNA), or not linked to helper viral DNA (e.g. deproteinized helper viral DNA). For example, terminal protein linked gutted viral DNA may be used in conjunction with adenovirus (e.g. transfection/infection protocol), deproteinized viral DNA or terminal transferase treated (see below) helper viral DNA. In some embodiments, the helper virus does not contain terminal protein. In other embodiments, the helper virus does not contain terminal protein and is used at a higher concentration than the gutted viral DNA. These sequence may also be mutated (e.g. directed evolution) to increase their ability to promote replication (See, e.g. U.S. Pat. No. 5,811,238, hereby incorporated by reference).

III. Template Strand Extended Adenoviral DNA

Figure 5:
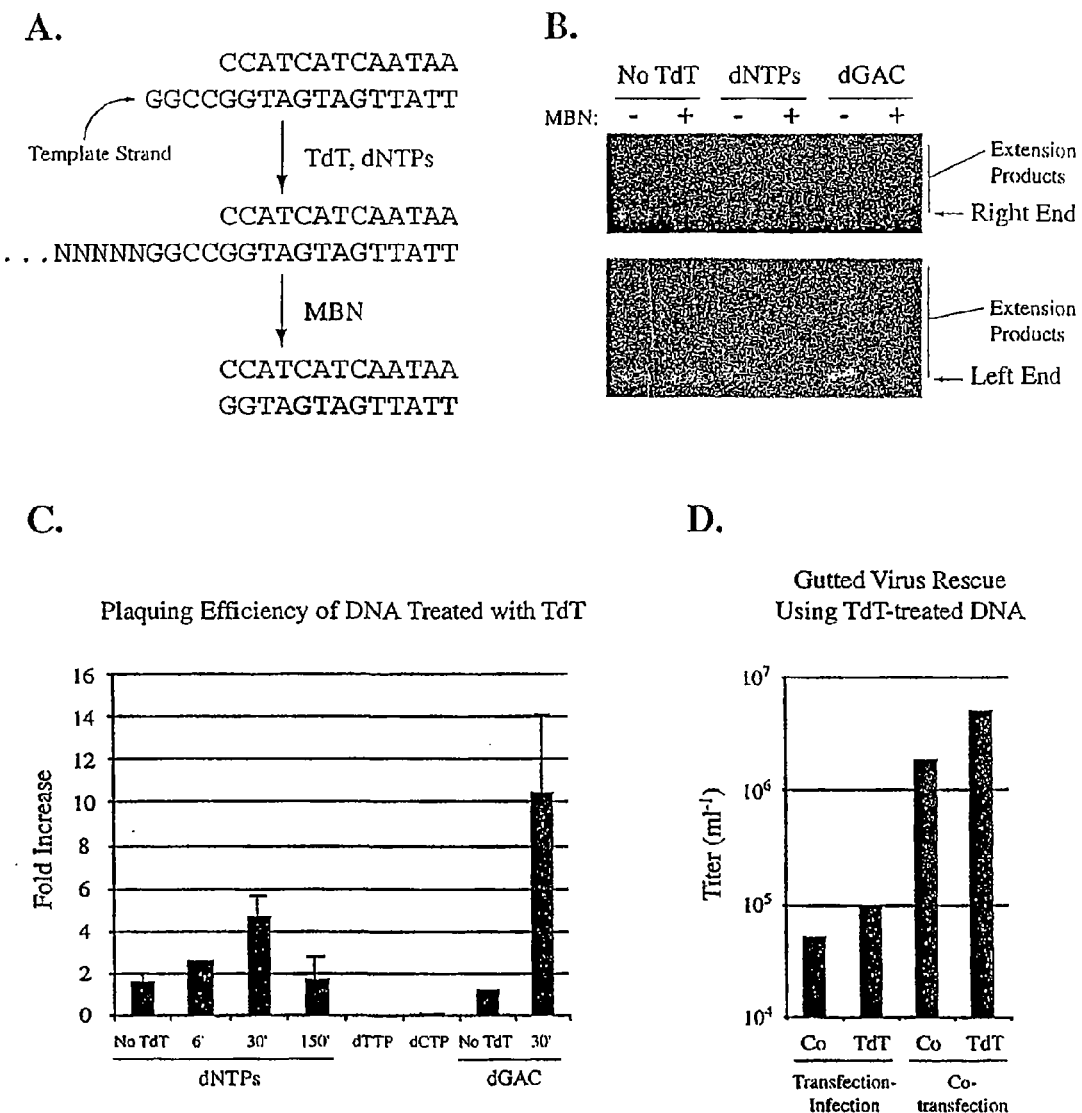
FIG. 5 (SEQ ID NOS:31-34) shows limited extension of template strand of the Ad origin increases plaquing efficiency and gutted virus recovery.

The present invention provides a further method for increasing gutted virus production (and recovery), as well as methods for increasing the plaquing efficiency of adenoviral DNA after transfection into cells. In particular, limited extension of adenoviral DNA termini (e.g. gutted adenoviral termini) increases plaquing efficiency (e.g. approximately 10 fold increase in efficiency, see Example 5 and FIG. 5) as well as increasing gutted virus recovery (e.g. an increase of 2.5 fold gutted viral recovery).

In preferred embodiments, the terminus of an adenoviral DNA is extended for a time sufficient to allow increased plaquing efficiency and/or gutted virus recovery. As demonstrated in Example 5, various time points may be tested to determine the appropriate limited template extension (e.g. in Example 5, approximately 30 minutes of extension in the presence of terminal transferase was optimal, with 6 minutes being less than optimal and 150 minutes being worse than no template extension). In some embodiments, adenoviral template DNA is extended from approximately 6 minutes to approximately 100 minutes. In preferred embodiments, the adenoviral DNA is extended for approximately 20 minutes to approximately 40 minutes. In particularly preferred embodiments, the adenoviral DNA is extended for approximately 30 minutes (e.g. 25-35 minutes). The time required to achieve a successful limited extension may be determined empirically employing methods similar to Example 5 and will vary depending on the conditions used (e.g. extending enzymes employed, concentrations of dNTPs, etc.).

Any type of enzyme capable of extending viral template DNA may be employed. For example, Taq polymerase, T4 polymerase, T4 DNA or RNA ligase, or terminal transferase may be used. In preferred embodiments, terminal transferase is employed. In some embodiments, the viral template DNA sequence is linearized by digesting with restriction enzyme(s) before template strand extension.

Template strand extension of viral DNA templates (e.g. gutted adenoviral DNA) employs molecule(s) capable of adding deoxyribonucleotide triphosphates (dNTPs) to the viral template DNA. In some embodiments, all four dNTPs are provided in the reaction mixture (i.e. guanine, cytosine, adenine, thymine). In other embodiments, only two or three of the dNTPs are provided (e.g. guanine and adenine, or guanine, adenine, and cytosine). In preferred embodiments, only guanine, adenine, and cytosine are supplied to the reaction mixture (i.e. not thymine).

Limited template extension of viral DNA increases plaquing efficiency and gutted virus recovery. In certain embodiments, the plaquing efficiency is increased two fold (i.e. the plaquing efficiency is double compared to controls that do not have limited extension of the template DNA). In preferred embodiments, the plaquing efficiency is more than doubled (e.g. 3 fold, 4 fold, and 5 fold increased efficiency). In particularly preferred embodiments, the plaquing efficiency is increased approximately 10 fold. In some embodiments, the recovery of gutted virus is increased two fold. In preferred embodiments, the recovery of gutted virus is increased more than two fold (e.g. 2.5 fold). In some embodiments, template extended gutted viral DNA is transfected into cells, followed later by infection by helper virus (i.e. a transfection/infection protocol is employed). In preferred embodiments, helper and gutted viral DNA are co-transfected into cells (See Example 5, and FIG. 5D).

Extensions of viral DNA may also be accomplished by ligating various length oligos to the viral origin (i.e. ligation of oligonucleotides is employed instead of or in addition to the methods described above). For example, T4 DNA ligase may be used to ligate various oligonucleotides (e.g. ranging from 2-100 base pairs in length, and mixtures of various lengths) to viral origins in order to increase the activity of these origins. Again, assays may be employed to determine the optimal length of oligonucleotides to employ and the amount of time ligation is allowed to proceed.

IV. Culturing Gutted and Helper Adenoviruses

Methods and compositions are also provided by the present invention to increase viral recovery. In particular, improved selection strategies are provided (particularly well suited for gutted and helper adenoviral DNA with identical or similar termini). The present invention also provides cells lines expressing protein IX (and methods for allowing cells to express factor IX) to increase viral recovery.

A. Regulated Expression of Site-Specific Recombinases

Site-specific recombinases have been used to reduce helper contamination and improve gutted virus titer during serial passage. In these systems, the packaging element of the helper virus is flanked by recognition sites for site-specific recombinases like Cre or Flp. In these systems, the yield of gutted virus after rescue from plasmid is low, so improvement in gutted virus titer during serial passage is paramount. Use of a site-specific recombinase improves gutted virus titer by improving the gutted:helper ratio after lysis of a plate, so that a higher percentage of particles produced contain gutted viral genomes. This method results in a higher gutted virus titer at the following passage, since each infected cell contains a higher proportion of gutted genomes.

Such systems are typically designed for infection of each producer cell by at least one helper virus particle. This protocol typically allows for complete lysis of the plate despite the action of recombinase, which acts to prevent packaging and spread of helper virus, but does not prevent death of infected cells. In these systems, high-level production of the site-specific recombinase is desirable. Since each cell is infected by helper virus, viral spread is not necessary; higher production of recombinase leads to lower contamination with helper virus but does not compromise gutted virus production.

As described above, gutted virus rescue is most efficient when gutted and helper viral genomes with identical origin structure are co-transfected into producer cells (see also, Example 2). Employing gutted and helper viral genomes with identical (or similar) origin structure, however, a smaller fraction of transfected cells convert the helper virus DNA into replicating virus. This fact is confirmed by the observation that lysis of transfected plates takes about a week, although the time for a single round of viral replication is on the order of 24 hours. Virus produced by those few cells that converted transfected DNA to replicating virus must spread through the plate before complete lysis occurs. Under these conditions, constitutive, high-level expression of recombinase is not appropriate (See Example 6). In the presence of high levels of recombinase, the few cells that can produce virus produce very little, which often is not sufficient to lyse the plate, typically a requirement for high titers of gutted virus.

Regulated expression of site specific recombinase is provided by the present invention in order to take advantage of the beneficial activity of site specific recombinases, yet avoid the detrimental results evidenced in cells expressing site specific recombinase constitutively. Site specific recombinase may be regulated in time, with minimal to no expression at early times after transfection and high expression at later time points. While not limited to any mechanism, it is believed that the expression of a site-specific recombinase is detrimental at early times after transfection, when transfected helper genomes are being converted to replicating virus, thus providing helper particles that should spread through the plate. At later time points, however, when helper and gutted virus particles are replicating in tandem, expression of site-specific recombinase could increase the proportion of viral particles that contain gutted genomes, thereby assisting in gutted virus recovery. One example of providing such temporal expression employs co-transfection of site specific expression vectors (e.g. Cre recombinase expression vector) with viral genomes (e.g. gutted and helper viral genomes with identical origins of replication) (See Example 6). In this manner, transfected cells are not expressing Cre at the time of transfection, and after transfection, some time will pass before the appearance of the first molecules of Cre protein, since RNA and then protein must be synthesized. Finally, the level of Cre will increase to some equilibrium level on a time scale that depends on the half life of the RNA, the half life of the protein, and the strength of the promoter used to drive Cre recombinase expression.

The amount of the recombinase expression vector employed will depend on many factors. Importantly, transfecting cells with a level of recombinase expression vector that is too high to allow the helper virus DNA to replicate at a high enough level to infect most of the cells, and lyse the plate is to be avoided (See Example 6, where 176 ng of pOG231 is less effective than providing no Cre at all). Likewise, transfecting cells with a level of recombinase expression vector that is too low to prevent the helper virus from dominating the type of virus being expressed is also to be avoided (See Example 6, where 1.41 ng of pOG231 was no more effective than providing no Cre at all). Determining the appropriate level of recombinase expression level to employ for a given type of cell type, recombinase, promoters employed, etc., is within the skill in the art. For example, a concentration type assay may be employed as exemplified in Example 6. As demonstrated in this example, various levels of recombinase expression vector may be tested to determine the optimal levels of starting recombinase expression vector that should be employed. Examples of appropriate levels of recombinase expression level are provided in Example 6 (for the types of conditions employed in this assay). For example, appropriate levels of pOG231, as determined in example 6 include approximately 5-37 ng of expression vector, preferably 7-36 ng of expression vector, more preferably 16-35 ng of expression vector. Of course, altering the type of vector, cells, conditions, etc., may change the appropriate level as described above.

B. Culturing Adenovirus in Cells Expressing Adenoviral Protein IX

In order to improve production, gutted and helper adenovirus are co-transfected in cells expressing adenoviral protein IX (pIX). The protein IX gene of the adenoviruses encodes a minor component of the outer adenoviral capsid which stabilizes the group-of-nine hexons which compose the majority of the viral capsid (See U.S. Pat. Nos. 5,932,210 and 5,824,544, hereby incorporated by reference). Based upon study of adenovirus deletion mutants, protein IX initially was thought to be a non-essential component of the adenovirus, although its absence was associated with greater heat lability than observed with wild-type virus. More recently it was discovered that protein IX is essential for packaging full length viral DNA into capsids and that in the absence of protein IX, only genomes at least 1 kb smaller than wild-type could be propagated as recombinant viruses.

In one embodiment, an expression vector encoding protein IX is co-transfected with the gutted and helper adenovirus. In some embodiments, gutted and helper adenovirus are transfected in a cell line that expresses adenoviral protein IX. In preferred embodiments, the cell stably and constitutively expresses adenoviral protein IX. In particularly preferred embodiments, the cell line also expresses E2B proteins. One example of a cell line expressing E2B proteins (adenoviral DNA polymerase and preterminal protein) is the C7 cell line (See, U.S. Pat. No. 6,083,750). Creating a cell line that stably and constitutively expresses adenoviral protein IX, in addition to adenoviral DNA polymerase and preterminal protein, may be accomplished, for example by stably transfecting C7 cells (or other cells expressing E2B proteins) with a vector expressing adenoviral protein IX (See Example 7, creating the D2104#10 cell line).

Additional cell lines that stably and constitutively expresses adenoviral protein IX, in addition to adenoviral DNA polymerase and preterminal protein are contemplated. For example, any type of cell known to effectively allow adenoviral replication may be transfected with an expression vector encoding adenoviral protein IX (preferably with a selectable marker). Preferably, the cells also express preterminal protein and adenoviral DNA polymerase. Transfected cells may be grown on selective media. Clones are then screened for expression by transfection with an adenoviral protein IX negative genome, and clones producing virus after transfection are isolated.

V. Heterologous Gene Sequences

As described above, the present invention is useful for the production of adenoviral vectors (e.g. helper-dependent adenoviral vectors). The adenoviral vectors produced, in preferred embodiments, comprise a heterologous gene sequence, such that the vectors may be useful for various applications (protein expression in vitro, therapeutic applications, etc). Suitable heterologous DNA sequences include, for example, nucleic acid sequences that encode a protein that is defective or missing in a recipient subject, or a heterologous gene that encodes a protein having a desired biological or therapeutic effect (e.g. an antibacterial, antiviral, or antitumor function). Other suitable heterologous nucleic acids include, but are not limited to, those encoding for proteins used for the treatment of endocrine, metaloic, hematologic, cardiovascular, neurologic, musculoskeletal, urologic, pulmonary, and immune disorders, including such disorders as inflammatory diseases, autoimmune disease, chronic and infectious diseases, such as AIDS, cancer, hypercholestemia, insulin disorders such as diabetes, growth disorders, various blood disorders including various enemias, thalassemias, and hemophilia; genetic defects such as cystic fibrosis, Gaucher's disease, Hurler's disease, adenosine deaminase (ADA) deficiency, and emphysema.

The therapeutic or diagnostic nucleic acid sequence, in some embodiments, will code for a protein antigen. The antigen may include a native protein or protein fragment, or a synthetic protein or protein fragment or peptide. Examples of antigens include, but are not limited to, those that are capable of eliciting an immune response against viral or bacterial hepatitis, influenza, diphtheria, tetanus, pertussis, measles, mumps, rubella, polio, pneumococcus, herpes, respiratory syncytial virus, hemophilus influenza type b, chlamydia, varicella-zoster virus or rabies. The nucleic acid sequence may also be a normal muscle gene that is effected in a muscle disease (e.g. muscular dystrophies like Duchenne muscular dystrophy, limb-girdle muscular dystrophy, Landouzy-Dejerine muscular dystrophy, Becker's muscular dystrophy, ocular myopathy, and myotonic muscular dystrophy). For such muscular dystrophies, the nucleic acid may be a heterologous gene encoding the full length dystrophin gene (or cDNA sequence), BMD-minigene, ΔH2-R19 minigene, Laminin-α2, utrophin, α-sarcoglycan, and emerin. BMD mini-gene refers to dystrophin cDNAs containing internal truncations corresponding to specific exons of the gene, in particular, a deletion of the sequences encoded on exons 17-48 [Amalfitano et al., in Lucy J, and Brown S. (eds): Dystrophin: Gene, Protein, and Cell Biology (Cambridge University Press, 1997), Chpt. 1, 1-26, herein incorporated by reference]. ΔH2-R19 refers to a specific dystrophin cDNA containing internal deletions corresponding to specific functional domains of the gene, in particular, a deletion of the sequences that encode 'hinge 2' through 'spectrin-like repeat' 19 [See Amalfitano et al.].

Nucleic acid sequences may also be antisense molecules (e.g. for blocking the expression of an abnormal muscle gene). The nucleic acid sequence may also code for proteins that circulate in mammalian blood or lymphatic systems. Examples of circulating proteins include, but are not limited to, insulin, peptide hormones, hemoglobin, growth factors, liver enzymes, clotting factors and enzymes, complement factors, cytokines, tissue necrosis factor and erythropoietin. Heterologous genes may also include gene encoding proteins that are to be produced (e.g. commercially produced) in muscle cells in vitro or in vivo. For example, the improved expressions systems of the present invention may be applied to preexisting, working muscle expression systems to improve the level of expression of protein product from a gene of interest. The present invention also contemplates employing any gene of interest (heterologous or endogenous).

VI. Using Adenoviral Vectors

The adenoviral vectors produced as described above may be used, for example, in drug screen or in gene therapy methods. In one screening method, an adenoviral vector (e.g. helper-dependent adenoviral vector, produced according to the above methods) contain adenoviral DNA operably linked to a heterologous gene encoding an factor (e.g. enzyme, protein, antisense molecule) with a known function (e.g. alcohol dehydrogenase), is contacted in vitro with a tissue culture sample (e.g. a muscle cell containing tissue culture) such that the heterologous gene is expressed. A candidate compound is added along with a substrate for the enzyme (e.g. ethanol), and a parallel assay is run without the candidate compound. The level of enzyme activity is detected (e.g. amount of substrate remaining over time) in each assay. The results of both assays are compared in order to determine the affect of the candidate compound on the activity of the enzyme. In other embodiments, the candidate compound many comprise a factor suspected of altering gene expression of the heterologous gene and the assay detects that degree and/or ability of the candidate compound to reduce the activity of the expressed factor. One of ordinary skill in the art will appreciate that many other screening methods can be used. The adenoviral vectors may also be used advantageously in gene therapy to replace a defective gene in subject with a heterologous gene.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); Sigma (Sigma Chemical Co., St. Louis, Mo.); and

EXAMPLE 1

Generating Gutted and Helper Virus with Identical Termini

This example describes the deletion of internal FseI sites in the nucleic acid sequence of an Ad5-based helper virus, and insertion of this nucleic acid sequence into a plasmid such that it is removable with FseI.

The FseI recognition sequence, "GGCCGGCC", contains cytosine residues and can be arranged to overlap with the first nucleotide of viral DNA so that only one additional base pair is attached to viral DNA removed from plasmid vectors with this enzyme (FIG. 1A). In addition, FseI is rare in cloning vector polylinkers and mammalian sequences, so it is ideal for removal of gutted viral genomes from plasmid vectors. FseI has been used previously for linearization of viral shuttle vectors, which contain a portion of the Ad genome; however, it could not be used to liberate the entire Ad5 genome from plasmid DNA, because the Ad5 genome contains two FseI sites.

Figure 10:
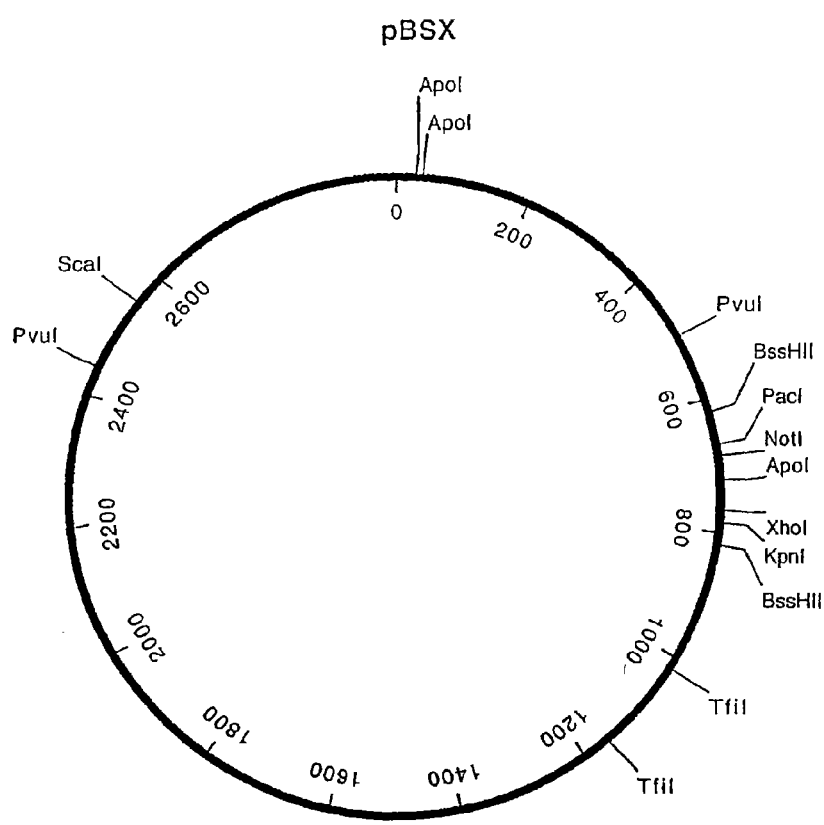
FIG. 10 show a restriction map of pBSX.

In order to remove the FseI sites in the (+)lox(+)pol helper virus DNA sequence (SEQ ID NO:1), mutations were created that destroy both FseI sites while maintaining the ability of the virus to replicate (transitions were made at nucleotides 12587 and 17756, creating SEQ ID NO:9, FIG. 11, see also FIG. 1B). The mutation at nucleotide 12587 was chosen so as to preserve the amino acid sequence of capsid protein IIIa. Primers 9252I, CGGAATTCGGATCCAGCGACCGC-GAGCTGAT (SEQ ID NO:2) and 9253I, CGGAATTCAGC-CGGCTTCGTCGGGCCGGATGGC (SEQ ID NO:3) were used in a PCR reaction to simultaneously amplify approximately 540 base pairs of the Ad5 sequence, to introduce the G to A transition at nucleotide 12587, and to flank the resulting DNA sequence with EcoRI sites. The product was digested with EcoRI and ligated to the large, approximately 2.2 kb ApoI fragment of pBSX (pBSX—SEQ ID NO:12, FIG. 9, which is a minor modification of a Bluescript vector, with alterations to the polylinker sequence, See FIG. 10) to yield pD1858#7. Primers 9254I, CGCGGATCCGCCGGCTACG-GCCTGACGGGCGG (SEQ ID NO:4) and 9255I, CGGAATTCACACACATACGACACGTTAG (SEQ ID NO:5) were used to amplify approximately 1 kb of Ad5 sequence, to introduce the C to T transition at nucleotide 17756, and to append an EcoRI site to the rightmost end of the resulting DNA fragment. The product was digested with EcoRI and NgoMI, then ligated to EcoRI-, NgoMI-digested pD1858#7 to yield pD1863#4. This plasmid was digested with NgoMI and ligated to the 5162-bp NgoMI fragment from the Ad5 genome, resulting in pD1866#17, which contains both transitions mentioned above. To create a virus lacking FseI sites, pD1866#17 was digested with EcoRI and co-transfected with FseI-digested terminal protein-DNA complex from (+)lox(+)pol Ecd-AP helper virus. The sequence for (+)lox(+)pol Ecd-AP is SEQ ID NO:1, FIG. 8. After one week of incubation, the transfected cells showed evidence of viral cytopathic effect, indicating that they contained replicating virus, designated ΔFseI.4 (SEQ ID NO:9, FIG. 1B). The DNA was extracted from these cells by Hirt prep (DNA episomal extraction method employing lysis in 0.6% SDS/10 mM EDTA, followed by addition of salt, incubation at 4° C., and centrifugation to remove contaminants, Hirt, B., *J. Mol. Biol.* 26:365 [1967]) and shown not to contain FseI sites by restriction digest.

To confirm that FseI could be used to release replication-competent viral DNA from flanking DNA sequences, ΔFseI.4 genomic DNA was cloned into a plasmid vector, where it was flanked by FseI sites (FIG. 1C). Primers 8270I, CGGAAT-TCGGCCGGCCATCATCAATAATATAC (SEQ ID NO:6) and 8274I, CGGTCGATTCAATTGCTGGCAAGCTTCG-GCCCTAGACAAATAT (SEQ ID NO:7) were used in a PCR reaction to amplify approximately 400 bp from the left end of (+)lox(+)pol Ecd-AP helper virus and to introduce flanking restriction sites: EcoRI and FseI at the left end of the fragment and HindIII, MfeI, and TfiI at the right end. The product was digested with EcoRI and TfiI and cloned into the 1.86 kb ApoI/TfiI fragment of pBSX (See, FIG. 9), generating pD1812#1. Primers 8270I (SEQ ID NO:6) and 8273I, CTAT-GCTAACCAGCGTAGC (SEQ ID NO:8) were used to amplify approximately 1 kb from the right end of (+)lox(+) pol Ecd-AP helper virus and to add FseI and EcoRI sites at the right end of the fragment. The product was digested with HindIII and EcoRI and cloned into HindIII-, MfeI-digested pD1812#1, generating pD1821#8. To clone ΔFseI.4 viral genomic DNA into pD1821#8, the plasmid was digested with HindIII and recombined with ΔFseI.4 Hirt prep DNA in BJ5183 bacterial cells (BJ5183 bacterial cells, see Hanahan, D., *J. Mol. Biol.*, 166:557 [1983]). The resulting plasmids, including pD1940#3 and pD1940#6, were shown by restriction digest to contain the entire ΔFseI.4 genome flanked by FseI sites (FIG. 1C). No internal FseI sites were detected, confirming that virus ΔFseI.4 contains mutations that destroy these sites.

To show that FseI digestion could release replication-competent Ad DNA from plasmids, pD1940#3 and pD1940#6 were digested with FseI and transfected into C7 cells (C7 cells express both Ad DNA polymerase and preterminal protein, see U.S. Pat. No. 6,083,750, hereby incorporated by reference). Plasmid pFG140 [See, Graham, F. L., *The EMBO J.*, 3:2917 (1984)] known to produce replicating adenovirus after transfection, was used as a control. Both sets of transfected cells were overlaid with agarose after transfection and stained with neutral red 10 days after overlay. It was determined that FseI-digested pD1940#3 and pD1940#6 produced 36 and 56 plaques per microgram, respectively; pFG140 produced 38 plaques per microgram. This result indicates that mutation of internal FseI sites did not prevent replication of adenovirus and that FseI is an appropriate enzyme for release of viral DNA from plasmids.

EXAMPLE 2

Figure 2:
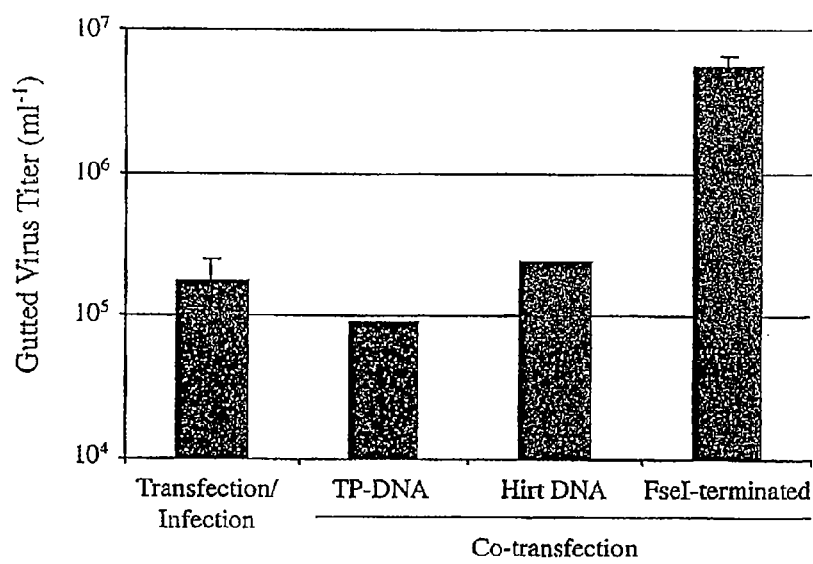
FIG. 2 shows improved gutted virus rescue that is achieved by co-transfection of matching plasmid-derived gutted and helper virus DNAs.
Figure 12:
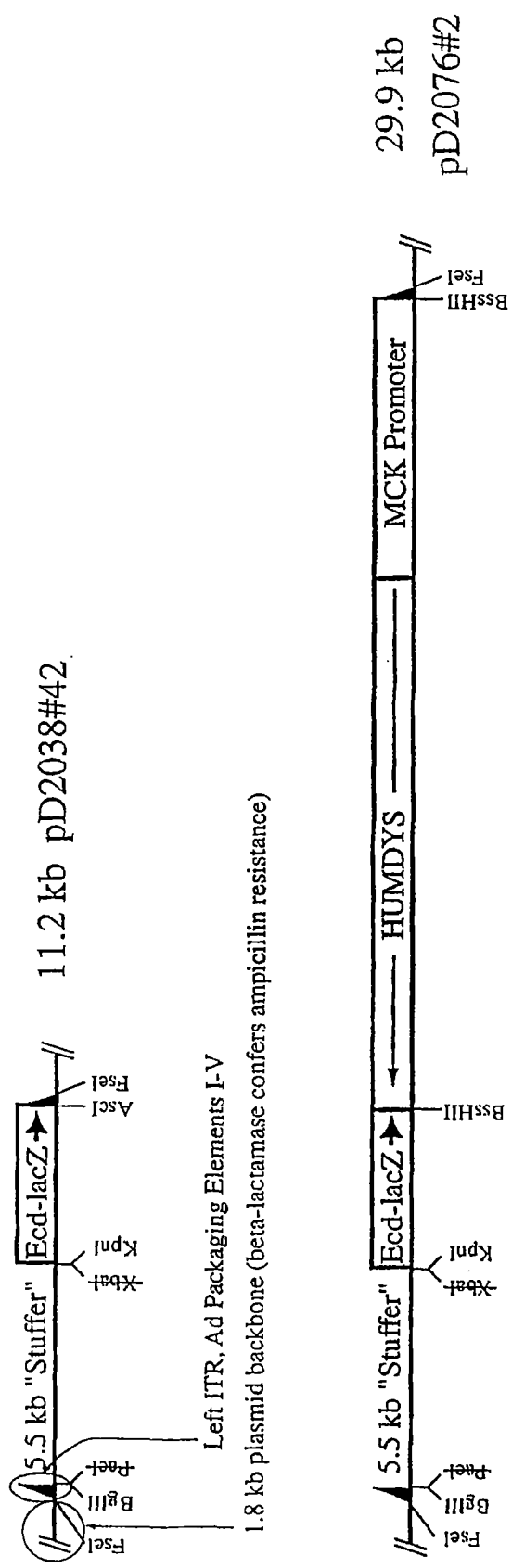
FIG. 12 shows pD2076#2.

Rescue of Helper-Dependent Ad Vectors Using Plasmid-Derived Substrates With Corresponding Termini This example describes the rescue of helper-dependent Ad vectors using plasmid-derived substrates with corresponding termini. To demonstrate that efficient gutted virus rescue depends on the relative specific activities of gutted and helper viral DNA, a FseI-terminated gutted virus was co-transfected with various forms of helper virus DNA or transfection/infection was performed (FIG. 2). The gutted adenovirus DNA employed was pD2076#2, which contains a gutted Ad genome flanked by FseI recognition sites and carries an inducible beta-galactosidase expression cassette (FIG. 12). This plasmid was digested with FseI, and 4.4 micrograms of digested DNA were transfected into C7 cells.

For co-transfection assays, 4.4. micrograms of helper viral DNA (either TP-DNA, Hirt DNA, or FseI-terminated DNA) were co-transfected with pD2076#2 DNA. For transfection/infection, helper virus particles were added immediately following transfection at an MOI of 10 transducing units per cell. For the TP-DNA complex co-transfection, terminal protein-DNA complex was isolated from (+)lox(+)pol helper virus (SEQ ID NO:1) was isolated and transfected into cells to provide helper activity (FIG. 13). For the Hirt DNA samples, ΔFseI.4 DNA (SEQ ID NO:9) was isolated from infected cells and deproteinized (FIG. 13). For FseI-terminated samples, pD1940#3 or pD1940#6 (See FIG. 13) was digested with FseI and the released DNA was used to provide helper activity (SEQ ID NO:13, FIG. 14). Digestion with FseI releases what is essentially ΔFseI.4 (SEQ ID NO:9), except with a couple of extra nucleotides at the end (as shown in FIG. 1).

Transfection/infection was found to be very inefficient (See FIG. 2), although it is the method most frequently reported in the literature. In co-transfections, an inverse correlation was observed between the specific activity of the helper virus DNA from and the yield of gutted virus produced. Co-transfection of gutted viral DNA with plasmid-derived helper viral DNA, carrying a physically identical origin of replication (constructed as described in Example 1), was by far the most efficient method for rescue of gutted adenovirus (See, FIG. 2). After co-transfection of plasmid-derived, FseI-terminated genomes, the average gutted viral titer observed was $5.6 \times 10^6$ ml$^{-1}$. This yield represents an improvement of approximately 30 fold over typical titers obtained by transfection/infection into C7 cells and 300 fold over typical titers obtained by transfection/infection into 293 cells.

EXAMPLE 3

Conversion of Plasmid-Derived Viral Replication Origins to Natural, Terminal Protein-Linked Origins.

This example describes the conversion of plasmid derived viral replication origins to natural, terminal protein-linked origins. This conversion employs "TP-primer", which is terminal protein DNA linked to single-stranded DNA from the non-template strand of an Ad ITR (FIG. 3A). TP Primer was prepared in the following manner. Terminal protein-DNA complex prepared from (+)lox(+)pol Ecd-AP virus was digested for at least 16 hours at 37° C. with 2.5 U/µg Bsh1236I, 1.33 U/µg AluI, and 0.69 U/µg HinfI. Bsh1236I cuts between base pairs 73 and 74 of the Ad5 ITR (CATCAT-CAATAATATACCTTATTTTGGAT-TGAAGCCAATATGATAATGAGGG GGTGGAGTTTGT-GACGTGGCGCGGGGCGTGGGAACGGGGCGGGTGA-CGTAG, SEQ ID NO:10), so this digestion results in terminal protein linked to a 73-bp, double-stranded DNA molecule (one of the two strands is as follows, CATCAT-CAATAATATACCTTATTTTGGAT-TGAAGCCAATATGATAATGAGGG GGTGGAGTTTGT-GACGTGGCG, SEQ ID NO:11). The products of restriction digestion were then treated with 2.5 U/µg DNA of lambda exonuclease for 20 minutes at 37° C. This enzyme catalyzes the removal of 5' mononucleotides from duplex DNA. Since the enzyme acts in a 5' to 3' direction, strands linked to terminal protein are not degraded; all other strands are degraded until a single-stranded region is reached.

The products of this digestion, therefore, include: 1) terminal protein linked to 73 unpaired bases (SEQ ID NO:11) of the non-template strand of the Ad5 ITR (TP-primer); 2) many random, small, single-stranded DNA molecules resulting from the degradation of approximately half of the restriction fragments present in the reaction; and 3) mononucleotides. The first of these is the desired and useful product; however, the other products do not interfere with subsequent steps. The enzymes in the reaction were then inactivated by incubation at 75° C. for 20 minutes.

TP-primer was then used to convert plasmid-derived gutted viral genomes to natural Ad origins by the following method (FIG. 3B). First, a plasmid containing gutted viral genomic DNA (pD2076#2), flanked by FseI sites, was digested with PseI to release gutted viral DNA. The products were subjected to very limited digestion with T7 gene 6 exonuclease (0.76 U/µg for 1 minute, 40 seconds) and the exonuclease was inactivated by incubation at 80° C. for 15 minutes. T7 gene 6 exonuclease, like lambda exonuclease, is a 5' to 3' exonuclease, so limited digestion with this enzyme exposes single-stranded regions near the gutted vector genomic termini. These regions are complementary to the single-stranded DNA found in the TP-primer reagent. Due to the long (73 bp) stretch of complementary DNA sequence and the absence of competing binding partners, the TP-primer reagent can bind efficiently to T7 gene 6-digested gutted DNA even at low molar ratios.

We added TP-primer reagent, prepared as described above, to the digested gutted DNA, raised the temperature of the mixture to 75° C., and allowed the temperature to fall slowly (over 2-3 hours) to room temperature. Hybridized TP-primer molecules were then extended using T4 DNA polymerase and nicks were repaired using T4 DNA ligase. This was accomplished by addition of 0.5 mM each dNTP, 1 mM ATP, 2.5 units T4 polymerase per μg DNA, and 2 Weiss units T4 ligase per μg DNA. A small amount of buffer (10 mM Tris-HCl, 10 mM MgCl$_2$, 50 mM NaCl, and 1 mM DTT, pH 7.9 at 25C) was also added such that the final concentration of gutted vector genomic DNA was 0.04 μg/μL when a 2:1 (TP-primer: gutted genome) ratio was used or 0.029 μg/μL when a 4:1 ratio was used. The reaction was then incubated for 5 minutes at 0° C., 5 minutes at room temperature, and 2 hours at 37° C. EDTA was added to a final concentration of 15 mM and the reaction was stored on ice.

An assay was performed to confirm the successful addition of terminal protein to the origin of replication of the gutted virus. Specifically, a restriction digest employing NotI was performed on circular pD2076#2, the TP-primer linked pD2076#2 (FseI digested), and FseI digested pD2076#2 (negative control). This digestion was followed by agarose gel electrophoresis (FIG. 4A). The results confirmed the successful addition of the TP-primer as approximately two-thirds of the gutted DNA terminal fragments were retained in the wells of the agarose gel, behavior that is typical of protein-linked DNA (FIG. 4A).

EXAMPLE 4

TP-Primer Increases the Specific Activity of Plasmid-Derived Ad DNA

This example describes the ability of TP-primer to increase the specific activity of plasmid derived Ad DNA. In particular, replication-competent helper virus genomes were excised from plasmids pD1940#3 or pD1940#6 and the origins of DNA replication were modified as described above (See Example 3, adding TP-primer to Ad DNA). Reaction mixtures were then diluted into 0.1× TE such that transfection mixtures contained either one microgram or 0.1 micrograms of modified plasmid DNA. Parallel transfection mixtures were prepared using unmodified FseI-digested pD1940 plasmid (SEQ ID NO:13, FIG. 14). The DNA was co-precipitated with calcium phosphate, and added to plates of C7 cells. Plates were washed 16 hours after addition of precipitates and overlayed with noble agar (See, Graham, F. L. and Prevec, L. *Manipulation of Adenovirus Vectors in Gene Transfer and Expression Protocols*, Clifton: The Humana Press, Inc., 1991). Eight to ten days after overlay, the plates were stained with neutral red and plaques were counted. Specific activity was calculated as the number of plaques observed divided by the weight of transfected DNA.

It was found that the specific activity of treated genomes was increased by an average of 24 or 27 fold after treatment with a 2:1 or 4:1 molar ratio of TP-primer, respectively. We also examined the effect of TP-primer treatment on the rescue of gutted Ad vectors from their plasmid-derived precursors. For these experiments, since large amounts of DNA were transfected, reaction mixtures were dialyzed against 1× HBS to avoid dilution. Conversion of gutted vector origins to natural, TP-linked form resulted in improved competition with helper virus DNA (FIG. 4B). Strikingly, co-transfection of TP-gutted DNA and untreated, FseI-terminated helper virus DNA prevented lysis of the transfected cells, indicating that the specific activity of TP-gutted DNA is high enough to prevent robust helper replication.

Co-transfection of TP-gutted DNA with terminal protein-DNA complex from helper virus resulted in an average gutted viral titer of 1.5×10$^7$ per ml. This titer represents an improvement of approximately 85 fold over typical titers obtained by transfection/infection into C7 cells, 850 fold over titers obtained by transfection/infection into 293 cells, and 2.7 fold over titers obtained by co-transfection of plasmid-derived, FseI-liberated gutted and helper genomes (See FIG. 4B).

EXAMPLE 5

Terminal Transferase Template Strand Extension of Adenoviral DNA

This example describes terminal transferase (TdT) template strand extension of adenoviral DNA, and how limited extensions increase the specific activity in plaque assays and allow for more efficient recovery of gutted adenovirus.

pD1940#3 or pD1940#6 viral DNA was digested to completion with FseI. The restriction enzyme reaction was diluted 3.125-fold into 1× TdT reaction buffer (Promega, Madison, Wis.) and supplemented with 80 micromolar dNTPs and 10 units TdT per picomole DNA termini. The reaction was mixed well, incubated for a variable length of time at 37° C., and the TdT was inactivated by incubation at 75° C. for 10 minutes. The reaction mixture was extracted with 0.5 volumes of phenol-chloroform and DNA was precipitated. Samples were resuspended in 0.1× TE and transfected into C7 cells using the calcium phosphate co-precipitation method.

To determine whether TdT treatment had improved the ability of viral DNA to replicate in cells, the specific activity of treated and untreated DNA in transfected cells was measured ('specific activity' was defined as the number of viral plaques observed per microgram of DNA transfected; higher specific activity indicates that a lesser weight of viral DNA must be transfected to produce actively replicating virus). The results of the this assay indicate that the specific activity of pD1940 DNA was increased by approximately 5 fold after 30 minutes of treatment but less so after 6 minutes or 2.5 hours (FIG. 5C). Control reactions lacking the TdT enzyme showed no evidence of increased plaquing efficiency (FIG. 5C).

To test whether the identity of added nucleotides is important for the observed effect, we supplemented individual TdT reactions with various single and mixed nucleotides. The various reactions were precipitated individually, transfected into cells, and developing viral plaques were counted after 7-10 days. The effectiveness of TdT treatment was found to vary with the identity of the nucleotides included in the reaction (FIG. 5C). It was determined that the addition of single nucleotides was not effective; in fact, addition of thymidine or cytosine residues alone markedly reduced plaquing efficiency. It was also determined that the most effective combination was addition of guanine, adenine, and cytosine (dGAC), which increased plaquing efficiency by approximately 10 fold (FIG. 5C and data not shown).

An assay was also conducted involving TdT treatment of gutted Ad virus, and rescue from bacterial plasmids. In this example, gutted Ad genomes excised from pD2076#2 with the restriction enzyme FseI were employed. These excised genomes were treated with the combination of guanine, adenine, and cytosine as described above. 8.8 micrograms of treated DNA were transfected into approximately 2 million C7 cells in a 60-mm plate. 16 hours later the cells were washed and then infected with 20 million transducing units of ΔFseI.4 helper virus (SEQ ID NO:9). Two to three days after this procedure, the plates displayed viral cytopathic effect and lysates were harvested. By measuring the titer of gutted virus in the recovered lysates, it was determined that TdT treatment of the gutted vector doubled the amount of gutted virus produced by the cells after rescue (FIG. 5D). By co-transfecting plasmid-derived helper and gutted DNAs, as described above, the baseline titer obtained without TdT treatment was increased (FIG. 5D). After treatment of gutted plasmid DNA with TdT, a further 2.5-fold increase in gutted virus titer was obtained (FIG. 5D).

EXAMPLE 6

Regulated Expression of Site-Specific Recombinase Improves Gutted Virus Rescue

This example describes the use of regulated expression of Cre recombinase to improve gutted virus rescue when gutted and helper virus with identical ends are co-transfected. Initially, the effect of constitutive expression of Cre recombinase in packing cells co-transfected with gutted and helper viruses with identical ends was examined. ΔFseI.4 helper virus (SEQ ID NO:9) is an E1-, E3-deleted virus that can be negatively selected using Cre recombinase and carries an alkaline phosphatase reporter gene in its E3 region. The packaging signal, which consists of packaging elements I-V, is flanked by loxP sites in direct repeat orientation, allowing removal of the packaging signal in the presence of Cre. The E1 region (map units 1-9.2) has been removed. The E3 region (map units 78.3-85.8) has also been removed and replaced with an expression cassette, oriented from left to right in the viral genome, that consists of the inducible ecdysone promoter, the coding region for human placental alkaline phosphatase, polyadenylation sequences from SV40, and approximately 2 kb of "stuffer" DNA derived from an intron of the human dystrophin gene. For these experiments, ΔFseI.4 genomes were released from pD1940#3 or pD1940#6 by digestion with FseI.

Figure 6:
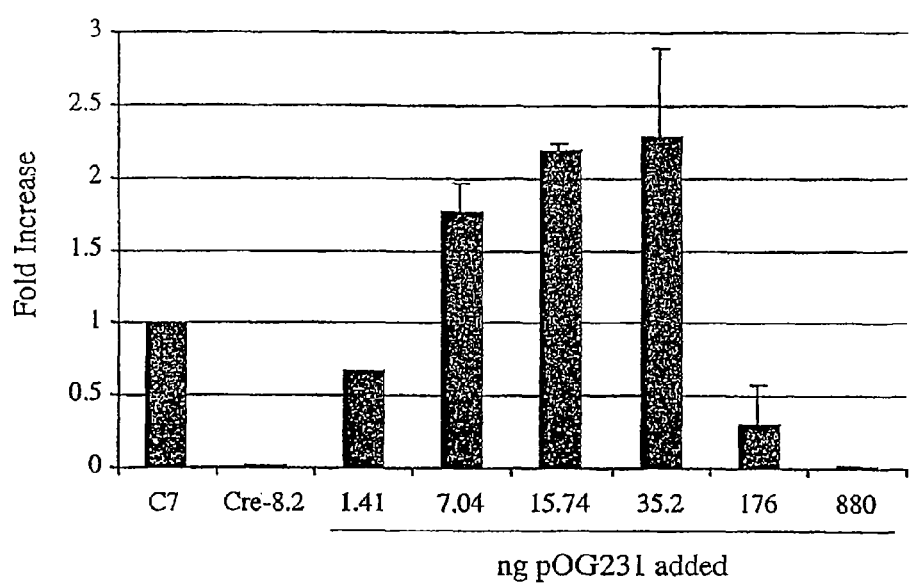
FIG. 6 shows that the regulated expression of Cre recombinase improves gutted virus recovery.

Specifically, FseI-terminated gutted and helper viral genomes were co-transfected into either C7 cells or C7-Cre-8.2 cells, which constitutively express Cre recombinase. The plate of transfected C7-Cre-8.2 cells showed no signs of lysis even after 12 days of incubation and the resulting titer of gutted virus was approximately 100 times lower than that observed in C7 cells (FIG. 6). This result indicates that when gutted and helper viral genomes with identical origin structures are co-transfected, constitutive expression Cre recombinase in the packaging cells is not desirable.

Cre recombinase, however, may still be employed to improve gutted virus recovery. Instead of constitutive expression of Cre recombinase, the recombinase expression is regulated over time. This was accomplished by co-transfection of a Cre recombinase expression vector (the level of Cre recombinase will increase gradually over time). Specifically, C7 cells were transfected with FseI-terminated gutted virus, FseI-terminated helper virus, and varying amounts of a Cre recombinase expression vector (pOG231). The results of this experiment show very low amounts of pOG231 had minimal effects on gutted virus production, with increasing amounts of pOG231, gutted virus production was improved (FIG. 6). The results also indicate that using the highest amounts of pOG231, little viral replication was observed and gutted virus titers were reduced (indicating that Cre protein levels increased to a level beyond which lysis could not proceed). Maximal improvement in gutted virus titers was observed using 16-35 ng of Cre expression vector, at which level average gutted titers more than doubled, to $1.3 \times 10^7$ ml-1 (FIG. 6). High levels of gutted virus were also observed using 7.04 ng of the Cre expression vector.

This selection strategy was also shown to be effective for gutted virus rescue from TdT-modified and TP-primer-modified genomes. For TdT-modified genomes, co-transfection with 35.2 ng Cre increased gutted virus production by an average of 3 fold. For TP-primer-modified genomes, use of 0.88 μg Cre approximately doubled gutted virus production, to $2.5 \times 10^7$ ml-1.

EXAMPLE 7

Generating An Adenoviral Protein IX Expressing Cell Line

Figure 16:
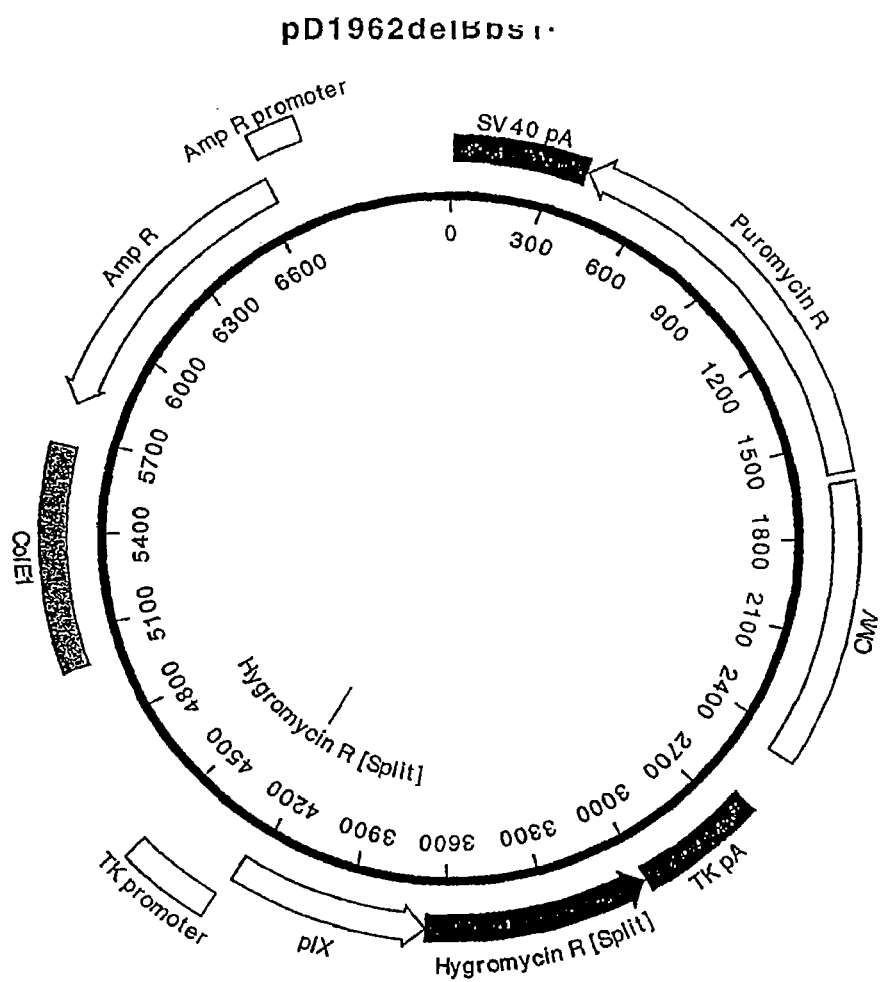
FIG. 16 shows a restriction map of pD1962delBsI.

This example describes the generation of a cell line expressing adenoviral protein IX (pIX), in addition to E2B proteins (adenoviral DNA polymerase and preterminal protein). C7 cells (that already express adenoviral DNA polymerase and preterminal protein) were transfected with PvuI-linearized pD1962delBbsI-pIX (SEQ ID NO:14, FIG. 15), a plasmid that contains expression cassettes directing expression of adenoviral protein IX and puromycin N-acetyl transferase (See FIG. 16). Positive clones were selected in the presence of 2 micrograms puromycin per milliliter of medium. Clones were screened for expression of pIX by transfection with FseI-digested HΔIX#3 (SEQ ID NO:15, FIG. 17), a plasmid that contains an E1-, E3-, and pIX-negative Ad genome of approximately 35.6 kb in size. Clone pD2104#10 produced virus after transfection with HΔIX#3.

Figure 7:
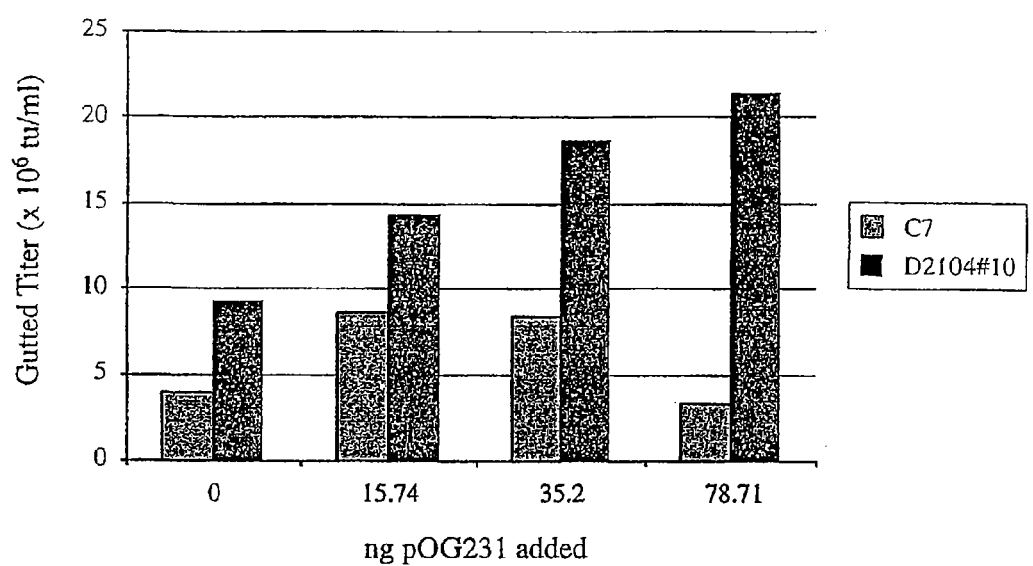
FIG. 7 shows the recovery of gutted virus in D2104#10 cells.

D2104#10 cells and C7 cells were then transfected with FseI-digested pD1940#6, which contains a pIX-positive Ad genome. The cells were then overlayed with agarose to allow for counting of plaques, each representing the successful conversion of a transfected genome to a replicating virus. It was determined that D2104#10 cells displayed three times as many plaques as C7 cells (FIG. 7). Additionally, plaques formed on D2104#10 cells were larger than those formed on C7 cells.

D2104#10 cells were then tested for the ability to rescue gutted virus from a plasmid-based precursor, either in the presence or absence of regulated Cre expression (FIG. 7). Plates of each cell type were transfected with FseI-terminated gutted and helper genomes at a 1:1 ratio, together with varying amounts (15.74 ng, 35.2 ng, and 78.71 ng) of the Cre expression plasmid pOG231. Plates of D2104#10 cells were found to lyse before plates of C7 cells that had been transfected under the same conditions, reflecting the higher proportion of transfected cells that initiated replication of the helper. The co-transfection of C7 cells in the presence of 79 ng of pOG231 failed to produce lysis even after 13 days, whereas D2104#10 cells lysed within 10 days. More gutted virus was produced in D2104#10 cells under all the conditions tested (FIG. 7). In the absence of Cre selection, D2104#10 cells produced twice as much virus as C7 cells. Examining the highest level of selection tested (79 ng), D2104#10 cells produced twice as much virus as C7 cells did under their highest selection conditions (16 ng).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

We claim:

1. A method for producing helper-dependent adenoviral vectors, wherein the method comprises:
   a) providing:
      i) a helper-dependent adenoviral DNA sequence comprising a first origin of replication operably linked to an adenoviral terminal protein sequence,
      ii) a helper adenoviral DNA sequence comprising a second origin of replication, wherein in a replication assay, the replication activity level of said second origin of replication comprises a 5 fold to 20 fold difference over the replication activity level of said first origin of replication, and
      iii) target cells, and
   b) transfecting said target cells with said helper-dependent adenoviral DNA sequence and said helper adenoviral DNA sequence under conditions such that the helper-dependent adenoviral vectors are produced.

2. The method of claim 1, wherein said helper-dependent adenoviral DNA sequence comprises a heterologous gene sequence.

3. The method of claim 1, wherein said first origin of replication and said second origin of replication have nucleic acid sequences that differ by no more than three bases.

4. The method of claim 1, wherein said terminal protein is selected from the group consisting of SEQ ID NOs: 18 and 20.

5. The method of claim 4, wherein said helper adenoviral DNA sequence comprises a crippling sequence.

6. The method of claim 4, wherein said helper adenoviral DNA sequence comprises recognition sites for site-specific recombinases.

7. The method of claim 6, further comprising: in a), providing iv) a second vector encoding a site-specific recombinase operably linked to an expression control sequence and wherein in step b) during the step of transfecting, further transfecting said target cells with said second vector.

8. The method of claim 7, further comprising recovering said helper-dependent adenoviral vectors.

9. The method of claim 8, wherein said helper-dependent adenoviral vectors have a first titer that is increased at least 20 fold over a second titer prepared using a transfection/infection method that comprises (1) transfecting said helper-dependent adenoviral DNA sequence into target cells expressing adenoviral DNA polymerase and preterminal protein, and (2) infecting said target cells with helper adenovirus.

10. The method of claim 4, wherein said target cells express adenoviral DNA polymerase and preterminal protein.

11. The method of claim 1, wherein said helper adenoviral DNA sequence comprises a crippling sequence.

12. The method of claim 1, wherein said helper adenoviral DNA sequence comprises recognition sites for site-specific recombinases.

13. The method of claim 12, further comprising: in a), providing iv) a second vector encoding a site-specific recombinase operably linked to an expression control sequence and wherein in step b) during the step of transfecting, further transfecting said target cells with said second vector.

14. The method of claim 13, further comprising recovering said helper-dependent adenoviral vectors.

15. The method of claim 14, wherein said helper-dependent adenoviral vectors have a first titer that is increased at least 20 fold over a second titer prepared using a transfection/infection method that comprises (1) transfecting said helper-dependent adenoviral DNA sequence into target cells expressing adenoviral DNA polymerase and preterminal protein, and (2) infecting said target cells with helper adenovirus.

16. The method of claim 1, wherein said target cells express adenoviral DNA polymerase and preterminal protein.

17. An isolated host cell comprising:
   a) a helper-dependent adenoviral DNA sequence comprising a first origin of replication, wherein said DNA sequence is linked to an adenoviral terminal protein sequence, and
   b) a helper adenoviral DNA sequence comprising a second origin of replication, wherein in a replication assay, the replication activity level of said second origin of replication comprises a 5 fold to 20 fold difference over the replication activity level of said first origin of replication.

* * * * *

UNITED STATES PATENT AND TRADEMARK OFFICE
CERTIFICATE OF CORRECTION

PATENT NO. : 7,820,441 B2
APPLICATION NO. : 10/381153
DATED : October 26, 2010
INVENTOR(S) : Jeffrey S. Chamberlain and Dennis J. Hartigan-O'Connor Page 1 of 1

It is certified that error appears in the above-identified patent and that said Letters Patent is hereby corrected as shown below:

Col. 1, Lines 6-8 should be deleted, and replaced with the following:

-- This invention was made with government support under AG015434 awarded by the National Institutes of Health. The government has certain rights in the invention. --

Signed and Sealed this
Eighth Day of February, 2011

David J. Kappos
*Director of the United States Patent and Trademark Office*